(12) United States Patent
Orlinger et al.

(10) Patent No.: US 11,554,169 B2
(45) Date of Patent: Jan. 17, 2023

(54) CMV VACCINES

(71) Applicant: Hookipa Biotech GmbH, Vienna (AT)

(72) Inventors: Klaus Orlinger, Vienna (AT); Karen Lingnau, Vienna (AT); Thomas Monath, Harvard, MA (US); Farshad Guirakhoo, Melrose, MA (US); Gerhard Fuhrmann, Vienna (AT); Katherine Cohen, Vienna (AT); Vera Baumgartl-Strasser, Purkersdorf (AT); Andreas Aspöck, Vienna (AT); Manuela Kainer, Neulengbach (AT); Bernhard Brim, Mauerbach (AT); Bettina Kiefmann, Vienna (AT); Elizabeth Watson, Vienna (AT); Mario Aistleithner, Vienna (AT); Katharina Bayer, Mistelbach (AT); Elsa Mühlbacher, Vienna (AT)

(73) Assignee: Hookipa Biotech GmbH, Vienna (AT)

( * ) Notice: Subject to any disclaimer, the term of this patent is extended or adjusted under 35 U.S.C. 154(b) by 0 days.

(21) Appl. No.: 16/137,323

(22) Filed: Sep. 20, 2018

(65) Prior Publication Data
US 2019/0247493 A1    Aug. 15, 2019

Related U.S. Application Data

(62) Division of application No. 15/101,363, filed as application No. PCT/EP2014/076466 on Dec. 3, 2014, now Pat. No. 10,111,945.

(60) Provisional application No. 62/055,699, filed on Sep. 26, 2014, provisional application No. 61/911,135, filed on Dec. 3, 2013.

(51) Int. Cl.
*A61K 39/245* (2006.01)
*C12N 15/86* (2006.01)
*A61K 39/12* (2006.01)
*C07K 14/005* (2006.01)
*C07K 16/10* (2006.01)
*C12N 7/00* (2006.01)
*A61K 39/00* (2006.01)

(52) U.S. Cl.
CPC ............ *A61K 39/245* (2013.01); *A61K 39/12* (2013.01); *C07K 14/005* (2013.01); *C07K 16/10* (2013.01); *C12N 7/00* (2013.01); *C12N 15/86* (2013.01); *A61K 2039/5254* (2013.01); *A61K 2039/5256* (2013.01); *A61K 2039/54* (2013.01); *A61K 2039/55566* (2013.01); *C07K 2319/00* (2013.01); *C12N 2710/16134* (2013.01); *C12N 2760/10021* (2013.01); *C12N 2760/10043* (2013.01); *C12N 2840/20* (2013.01); *C12N 2840/206* (2013.01)

(58) Field of Classification Search
CPC .................. A61K 39/245; A61K 39/12; A61K 2039/5254; A61K 2039/5256; A61K 2039/54; A61K 2039/55566; C07K 14/005; C07K 16/10; C07K 2319/00; C12N 7/00; C12N 15/86; C12N 2710/16134; C12N 2760/10021; C12N 2760/10043; C12N 2840/20; C12N 2840/206; A61P 31/22; A61P 37/04
See application file for complete search history.

(56) References Cited

U.S. PATENT DOCUMENTS

| 5,057,540 | A | 10/1991 | Kensil et al. |
| 8,592,205 | B2 | 11/2013 | Pinschewer et al. |
| 8,834,307 | B2 | 9/2014 | Itoo et al. |
| 9,309,289 | B2 | 4/2016 | Pinschewer et al. |
| 9,809,801 | B2 | 11/2017 | Belnoue et al. |
| 9,944,952 | B2 | 4/2018 | Pinschewer et al. |
| 10,111,945 | B2 | 10/2018 | Orlinger et al. |
| 10,655,145 | B2 | 5/2020 | Pinschewer et al. |
| 10,669,315 | B2 | 6/2020 | Orlinger et al. |
| 10,722,564 | B2 | 7/2020 | Pinschewer et al. |
| 11,266,727 | B2 | 3/2022 | Schmidt et al. |
| 11,214,598 | B2 | 4/2022 | Monath et al. |
| 2009/0148451 | A1 | 6/2009 | Nicolette |
| 2010/0297172 | A1 | 11/2010 | Pinschewer et al. |
| 2010/0316667 | A1 | 12/2010 | Diamond et al. |
| 2012/0093848 | A1 | 4/2012 | Lian et al. |
| 2014/0050760 | A1 | 2/2014 | Pinschewer et al. |
| 2016/0024476 | A1 | 1/2016 | Belnoue et al. |

(Continued)

FOREIGN PATENT DOCUMENTS

| JP | 2011-507536 A | 3/2011 |
| WO | WO 2006/008074 A1 | 1/2006 |
| WO | WO 2007/109812 A2 | 9/2007 |
| WO | WO 2007/109813 A1 | 9/2007 |
| WO | WO 2009/083210 A1 | 7/2009 |

(Continued)

OTHER PUBLICATIONS

Chee MS, et. al. RecName: Full=Envelope glycoprotein B; Short=gB; Flags: Precursor UniProtKB/Swiss-Prot: P06473.1. Dep. May 1, 1992.*

(Continued)

*Primary Examiner* — Rachel B Gill
(74) *Attorney, Agent, or Firm* — Jones Day

(57) ABSTRACT

Provided herein are genetically modified arenaviral vectors suitable as vaccines for prevention and treatment of cytomegalovirus infections and reactivation. Also provided herein are pharmaceutical compositions and methods for the treatment of cytomegalovirus infections and reactivation. Specifically, provided herein are pharmaceutical compositions, vaccines, and methods of treating cytomegalovirus infections and reactivation.

Figure 1:
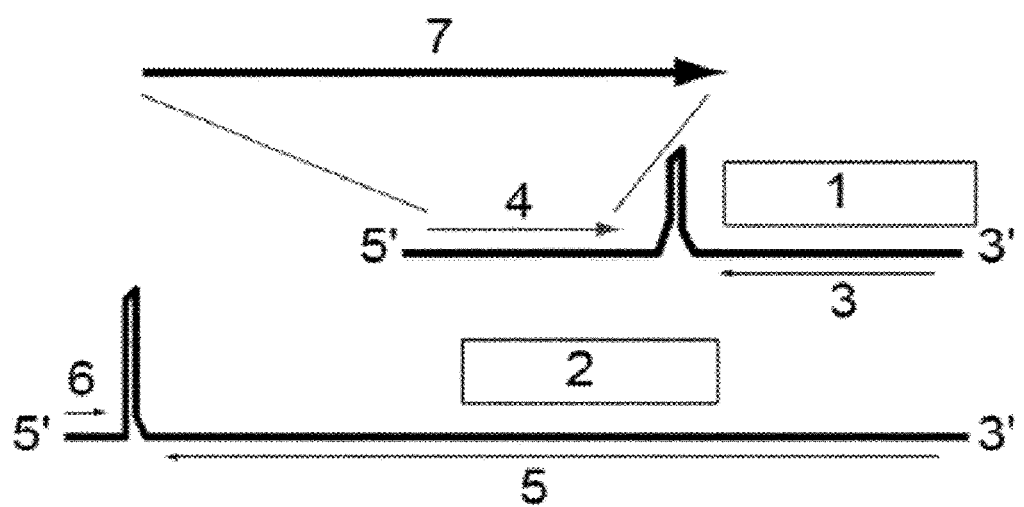

55 Claims, 35 Drawing Sheets
Specification includes a Sequence Listing.

(56) References Cited

U.S. PATENT DOCUMENTS

| | | | |
|---|---|---|---|
| 2016/0159864 A1* | 6/2016 | Carfi | A61K 39/12 435/325 |
| 2016/0194663 A1 | 7/2016 | Pinschewer et al. | |
| 2016/0296619 A1 | 10/2016 | Orlinger et al. | |
| 2017/0319673 A1 | 11/2017 | Pinschewer et al. | |
| 2018/0179257 A1 | 6/2018 | Orlinger et al. | |
| 2018/0319845 A1 | 11/2018 | Monath et al. | |
| 2018/0344830 A1 | 12/2018 | Schmidt et al. | |
| 2019/0062784 A1 | 2/2019 | Pinschewer et al. | |
| 2019/0135875 A1 | 5/2019 | Bonilla et al. | |
| 2020/0113995 A1 | 4/2020 | Orlinger et al. | |
| 2020/0206334 A1 | 7/2020 | Schmidt et al. | |
| 2021/0024584 A1 | 1/2021 | Orlinger et al. | |
| 2021/0071198 A1 | 3/2021 | Pinschewer et al. | |
| 2021/0145950 A1 | 5/2021 | Pinschewer et al. | |
| 2022/0073568 A1 | 3/2022 | Monath et al. | |

FOREIGN PATENT DOCUMENTS

| | | | |
|---|---|---|---|
| WO | WO 2012/049317 A2 | 4/2012 | |
| WO | WO 2012/093340 A2 | 7/2012 | |
| WO | WO 2012/162428 A1 | 11/2012 | |
| WO | WO 2013/006838 | 1/2013 | |
| WO | WO 2013/054199 A2 | 4/2013 | |
| WO | WO 2015/082570 A1 | 6/2015 | |
| WO | WO-2016075250 A1 * | 5/2016 | A61K 39/0011 |
| WO | WO 2021/089853 | 5/2021 | |
| WO | WO 2021/239471 | 12/2021 | |

OTHER PUBLICATIONS

Davison AJ. UL55; gB [Human herpesvirus 5]. NCBI Reference Sequence: YP_081514.1. Dep. Sep. 16, 2004.*

Dolan A, Cunningham C, Hector RD, Hassan-Walker AF, Lee L, Addison C, Dargan DJ, McGeoch DJ, Gatherer D, Emery VC, Griffiths PD, Sinzger C, McSharry BP, Wilkinson GW, Davison AJ. Genetic content of wild-type human cytomegalovirus. J Gen Virol. May 2004;85(Pt 5):1301-12.*

Chee MS, et. al. RecName: Full=65 kDa phosphoprotein; Short=pp65; AltName: Full=65 kDa matrix phosphoprotein; AltName: Full=Phosphoprotein UL83; AltName: Full=Tegument protein UL83. UniProtKB/Swiss-Prot: P06725.2. Dep. Feb. 1, 1991.*

Flatz L, et. al., Nabel GJ, Pinschewer DD. Development of replication-defective lymphocytic choriomeningitis virus vectors for the induction of potent CD8+ T cell immunity. Nat Med. Mar. 2010;16(3):339-45. Epub Feb. 7, 2010.*

Sung H, Schleiss MR. Update on the current status of cytomegalovirus vaccines. Expert Rev Vaccines. 2010;9(11):1303-1314.*

Jefferys R. The Promise and Pitfalls of Adenoviruses as Vaccine Vectors. TAG HIV Basic Science, Vaccines, and Cure Project Blog. Pub. Jan. 20, 2012.*

Lasaro MO, Ertl HC. New insights on adenovirus as vaccine vectors. Mol Ther. 2009;17(8):1333-1339.*

Flatz L, Hegazy AN, Bergthaler A, et al. Development of replication-defective lymphocytic choriomeningitis virus vectors for the induction of potent CD8+ T cell immunity. Nat Med. 2010;16(3):339-345.*

Bergthaler A, Gerber NU, Merkler D, Horvath E, de la Torre JC, Pinschewer DD. Envelope exchange for the generation of live-attenuated arenavirus vaccines. PLoS Pathog. Jun. 2006;2(6):e51. Epub Jun. 2, 2006.*

Emonet SF, Garidou L, McGavern DB, de la Torre JC. Generation of recombinant lymphocytic choriomeningitis viruses with trisegmented genomes stably expressing two additional genes of interest. Proc Natl Acad Sci U S A. Mar. 3, 2009;106(9):3473-8. Epub Feb. 10, 2009.*

Von Messling V, Cattaneo R. Toward novel vaccines and therapies based on negative-strand RNA viruses. Curr Top Microbiol Immunol. 2004;283:281-312.*

Bouard D, Alazard-Dany D, Cosset FL. Viral vectors: from virology to transgene expression. Br J Pharmacol. May 2009;157(2):153-65.*

Buchbinder SP, Mehrotra DV, Duerr A, Fitzgerald DW, Mogg R, Li D, Gilbert PB, Lama JR, et. al. Efficacy assessment of a cell-mediated immunity HIV-1 vaccine (the Step Study): a double-blind, randomised, placebo-controlled, test-of-concept trial. Lancet. Nov. 29, 2008;372(9653):1881-1893. Epub Nov. 13, 2008.).*

Marshall E. Gene therapy death prompts review of adenovirus vector. Science. Dec. 17, 1999;286(5448):2244-5.*

WHO Informal Consultation: Development of Viral Vectored Vaccines for HIV, Malaria, Tuberculosis and other Indications Geneva, Oct. 1-2, 2013. (Year: 2013).*

Cines DB, Bussel JB. SARS-CoV-2 Vaccine-Induced Immune Thrombotic Thrombocytopenia. N Engl J Med. Apr. 16, 2021: NEJMe2106315. doi: 10.1056/NEJMe2106315. Epub ahead of print. (Year: 2021).*

Pai M, Chan B, Stall NM, et al. Vaccine-induced immune thrombotic thrombocytopenia (VITT) following adenovirus vector COVID-19 vaccination. Science Briefs of the Ontario COVID-19 Science Advisory Table. 2021;2(17). (Year: 2021).*

Hallam SJ, Koma T, Maruyama J, Paessler S. Review of Mammarenavirus Biology and Replication. Front Microbiol. Aug. 3, 2018;9:1751. (Year: 2018).*

Sarute N, Ross SR. New World Arenavirus Biology. Annu Rev Virol. Sep. 29, 2017;4(1):141-158. Epub Jun. 23, 2017. (Year: 2017).*

Wingerath J, Ostroumov D, Woller N, Manns MP, Pinschewer DD, Orlinger K, Berka U, Kühnel F, Wirth TC. Recombinant LCMV Vectors Induce Protective Immunity following Homologous and Heterologous Vaccinations. Mol Ther. Nov. 1, 2017;25(11):2533-2545. Epub Jul. 20, 2017. (Year: 2017).*

Schleiss MR, Berka U, Watson E, Aistleithner M, Kiefmann B, Mangeat B, Swanson EC, et. al. Additive Protection against Congenital Cytomegalovirus Conferred by Combined Glycoprotein B/pp65 Vaccination Using a Lymphocytic Choriomeningitis Virus Vector. Clin Vaccine Immunol. Jan. 5, 2017;24(1):e00300-16. (Year: 2017).*

Schleiss MR, Bourne N, Bernstein DI. Preconception vaccination with a glycoprotein B (gB) DNA vaccine protects against cytomegalovirus (CMV) transmission in the guinea pig model of congenital CMV infection. J Infect Dis. Dec. 15, 2003;188(12):1868-74. Epub Dec. 9, 2003. (Year: 2003).*

Adler SP. Immunization to prevent congenital cytomegalovirus infection. Br Med Bull. 2013;107:57-68. Epub Aug. 16, 2013. (Year: 2013).*

Anderholm KM, Bierle CJ, Schleiss MR. Cytomegalovirus Vaccines: Current Status and Future Prospects. Drugs. Nov. 2016;76(17):1625-1645. (Year: 2016).*

Kallert SM, Darbre S, Bonilla WV, Kreutzfeldt M, Page N, Müller P, Kreuzaler M, Lu M, Favre S, Kreppel F, Löhning M, et. al. Replicating viral vector platform exploits alarmin signals for potent CD8+ T cell-mediated tumour immunotherapy. Nat Commun. May 26, 2017;8:15327. (Year: 2017).*

Chare ER, Gould EA, Holmes EC. Phylogenetic analysis reveals a low rate of homologous recombination in negative-sense RNA viruses. J Gen Virol. Oct. 2003;84(Pt 10):2691-2703. (Year: 2003).*

Bergthaler A, Gerber NU, Merkler D, Horvath E, de la Torre JC, Pinschewer DD. Envelope exchange for the generation of live-attenuated arenavirus vaccines. PLoS Pathog. Jun. 2006;2(6):e51. Epub Jun. 2, 2006. (Year: 2006).*

Ortiz-Riaño E, Cheng BYH, Carlos de la Torre J, Martínez-Sobrido L. Arenavirus reverse genetics for vaccine development. J Gen Virol. Jun. 2013;94(Pt 6):1175-1188. Epub Jan. 30, 2013. (Year: 2013).*

Altman et al., "Phenotypic analysis of antigen-specific T lymphocytes," Science, 274(5284):94-96 (1996).

Bate et al., "Cytomegalovirus seroprevalence in the United States: the national health and nutrition examination surveys, 1988-2004," Clin. Infect. Dis., 50(11):1439-1447 (2010).

Bonilla et al., "Interpretation of lymphocyte proliferation tests," Ann. Allergy Asthma Immunol., 101(1):101-104 (2008).

(56) References Cited

OTHER PUBLICATIONS

Bonilla et al., "Practice parameter for the diagnosis and management of primary immunodeficiency," Ann. Allergy Asthma Immunol., 94(5 Suppl. 1):S1-S63 (2005).
Bourne et al., "Effect of antibody alone and combined with acyclovir on neonatal herpes simplex virus infection in guinea pigs," J. Infect. Dis., 173:1-6 (1996).
Cannon et al., "Washing our hands of the congenital cytomegalovirus disease epidemic," BMC Public Health, 5:70 (2005).
Cardin et al., "Replication-defective lymphocytic choriomeningitis virus vectorsexpressing guinea pig cytomegalovirus gB and pp65 homologs areprotective against congenital guinea pig cytomegalovirus infection," Vaccine, 34:1993-1999 (2016).
Caruso et al., "Flow cytometric analysis of activation markers on stimulated T cells and their correlation with cell proliferation," Cytometry, 27(1):1-6 (1997).
Chou et al., "Analysis of interstrain variation in cytomegalovirus glycoprotein B sequences encoding neutralization-related epitopes," J. Infect. Dis., 163(6):1229-1234 (1991).
Czerkinsky et al., "A solid-phase enzyme-linked immunospot (ELISPOT) assay for enumeration of specific antibody-secreting cells," J. Immunol. Methods, 65(1-2):109-121 (1983).
Einsele et al., "Infusion of cytomegalovirus (CMV)-specific T cells for the treatment of CMV infection not responding to antiviral chemotherapy," Blood, 99(11):3916-3922 (2002).
Fang et al., "An antibody delivery system for regulated expression of therapeutic levels of monoclonal antibodies in vivo," Mol. Ther., 15(6):1153-1159 (2007).
Flatz et al., "Recovery of an arenavirus entirely from RNA polymerase I/II-driven cDNA," Proc. Natl. Acad. Sci. USA, 103(12):4663-4668 (2006).
Flatz et al., "Development of replication-defective lymphocytic choriomeningitis virus vectors for the induction of potent CD8+ T cell immunity", Nature Medicine; 16(3):339-345 (2010).
Fouts et al., "Antibodies against the gH/gL/UL128/UL130/UL131 complex comprise the majority of the anti-cytomegalovirus (anti-CMV) neutralizing antibody response in CMV hyperimmune globulin," J. Virol., 86(13):7444-7447 (2012).
Gao et al., "Towards optimising the production of and expression from polycistronic vectors in embryonic stem cells," PLoS One, 7(11):e48668 (2012).
Genbank Accession No. 60926.2, Apr. 11, 2014.
Genbank Accession No. M60929.1, Aug. 2, 1993.
Genbank Accession No. M85228.1, Aug. 2, 1993.
Ghanekar et al., "Gamma interferon expression in $CD8^+$ T cells is a marker for circulating cytotoxic T lymphocytes that recognize an HLA A2-restricted epitope of human cytomegalovirus phosphoprotein pp65," Clin. Diagn. Lab. Immunol., 8(3):628-631 (2001).
Hicks et al., "Age-related changes in mitogen-induced lymphocyte function from birth to old age," Am. J. Clin. Pathol., 80(2):159-163 (1983).
Hutchings et al., "The detection and enumeration of cytokine-secreting cells in mice and man and the clinical application of these assays," J. Immunol. Methods, 120(1):1-8 (1989).
Kensil et al., "Structural and Immunological Characterization of the Vaccine Adjuvant QS-21," in: Powell M.F., Newman M.J. (eds) Vaccine Design. Pharmaceutical Biotechnology, vol. 6. Springer, Boston, MA, Chapter 22, pp. 525-541 (1995).
Kim et al., "High cleavage efficiency of a 2A peptide derived from porcine teschovirus-1 in human cell lines, zebrafish and mice," PLoS One, 6(4):e18556 (2011).
La Rosa et al., "The immune response to human CMV," Future Virol., 7(3):279-293 (2012).
Meyer-König et al., "An antibody delivery system for regulated expression of therapeutic levels of monoclonal antibodies in vivo," J. Infect. Dis., 177(5):1162-1169 (1998).
Micklethwaite et al., "Prophylactic infusion of cytomegalovirus-specific cytotoxic T lymphocytes stimulated with Ad5f35pp65 gene-modified dendritic cells after allogeneic hemopoietic stem cell transplantation," Blood, 112(10):3974-3981 (2008).

Murali-Krishna et al., "Counting antigen-specific CD8 T cells: a reevaluation of bystander activation during viral infection," Immunity, 8(2):177-187 (1998).
Nomura et al., "Optimization of whole blood antigen-specific cytokine assays for CD4(+) T cells," Cytometry, 40(1):60-68 (2000).
Ortiz-Riano et al., "Arenavirus reverse genetics for vaccine development," J. Gen. Virol., 94(Pt 6):1175-1188 (2013).
Pass et al., "Development and evidence for efficacy of CMV glycoprotein B vaccine with MF59 adjuvant," J. Clin. Virol., 46(Suppl. 4):S73-S76 (2009).
Pass et al., "Vaccine prevention of maternal cytomegalovirus infection," N. Engl. J. Med., 360(12):1191-1199 (2009).
Patent Cooperation Treaty, International Search Report for PCT/EP2014/076466, dated May 6, 2015.
Peggs et al., "Directly selected cytomegalovirus-reactive donor T cells confer rapid and safe systemic reconstitution of virus-specific immunity following stem cell transplantation," Clin. Infect. Dis., 52(1):49-57 (2011).
Perfetto et al., "Seventeen-colour flow cytometry: unravelling the immune system," Nat. Rev. Immunol., 4(8):648-655 (2004).
Pipeling et al., "Primary cytomegalovirus phosphoprotein 65-specific CD8+ T-cell responses and T-bet levels predict immune control during early chronic infection in lung transplant recipients," J. Infect. Dis., 204(11):1663-1671 (2011).
Ryckman et al., "Characterization of the human cytomegalovirus gH/gL/UL128-131 complex that mediates entry into epithelial and endothelial cells," J. Virol., 82(1):60-70 (2008).
Sanchez et al., "Rescue of the prototypic Arenavirus LCMV entirely from plasmid," Virology, 350(2):370-380 (2006).
Schleiss et al., "Additive protection against congenital cytomegalovirus conferred by combined glycoprotein B/pp65 vaccination using a lymphocytic choriomeningitis virus vector," Clin. Vaccine Immunol., 24(1):e00300-16 (2017).
Schleiss et al., "Immunogenicity evaluation of DNA vaccines that target guinea pig cytomegalovirus proteins glycoprotein B and UL83," Viral Immunol., 13(2):155-167 (2000).
Schleiss et al., "Preconception vaccination with a glycoprotein B (gB) DNA vaccine protects against cytomegalovirus (CMV) transmission in the guinea pig model of congenital CMV infection," J. Infect. Dis., 188(12):1868-1874 (2003).
Selinsky et al., "A DNA-based vaccine for the prevention of human cytomegalovirus-associated diseases," Human Vaccines, 1(1):16-23 (2005).
Shedlock et al., "Vaccination with synthetic constructs expressing cytomegalovirus immunogens is highly T cell immunogenic in mice," Human Vaccines & Immunotherapeutics 8(11):1668-1681 (2012).
Stoute et al., "A preliminary evaluation of a recombinant circumsporozoite protein vaccine against Plasmodium falciparum malaria.," N. Engl. J. Med., 336(2):86-91 (1997).
Suni et al., "Detection of antigen-specific T cell cytokine expression in whole blood by flow cytometry," J. Immunol. Methods, 212(1):89-98 (1998).
Swanson et al., "Comparison of monovalent glycoprotein B with bivalent gB/pp65 (GP83) vaccine for congenital cytomegalovirus infection in a guinea pig model: Inclusion of GP83 reduces gB antibody response but both vaccine approaches provide equivalent protection against pup mortality," Vaccine, 33(32):4013-4018 (2015).
Wang et al., "Human cytomegalovirus virion protein complex required for epithelial and endothelial cell tropism," Proc. Natl. Acad. Sci. USA, 102(50):18153-18158 (2005).
Wills et al., "The human cytotoxic T-lymphocyte (CTL) response to cytomegalovirus is dominated by structural protein pp65: frequency, specificity, and T-cell receptor usage of pp65-specific CTL," J. Virol., 70(11):7569-7579 (1996).
Wussow et al., "A vaccine based on the rhesus cytomegalovirus UL128 complex induces broadly neutralizing antibodies in rhesus macaques," J. Virol., 87(3):1322-1332 (2013).
Zhong et al., "Induction of pluripotent protective immunity following immunisation with a chimeric vaccine against human cytomegalovirus," PLoS One, 3(9):e3256 (2008).
U.S. Appl. No. 16/861,758, filed Apr. 29, 2020, Pinschewer et al.

(56) References Cited

OTHER PUBLICATIONS

Hartikka et al., "Preclinical evaluation of the immunogenicity and safety of plasmid DNA-based prophylactic vaccines for human cytomegalovirus," *Humam Vaccines Immunotherap.*, 8(11):1595-1606 (2012).
Bergthaler et al., "Envelope exchange for the generation of live-attenuated arenavirus vaccines," PLOS Pathogen, 2(6):501-512 (2006).
Buchmeier et al., "Arenaviridae: The Viruses and Their Replication," Fields Virol., 2:1635-1668 (2001).
Buchmeier et al., eds., 2007, "Arenaviridae: the viruses and their replication," Fields Virology; Philadelphia, PA, USA: Wolter Kluwer Lippincott Williams & Wilkins. 2:1791-1827 (2007).
Charrel et al., 2003, "New insights into the evolutionary relationships between arenaviruses provided by comparative analysis of small and large segment sequences," Virology, 317:191-196.
International Search Report and Written Opinion dated May 16, 2015 for PCT/EP2014/076466 (14 pages).
Remy-Ziller et al., "Immunological Characterization of a Modified Vaccinia Virus Ankara Vector Expressing the Human Papillomavirus 16 E1 Protein," Clinical and Vaccine Immunology, 21(2):147-155 (2014).

\* cited by examiner

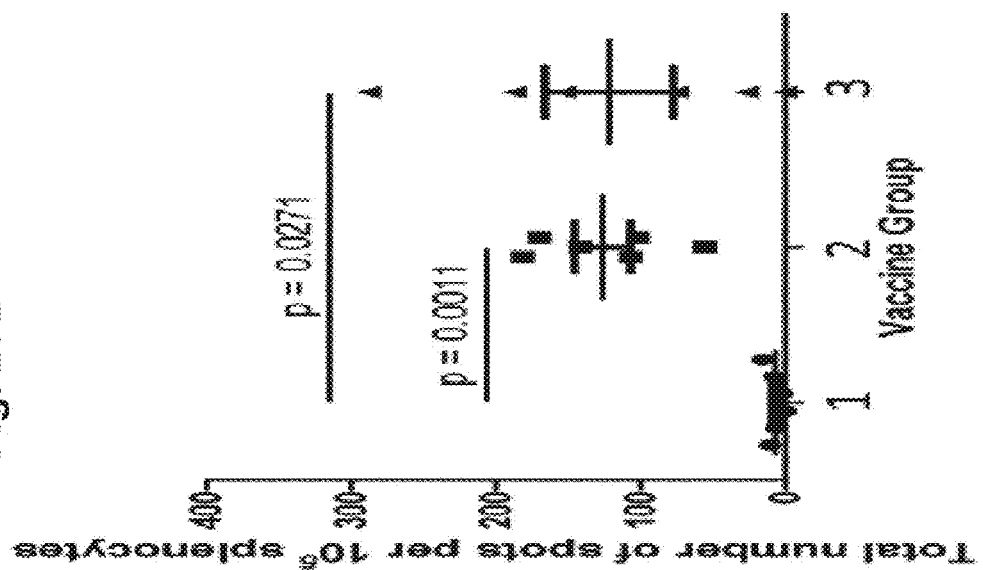
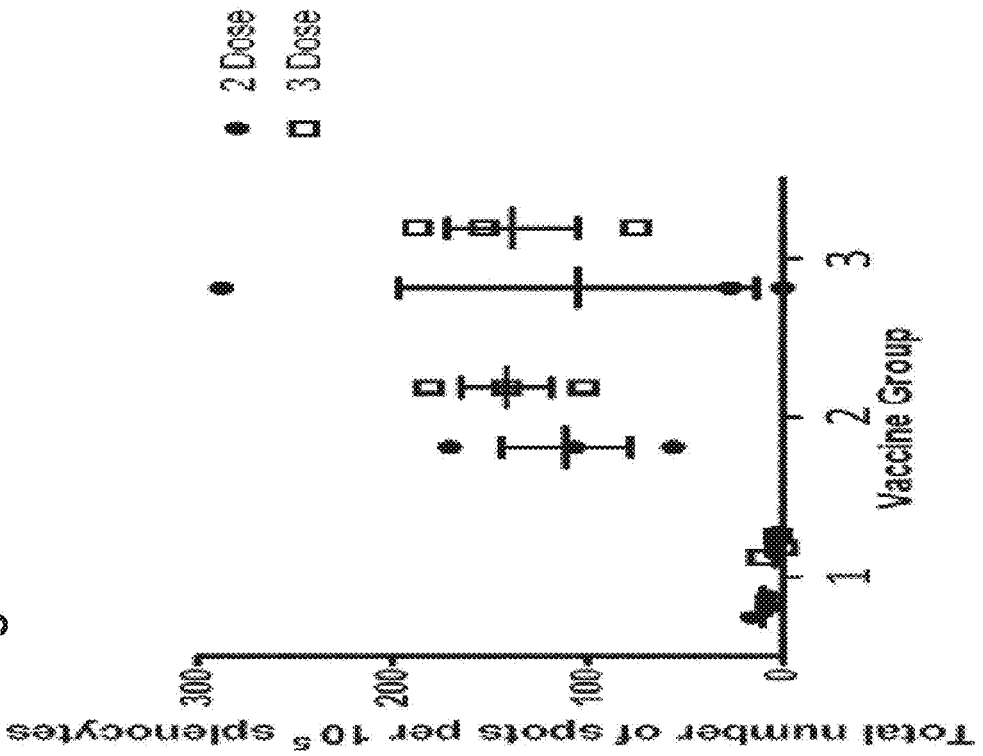
Fig. 27A
Fig. 27B

CMV VACCINES

CROSS REFERENCE TO RELATED APPLICATION

The present application is a divisional of U.S. patent application Ser. No. 15/101,363, filed Jun. 2, 2016, which is a U.S. National Stage Application under 35 U.S.C. § 371 of International Patent Application No. PCT/EP2014/076466, filed Dec. 3, 2014, which claims the benefit of U.S. Provisional Application No. 61/911,135 filed on Dec. 3, 2013 and U.S. Provisional Application No. 62/055,699 filed on Sep. 26, 2014, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Sep. 19, 2018, is named 13194-030-999_SEQ_LISTING.txt and is 292,057 bytes in size.

1. INTRODUCTION

The invention relates to genetically modified arenaviruses suitable as vaccines for prevention and treatment of cytomegalovirus infections and reactivation. The invention also relates to pharmaceutical compositions and methods for the treatment of cytomegalovirus infections and reactivation. Specifically, provided herein are pharmaceutical compositions, vaccines, and methods of treating cytomegalovirus infections and reactivation.

2. BACKGROUND

2.1 Medical Need

Human cytomegalovirus (HCMV) is a ubiquitous beta-herpes virus that typically causes chronic latent, asymptomatic infection in healthy individuals, with overall age-adjusted CMV seroprevalence in the developed world of above 50% (Bate et al., Clin. Infect. Dis., 2010, 50(11):1439; La Rosa & Diamond, Future Virol., 2012, 7(3):279). However, in immunocompromised patients, especially transplant recipients, HIV-infected persons, and congenitally infected newborns, CMV causes significant morbidity and mortality and therefore poses an important public health problem.

HCMV infection is the most common cause of congenital viral infection in the developed world. Approximately 40,000 congenitally infected infants are born in the United States per year. Congenital CMV infection can result in a wide range of neurodevelopmental disabilities, and it presents the most common infectious cause of hearing loss in children. The large public health impact of HCMV is demonstrated by the fact that more children suffer from long-term sequelae as a result of congenital CMV infection than either Down syndrome or fetal alcohol syndrome (Cannon et al., BMC Public Health, 2005, 5:70).

In addition to its impact as a perinatal infection, HCMV is also an important cause of infectious complications in transplant patients, causing pneumonitis, hepatitis, gastrointestinal ulceration, retinitis and death. Although nowadays these severe forms of end organ disease can be prevented in most cases by the cost-intensive, routine use of preemptive therapy with antiviral drugs, late reactivation of CMV infection is still a problem. Furthermore, CMV triggers indirect effects such as graft rejection, accelerated atherosclerosis after heart or lung transplant or immunosuppression.

Moreover, CMV infection and/or reactivation are also significantly associated with mortality in HIV patients as well as in patients admitted to intensive care units.

2.2 HCMV Immunity and Vaccine Development

The significant public health impact of congenital CMV has led the US Institute of Medicine to rank development of a CMV vaccine as a top priority in its recent report "Vaccines for the 21st Century". Although vaccine development efforts have been going on for several decades; so far there is no licensed CMV vaccine available. Development of an efficacious vaccine has been proven difficult as there are still critical gaps in the understanding of CMV epidemiology and transmission.

CMV rarely elicits disease in healthy immunocompetent hosts, where immunity against CMV provides some level of protection and plays an essential role in maintaining asymptomatic infection. However, the human immune system is unable to clear the infection and CMV usually establishes chronic infections that can persist lifelong despite host immunity. In contrast, uncontrolled CMV viremia and life-threatening symptoms readily occur after immunosuppression and in the immature host.

Several vaccine candidates based on different technologies have already been studied in clinical trials. Partial protection by vaccination has been demonstrated with both live-attenuated and glycoprotein vaccine candidates inducing CMV-specific antibody responses. Passive immunization with antibodies has also been shown to provide some protection. However, once latent infection has been established, strong induction of CMV-specific T cells seems to be necessary to control reactivation and disease.

2.3 HCMV Vaccine Antigens

Several data indicate that neutralizing antibodies inhibiting CMV entry into host cells play an important role for prevention of horizontal and vertical virus transmission. Studies based on neutralization of fibroblast infection have defined the major envelope glycoprotein B (gB) as one of the dominant targets of neutralizing antibodies. The inclusion of gB in a human CMV vaccine candidate is further supported by clinical phase II data showing that a subunit vaccine based on gB in combination with MF59 adjuvant is able to confer partial protection in seronegative women (Pass, J. Clin. Virol., 2009, 46(Suppl 4):573; Pass et al., N. Eng. J. Med., 2009, 360(12):1191).

Though vaccine candidates based on recombinant gB elicit high titers of neutralizing antibodies preventing HCMV infection, other HCMV antigens may elicit higher titers of antibodies that inhibit HCMV infection of particular cell types, such as epithelial and endothelial cells. A vaccine strategy for effective prevention of HCMV infection will likely depend on the ability to induce potent neutralizing antibodies inhibiting virus entry into various cell types. Recent studies have shown that a pentameric complex formed by the glycoproteins gH/gL (UL75/UL115), UL128, UL130, and UL131A is required for HCMV entry into epithelial and endothelial cells and is the target of potent neutralizing antibodies in HCMV-seropositive individuals (Ryckman et al., J. Virol., 2008, 82(1):60; Wang & Shenk, Proc. Natl. Acad. Sci. USA, 2005, 102:18153; Wussow, et al., J. Virol., 2013, 87(3):1322).

A potential vaccine antigen for the induction of protection against CMV disease mediated by cytotoxic T cells, is the tegument protein pp65 which is an immunodominant CD8+ T-cell antigen (Wills et al., J. Virol., 1996, 70(11):7569). pp65-specific CD8+ T-cell frequencies have been associated with immune control of CMV in transplant patients (Pipeling et al., J. Infect. Dis., 2011, 204(11):1663) and adaptive transfer of pp65-specific T cells appears to have therapeutic utility in hematopoietic stem cell transplant recipients (Peggs et al., Clin Infect Dis 2011, 52(1):49; Einsele et al., Blood, 2002, 99(11):3916; Micklethwaite et al., Blood, 2008, 112(10):3974). Taken together these findings suggest that a CMV vaccine designed to prevent CMV disease in transplant patients requires inclusion of pp65.

3. SUMMARY OF THE INVENTION

The invention relates to an infectious, replication-deficient arenavirus viral vector comprising a nucleotide sequence selected from the group consisting of:
a. a nucleotide sequence encoding a CMV glycoprotein gB or an antigenic fragment thereof;
b. a nucleotide sequence encoding a CMV tegument protein pp65 or an antigenic fragment thereof;
c. a nucleotide sequence encoding a CMV glycoprotein gH or an antigenic fragment thereof;
d. a nucleotide sequence encoding a CMV glycoprotein gL or an antigenic fragment thereof;
e. a nucleotide sequence encoding a CMV UL128 protein or an antigenic fragment thereof;
f. a nucleotide sequence encoding a CMV UL130 protein or an antigenic fragment thereof; and
g. a nucleotide sequence encoding a CMV UL131A protein or an antigenic fragment thereof.

In certain embodiments, a viral vector as provided herein is infectious, i.e., is capable of entering into or inject its genetic material into a host cell. In certain more specific embodiments, a viral vector as provided herein is infectious, i.e., is capable of entering into or inject its genetic material into a host cell followed by amplification and expression of its genetic information inside the host cell.

In certain embodiments, the CMV glycoprotein gB or the antigenic fragment thereof is selected from SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, and SEQ ID NO: 30 SEQ ID NO: 60, and SEQ ID NO: 63. In certain embodiments, the antigenic fragment is at least 10, 25, 50, 75, 100, 150, 200, 250, 300, 350, 400, 450, 500, 600, 700, 800, or at least 900 amino acids long. In certain embodiments, the fragment is antigenic when it is capable of (i) eliciting an antibody immune response in a host (e.g., mouse, rabbit, goat, or donkey) wherein the resulting antibodies bind specifically to human CMV glycoprotein gB; and/or (ii) eliciting a specific T cell immune response.

In certain embodiments, the gB antigen comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the gB antigen or to an antigenic fragment selected from SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 60, and SEQ ID NO: 63.

In certain embodiments, the pp65 antigen comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the pp65 antigen or antigenic fragment of SEQ ID NO: 36. In certain embodiments, the antigenic fragment is at least 10, 25, 50, 75, 100, 150, 200, 250, 300, 350, 400, 450, or at least 500 amino acids long. In certain embodiments, the fragment is antigenic when it is capable of (i) eliciting an antibody immune response in a host (e.g., mouse, rabbit, goat, or donkey) wherein the resulting antibodies bind specifically to human CMV pp65; and/or (ii) eliciting a specific T cell immune response.

In certain embodiments, the glycoprotein gH comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the glycoprotein gH or antigenic fragment selected from SEQ ID NO: 39 and SEQ ID NO: 52. In certain embodiments, the antigenic fragment is at least 10, 25, 50, 75, 100, 150, 200, 250, 300, 350, 400, 450, 500, 600, 700, or at least 750 amino acids long. In certain embodiments, the fragment is antigenic when it is capable of (i) eliciting an antibody immune response in a host (e.g., mouse, rabbit, goat, or donkey) wherein the resulting antibodies bind specifically to human CMV glycoprotein gH; and/or (ii) eliciting a specific T cell immune response.

In certain embodiments, the glycoprotein gL comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the glycoprotein gL or antigenic fragment of SEQ ID NO: 41. In certain embodiments, the antigenic fragment is at least 10, 25, 50, 75, 100, 150, 200, 250, or at least 300 amino acids long. In certain embodiments, the fragment is antigenic when it is capable of (i) eliciting an antibody immune response in a host (e.g., mouse, rabbit, goat, or donkey) wherein the resulting antibodies bind specifically to human CMV glycoprotein gL; and/or (ii) eliciting a specific T cell immune response.

In certain embodiments, the UL128 comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the UL128 or antigenic fragment of SEQ ID NO: 43. In certain embodiments, the antigenic fragment is at least 10, 25, 50, 75, 100, at least 150 amino acids long. In certain embodiments, the fragment is antigenic when it is capable of (i) eliciting an antibody immune response in a host (e.g., mouse, rabbit, goat, or donkey) wherein the resulting antibodies bind specifically to human CMV UL128; and/or (ii) eliciting a specific T cell immune response.

In certain embodiments, the UL130 comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the UL130 or antigenic fragment of SEQ ID NO: 46. In certain embodiments, the antigenic fragment is at least 10, 25, 50, 75, 100, 150, 200, at least 250 amino acids long. In certain embodiments, the fragment is antigenic when it is capable of (i) eliciting an antibody immune response in a host (e.g., mouse, rabbit, goat, or donkey) wherein the resulting antibodies bind specifically to human CMV UL130; and/or (ii) eliciting a specific T cell immune response.

In certain embodiments, the UL131A comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the UL131A or antigenic fragment of SEQ ID NO: 48. In certain embodiments, the antigenic fragment is at least 10, 25, 50, 75, at least 100 amino acids long. In certain embodiments, the fragment is antigenic when it is capable of (i) eliciting an antibody immune response in a host (e.g., mouse, rabbit, goat, or donkey) wherein the resulting antibodies bind specifically to human CMV UL131A; and/or (ii) eliciting a specific T cell immune response.

In certain embodiments, the viral vector comprises at least two of:
  a. a nucleotide sequence encoding a CMV glycoprotein gH or an antigenic fragment thereof;
  b. a nucleotide sequence encoding a CMV glycoprotein gL or an antigenic fragment thereof;
  c. a nucleotide sequence encoding a CMV UL128 protein or an antigenic fragment thereof;
  d. a nucleotide sequence encoding a CMV UL130 protein or an antigenic fragment thereof; and
  e. a nucleotide sequence encoding a CMV UL131A protein or an antigenic fragment thereof,
wherein the two nucleotide sequences selected from a. to e. above are separated by a nucleotide sequence that encodes a self-cleaving peptide or an amino acid sequence that leads to release of the upstream amino acid sequence by "ribosome skipping" or a sequence element leading to binding of the ribosome and translation of the downstream sequence such as "internal ribosome entry sites".

In certain embodiments, the viral vector comprises at least three of:
  a. a nucleotide sequence encoding a CMV glycoprotein gH or an antigenic fragment thereof;
  b. a nucleotide sequence encoding a CMV glycoprotein gL or an antigenic fragment thereof;
  c. a nucleotide sequence encoding a CMV UL128 protein or an antigenic fragment thereof;
  d. a nucleotide sequence encoding a CMV UL130 protein or an antigenic fragment thereof; and
  e. a nucleotide sequence encoding a CMV UL131A protein or an antigenic fragment thereof,
wherein the three nucleotide sequences selected from a. to e. above are separated by a nucleotide sequence that encodes a self-cleaving peptide or an amino acid sequence that leads to release of the upstream amino acid sequence by "ribosome skipping" or a sequence element leading to binding of the ribosome and translation of the downstream sequence such as "internal ribosome entry sites".

In certain embodiments, the viral vector comprises at least four of:
  a. a nucleotide sequence encoding a CMV glycoprotein gH or an antigenic fragment thereof;
  b. a nucleotide sequence encoding a CMV glycoprotein gL or an antigenic fragment thereof;
  c. a nucleotide sequence encoding a CMV UL128 protein or an antigenic fragment thereof;
  d. a nucleotide sequence encoding a CMV UL130 protein or an antigenic fragment thereof; and
  e. a nucleotide sequence encoding a CMV UL131A protein or an antigenic fragment thereof,
wherein the four nucleotide sequences selected from a. to e. above are separated by a nucleotide sequence that encodes a self-cleaving peptide or an amino acid sequence that leads to release of the upstream amino acid sequence by "ribosome skipping" or a sequence element leading to binding of the ribosome and translation of the downstream sequence such as "internal ribosome entry sites".

In certain embodiments, the viral vector comprises:
  a. a nucleotide sequence encoding a CMV glycoprotein gH or an antigenic fragment thereof;
  b. a nucleotide sequence encoding a CMV glycoprotein gL or an antigenic fragment thereof;
  c. a nucleotide sequence encoding a CMV UL128 protein or an antigenic fragment thereof;
  d. a nucleotide sequence encoding a CMV UL130 protein or an antigenic fragment thereof; and
  e. a nucleotide sequence encoding a CMV UL131A protein or an antigenic fragment thereof,
wherein the five nucleotide sequences a. to e. above are separated by a nucleotide sequence that encodes a self-cleaving peptide or an amino acid sequence that leads to release of the upstream amino acid sequence by "ribosome skipping" or a sequence element leading to binding of the ribosome and translation of the downstream sequence such as "internal ribosome entry sites".

In certain embodiments, the self-cleaving peptide (or the ribosome-skipping sequence) can be obtained from a 2A protein from a member of the virus family Picornaviridae. In certain specific embodiments, the self-cleaving peptide (or the ribosome-skipping sequence) is obtained from (or derived from) Porcine teschovirus-1 2A, Thoseaasignavirus 2A, or Foot-and-mouth disease virus 2A peptide.

In certain embodiments, an open reading frame (ORF) of the arenavirus is deleted or functionally inactivated. In a specific embodiment, the ORF that encodes the glycoprotein GP of the arenavirus is deleted or functionally inactivated. In certain embodiments, functional inactivation of a gene eliminates any translation product. In certain embodiments, functional inactivation refers to a genetic alteration that allows some translation, the translation product, however, is not longer functional and cannot replace the wild type protein.

In certain embodiments, the viral vector can amplify and express its genetic information in a cell that has been infected by the viral vector but the viral vector is unable to produce further infectious progeny particles in a non-complementing cell. In certain embodiments, a viral vector as provided herein is infectious, i.e., is capable of entering into or inject its genetic material into a host cell. In certain more specific embodiments, a viral vector as provided herein is infectious, i.e., is capable of entering into or inject its genetic material into a host cell followed by amplification and expression of its genetic information inside the host cell.

In certain embodiments, the genomic information encoding the infectious, replication-deficient arenavirus particle is derived from the lymphocytic choriomeningitis virus (LCMV) Clone 13 strain or the LCMV MP strain. The nucleotide sequence of the S segment and of the L segment of Clone 13 are set forth in SEQ ID NOs: 32 and 33, respectively.

In certain embodiments, provided herein is a viral vector whose genome is or has been derived from the genome of Clone 13 (SEQ ID NOs: 32 and 33) by deleting an ORF of the Clone 13 genome (e.g., the ORF of the GP protein) and replacing it with a heterologous ORF that encodes an antigen (e.g., a CMV antigen) such that the remaining LCMV genome is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the nucleotide sequence of Clone 13 (SEQ ID NOs: 32 and 33).

In certain embodiments, provided herein is a viral vector whose genome has been derived from the genome of the LCMV strain MP (SEQ ID NOs: 49 and 53) by deleting an ORF of the LCMV strain MP genome (e.g., the ORF of the GP protein) and replacing it with a heterologous ORF that encodes an antigen (e.g., a CMV antigen) such that the remaining LCMV genome is at least 80%, 81%, 82%, 83%, 84%, 85%, 86%, 87%, 88%, 89%, 90%, 91%, 92%, 93%, 94%, 95%, 96%, 97%, 98%, at least 99%, 99.1%, 99.2%, 99.3%, 99.4%, 99.5%, 99.6%, 99.7%, 99.8%, at least 99.9% or 100% identical to the nucleotide sequence of LCMV strain MP (SEQ ID NOs: 49 and 53).

In a more specific embodiment, the viral vector comprises a genomic segment, wherein the genomic segment comprises a nucleotide sequence that is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the sequence of nucleotide 1639 to 3315 of SEQ ID NO: 31 or 1640 to 3316 of SEQ ID NO: 32. In certain embodiments, the viral vector comprises a genomic segment comprising a nucleotide sequence encoding an expression product whose amino acid sequence is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the amino acid sequence encoded by 1639 to 3315 of SEQ ID NO: 31 or 1640 to 3316 of SEQ ID NO: 32.

The invention also relates to an infectious, replication-deficient arenavirus particle comprising a nucleotide sequence encoding a CMV glycoprotein gB wherein the cytoplasmic domain of the glycoprotein gB has been deleted. In specific embodiments, the cytoplasmic domain of gB has been deleted. In other specific embodiments, the cytoplasmic domain of gB has been substituted with the cytoplasmic domain of a heterologous protein. In even other specific embodiments, the cytoplasmic domain and the transmembrane domain of gB have been substituted with the cytoplasmic domain and the transmembrane domain of a heterologous protein. In certain embodiments, the heterologous protein is the G protein of the Vesicular Stomatitis Virus (VSV) or the hemagglutinin protein of influenza virus. In certain embodiments, the growth or infectivity of the arenavirus is not affected by the heterologous amino acids. In specific embodiments, the transmembrane domain of the gB protein is deleted.

Also provided herein are nucleic acids encoding a fusion protein comprising a CMV glycoprotein gB or a fragment thereof and a heterologous polypeptide. In certain embodiments, the cytoplasmic domain of the glycoprotein gB has been deleted. In certain embodiments, the cytoplasmic domain of the glycoprotein gB has been substituted with the cytoplasmic domain of a heterologous protein. In even other specific embodiments, the cytoplasmic domain and the transmembrane domain of gB have been substituted with the cytoplasmic domain and the transmembrane domain of a heterologous protein. In certain embodiments, the heterologous protein is the G protein of VSV or the hemagglutinin protein of influenza virus. In certain embodiments, the transmembrane domain of the gB protein is deleted.

Also provided herein are fusion proteins comprising a CMV glycoprotein gB or a fragment thereof and a heterologous polypeptide. In certain embodiments, the cytoplasmic domain of the glycoprotein gB has been deleted. In certain embodiments, the cytoplasmic domain of the glycoprotein gB has been substituted with the cytoplasmic domain of the heterologous protein. In even other specific embodiments, the cytoplasmic domain and the transmembrane domain of gB have been substituted with the cytoplasmic domain and the transmembrane domain of a heterologous protein. In certain embodiments, the heterologous protein is the G protein of VSV or the hemagglutinin protein of influenza virus. In certain embodiments, the transmembrane domain of the gB protein is deleted.

Also provided herein are isolated nucleic acids, wherein the nucleic acid encodes an arenavirus genomic segment wherein one ORF of the genomic segment is deleted or functionally inactivated and wherein the genomic segment comprises one or any combination of:
  a. a nucleotide sequence encoding a CMV glycoprotein gB or an antigenic fragment thereof;
  b. a nucleotide sequence encoding a CMV tegument protein pp65 or an antigenic fragment thereof;
  c. a nucleotide sequence encoding a CMV glycoprotein gH or an antigenic fragment thereof
  d. a nucleotide sequence encoding a CMV glycoprotein gL or an antigenic fragment thereof
  e. a nucleotide sequence encoding a CMV UL128 protein or an antigenic fragment thereof
  f. a nucleotide sequence encoding a CMV UL130 protein or an antigenic fragment thereof and
  g. a nucleotide sequence encoding a CMV UL131A protein or an antigenic fragment thereof.

In certain embodiments, the genomic segment encoded by the isolated nucleic acid is the short segment, wherein the ORF encoding the GP is deleted. In certain embodiments, the genomic segment comprises a CMV glycoprotein gB or a fragment thereof. In certain embodiments, the cytoplasmic domain of the glycoprotein gB has been deleted. In certain embodiments, the cytoplasmic domain of the glycoprotein gB has been substituted with the cytoplasmic domain of a heterologous protein. In specific embodiments, the heterologous protein is the G protein of VSV or the hemagglutinin protein of influenza virus. In certain embodiments, the transmembrane domain of the gB protein is deleted. In certain embodiments, the cytoplasmic and transmembrane domains of the glycoprotein gB have been substituted with the cytoplasmic domain and the transmembrane domain of the heterologous protein.

In one aspect, provided herein are methods for generating an infectious, replication-deficient arenavirus particle comprising:
  a. transfecting into a host cell a nucleic acid described herein;
  b. maintaining the host cell under conditions suitable for virus formation; and
  c. harvesting the infectious, replication-deficient arenavirus particle;
wherein the host cell expresses the ORF that is deleted or functionally inactivated on the genomic segment. In certain embodiments, any additional nucleic acids required for the rescue of a viral particle are also transfected into the host cell in step a. Such additional nucleic acids can be: the cDNA of the second arenavirus genomic segment, a nucleic acid encoding the L ORF, and/or a nucleic acid encoding the N ORF.

In another aspect, provided herein are compositions, e.g., pharmaceutical, immunogenic or vaccine compositions, comprising a viral vector described herein and a pharmaceutically acceptable carrier. Also provided herein are compositions (e.g., vaccine compositions) that comprise two or more different viral vectors described herein (i.e., wherein the viral vectors encode different CMV antigens). In certain embodiments, the pharmaceutical composition comprises a nucleic acid or fusion protein described herein.

In a further aspect, provided herein are methods of treating or preventing CMV infection or reactivation in a patient, comprising administering to the patient a viral vector, a pharmaceutical composition, an immunogenic composition, or a vaccine described herein. In yet another aspect, provided herein is use of a viral vector, a pharmaceutical composition, an immunogenic composition, or a vaccine described herein for the treatment or prevention of CMV infection or reactivation in a patient. In certain embodiments, an infectious, replication-deficient arenavirus expressing a CMV antigen or a fragment thereof is capable of preventing transmission and/or infection of CMV from a mother to an unborn child. In certain embodiments, one or more infectious, replication-deficient arenaviruses expressing a CMV antigen or a fragment thereof are capable of preventing transmission and/or infection of CMV from a mother to an unborn child.

In certain embodiments, administering to a patient an infectious, replication-deficient arenavirus expressing a CMV antigen or a fragment thereof induces a long-lasting immune response.

In certain embodiments, provided herein are methods of treating and or preventing CMV infection or reactivation in a patient, comprising administering to the patient two or more replication-deficient arenaviruses expressing a CMV antigen or fragment thereof. In a more specific embodiment, each replication-deficient arenavirus expresses a different CMV antigen or fragment thereof. In other embodiments, each replication-deficient arenavirus expresses a CMV antigen or a derivative thereof. In some embodiments the derivative thereof is a CMV antigen fragment. In yet another embodiment provided herein are compositions that comprise two or more replication-deficient arenaviruses each expressing a different CMV antigen or fragment thereof.

3.1 Conventions and Abbreviations

| | |
|---|---|
| APC | Antigen presenting cells |
| C-cell | Complementing cell line |
| CD4 | Cluster of Differentiation 4 |
| CD8 | Cluster of Differentiation 8 |
| CMI | Cell-mediated immunity |
| CMV | Cytomegalovirus |
| Flu-HA | Influenza hemagglutinin |
| gB | Glycoprotein B |
| GP | Glycoprotein |
| GS-plasmid | Plasmid expressing genome segments |
| HRP | Horse radish peroxidase |
| IFN-γ | Interferon-γ |
| LCMV | Lymphocytic choriomeningitis virus |
| MHC | Major Histocompatibility Complex |
| NP | Nucleoprotein |
| ORF | Open reading frame |
| T2A | Teschovirus 2A |
| TF-plasmid | Plasmid expressing transacting factors |
| TNF-α | Tumor necrosis factor-α |
| UTR | Untranslated region |
| VSV-G | Vesicular stromatitis virus protein G |
| Z | Matrix Protein from LCMV |
| HK1 constructs (ie, name includes HK1) | Obtained or derived from LCMV Clone 13 |
| HK3 constructs (ie, name includes HK3) | Obtained or derived from MP strain of LCMV |

4. DESCRIPTION OF THE SEQUENCE LISTING

The following sequences are illustrative amino acid sequences and nucleotide sequences that can be used with the methods and compositions described herein. In some instances a DNA sequence is used to describe the RNA sequence of a viral genomic segment. The RNA sequence can be readily deduced from the DNA sequence.

SEQ ID NO: 1 is the nucleotide sequence of HK1-HgB (FL) genomic segment. The genomic segment is RNA, the sequence in SEQ ID NO: 1 is shown for DNA; however, exchanging all thymidines ("T") in SEQ ID NO: 1 for uridines ("U") provides the RNA sequence.

SEQ ID NO: 2 is the nucleotide sequence for HgB(FL) cDNA.

SEQ ID NO: 3 is the amino acid sequence for HgB(FL).

SEQ ID NO: 4 is the nucleotide sequence of HK1-HgB (dTM) genomic segment. The genomic segment is RNA, the sequence in SEQ ID NO: 4 is shown for DNA; however, exchanging all thymidines ("T") in SEQ ID NO: 4 for uridines ("U") provides the RNA sequence.

SEQ ID NO: 5 is the nucleotide sequence for HgB(dTM) cDNA.

SEQ ID NO: 6 is the amino acid sequence for HgB(dTM).

SEQ ID NO: 7 is the nucleotide sequence of HK1-HgB (1-706) genomic segment. The genomic segment is RNA, the sequence in SEQ ID NO:7 is shown for DNA; however, exchanging all thymidines ("T") in SEQ ID NO:7 for uridines ("U") provides the RNA sequence.

SEQ ID NO: 8 is the nucleotide sequence for HgB(1-706) cDNA.

SEQ ID NO: 9 is the amino acid sequence for HgB(1-706).

SEQ ID NO: 10 is the nucleotide sequence of HK1-HgB (1-691) genomic segment. The genomic segment is RNA, the sequence in SEQ ID NO:10 is shown for DNA; however, exchanging all thymidines ("T") in SEQ ID NO: 10 for uridines ("U") provides the RNA sequence.

SEQ ID NO: 11 is the nucleotide sequence for HgB(1-691) cDNA.

SEQ ID NO: 12 is the amino acid sequence for HgB(1-691).

SEQ ID NO: 13 is the nucleotide sequence of HK1-HgB (1-447) genomic segment. The genomic segment is RNA, the sequence in SEQ ID NO: 13 is shown for DNA; however, exchanging all thymidines ("T") in SEQ ID NO: 13 for uridines ("U") provides the RNA sequence.

SEQ ID NO: 14 is the nucleotide sequence for HgB(1-447) cDNA.

SEQ ID NO: 15 is the amino acid sequence for HgB(1-447).

SEQ ID NO: 16 is the nucleotide sequence of HK1-HgB (dCt) genomic segment. The genomic segment is RNA, the sequence in SEQ ID NO:16 is shown for DNA; however, exchanging all thymidines ("T") in SEQ ID NO:16 for uridines ("U") provides the RNA sequence.

SEQ ID NO: 17 is the nucleotide sequence for HgB(dCt) cDNA.

SEQ ID NO: 18 is the amino acid sequence for HgB(dCt).

SEQ ID NO: 19 is the nucleotide sequence of HK1-HgB (VSV-G-1) genomic segment. The genomic segment is RNA, the sequence in SEQ ID NO:19 is shown for DNA; however, exchanging all thymidines ("T") in SEQ ID NO:19 for uridines ("U") provides the RNA sequence.

SEQ ID NO: 20 is the nucleotide sequence for HgB(VSV-G-1) cDNA.

SEQ ID NO: 21 is the amino acid sequence for HgB (VSV-G-1).

SEQ ID NO: 22 is the nucleotide sequence of HK1-HgB (VSV-G-2) genomic segment. The genomic segment is RNA, the sequence in SEQ ID NO:22 is shown for DNA; however, exchanging all thymidines ("T") in SEQ ID NO:22 for uridines ("U") provides the RNA sequence.

SEQ ID NO: 23 is the nucleotide sequence for HgB(VSV-G-2) cDNA.

SEQ ID NO: 24 is the amino acid sequence for HgB (VSV-G-2).

SEQ ID NO: 25 is the nucleotide sequence of HK1-HgB (H3-1) genomic segment. The genomic segment is RNA, the sequence in SEQ ID NO: 25 is shown for DNA; however, exchanging all thymidines ("T") in SEQ ID NO: 25 for uridines ("U") provides the RNA sequence.

SEQ ID NO: 26 is the nucleotide sequence for HgB(H3-1) cDNA.

SEQ ID NO: 27 is the amino acid sequence for HgB(H3-1).

SEQ ID NO: 28 is the nucleotide sequence of HK1-HgB (H3-2) genomic segment. The genomic segment is RNA, the sequence in SEQ ID NO: 28 is shown for DNA; however, exchanging all thymidines ("T") in SEQ ID NO: 28 for uridines ("U") provides the RNA sequence.

SEQ ID NO: 29 is the nucleotide sequence for HgB(H3-2) cDNA.

SEQ ID NO: 30 is the amino acid sequence for HgB(H3-2).

SEQ ID NO: 31 is the lymphocytic choriomeningitis virus segment S, complete sequence. The genomic segment is RNA, the sequence in SEQ ID NO: 31 is shown for DNA; however, exchanging all thymidines ("T") in SEQ ID NO:31 for uridines ("U") provides the RNA sequence.

SEQ ID NO: 32 is the lymphocytic choriomeningitis virus clone 13 segment S, complete sequence (GenBank: DQ361065.2). The genomic segment is RNA, the sequence in SEQ ID NO: 32 is shown for DNA; however, exchanging all thymidines ("T") in SEQ ID NO: 32 for uridines ("U") provides the RNA sequence.

SEQ ID NO: 33 is the lymphocytic choriomeningitis virus clone 13 segment L, complete sequence (GenBank: DQ361066.1). The genomic segment is RNA, the sequence in SEQ ID NO: 33 is shown for DNA; however, exchanging all thymidines ("T") in SEQ ID NO: 33 for uridines ("U") provides the RNA sequence.

SEQ ID NO: 34 is the nucleotide sequence of HK1-Hpp65 genomic segment. The genomic segment is RNA, the sequence in SEQ ID NO: 34 is shown for DNA; however, exchanging all thymidines ("T") in SEQ ID NO: 34 for uridines ("U") provides the RNA sequence.

SEQ ID NO: 35 is the nucleotide sequence for Hpp65 cDNA.

SEQ ID NO: 36 is the amino acid sequence for Hpp65.

SEQ ID NO: 37 is the nucleotide sequence of HK1-HgH genomic segment. The genomic segment is RNA, the sequence in SEQ ID NO: 37 is shown for DNA; however, exchanging all thymidines ("T") in SEQ ID NO: 37 for uridines ("U") provides the RNA sequence.

SEQ ID NO: 38 is the nucleotide sequence for HgH cDNA.

SEQ ID NO: 39 is the amino acid sequence for HgH.

SEQ ID NO: 40 is the nucleotide sequence for HgL cDNA.

SEQ ID NO: 41 is the amino acid sequence for HgL.

SEQ ID NO: 42 is the nucleotide sequence for HUL128 cDNA.

SEQ ID NO: 43 is the amino acid sequence for HUL128.

SEQ ID NO: 44 is the nucleotide sequence of HK1-HUL130 genomic segment. The genomic segment is RNA, the sequence in SEQ ID NO: 44 is shown for DNA; however, exchanging all thymidines ("T") in SEQ ID NO: 44 for uridines ("U") provides the RNA sequence.

SEQ ID NO: 45 is the nucleotide sequence for HUL130 cDNA.

SEQ ID NO: 46 is the amino acid sequence for HUL130.

SEQ ID NO: 47 is the nucleotide sequence for HUL131A cDNA.

SEQ ID NO: 48 is the amino acid sequence for HUL131A.

SEQ ID NO: 49 is the lymphocytic choriomeningitis strain MP segment L, complete sequence. The genomic segment is RNA, the sequence in SEQ ID NO:49 is shown for DNA; however, exchanging all thymidines ("T") in SEQ ID NO:49 for uridines ("U") provides the RNA sequence.

SEQ ID NO: 50 is the nucleotide sequence of HK1-HgH (dTM) genomic segment. The genomic segment is RNA, the sequence in SEQ ID NO:50 is shown for DNA; however, exchanging all thymidines ("T") in SEQ ID NO:50 for uridines ("U") provides the RNA sequence.

SEQ ID NO: 51 is the nucleotide sequence for HgH(dTM) cDNA.

SEQ ID NO: 52 is the amino acid sequence for HgH (dTM).

SEQ ID NO: 53 is the lymphocytic choriomeningitis strain MP segment S, complete sequence. The genomic segment is RNA, the sequence in SEQ ID NO:53 is shown for DNA; however, exchanging all thymidines ("T") in SEQ ID NO:53 for uridines ("U") provides the RNA sequence.

SEQ ID NO: 54 is the amino acid sequence of the NP protein of the MP strain of LCMV.

SEQ ID NO: 55 is the amino acid sequence of the GP protein of the MP strain of LCMV.

SEQ ID NO: 56 is the amino acid sequence of the L protein of the MP strain of LCMV.

SEQ ID NO: 57 is the amino acid sequence of the Z protein of the MP strain of LCMV.

SEQ ID NO: 58 is the sequence of LCMV clone 13 S-Segment encoding HCMV strain Merlin gB; full-length wildtype. The genomic segment is RNA, the sequence in SEQ ID NO: 58 is shown for DNA; however, exchanging all thymidines ("T") in SEQ ID NO: 58 for uridines ("U") provides the RNA sequence.

SEQ ID NO: 59 is the cDNA sequence of HCMV strain Merlin gB(FL) ORF.

SEQ ID NO: 60 is the amino acid sequence of HCMV strain Merlin gB(FL).

SEQ ID NO: 61 is the sequence of LCMV clone 13 S-Segment encoding HCMV strain Merlin gB sequence; deletion of transmembrane region (dTM). The genomic segment is RNA, the sequence in SEQ ID NO: 61 is shown for DNA; however, exchanging all thymidines ("T") in SEQ ID NO: 61 for uridines ("U") provides the RNA sequence.

SEQ ID NO: 62 is the cDNA sequence of HCMV strain Merlin gB(dTM) ORF.

SEQ ID NO: 63 is the amino acid sequence of HCMV strain Merlin gB(dTM).

5. BRIEF DESCRIPTION OF THE FIGURES

FIG. 1: The genome of wild type arenaviruses consists of a short (1; ~3.4 kb) and a large (2; ~7.2 kb) RNA segment. The short segment carries ORFs encoding the nucleoprotein (3) and glycoprotein (4). The large segment encodes the RNA-dependent RNA polymerase L (5) and the matrix protein Z (6). Wild type arenaviruses can be rendered replication-deficient vaccine vectors by deleting the glycoprotein gene and inserting, instead of the glycoprotein gene, antigens of choice (7) against which immune responses are to be induced.

Figure 2:
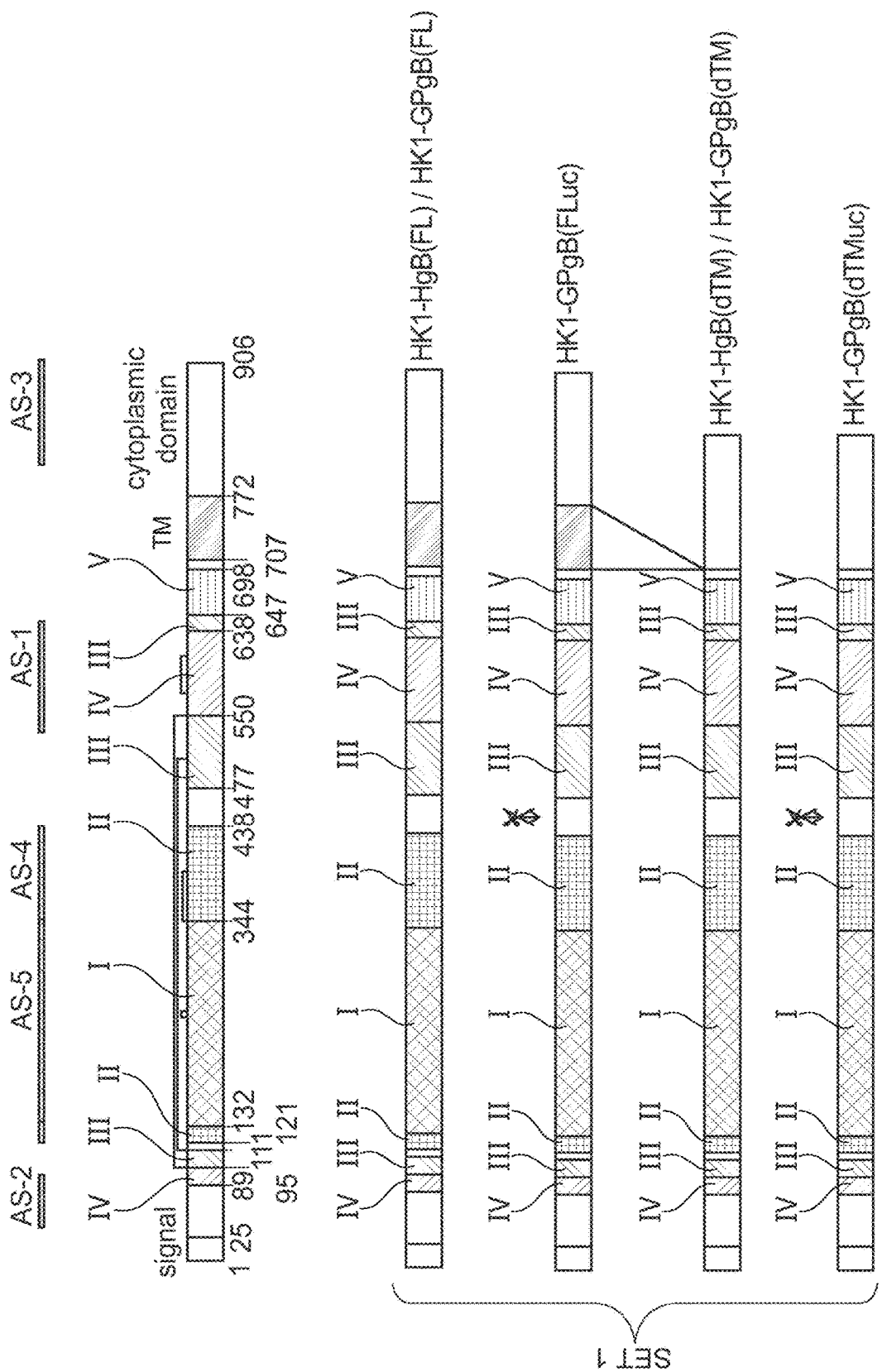
Figure 2:
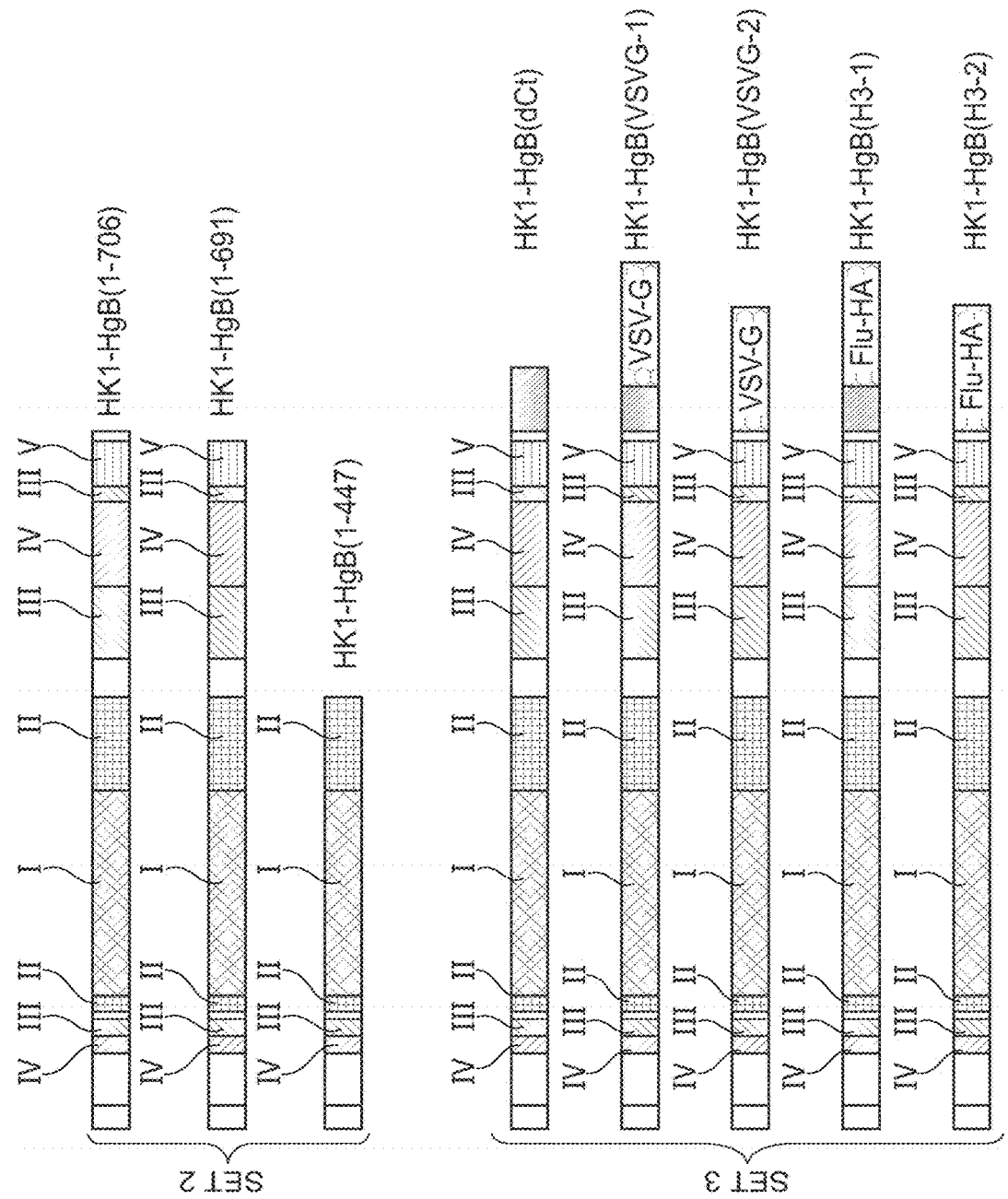

FIG. 2: (Adapted from Pötzsch, et al., 2011) Antigenic sites of gB protein expressed in various different rLCMV-gB vectors; AS-1/5 refer to the antigenic sites 1-5 of glycoprotein B. TM indicates the transmembrane domain of gB. Crossed-out scissors indicate a mutation in the furin-cleavage site located within the ectodomain of gB. "H" in vector names (e.g. HK1-HgB(FL)) indicate human CMV gB sequences; "GP" in vector names (e.g. HK1-GPgB(FL)) indicate guinea pig CMV gB sequences.

Figure 3A:
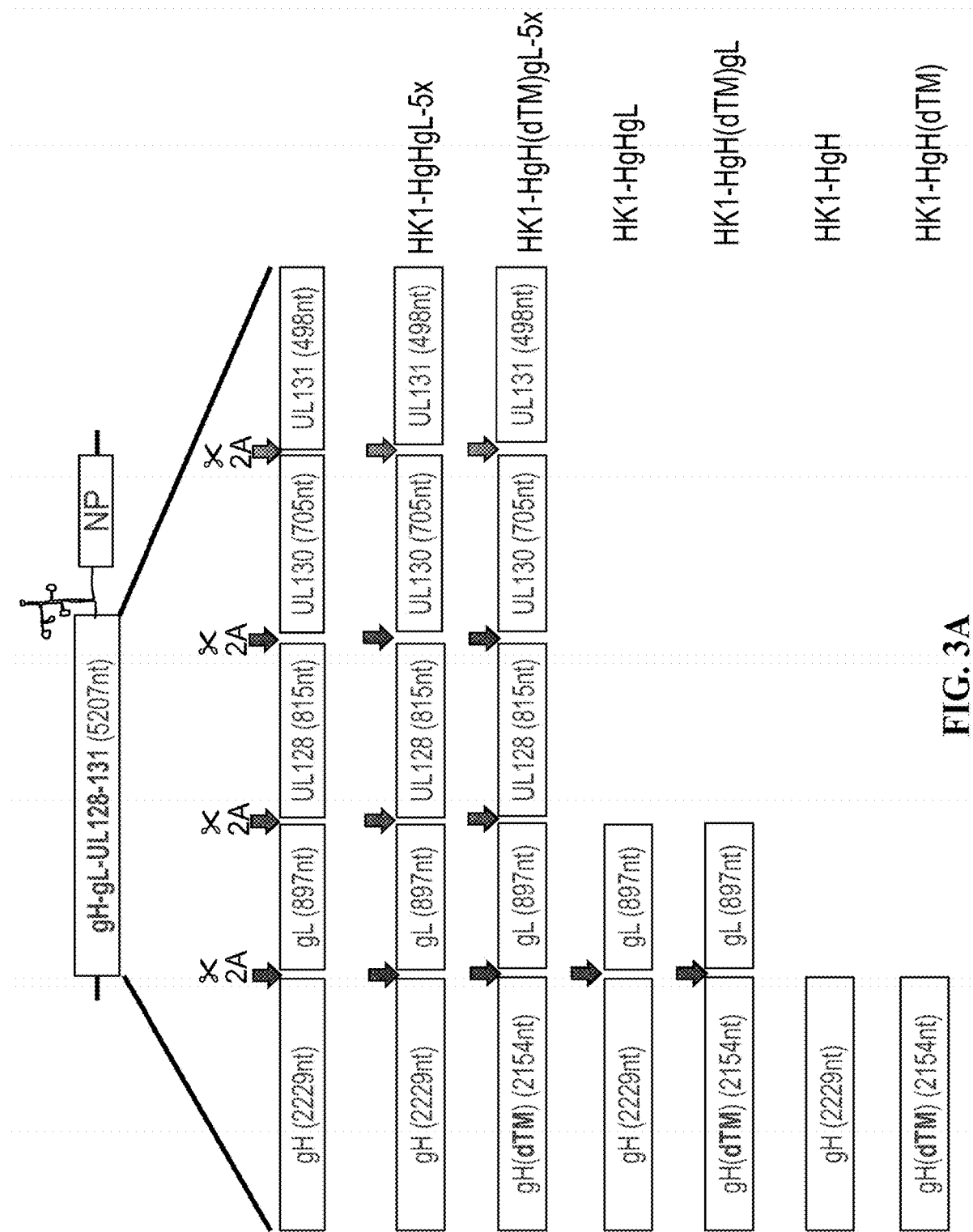

FIG. 3A: Different rLCMV-PC vectors are generated for the expression of membrane-anchored (wildtype) or non-anchored (transmembrane domain deleted) forms of either the entire pentameric complex or just parts thereof. Arrows in individual colors indicate 2A self-cleaving sequences. The 2A nucleotide sequence was wobbled to avoid homologous recombination while plasmid cloning or in the context of the vector backbone.

Figure 3B:
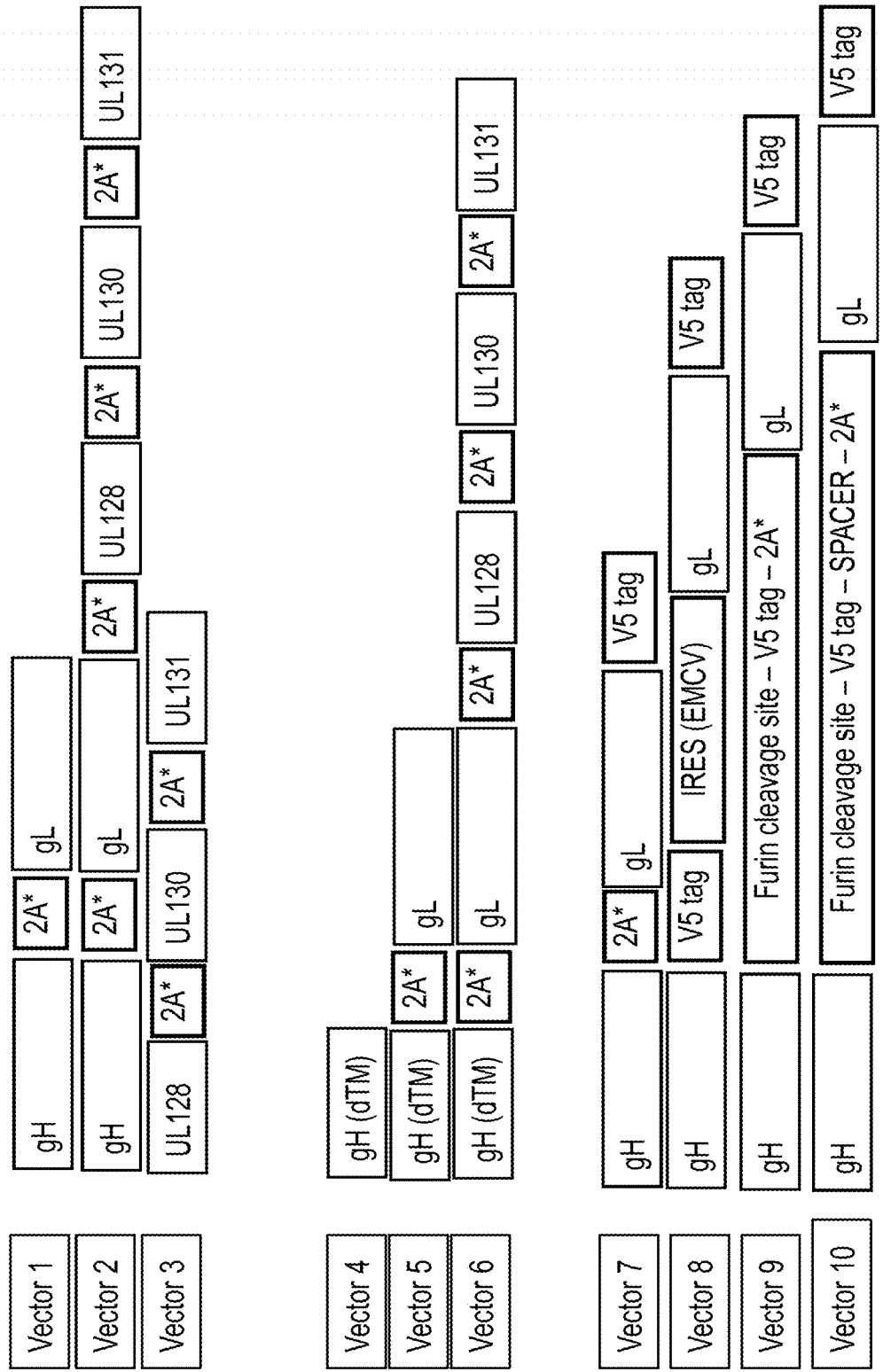

FIG. 3B: Different rLCMV-PC vectors are generated for the expression of membrane-anchored (wildtype) or non-anchored (transmembrane domain deleted) forms of either the entire pentameric complex or just parts thereof. 2A self-cleaving sequences separating the individual PC components were wobbled for the reasons outlined above. Alternatively, an IRES sequence was placed between two open reading frames (ORF) leading to translation of the downstream ORF. Further, a protein tag (V5) was fused to individual pentamer complex proteins to facilitate detection in Western blotting. 2A*: 2A peptide derived from a 2A protein from a member of the virus family Picornaviridae (e.g., Porcine teschovirus-1 2A, Thosea asigna virus 2A).

Figure 4A:
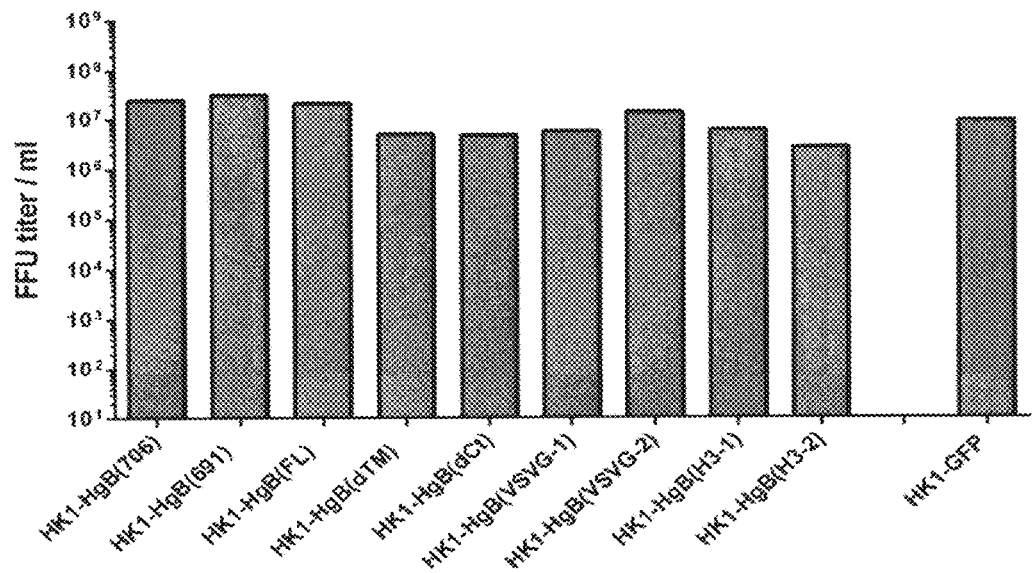
Figure 4B:
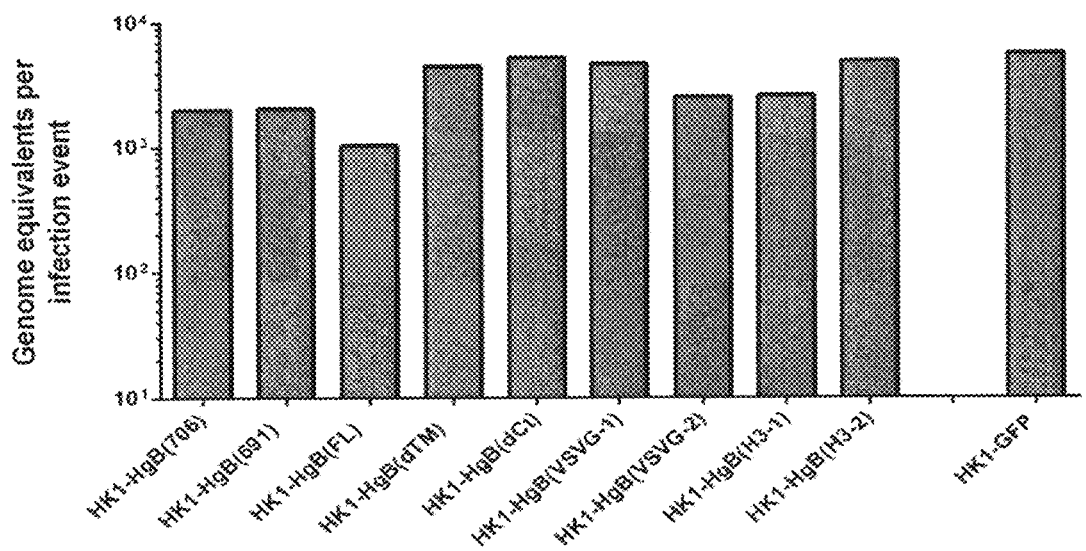

FIG. 4A and FIG. 4B: LCMV GP expressing HEK 293 suspension cultures were infected with rLCMV vectors HK1-HgB(FL), HK1-HgB(dTM), HK1-HgB(706), HK1-HgB(691), HK1-HgB(dCt), HK1-HgB(VSVG-1), HK1-HgB(VSVG-2), HK1-HgB(H3-1) and HK1-HgB(H3-2) (MOI of 0.001). A corresponding rLCMV vector expressing the green-fluorescent-protein (HK1-GFP) has been used as control. (FIG. 4A) Viral infection was monitored in focus forming units (FFU) assay by counting stained foci after 72 h or 96 h of incubation. Results were used to determine the viral titer by calculating the number of focus forming units per milliliter (FFU/ml). (FIG. 4B) To assess the infectivity of vector particles, vector RNA was isolated from stock preparations and the amount of genome equivalents was determined using quantitative real time PCR (qPCR). Respective results were put in correlation with FFU titers established in (FIG. 4A) to calculate the specific infectivity of the vector constructs.

Figure 5:
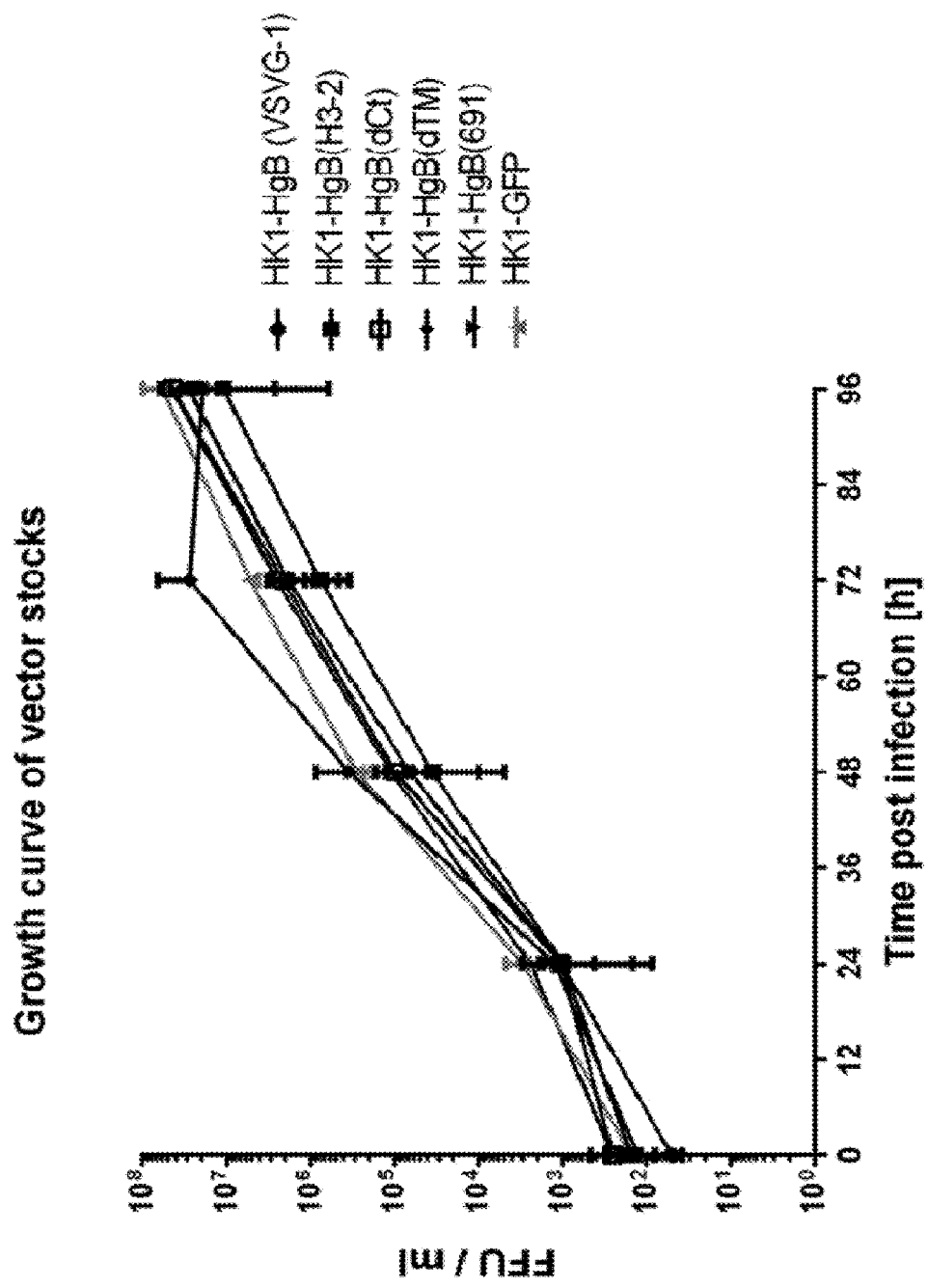

FIG. 5: In order to analyze vector replication, growth curves were performed using suspension HEK 293 cells expressing LCMV GP. Respective cells were seeded with cell density of $3 \times 10^5$ cells/ml and infected with individual vectors (HK1-HgB(dTM), HK1-HgB(dCt), HK1-HgB (VSVG-1), HK1-HgB(H3-2) and HK1-HgB(691)) at MOI of 0.001. Samples were drawn every 24 hours and analysed by FFU assay. All tested vectors exhibited similar growth kinetics and peak titers compared to HK1-GFP indicating that the individual gB transgenes did not interfere with vector replication to a greater extent than the small reporter-gene GFP.

Figure 6:
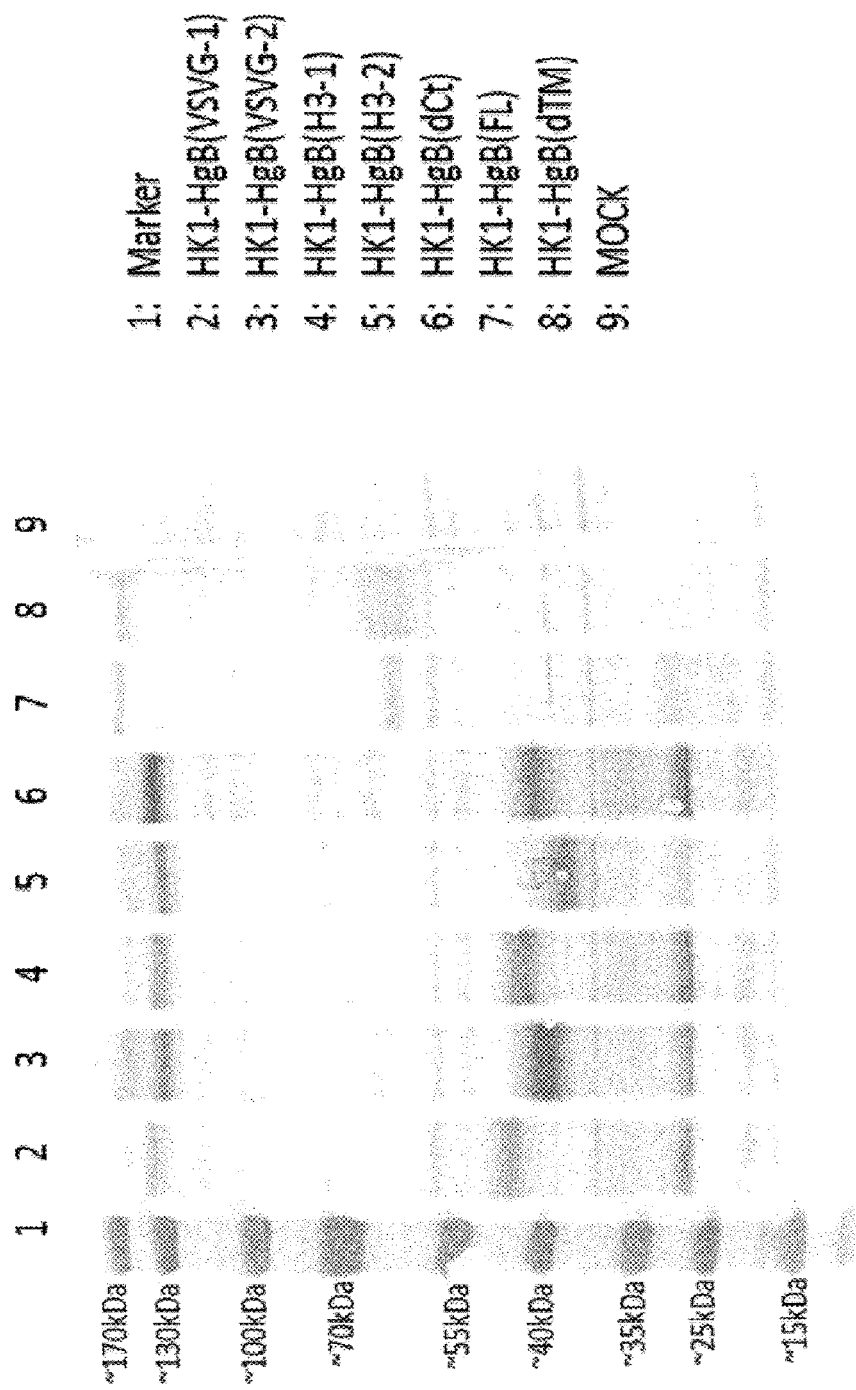

FIG. 6: HEK 293 cells expressing LCMV GP were infected with individual rLCMV-gB constructs (HK1-HgB (VSVG-1), HK1-HgB(VSVG-2), HK1-HgB(H3-1), HK1-HgB(H3-2), HK1-HgB(dCt), HK1-HgB(FL), HK1-HgB (dTM)) at a multiplicity of infection (MOI) of 0.001. Cells were analyzed 96 h post infection. Proteins were separated on SDS gels, transferred to nitrocellulose membranes and gB protein expression was detected with transgen specific primary (Mouse monoclonal antibody to human CMV gB) and appropriate secondary antibody. Uncleaved precursors of full length gB are expected to band at ~160 kDa whereas cleaved gB contains a surface component with an estimated molecular mass of 116 kDa that is linked by disulfide bonds to a transmembrane component with an estimated molecular mass of 55 kDa. However, due to use of a monoclonal primary antibody only two bands representing the uncleaved gB protein and the smaller cleavage product of gB are expected to be visible on the blot. As expected, full length gB (lane 7) banded at ~160 kDa, whereas all remaining constructs showed bands of lower size which can be explained by the deletion or exchange of at least parts of the gB cytoplasmic domain. Analogously, the transmembrane part of full length gB (lane 7) bands at ~60 kDa (slightly higher than expected) and all gB derivates exhibit cleavage products of lower size. In general HK1-gB(FL) and HK1-gB(dTM) exhibited weaker gB bands compared to all other vectors.

Figure 7:
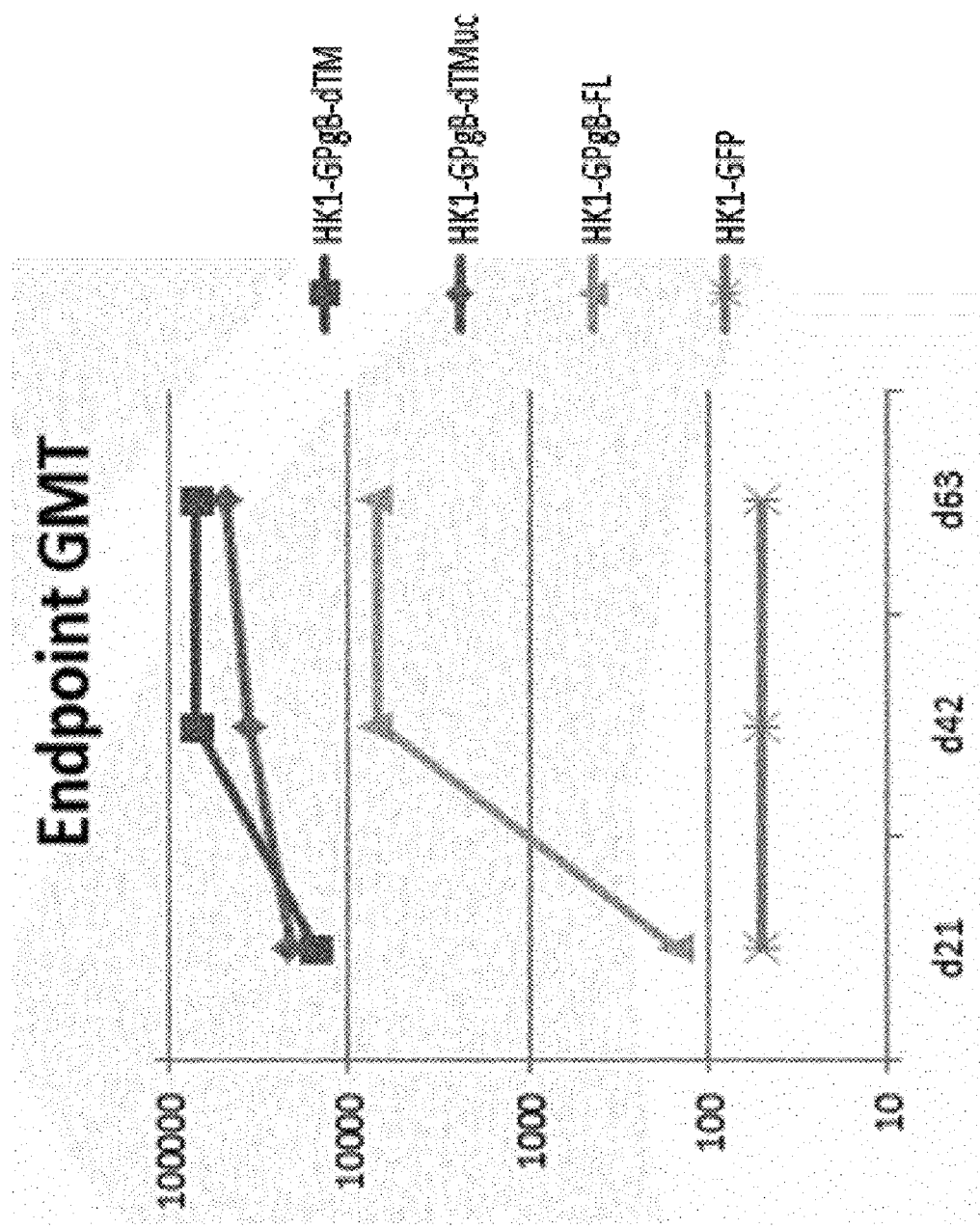

FIG. 7: C57BL/6 mice were immunized subcutaneously 3 times on days 0, 21 and 42 of the experiment with $6.7 \times 10^4$ FFU/dose of each of HK1-GPgB-dTM, HK1-GPgB-dTMuc, HK1-GPgB-FL and with $9.2 \times 10^5$ FFU/dose of HK1-GFP. Sera of immunized mice were collected on days 21, 42 and 63 of the experiment and anti-GPgB IgG antibody titers were determined by ELISA. Endpoint GMTs are shown.

Figure 8A:
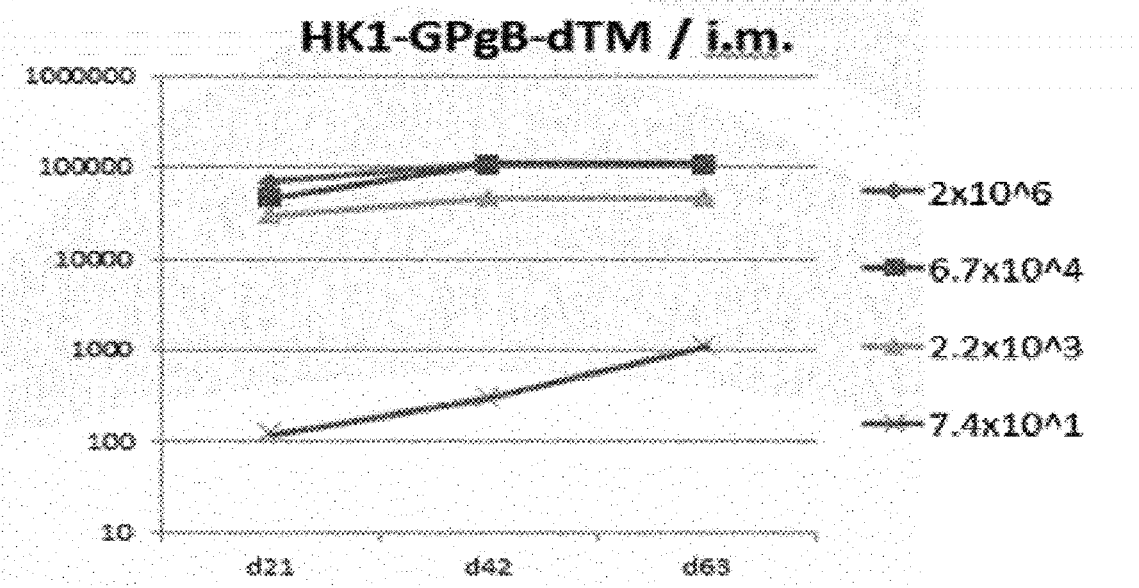
Figure 8B:
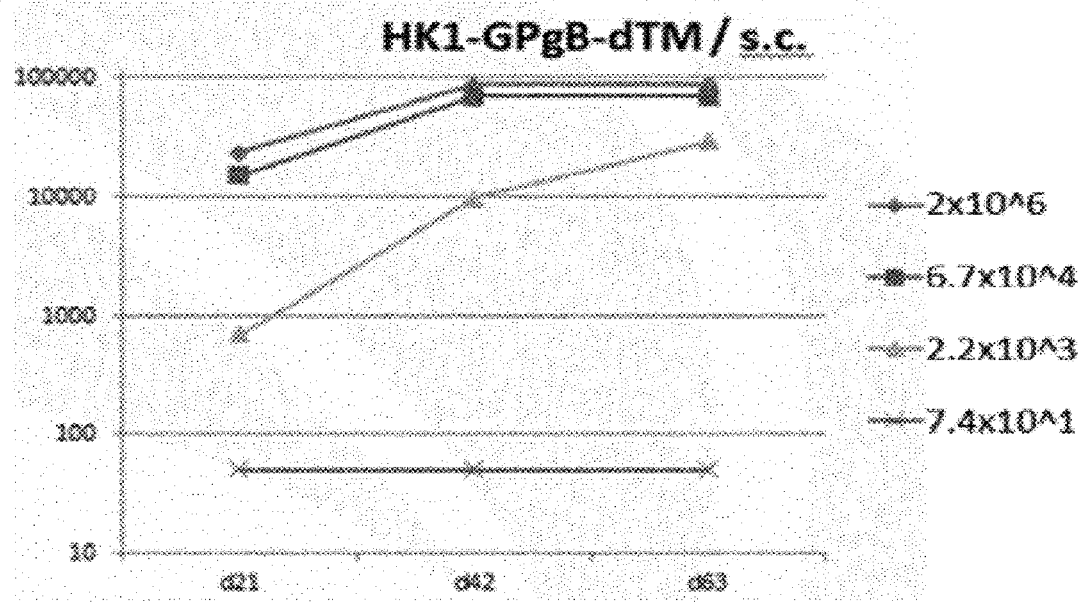

FIG. 8A and FIG. 8B: C57BL/6 mice were immunized 3 times on days 0, 21 and 42 of the experiment either via the intramuscular route (FIG. 8A) or by subcutaneous injections (FIG. 8B) with different concentrations ($7.4 \times 10^1$, $2.2 \times 10^3$, $6.7 \times 10^4$ and $2 \times 10^6$ FFU/dose) of HK1-GPgB-dTM. Sera of immunized mice were collected on days 21, 42 and 63 of the experiment and anti-GPgB IgG antibody titers were determined by ELISA. Endpoint GMTs are shown.

Figure 8C:
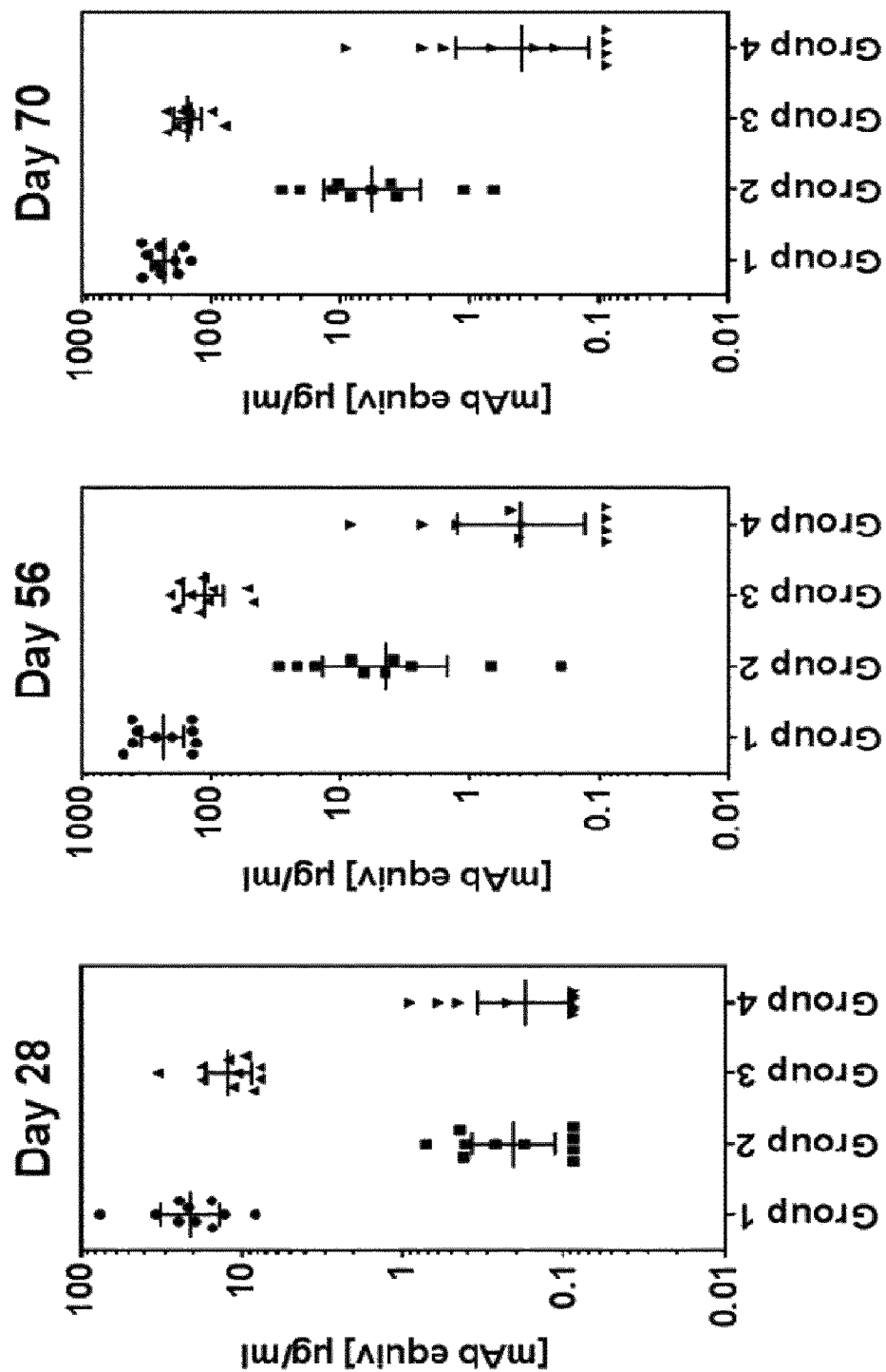

FIG. 8C: C57BL/6 mice were immunized with $5.6 \times 10^5$ (groups 1 and 3) or $3.2 \times 10^3$ (groups 2 and 4) FFU/dose of HK1-HgB(dCt) on days 0 and 28 via the intramuscular (Groups 1 and 2) or the intradermal (Groups 3 and 4) route. Sera of immunized mice were collected on day 28, 56 and 70 and anti-HCMVgB IgG antibody titers were measured by ELISA. Monoclonal antibody equivalent concentrations (μg/ml) are shown; a monoclonal anti-gB antibody (mIgG1) has been used for standard curve generation.

Figure 8D:
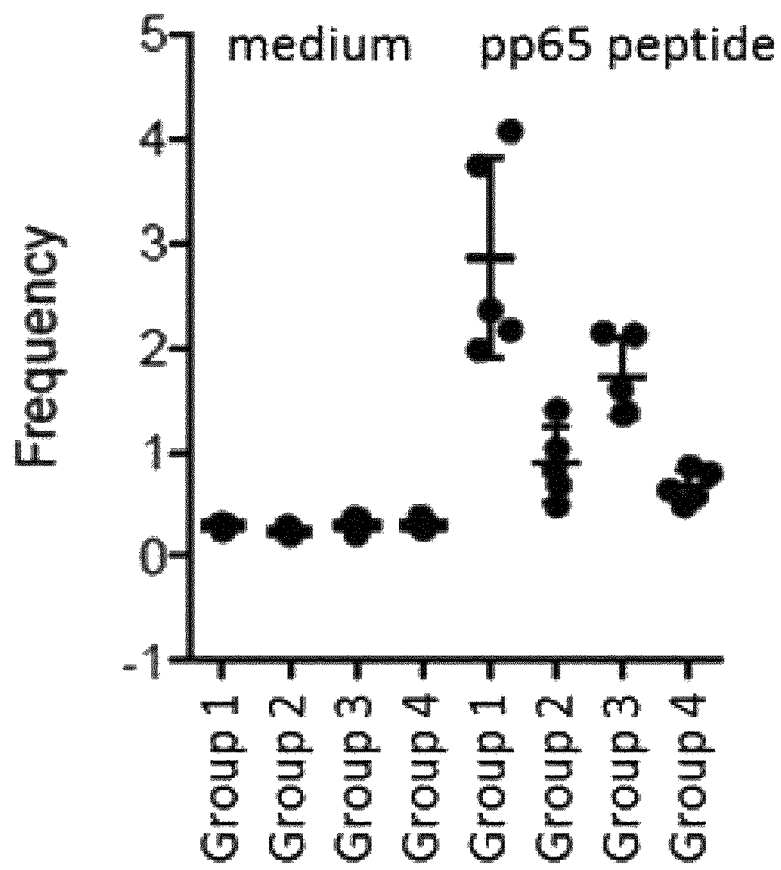

FIG. 8D: C57BL/6 mice were immunized with $6.7 \times 10^5$ (Groups 1 and 3) or $3.5 \times 10^3$ (Groups 2 and 4) FFU/dose of HK1-Hpp65 on days 0 and 28 via the intramuscular (Groups 1 and 2) or the intradermal (Groups 3 and 4) route. CD8+ T cell responses were analyzed by flow cytometry restimulating spleen cells with a pool of peptides generated based on Shedlock D. et al (Human Vaccines & Immunotherapeutics 2012; 8:11, 1-14) on day 38. Control cells were stimulated with medium only. After incubation with medium (lanes 1-4) or with specific peptides (lanes 5-8) cells were stained for flow cytometric analysis of CD8+ T cells. Expression of IL-2, IFN-g and TNF was analyzed.

Figure 9:
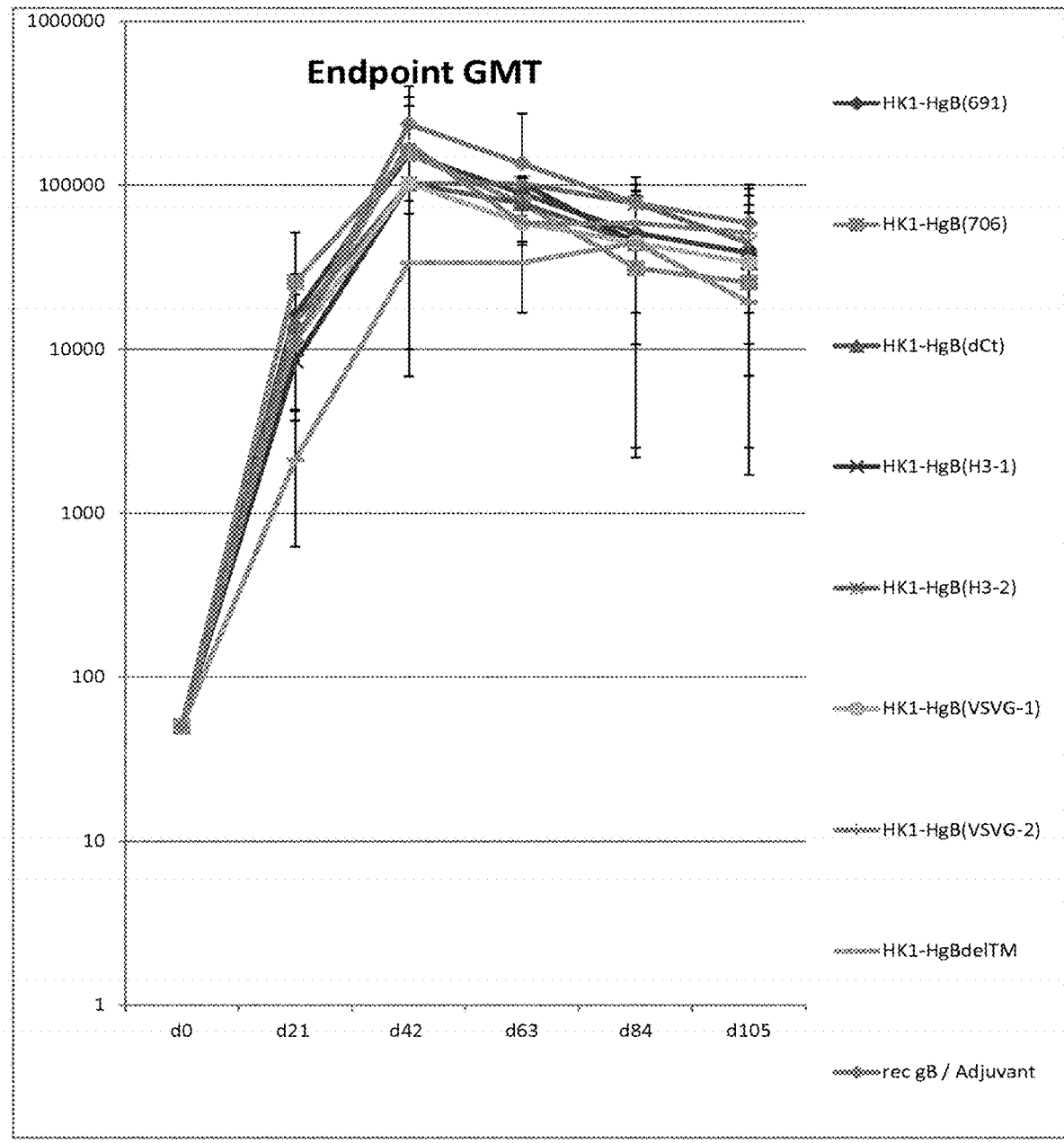

FIG. 9: C57BL/6 mice were immunized intramuscularly with $1 \times 10^5$ FFU/dose of HK1-HgB(691), HK1-HgB(706), HK1-HgB(dCt), HK1-HgB(H3-1), HK1-HgB(H3-2), HK1-HgB(VSVG-1), HK1-HgB(VSVG-2), HK1-HgB(dTM) and recombinant gB/adjuvant on days 0 and 21. Sera of immunized mice were collected on days 0, 21, 42, 63, 84 and 105 of the experiment and anti-HCMVgB IgG antibody titers were measured by ELISA. Endpoint GMTs are shown.

Figure 10:
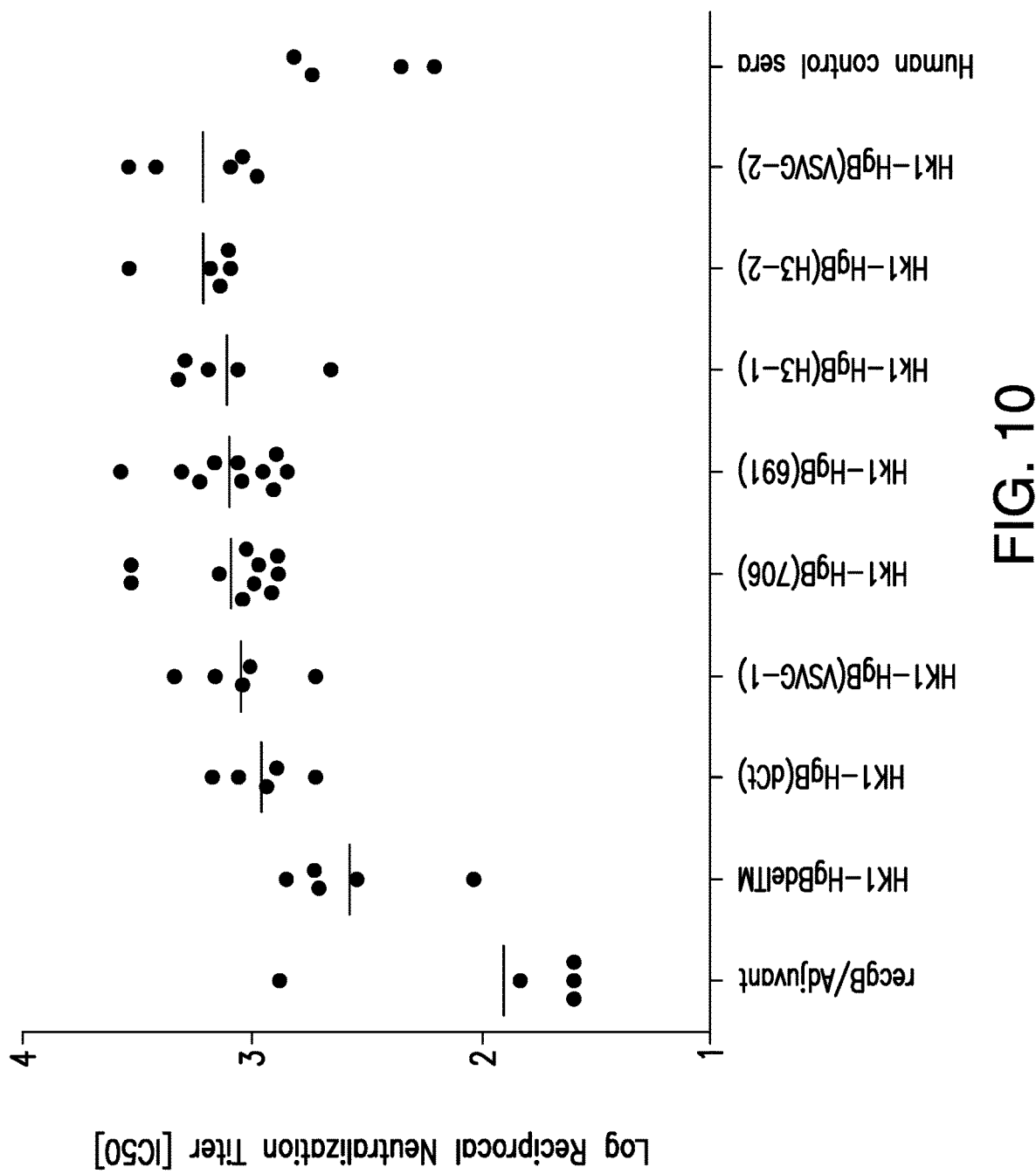

FIG. 10: C57BL/6 mice were immunized intramuscularly with $1 \times 10^5$ FFU/dose of HK1-HgB(691), HK1-HgB(706), HK1-HgB(dCt), HK1-HgB(H3-1), HK1-HgB(H3-2), HK1-HgB(VSVG-1), HK1-HgB(VSVG-2), HK1-HgB(dTM) and recombinant gB/adjuvant on days 0 and 21. Sera collected on day 42 were mixed with media containing guinea pig complement (final concentration: 5%) and GFP-tagged HCMV strain TS15-rN. Serum/media mixtures were incubated for 60 min at 37° C., and then transferred to wells of a 384-well plate containing ARPE-19 cells. Representative micrographs were taken on day 4 and GFP was quantitated on day 7 post infection. GFP values were plotted vs. serum concentration and analyzed using four-parameter curve fitting to determine approximate dilutions that result in 50% inhibition. Logarithmic reciprocal neutralization titers (IC50) are presented.

Figure 11:
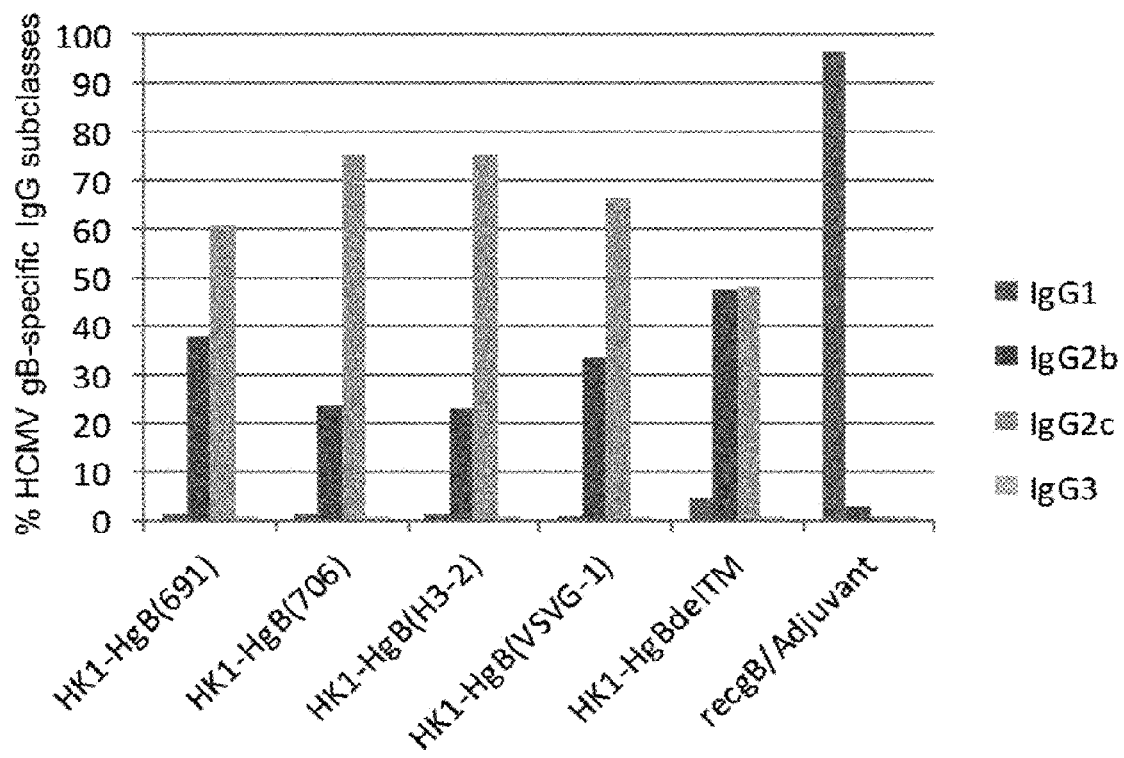

FIG. 11: C57BL/6 mice were immunized intramuscularly with $1\times10^5$ FFU/dose of HK1-HgB(691), HK1-HgB(706), HK1-HgB(H3-2), HK1-HgB(VSVG-1), HK1-HgB(dTM) and recombinant gB/adjuvant on days 0 and 21. Sera collected on day 42 were analyzed by HCMVgB-specific IgG subclass ELISA. The percentage of HCMVgB-specific IgG subclasses was calculated as the ratio of the individual subclass Endpoint Titer GMT divided by the total Endpoint Titer GMT of all subclasses.

Figure 12:
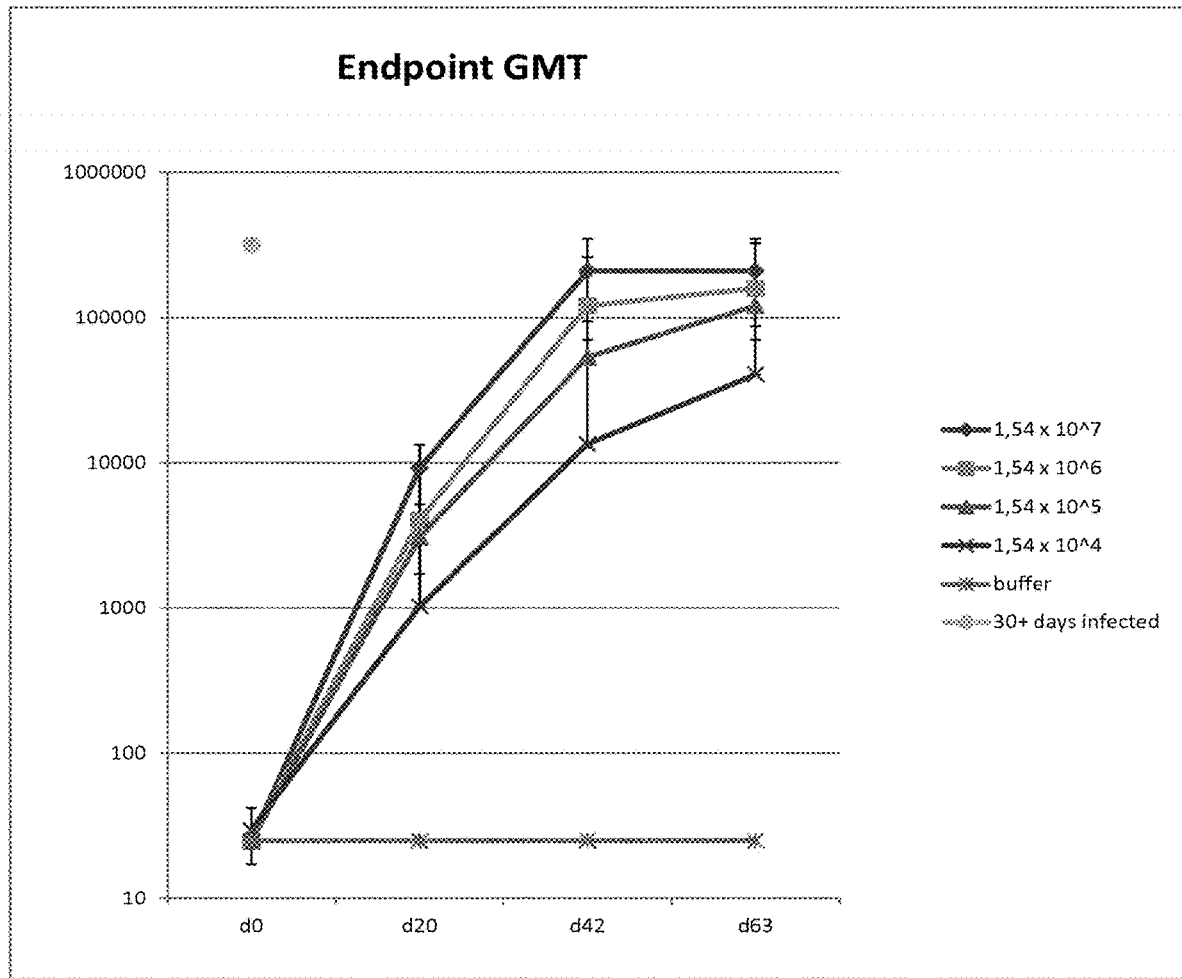

FIG. 12: Hartley guinea pigs (4 animals/group) were immunized intramuscularly with different concentrations ($1.54\times10^7$, $1.54\times10^6$, $1.54\times10^5$ and $1.54\times10^4$ FFU/dose) of HK1-GPgB-dTM on days 0, 21 and 42. Sera of immunized animals were collected on days 0, 21, 42 and 63 of the experiment and anti-gB antibody titers were analyzed by GPgB-specific IgG ELISA. Endpoint GMTs are shown. The lone filled circle indicates GPCMV positive control serum.

Figure 13:
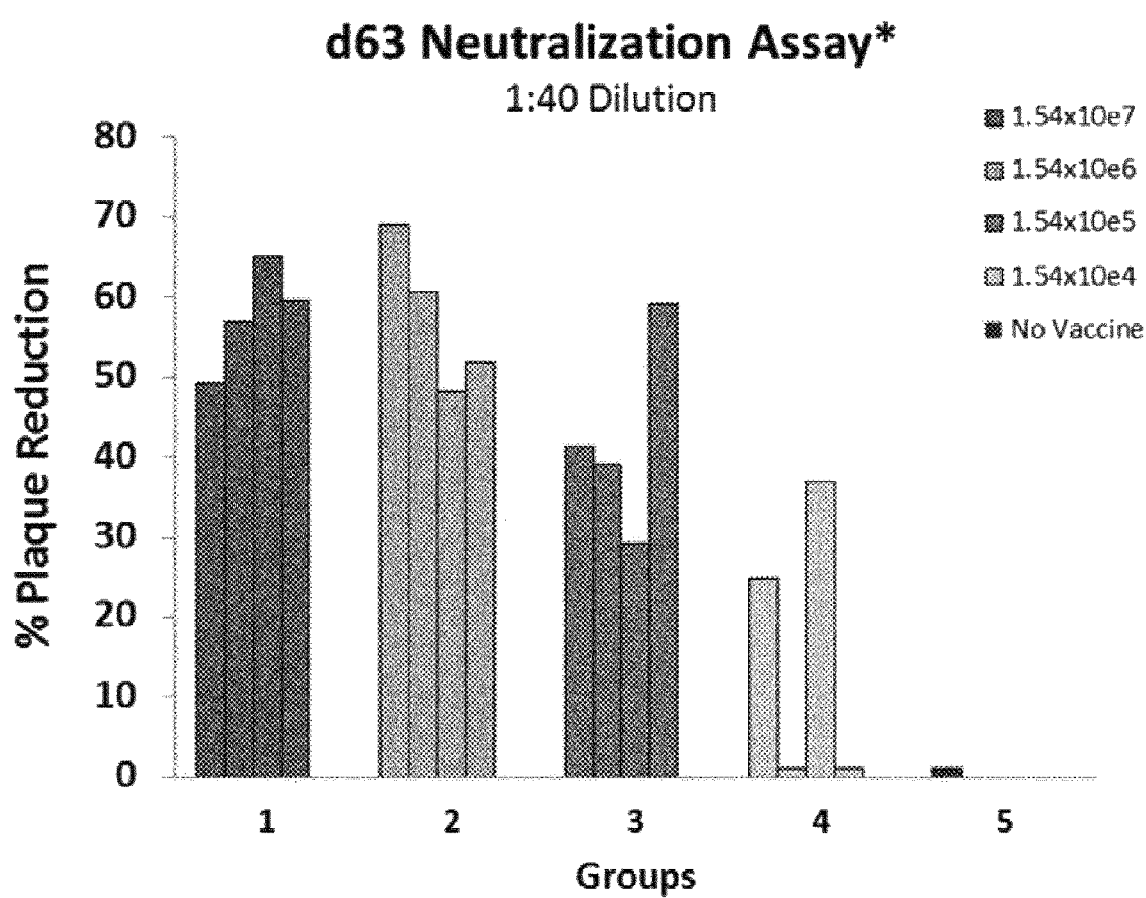

FIG. 13: Hartley guinea pigs (4 animals/group) were immunized intramuscularly with different concentrations ($1.54\times10^7$, $1.54\times10^6$, $1.54\times10^5$ and $1.54\times10^4$ FFU/dose) of HK1-GPgB-dTM on days 0, 21 and 42. The neutralizing activity of anti-GPgB antibodies in the sera of immunized animals collected on day 63 of the experiment was analyzed by plaque reduction assay.

Figure 14A:
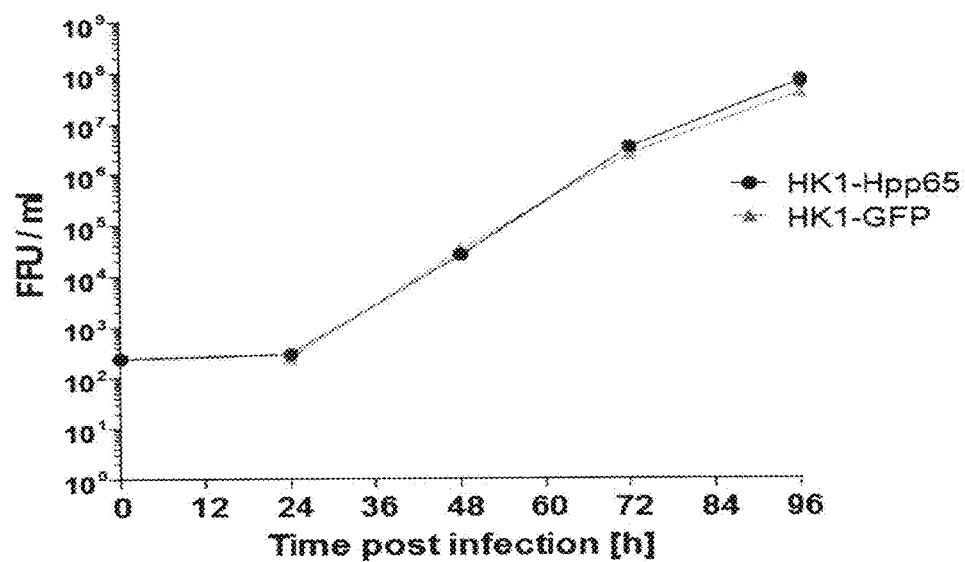
Figure 14B:
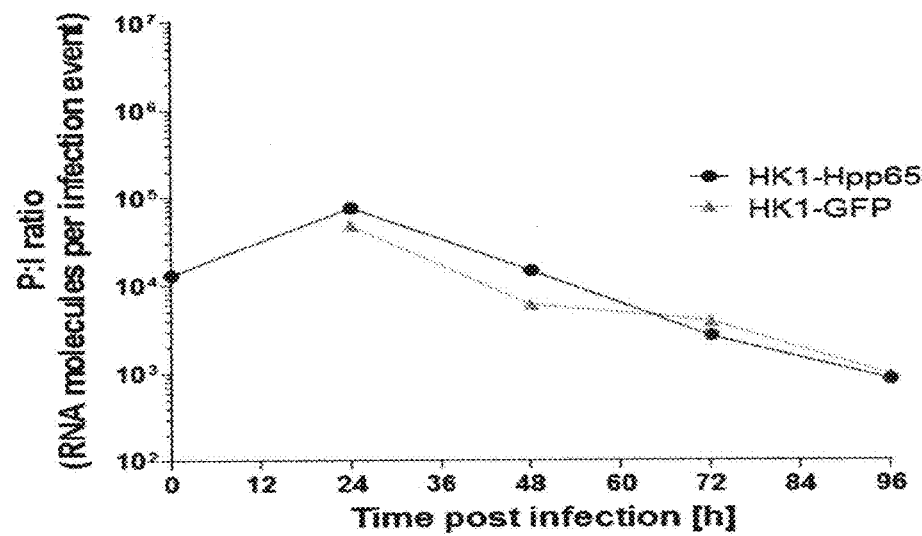

FIG. 14A and FIG. 14B: LCMV GP-expressing HEK 293 suspension cells were infected with rLCMV vector HK1-Hpp65 (MOI=0.001). A rLCMV vector expressing GFP (HK1-GFP) was used as a control. Samples were drawn at indicated time points and were analyzed by FFU assay (FIG. 14A) to calculate the number of focus forming units (FFU) per sample unit volume (FFU/ml) and by qPCR to calculate the specific infectivity of the vector constructs (FIG. 14B).

Figure 15:
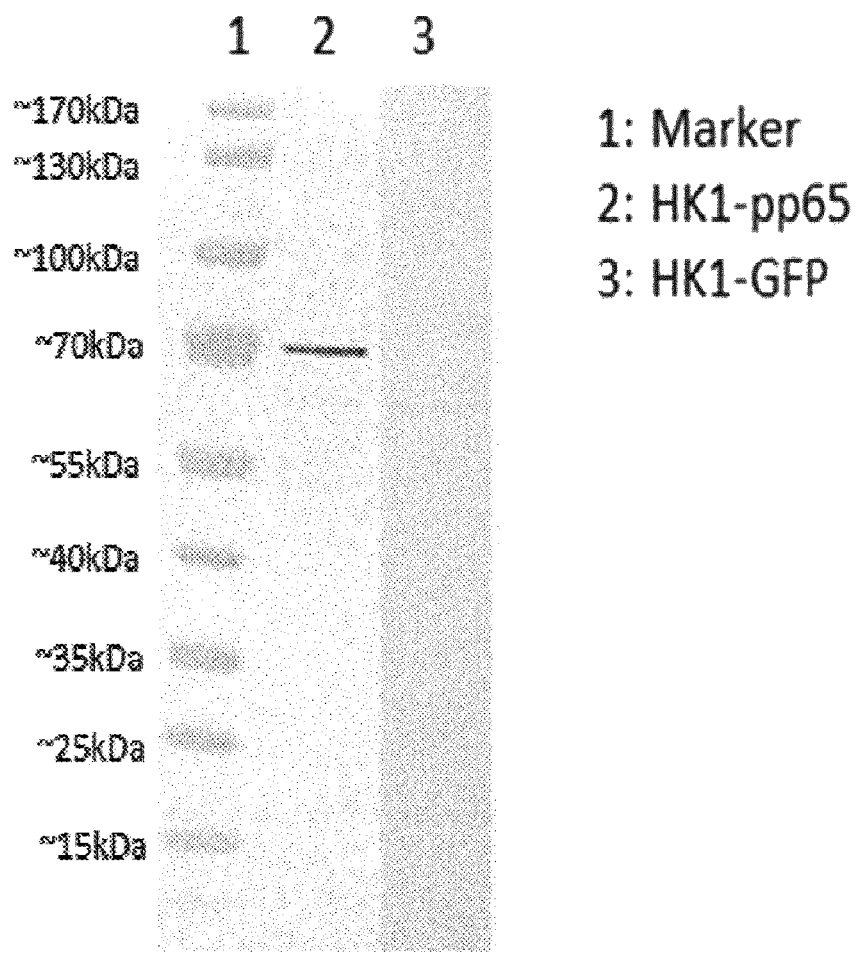

FIG. 15: LCMV GP-expressing HEK 293 suspension cells were infected with HK1-Hpp65 or a negative control vector HK1-GFP, harvested and lysed 96 h post infection, separated on SDS gels, transferred to nitrocellulose membranes and probed with anti-pp65 primary and appropriate alkaline phosphatase conjugated secondary antibody. Human CMV pp65 protein is expected to band in the range of 65 kDa, corresponding to the main band of HK1-Hpp65 in Western Blot.

Figure 16A:
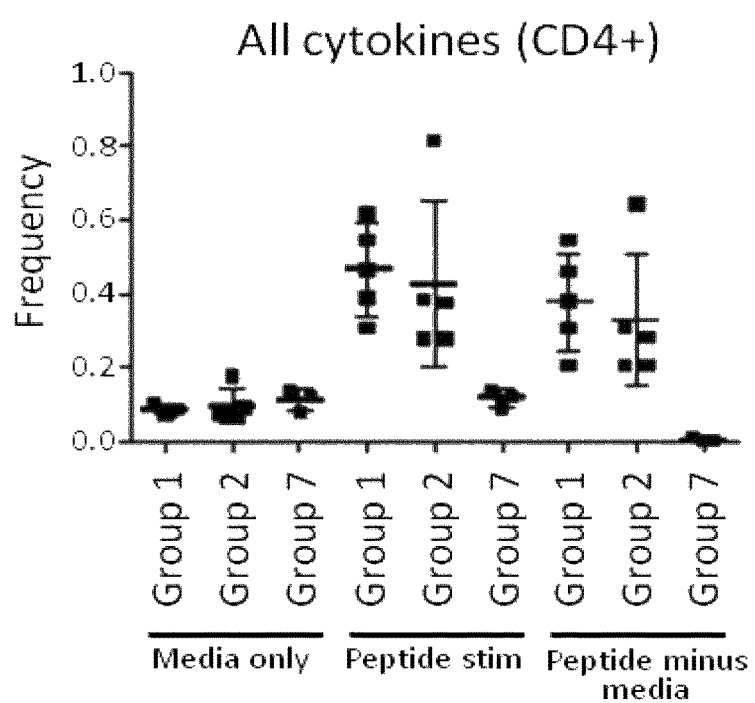
Figure 16B:
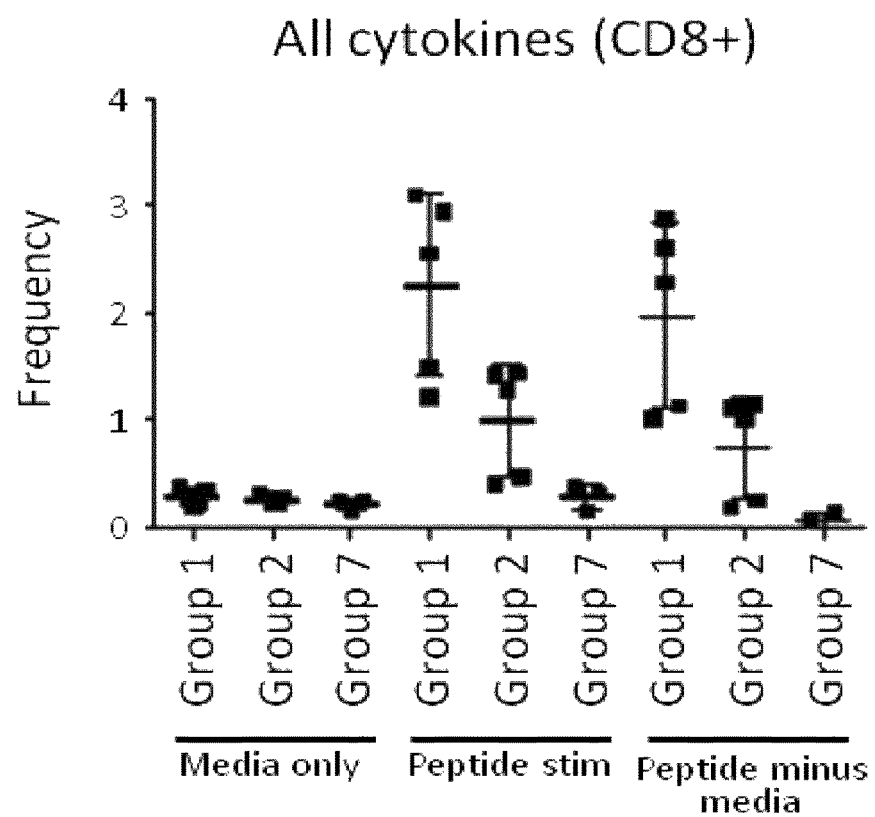
Figure 16C:
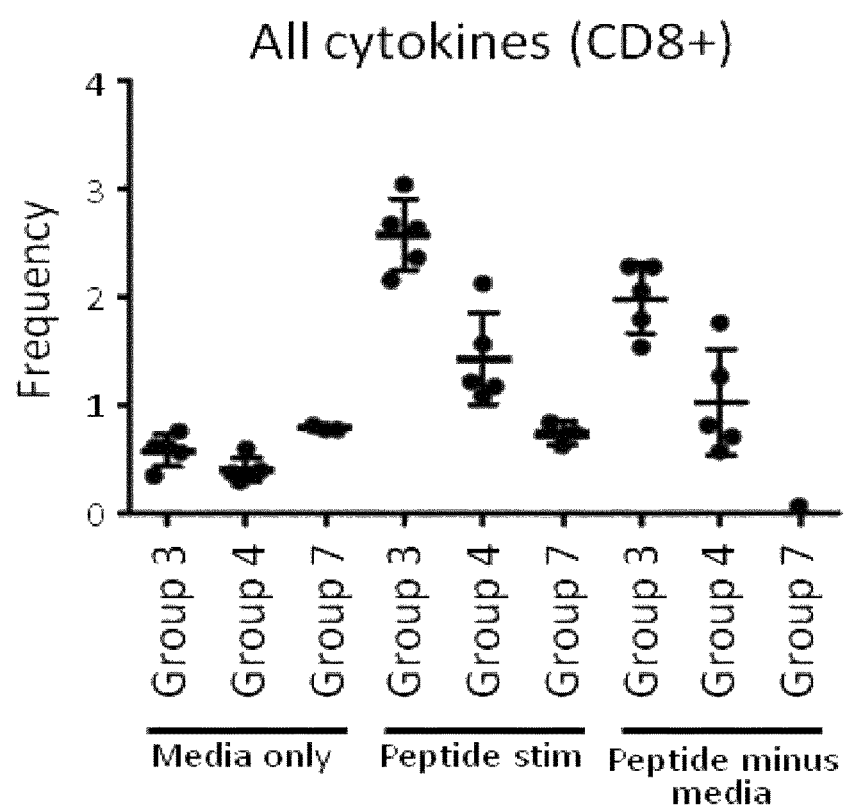

FIGS. 16A-16C: (FIG. 16A) and (FIG. 16B) Groups of 15 C57BL/6 mice were vaccinated intramuscularly (100 μL/mouse in total; 50 μL/thigh) with a target dose of $1\times10^4$ of HK1-Hpp65 (Group 1) or HK3-Hpp65 (Group 2). Non-vaccinated mice (Group 7) were used as a control. For the determination of T cell responses cytokines were analysed by flow cytometry. On day 10 after immunization, 5 mice/group were sacrificed and single cell suspension of spleen cells were restimulated with a pool of peptides generated based on Shedlock D. et al (Human Vaccines & Immunotherapeutics 2012; 8:11, 1-14). After 5 hrs stimulation time the cells were stained for flow cytometric analysis of CD4+ and CD8+ T cells. The cells were stained for the surface marker CD3, CD4 and CD8. After 30 min of surface staining, the cells were permeabilized with 2% PFA (15 min) and treated with saponin to ensure that the cell surface stays permeable. After 30 min intracellular staining (IL-2, IFN-g and TNF-a) samples were washed and measured with FACS Gallios. The frequency of cytokine-expressing CD4+ (A) or CD8+ T (B) cells is reported. (FIG. 16C) Groups of 10 C57BL/6 mice were vaccinated twice by the intramuscular route with a target dose of $1\times104$ of HK1-HgB(dTM) on days 0 and 28 of the experiment. On day 56 of the experiment mice were vaccinated intramuscularly with a target dose of $1\times10^4$ of HK1-Hpp65 (Group 3) or HK3-Hpp65 (Group 4). Non-vaccinated mice (Group 7) were used as a control. On day 66 of the experiment T cell responses were analysed by measuring cytokines by flow cytometry. Single cell suspension of spleen cells from sacrificed mice (5/group) were restimulated with the same pool of peptides. After 5 hrs stimulation time the cells were stained for flow cytometric analysis of CD8+ T cells. The cells were stained for the surface marker CD3, CD4 and CD8. After 30 min surface staining, the cells were permeabilized with 2% PFA (15 min) and treated with saponin to ensure that the cell surface stays permeable. After 30 min intracellular staining (IL-2, IFN-g and TNF-α) samples were washed and measured with FACS Gallios. The frequency of cytokine-expressing CD8+ T cells is reported.

Figure 17:
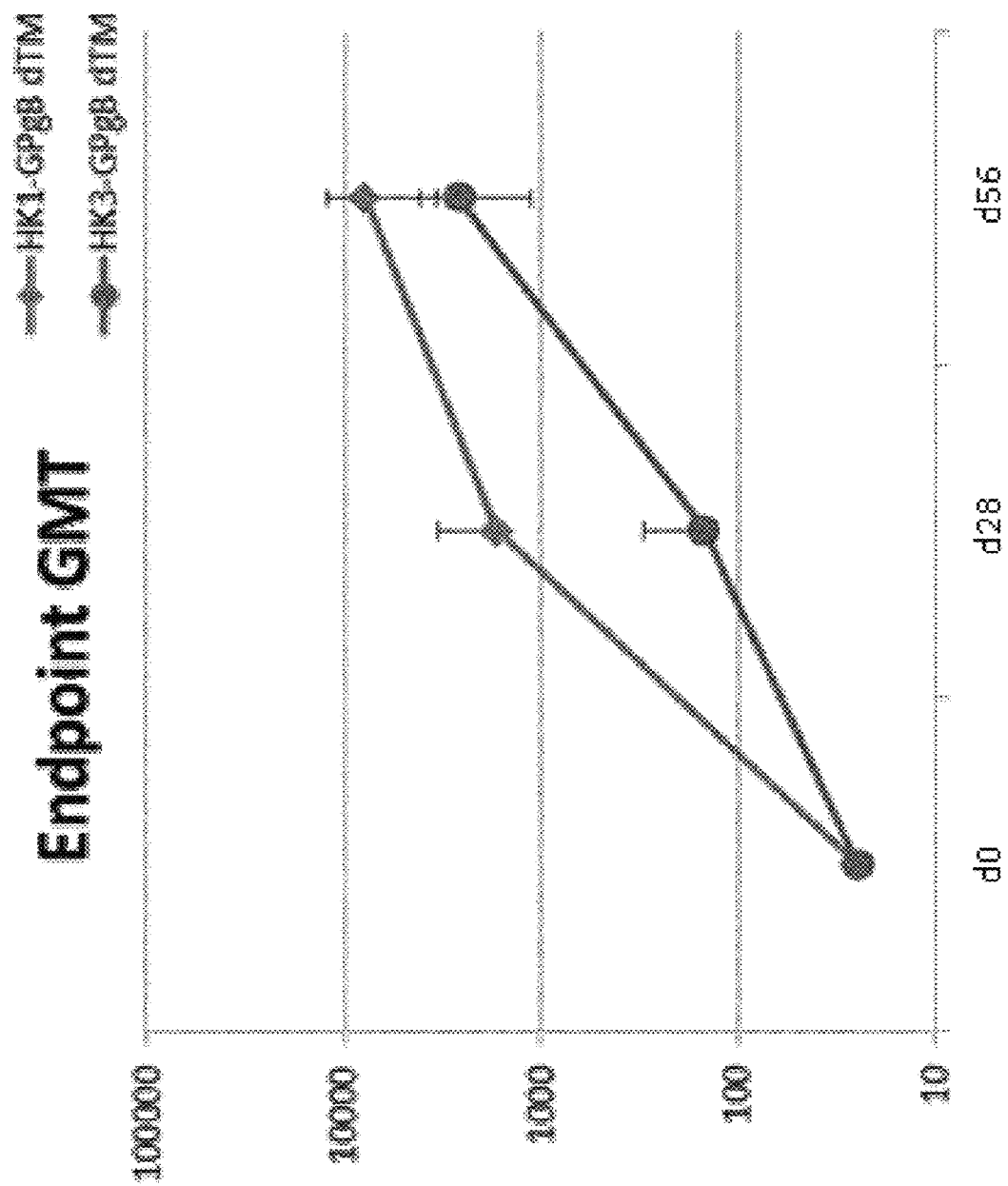

FIG. 17: C57BL/6 mice were vaccinated intramuscularly (100 μL/mouse in total; 50 μL/thigh) on days 0 and 28 of the experiment with a target dose of $1\times10^4$ of HK1-GPgB(dTM) and HK3-GPgB(dTM). Sera from individual animals were generated prior to each vaccine dose (days 0, 28) as well as four weeks (day 56) after the last (second) injection. All sera were tested for the level of GPgB-specific IgG antibodies by ELISA; ELISA data are expressed as geometric mean GPgB-specific IgG endpoint titer.

Figure 18:
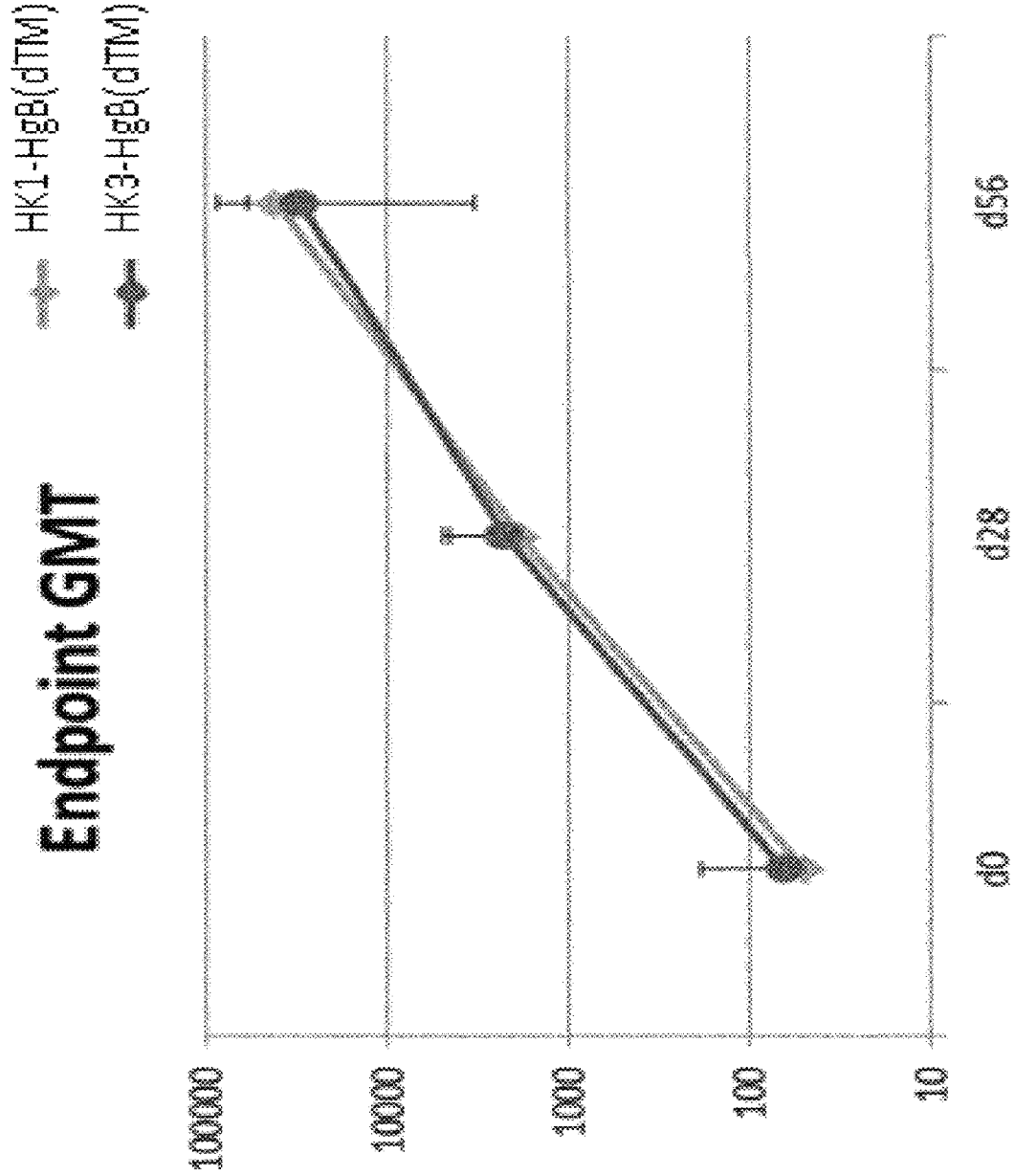

FIG. 18: C57BL/6 mice were vaccinated intramuscularly (100 μL/mouse in total; 50 μL/thigh) on days 0 and 28 of the experiment with a target dose of $1\times10^4$ of HK1-HgB(dTM) and HK3-HgB(dTM). Sera from individual animals were generated prior to each vaccine dose (days 0, 28) as well as four weeks (day 56) after the last (second) injection. All sera were tested for the level of HgB-specific IgG antibodies by ELISA; ELISA data are expressed as geometric mean HgB-specific IgG endpoint titer.

Figure 19:
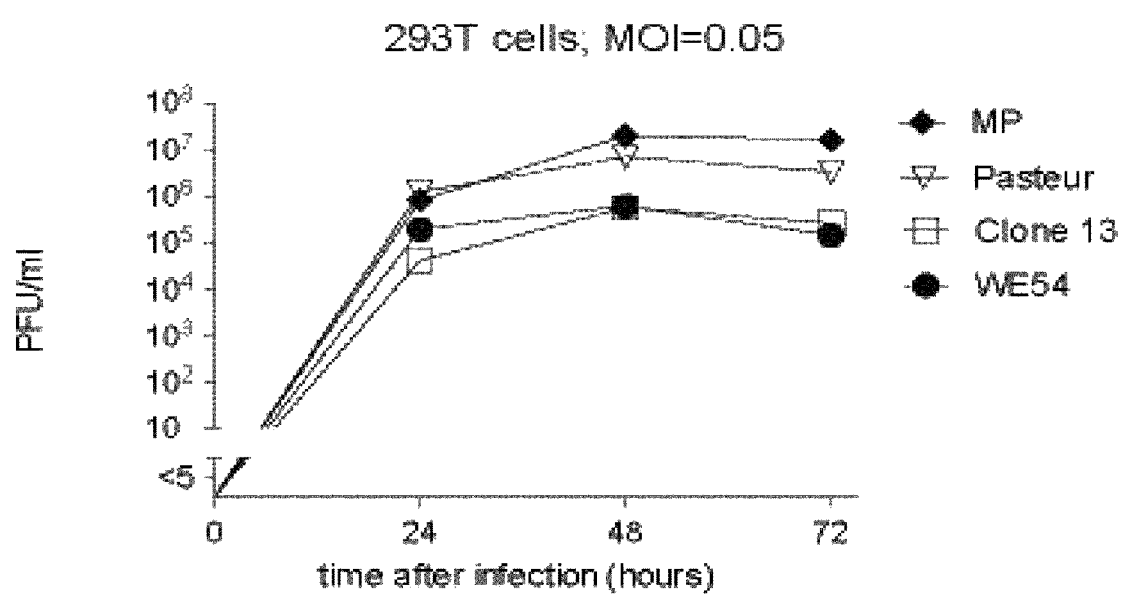

FIG. 19: HEK 293T cells were seeded in M6 well culture wells at a density of 500,000 cells per well. The next day, cells were infected with different LCMV strains at a multiplicity of infection of 0.05. Supernatant was harvested at the indicated time points and viral titres were determined by immunofocus assay. Symbols represent the mean of two wells.

Figure 20:
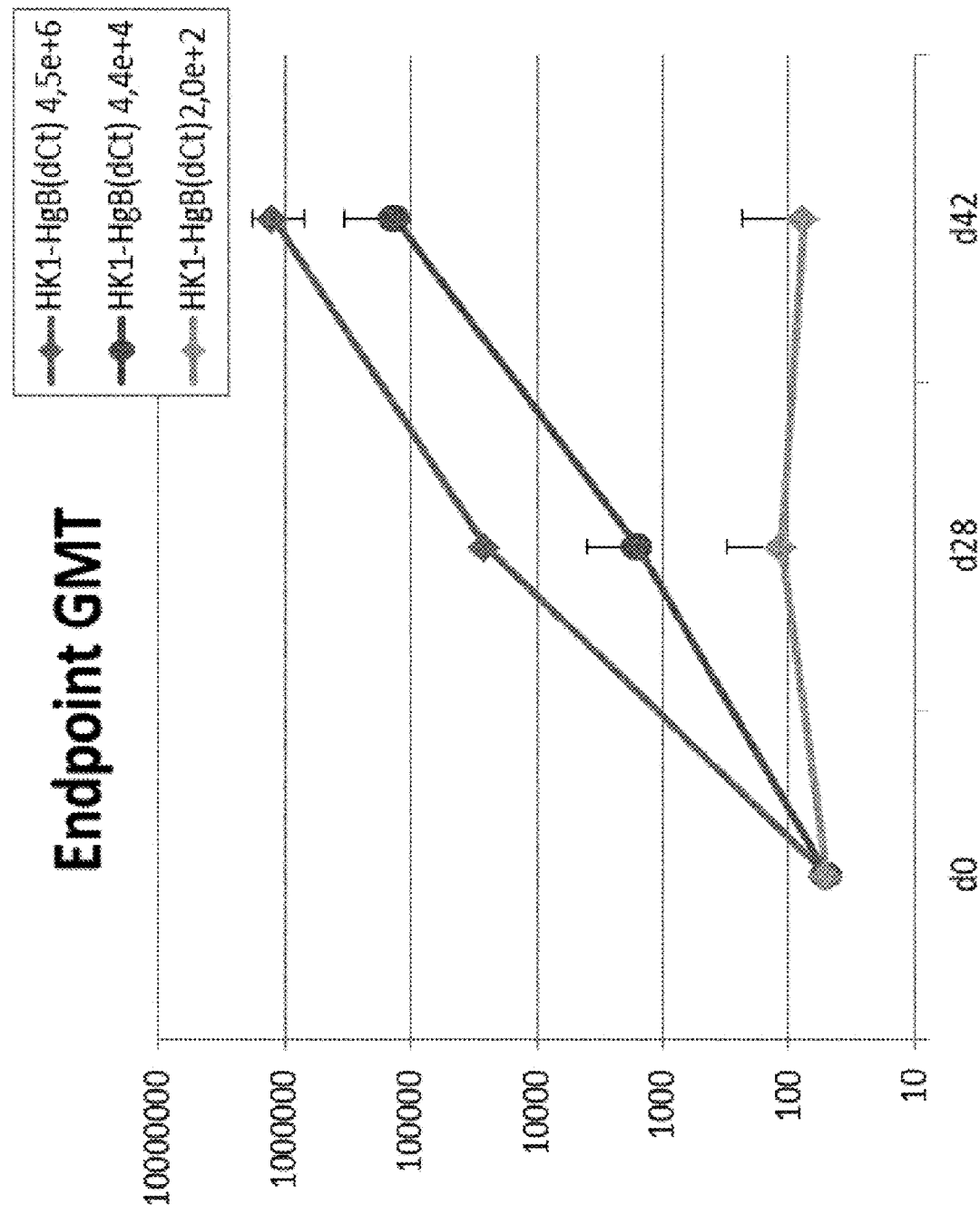

FIG. 20: Groups of 5 New Zealand white rabbits were immunized intramuscularly with different doses ($2.0\times10^2$, $4.4\times10^4$ and $4.5\times10^6$ FFU/dose) of HK1-HgB(dCt) on days 0 and 28. Sera were collected on days 0, 28 and 42 and anti-HCMVgB IgG antibody titers were measured by ELISA. Endpoint GMTs are shown.

Figure 21A:
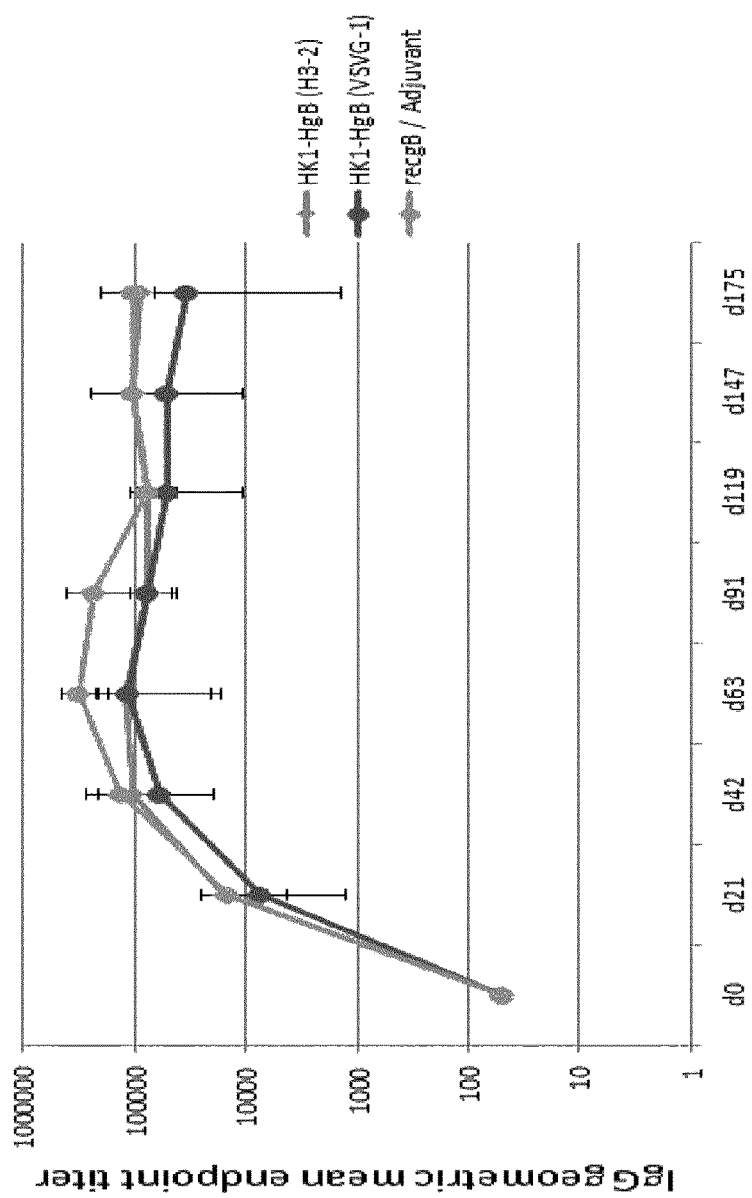

FIG. 21A: C57BL/6 mice were immunized intramuscularly with $1\times10^5$ FFU/dose of HK1-HgB(H3-2), HK1-HgB (VSVG-1) and recombinant gB/adjuvant on days 0, 21 and 42. Sera of immunized mice were collected on days 21, 42, 63, 91, 119, 147 and 175 and anti-HCMVgB IgG antibody titers were measured by ELISA. Endpoint GMTs are shown.

Figure 21B:
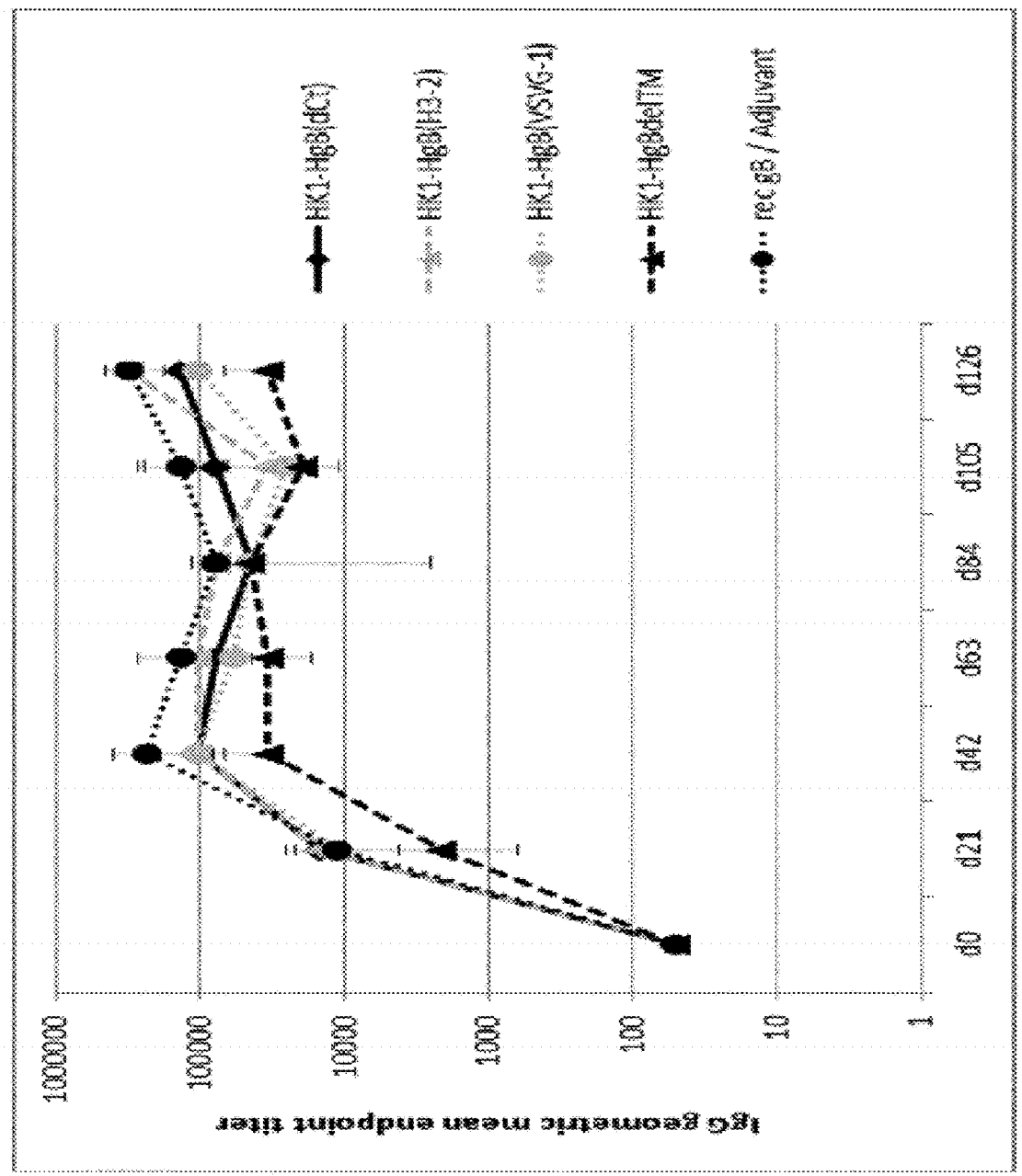

FIG. 21B: C57BL/6 mice were immunized intramuscularly with $1\times10^5$ FFU/dose of HK1-HgB(H3-2), HK1-HgB (VSVG-1), HK1-HgB(dTM), HK1-HgB(dCt) and recombinant gB/adjuvant on days 0, 21 and 105. Sera of immunized mice were collected on days 21, 42, 63, 84, 105 and 126 and anti-HCMVgB IgG antibody titers were measured by ELISA. Endpoint GMTs are shown.

Figure 22A:
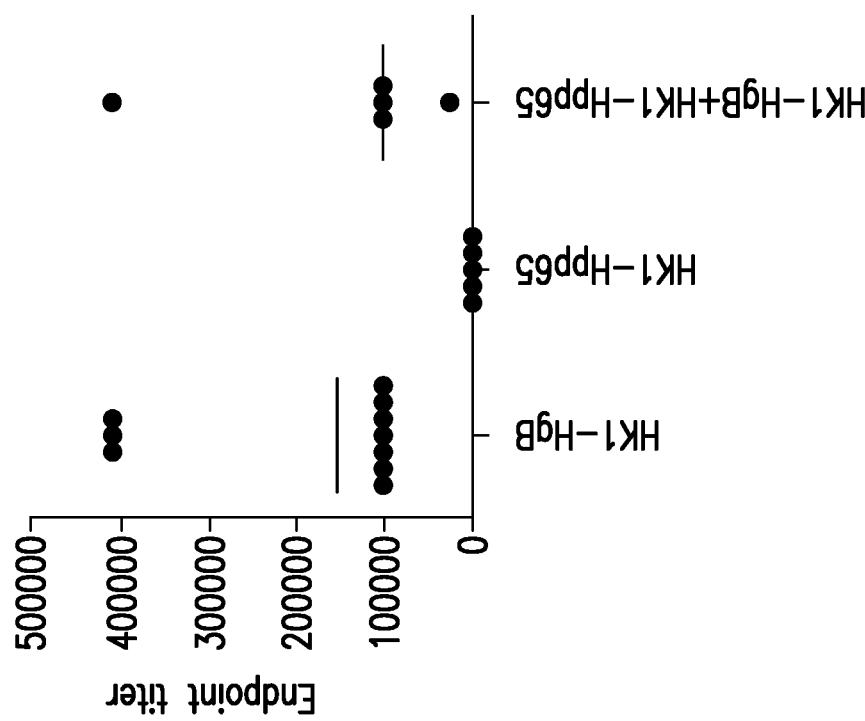
Figure 22B:
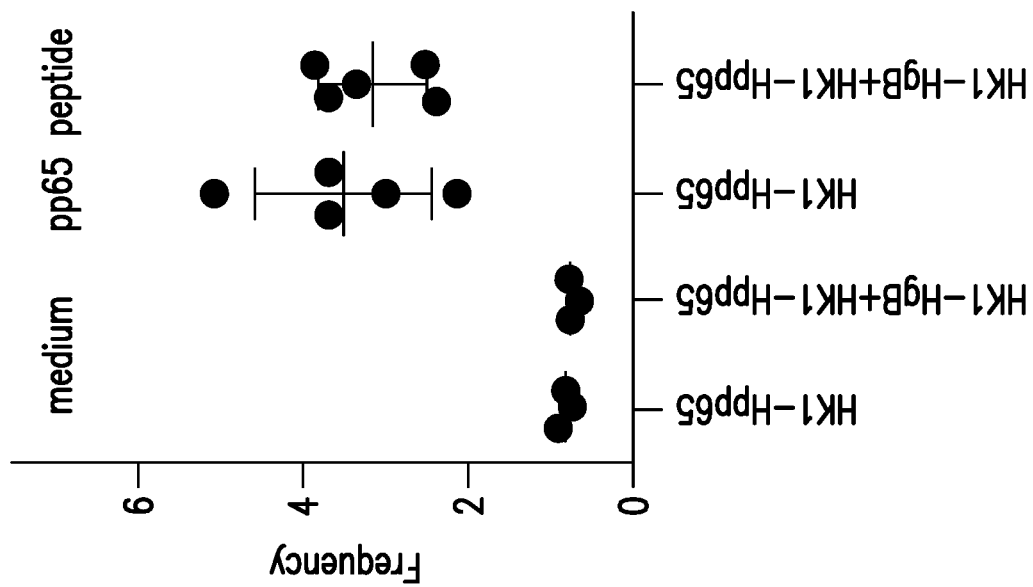

FIG. 22A and FIG. 22B: Groups of 10 C57BL/6 mice were immunized intramuscularly with $9\times10^4$ FFU/dose of HK1-HgB(dCt) alone or 9×10$^4$ FFU/dose of HK1-Hpp65 alone or with 9×10$^4$ FFU/dose of each HK1-HgB(dCt) and HK1-Hpp65 together on days 0 and 28. (FIG. 22A) Sera of immunized mice were collected on day 49 and anti-HCMVgB IgG antibody titers were measured by ELISA. (FIG. 22B) For the determination of T cell responses cytokines were analysed by flow cytometry. On day 49 after immunization, mice were sacrificed and single cell suspension of spleen cells were restimulated with a pool of peptides generated based on Shedlock D. et al (Human Vaccines & Immunotherapeutics 2012; 8:11, 1-14). Control cells were stimulated with medium only. After incubation with medium (lanes 1 and 2) or with specific peptides (lanes 3 and 4) cells were stained for flow cytometric analysis of CD8+ T cells. Expression of IL-2, IFN-g and TNF was analyzed.

Figure 23:
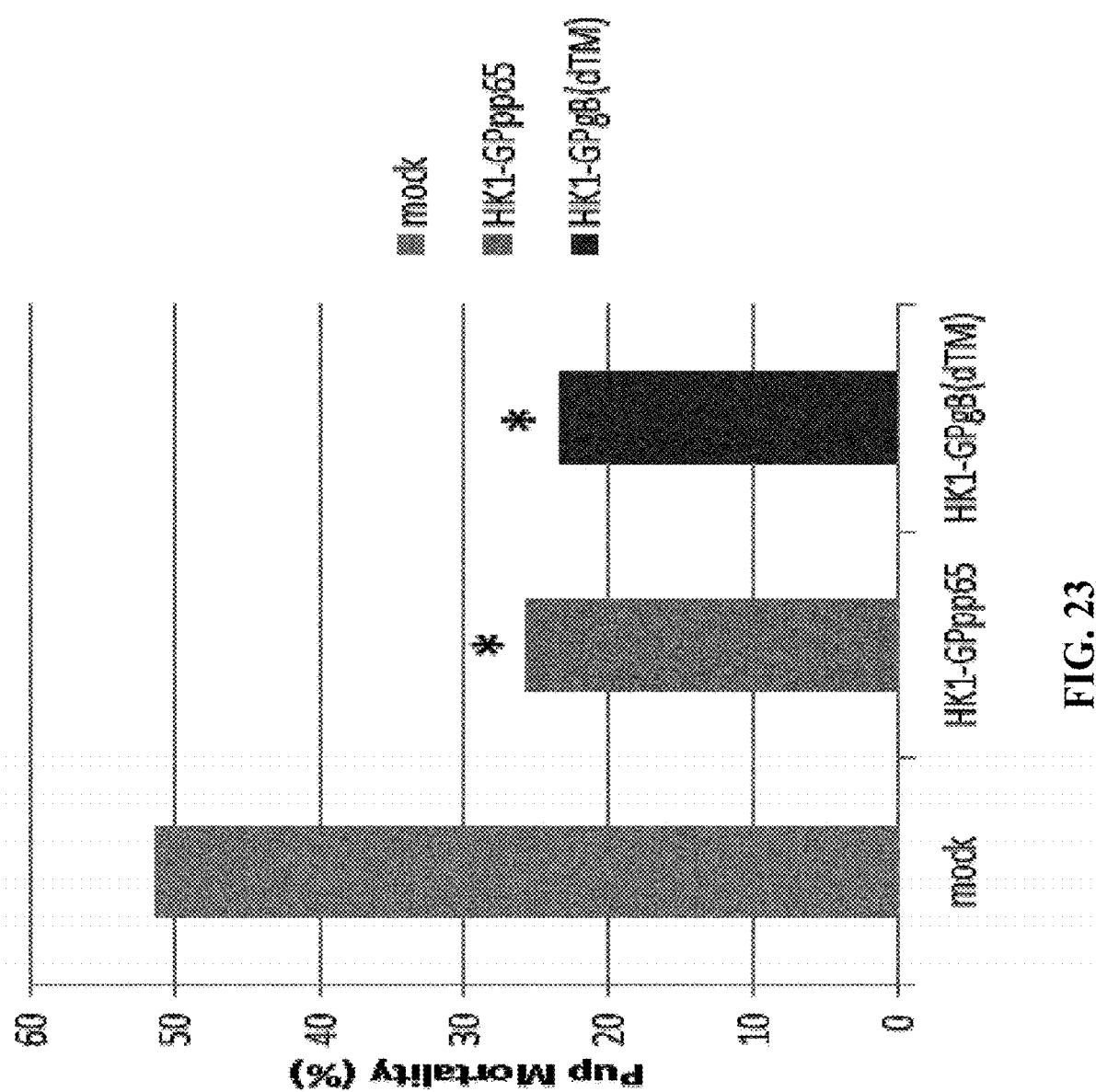

FIG. 23: Hartley guinea pigs (11 animals/group) were immunized intramuscularly three times (on days 0, 21 and 42) with 1.54×10$^6$ FFU/dose of either HK1-GPgB-dTM or HK1-GPpp65 in advance of breeding. Control animals (10/group) received buffer instead of rLCMV vector constructs. Animals were bred on day 63+ of the experiment. ~45 days after gestation guinea pigs were challenged subcutaneously with 1×10$^5$ pfu of guinea pig CMV. Pup mortality was measured at parturition and protection rates were determined by comparison of treatment groups for viremia and rates of pup death, * indicates significant (p<0.05) reduction.

Figure 24A:
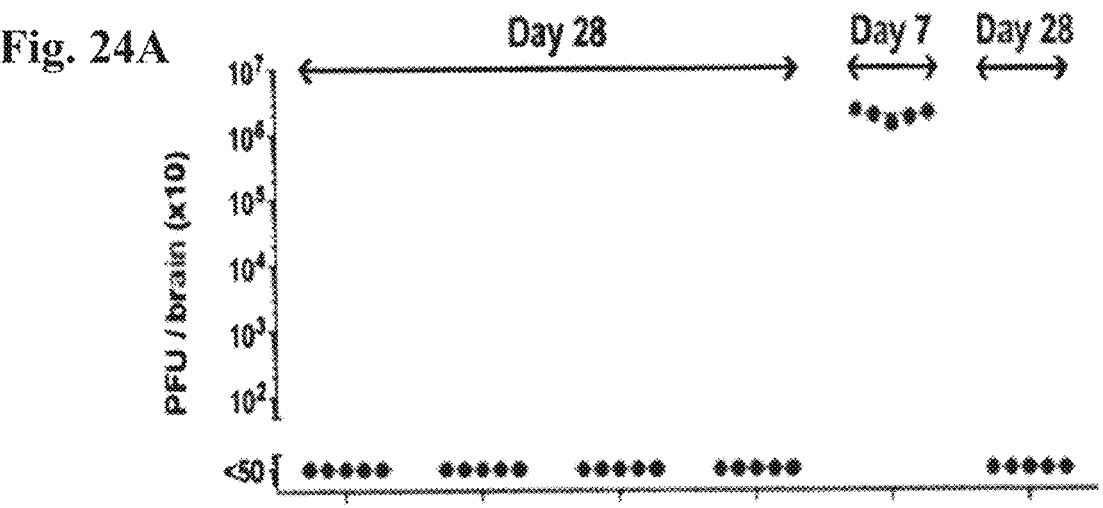
Figure 24B:
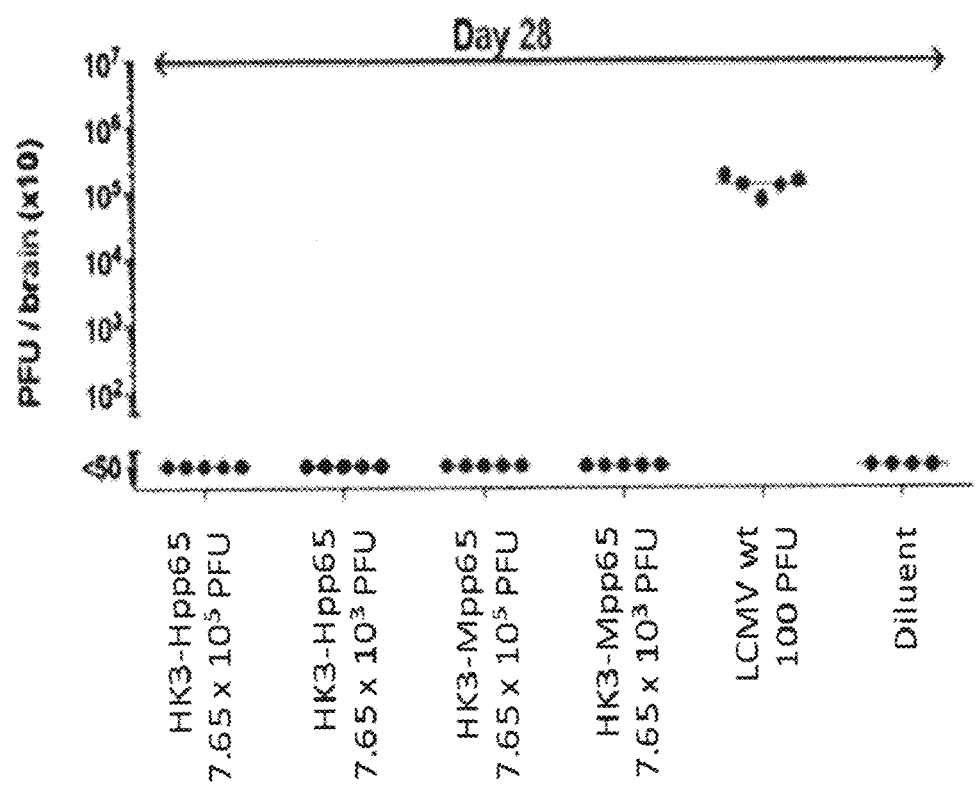

FIG. 24A and FIG. 24B: IFN α/β and γ receptors deficient AG129 mice (FIG. 24A) as well as T and B cell deficient RAG−/− mice (FIG. 24B) were inoculated intracerebrally with 7.65×10$^5$ as well as 7.65×10$^3$ FFU/dose of either HK3-Hpp65 or the mouse analogue HK3-Mpp65 on day 0. Control groups of mice received either 100 FFU/dose of wildtype LCMV or diluent only. Mice were subsequently monitored for signs of illness and brain tissue were collected on the indicated days and analyzed for the presence of infectious virus.

Figure 25:
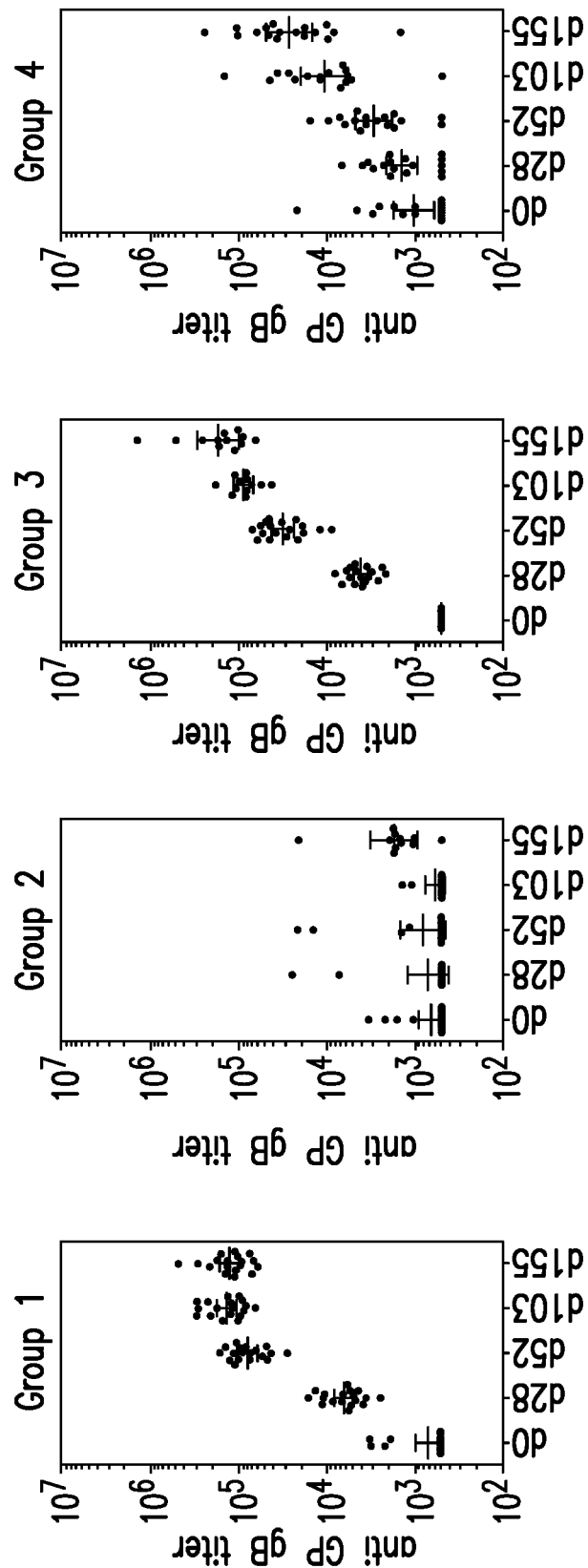

FIG. 25: Hartley guinea pigs (18 animals/group) were immunized intramuscularly with 8×10$^5$ FFU/dose of HK1-GPgB(dCt) (group 1), 8×10$^5$ FFU/dose of HK1-GPpp65 (group 2), or 8×10$^5$ FFU/dose of each HK1-GPgB(dCt) and HK1-GPpp65 (group 3) on days 0, 31 and 72 (group 1)/days 0, 31 and 70 (group 2)/days 0, 34 and 70 (group 3) of the experiment. In addition, Hartley guinea pigs (18 animals/group) were immunized subcutaneously with 50 μg of subunit gB protein, formulated in Complete Freund's Adjuvant (group 4) on days 0, 46 and 76. Sera of immunized animals were collected on days 0, 28, 52, 103 and 155 of the experiment and anti-gB antibody titers were analyzed by GPgB-specific IgG ELISA using a sera pool with assigned anti-gB antibody titer as a reference standard.

Figure 26:
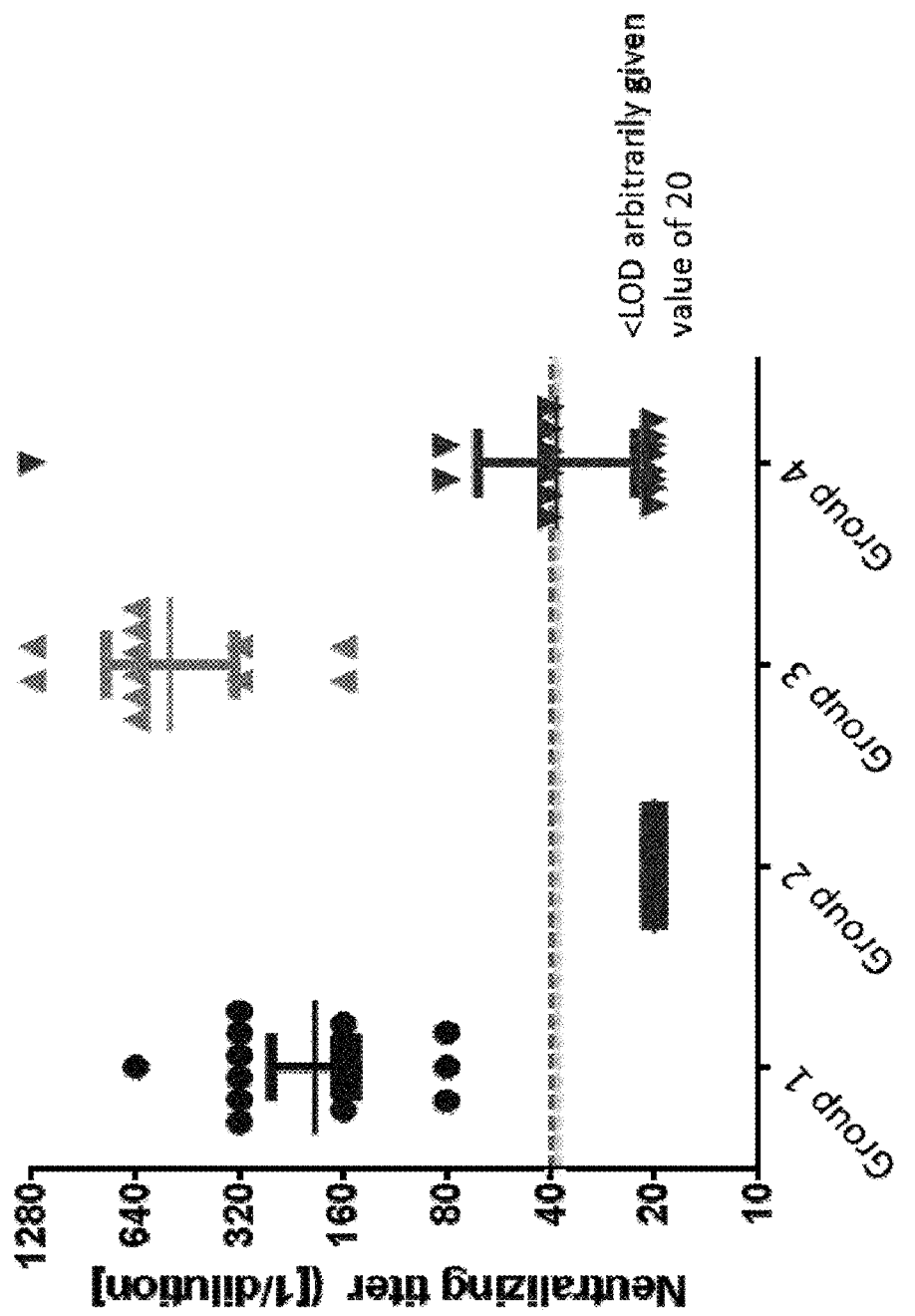

FIG. 26: Hartley guinea pigs (18 animals/group) were immunized intramuscularly with 8×10$^5$ FFU/dose of HK1-GPgB(dCt) (group 1), 8×10$^5$ FFU/dose of HK1-GPpp65 (group 2), or 8×10$^5$ FFU/dose of each HK1-GPgB(dCt) and HK1-GPpp65 (group 3) on days 0, 31 and 72 (group 1)/days 0, 31 and 70 (group 2)/days 0, 34 and 70 (group 3). In addition, Hartley guinea pigs (18 animals/group) were immunized subcutaneously with 50 μg of subunit gB protein, formulated in Complete Freund's Adjuvant (group 4) on days 0, 46 and 76. Sera of immunized animals were collected on day 103 and the neutralizing activity of the sera of the experiment was analyzed. Dotted line indicates limit of detection. Sera samples that failed to reach the limit of detection in the assay were arbitrarily assigned a value of 20 for graphing and statistical calculations.

FIG. 27A and FIG. 27B: Splenocytes were isolated from Hartley guinea pigs immunized intramuscularly with 8×10$^5$ FFU/dose of HK1-GFP (group 1), 8×10$^5$ FFU/dose of HK1-GPpp65 (group 2) or 8×10$^5$ FFU/dose of each HK1-GPgB (dCt) and HK1-GPpp65 (group 3) and analyzed by ELISPOT assay. Three animals from each vaccine group were sacrificed after 2 doses of vaccine and three additional animals from each vaccine group were sacrificed after 3 vaccine doses. The magnitude of the pp65-specific splenocyte response for each animal was calculated using Prism6 as the "area under the curve" above the DMSO control of each animal's response to all pp65 peptide pools. (FIG. 27A) Average number of spots per animal is represented by data points for either 2 doses (circles) or 3 doses (boxes) of vaccine (Bars represent group mean and ±SEM). (FIG. 27B) Average number of spots per animal is represented by data points for HK1-GFP (circles), HK1-GPpp65 (squares), or HK1-GPgB(dCt)/HK1-GPpp65 (triangles) vaccinated animals (Bars represent group mean and ±SEM). P-values shown on figure were calculated using a Mann-Whitney U-test (Wilcoxon, Biometrics Bulletin, 1945, 1: 80-83; Mann & Whitney, Annals of mathematical Statistics, 1947, 18: 50-60).

Figure 28:
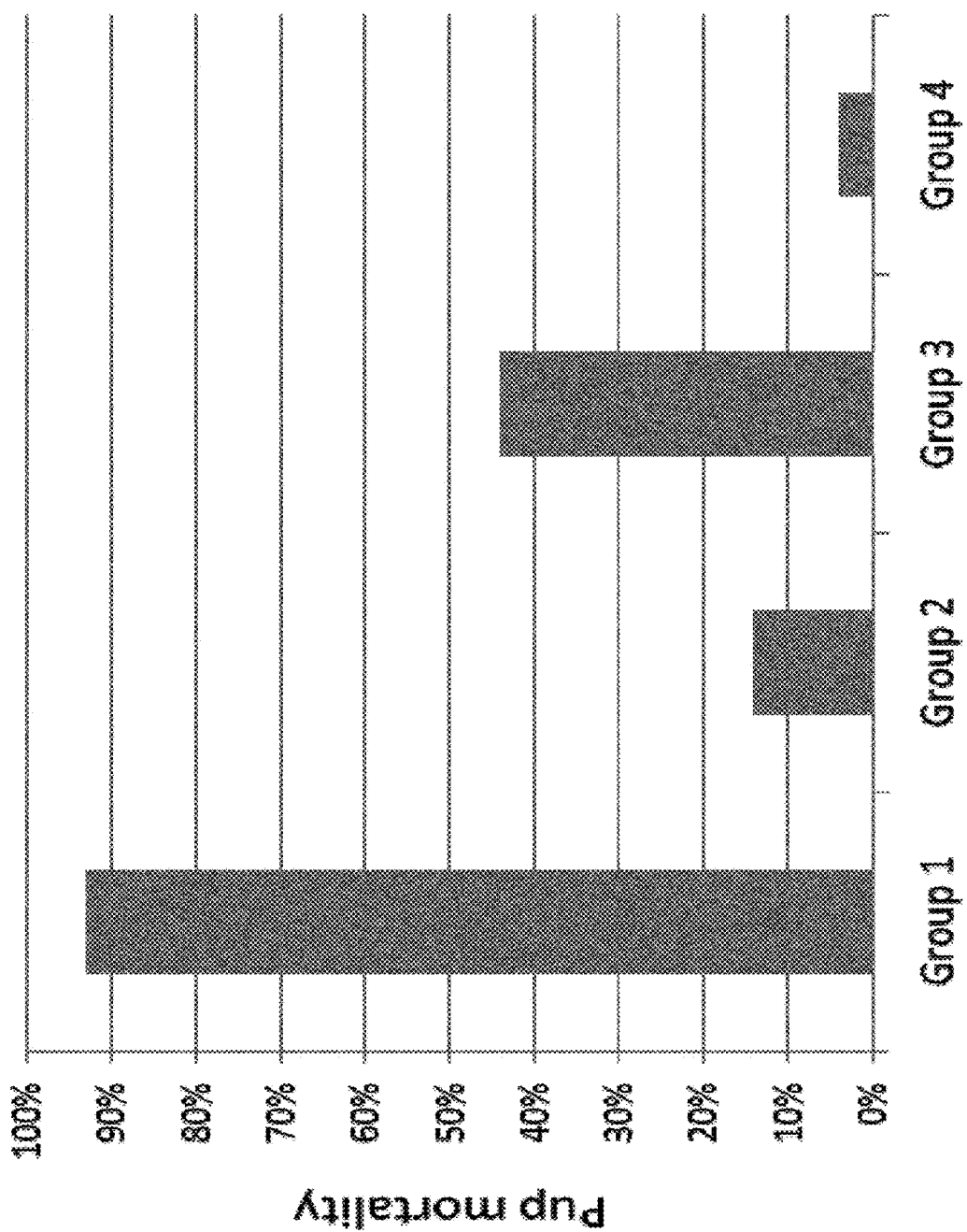

FIG. 28: Hartley guinea pigs were immunized intramuscularly three times with 8×10$^5$ FFU/dose of either HK1-GFP (group1), HK1-GPgB(dCt) (group 2), HK1-GPpp65 (group 3) or 8×10$^5$ FFU/dose of each HK1-GPgB(dCt) and HK1-GPpp65 in combination (group 4) in advance of breeding. About one month after the last vaccine dose animals were allowed to breed. Pregnancies in guinea pig dams were confirmed and monitored by palpitation. Pregnant dams were challenged in the third trimester of gestation with 10$^5$ plaque-forming units of salivary gland passaged guinea pig CMV and were subsequently monitored until delivery. Pup mortality was measured at parturition and protection rates were determined by comparison of treatment groups for rates of pup mortality.

6. DETAILED DESCRIPTION OF THE INVENTION

Provided herein are methods and compositions for the treatment or prevention of infection of a subject with CMV, or of reactivation of CMV in a subject. More specifically, provided herein are infectious, replication-deficient arenaviruses that comprise a nucleotide sequence encoding a CMV antigen. These viruses can be administered to a subject for the treatment or prevention of CMV infection or reactivation. The generation of infectious, replication-deficient arenavirus vectors for use with the present invention is described in more detail in Section 6.3.

Provided herein is a genetically modified arenavirus, where the arenavirus:
  is infectious;
  cannot form infectious progeny virus in a non-complementary cell (i.e., a cell that does not express the functionality that is missing from the replication-deficient arenavirus and causes it to be replication-deficient);
  is capable of replicating its genome and expressing its genetic information; and
  encodes a CMV antigen or a fragment thereof.

A genetically modified arenavirus described herein is infectious, i.e., it can attach to a host cell and release its genetic material into the host cell. A genetically modified arenavirus described herein is replication-deficient, i.e., the arenavirus is unable to produce further infectious progeny particles in a non-complementing cell. In particular, the genome of the arenavirus is modified (e.g., by deletion or functional inactivation of an ORF) such that a virus carrying the modified genome can no longer produce infectious progeny viruses. A non-complementing cell is a cell that does not provide the functionality that has been eliminated from the replication-deficient arenavirus by modification of the virus genome (e.g., if the ORF encoding the GP protein is deleted or functionally inactivated, a non-complementing cell does not provide the GP protein). However, a genetically modified arenavirus provided herein is capable of producing infectious progeny viruses in complementing cells. Complementing cells are cells that provide (in trans) the functionality that has been eliminated from the replication-deficient arenavirus by modification of the virus genome (e.g., if the ORF encoding the GP protein is deleted or functionally inactivated, a complementing cell does provide the GP protein). Expression of the complementing functionality (e.g., the GP protein) can be accomplished by any method known to the skilled artisan (e.g., transient or stable expression). A genetically modified arenavirus described herein can amplify and express its genetic information in a cell that has been infected by the virus. A genetically modified arenavirus provided herein comprises a nucleotide sequence that encodes a CMV antigen such as but not limited to the CMV antigens described in Section 6.2.

In certain embodiments, provided herein is a genetically modified arenavirus in which an ORF (ORF) of the arenavirus genome is deleted or functionally inactivated such that the resulting virus cannot produce further infectious progeny virus particles in non-complementing cells. An arenavirus particle comprising a genetically modified genome in which an ORF deleted or functionally inactivated can be produced in complementing cells (i.e., in cells that express the arenaviral ORF that has been deleted or functionally inactivated) (see Section 6.3). The genetic material of the resulting arenavirus particles can be transferred upon infection of a host cell into the host cell, wherein the genetic material can be expressed and amplified. In addition, the genome of the genetically modified arenavirus particles provided herein encodes a CMV antigen that can be expressed in the host cell.

In certain embodiments, the ORF that encodes the glycoprotein (GP) gene of the arenavirus is deleted to generate a replication-deficient arenavirus for use with the present invention. In a specific embodiment, the replication-deficient arenavirus comprises a genomic segment comprising a nucleotide sequence encoding a CMV antigen. Thus, in certain embodiments, a genetically modified arenavirus particle provided herein comprises a genomic segment that a) has a deletion or functional inactivation of an ORF that is present in the wild type form of the genomic segment; and b) encodes (either in sense or antisense) a CMV antigen (see Section 6.3).

In certain embodiments, the antigen encoded by the nucleic acid that is inserted into the genome of replication-deficient arenavirus can encode, for example, a CMV antigen or combinations of CMV antigens including, but not limited to:

a. a nucleotide sequence encoding a CMV glycoprotein gB or an antigenic fragment thereof;
b. a nucleotide sequence encoding a CMV tegument protein pp65 or an antigenic fragment thereof;
c. a nucleotide sequence encoding a CMV glycoprotein gH or an antigenic fragment thereof;
d. a nucleotide sequence encoding a CMV glycoprotein gL or an antigenic fragment thereof
e. a nucleotide sequence encoding a CMV UL128 protein or an antigenic fragment thereof
f. a nucleotide sequence encoding a CMV UL130 protein or an antigenic fragment thereof
g. a nucleotide sequence encoding a CMV UL131A protein or an antigenic fragment thereof.

A detailed description of the antigens described herein is provided in Section 6.2.

In certain embodiments, the arenaviruses used according to the invention described herein can be Old World viruses, for example, Lymphocytic choriomeningitis virus (LCMV). More detailed description of the arenaviruses described herein is provided in Section 6.1.

Provided herein are nucleic acids encoding the genome of such replication-deficient arenaviruses. In certain aspects, an infectious, replication-deficient arenavirus particle comprises a genomic segment comprising a nucleotide sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 34, SEQ ID NO: 37, SEQ ID NO: 40, SEQ ID NO: 44, or SEQ ID NO: 49, or SEQ ID NO: 50.

Provided herein is an expression plasmid that encodes one or more components required for the generation of a viral vector described herein. Specifically, provided herein is an expression vector that encodes an LCMV S segment wherein the ORF for the GP protein has been deleted from the S segment and has been replaced with the ORF of human CMV glycoprotein gB with a truncation of the carboxy-terminus (e.g., having the amino acid sequence of SEQ ID NO: 18 or an amino acid sequence that is 80%, 81%, 82%, 83%, 84%, 85%, 86%, 87%, 88%, 89%, 90%, 90%, 91%, 92%, 93%, 94%, 95%, 96%, 97%, 98%, 99%, or 100% identical to SEQ ID NO: 18).

Provided herein are kits comprising one or two of the vector plasmids described herein. In certain embodiments, provided herein is a kit that comprises a) an expression plasmid that encodes the S segment of an LCMV vector; b) an expression plasmid that encodes the L segment of an LCMV vector; and c) an expression plasmid that encodes the complementing functionality. In a specific embodiment, provided herein is a kit comprising a) an expression vector that encodes an LCMV S segment wherein the ORF for the GP protein has been deleted from the S segment and has been replaced with the ORF of human CMV glycoprotein gB with a truncation of the carboxy-terminus (e.g., having the amino acid sequence of SEQ ID NO: 18 or an amino acid sequence that is 80%, 81%, 82%, 83%, 84%, 85%, 86%, 87%, 88%, 89%, 90%, 90%, 91%, 92%, 93%, 94%, 95%, 96%, 97%, 98%, 99%, or 100% identical to SEQ ID NO: 18); b) an expression plasmid that encodes the L segment of an LCMV vector; and c) an expression plasmid that encodes the LCMV GP protein (or a cell line that expresses LCMV GP protein).

Also provided herein are cell lines, cultures and methods of culturing cells infected with nucleic acids, vectors, and compositions provided herein. More detailed description of the nucleic acids, vector systems and cell lines described herein is provided in Section 6.4.

The invention relates to such genetically modified replication-deficient arenaviruses suitable as vaccines and to methods of using such arenaviruses in vaccination and treatment or prevention of infections by CMV or reactivation of CMV. More detailed description of methods of using such arenaviruses described herein is provided in Section 6.5.

In certain embodiments, immunization with an infectious, replication-deficient arenavirus that expresses a CMV antigen or a fragment thereof, as described herein provides a long-lasting immune response. In certain embodiments, maximal antibody levels can be achieved after two immunizations. In another embodiment, a third immunization can be administered for a boosting effect. In more specific embodiments, provided herein are administration schedules using the infectious, replication-deficient arenavirus in a vaccination for the treatment and/or prevention of infections by CMV or reactivation of CMV. A more detailed description of administration schedules using an infectious, replication-deficient arenavirus as described herein is provided in Section 6.5.

In certain embodiments, administering to a seronegative subject an infectious, replication-deficient arenavirus expressing a CMV antigen or a fragment thereof, as described herein induces a detectable antibody titer for a minimum of at least 4 weeks. In another embodiment, administering to a subject infected with a CMV infection an infectious, replication-deficient arenavirus expressing a CMV antigen or a fragment thereof, as described herein increases the antibody titer by at least 100%, at least 200%, at least 300%, at least 400%, at least 500%, or at least 1000%. In certain embodiments, primary antigen exposure elicits a functional, (neutralizing) and minimum antibody titer of at least 50%, at least 100%, at least 200%, at least 300%, at least 400%, at least 500%, or at least 1000% of mean control sera from infection-immune human subjects. In more specific embodiments, the primary neutralizing geometric mean antibody titer increases up to a peak value of at least 1:50, at least 1:100, at least 1:200, or at least 1:1000 within at least 4 weeks post-immunization. In another embodiment, immunization with an infection, replication-deficient arenavirus expressing a CMV antigen or a fragment thereof, as described herein produces high titers of antibodies that last for at least 4 weeks, at least 8 weeks, at least 12 weeks, at least 6 months, at least 12 months, at least 2 years, at least 3 years, at least 4 years, or at least 5 years post-immunization following a single administration of the vaccine.

In yet another embodiment, secondary antigen exposure increases the antibody titer by at least 100%, at least 200%, at least 300%, at least 400%, at least 500%, or at least 1000%. In another embodiment, secondary antigen exposure elicits a functional, (neutralizing) and minimum antibody titer of at least 50%, at least 100%, at least 200%, at least 300%, at least 400%, at least 500%, or at least 1000% of mean control sera from infection-immune human subjects. In more specific embodiments, the secondary neutralizing geometric mean antibody titer increases up to a peak value of at least 1:50, at least 1:100, at least 1:200, or at least 1:1000 within at least 4 weeks post-immunization. In another embodiment, a second immunization with an infection, replication-deficient arenavirus expressing a CMV antigen or a fragment thereof, as described herein produces high titers of antibodies that last for at least 4 weeks, at least 8 weeks, at least 12 weeks, at least 6 months, at least 12 months, at least 2 years, at least 3 years, at least 4 years, or at least 5 years post-immunization.

In yet another embodiment, a third boosting immunization increases the antibody titer by at least 100%, at least 200%, at least 300%, at least 400%, at least 500%, or at least 1000%. In another embodiment, the boosting immunization elicits a functional, (neutralizing) and minimum antibody titer of at least 50%, at least 100%, at least 200%, at least 300%, at least 400%, at least 500%, or at least 1000% of mean control sera from infection-immune human subjects. In more specific embodiments, the third boosting immunization elicits a functional, (neutralizing), and minimum antibody titer of at least 50%, at least 100%, at least 200%, at least 300%, at least 400%, at least 500%, or at least 1000% of mean control sera from infection-immune human subjects. In another embodiment, a third boosting immunization prolongs the antibody titer by at least 4 weeks, at least 8 weeks, at least 12 weeks, at least 6 months, at least 12 months, at least 2 years, at least 3 years, at least 4 years, or at least 5 years post-immunization In certain embodiments, the infectious replication-deficient arenavirus expressing a CMV antigen or fragment thereof, elicits a T cell independent or T cell dependent response. In other embodiments, the infectious, replication-deficient arenavirus expressing a CMV antigen or a fragment thereof, elicits a T cell response. In other embodiments, the infections, replication-deficient arenavirus expressing a CMV antigen or a fragment thereof, as described herein elicits a T helper response. In another embodiment, the infectious, replication-deficient arenavirus expressing a CMV antigen or a fragment thereof, as described herein elicits a Th1-orientated response or a Th2-orientated response.

In more specific embodiments, the Th1-orientated response is indicated by a predominance of IgG1 antibodies versus IgG2. In other embodiments the ratio of IgG1:IgG2 is greater than 1:1, greater than 2:1, greater than 3:1, or greater than 4:1. In another embodiment the infectious, replication-deficient arenavirus expressing a CMV antigen or a fragment thereof, as described hereon is indicated by a predominance of IgG3 antibodies.

In some embodiments, the infectious, replication-deficient arenavirus expressing a CMV antigen or a fragment thereof elicits a CD8+ T cell response. In other embodiments, the infectious, replication-deficient arenavirus expressing a CMV antigen or a fragment thereof elicits a regulatory T cell response. In more specific embodiments, the regulatory T cell response maintains immune tolerance. In another embodiment, the infectious, replication-deficient arenavirus expressing a CMV antigen or a fragment there of elicits both CD4+ and CD8+ T cell responses.

In certain embodiments, the infectious, replication-deficient arenavirus expressing a CMV antigen or fragment thereof, as described herein elicits high titers of neutralizing antibodies. In another embodiment, the infectious replication-deficient arenavirus expressing a CMV antigen or fragment thereof, as described herein elicits high titers of neutralizing antibodies than expression of the protein complex components individually.

In other embodiments, two or more infections, replication-deficient arenavirus expressing a CMV antigen elicits high titers of neutralizing antibodies. In a more specific embodiment, two or more infections, replication-deficient arenavirus expressing a CMV antigen elicit higher titers of neutralizing antibodies than an infectious, replication-deficient arenavirus expressing one CMV antigen or fragment thereof.

In another embodiment, the infectious, replication-deficient arenavirus expressing two, three, four, five, or more CMV antigens elicits higher titers of neutralizing antibodies than an infectious replication-deficient arenavirus expressing one CMV antigen or fragment thereof.

6.1 Infectious, Replication-Deficient Arenavirus Vectors Expressing a CMV Antigen Arenaviruses for use with the methods and compositions provided herein can be of Old World viruses, for example Lassa virus, Lymphocytic choriomeningitis virus (LCMV), Mobala virus, Mopeia virus, or Ippy virus, or New World viruses, for example Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Bear Canyon virus, or Whitewater Arroyo virus. The genetically modified arenavirus can be generated as described in Section 6.3.

The wild type arenavirus genome consists of a short (~3.4 kb) and a large (~7.2 kb) RNA segment. The short segment carries the ORFs encoding the nucleoprotein NP and glycoprotein GP genes. The large segment encodes the RNA-dependent RNA polymerase L and the matrix protein Z genes. Wild type arenaviruses can be rendered replication-deficient to generate vaccine vectors by substituting the glycoprotein gene for one or more CMV antigens, against which immune responses are to be induced.

Infectious, replication-deficient arenavirus vectors expressing a CMV antigen, or a combination of CMV antigens as described herein, can be used to immunize (in a preventive manner) or treat (in an immunotherapeutic manner) subjects against CMV infection or reactivation. In a specific embodiment, a combination of gB and pp65 is used.

Arenavirus disease and immunosuppression in wild type arenavirus infection are known to result from unchecked viral replication. By abolishing replication, i.e., the ability to produce infectious progeny virus particles, of arenavirus vectors by deleting from their genome, e.g., the Z gene which is required for particle release, or the GP gene which is required for infection of target cells, the total number of infected cells can be limited by the inoculum administered, e.g., to a vaccine recipient, or accidentally transmitted to personnel involved in medical or biotechnological applications, or to animals. Therefore, abolishing replication of arenavirus vectors prevents pathogenesis as a result of intentional or accidental transmission of vector particles. In this invention, one important aspect consists in exploiting the above necessity of abolishment of replication in a beneficial way for the purpose of expressing a CMV antigen. In certain embodiments, an arenavirus particle is rendered replication deficient by genetic modification of its genome. Such modifications to the genome can include:

- deletion of an ORF (e.g., the ORF encoding the GP, NP, L, or Z protein);
- functional inactivation of an ORF (e.g., the ORF encoding the GP, NP, L, or Z protein). For example, this can be achieved by introducing a missense or a nonsense mutation;
- change of the sequence of the ORF (e.g., the exchange of an S1P cleavage site with the cleavage site of another protease);
- mutagenesis of one of the 5' or 3' termini of one of the genomic segments;
- mutagenesis of an intergenic region (i.e., of the L or the S genomic segment).

In certain embodiments, an infectious, replication-deficient arenavirus expressing a CMV antigen described herein is a Lymphocytic choriomeningitis virus (LCMV) wherein the S segment of the virus is modified by substituting the ORF encoding the GP protein with an ORF encoding a CMV antigen.

In certain embodiments, a wild type arenavirus vector genome (FIG. 1) can be designed to retain at least the essential regulatory elements on the 5' and 3' untranslated regions (UTRs) of both segments, and/or also the intergenic regions (IGRs). Without being bound by theory, the minimal transacting factors for gene expression in infected cells remain in the vector genome as ORFs that can be expressed, yet they can be placed differently in the genome and can be placed under control of a different promoter than naturally, or can be expressed from internal ribosome entry sites. In certain embodiments, the nucleic acid encoding a CMV antigen is transcribed from one of the endogenous arenavirus promoters (i.e., 5' UTR, 3' UTR of the S segment, 5' UTR, 3' UTR of the L segment). In other embodiments, the nucleic acid encoding a CMV antigen is expressed from a heterologous introduced promoter sequences that can be read by the viral RNA-dependent RNA polymerase, by cellular RNA polymerase I, RNA polymerase II or RNA polymerase III, such as duplications of viral promoter sequences that are naturally found in the viral UTRs, the 28S ribosomal RNA promoter, the beta-actin promoter or the 5S ribosomal RNA promoter, respectively. In certain embodiments ribonucleic acids coding for CMV antigens are transcribed and translated either by themselves or as readthrough by fusion to arenavirus protein ORFs, and expression of proteins in the host cell may be enhanced by introducing in the viral transcript sequence at the appropriate place(s) one or more, e.g., two, three or four, internal ribosome entry sites.

In certain embodiments, the vector generated to encode one or more CMV antigens may be based on a specific strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In certain embodiments, the vector generated to encode one or more CMV antigens may be based on LCMV Clone 13. In other embodiments, the vector generated to encode one or more CMV antigens may be based on LCMV MP strain. The sequence of the S segment of LCMV Clone 13 is listed as SEQ ID NO: 32. In certain embodiments, the sequence of the S segment of LCMV Clone 13 is the sequence set forth in SEQ ID NO: 31. The sequence of the L segment of LCMV Clone 13 is listed as SEQ ID NO: 33. The sequence of the S segment of LCMV strain MP is listed as SEQ ID NO: 53. The sequence of the L segment of LCMV strain MP is listed as SEQ ID NO: 49.

In certain embodiments, described herein is an infectious, replication-deficient arenavirus particle comprising a nucleotide sequence or fragment thereof selected from SEQ ID NO: 49, SEQ ID NO: 53, or a combination thereof.

In certain embodiments, described herein is infectious, replication-deficient arenavirus particle comprising a nucleotide sequence, or a combination of nucleotide sequences, selected from the group consisting of:

- a nucleotide sequence encoding a cytomegalovirus glycoprotein gB or an antigenic fragment thereof;
- a nucleotide sequence encoding a cytomegalovirus tegument protein pp65 or an antigenic fragment thereof;
- a nucleotide sequence encoding a cytomegalovirus glycoprotein gH or an antigenic fragment thereof;
- a nucleotide sequence encoding a cytomegalovirus glycoprotein gL or an antigenic fragment thereof;
- a nucleotide sequence encoding a cytomegalovirus UL128 protein or an antigenic fragment thereof
- a nucleotide sequence encoding a cytomegalovirus UL130 protein or an antigenic fragment thereof; and
- a nucleotide sequence encoding a cytomegalovirus UL131A protein or an antigenic fragment thereof.

6.2 CMV Antigens

In certain embodiments, antigens for use with the methods and compositions described herein are CMV antigens.

In certain embodiments, the ORFs encoding two, three, four, or five or more CMV antigens described are transcribed as a single transcript. In certain embodiments, the ORFs encoding the CMV antigens on that transcript are separated by a nucleic acid encoding a self-cleaving peptide or a ribosome-skipping sequence. In certain embodiments, the self-cleaving peptide (or the ribosome-skipping sequence) can be obtained from a 2A protein from a member of the virus family Picornaviridae. In certain specific embodiments, the self-cleaving peptide is obtained from (or derived from) Porcine teschovirus-1 2A, Thoseaasignavirus 2A, Foot-and-mouth disease virus 2A peptide, or equine rhinitis A virus 2A peptide. In certain specific embodiments, the 2A peptide obtained from (or derived from) the porcine teschovirus-1 2A has the highest cleavage efficiency. In certain embodiments, the 2A peptide has a high cleavage efficiency in combination with the CMV antigens described herein upstream or downstream of the 2A peptide.

In certain embodiments, the ORFs encoding two, three, four, or five or more CMV antigens are separated by a ribosome-skipping sequence. In more specific embodiments, the ribosome-skipping sequence is a cis-acting hydrolase element sequence.

In certain embodiments, the ORFs encoding two, three, four, or five, or more CMV antigens are separated by a self-cleaving protease obtained from (or derived from) tobacco etch viruses (TEVs) of the Potyviridae family.

In certain embodiments, a Gly-Ser-Gly linker is inserted at the N-terminus and C-terminus of the 2A peptide. In more specific embodiments, the Gly-Ser-Gly linker is inserted at the N-terminus of the 2A peptide. In more specific embodiments, the Gly-Ser-Gly linker is inserted at the C-terminus of the 2A peptide. In certain embodiments, the Gly-Ser-Gly linker improves the efficiency of cleavage by the 2A peptide.

In certain embodiments, the ORFs encoding two, three, four, or five or more CMV antigens are separated by an internal ribosome entry site. In certain embodiments, the internal ribosome entry site functions under the control of an upstream promoter. In certain embodiments the internal ribosome entry site is obtained from (or derived from) the encephalomyocarditis virus.

In certain embodiments the ORFs encoding two, three, four, or five, or more CMV antigens are separated by a 2A peptide and a furin cleavage site. In certain embodiments, the 2A peptide is flanked by a furin cleavage site. In certain embodiments, the furin cleavage site is located between an ORF encoding a CMV antigen and the 2A peptide. In certain embodiments the furin cleavage site is added upstream of the 2A peptide. In certain embodiments the furin cleavage site is added downstream of the 2A peptide. In certain embodiments, the furin cleavage site is located in the vector with the ORFs encoding two, three, four, or five, or more CMV antigens, a self-cleaving peptide, and combinations thereof. In certain embodiments, the furin cleavage site consensus sequence is R-X-K-/R-R. In a more specific embodiment the furin cleavage site is cleaved by the furin protein in the trans golgi network. In another embodiment the furin cleavage site removes the 2A peptide sequence. In yet another embodiment the furin cleavage site removes the self-cleaving peptide sequence at the C-terminus. For example, see Fang et al., Molecular Therapy. 2007; 15(6): 1153-1159.

The certain embodiments, the ORFs encoding two, three, four, or five, or more CMV antigens are separated by the 2A peptide and a tag. In certain embodiments, the tag is linked to the 2A peptide. In certain embodiments, the tag is located between the 2A peptide and the furin cleavage site. In certain embodiments the tag is located at the C-terminus or N-terminus of the downstream ORF encoding the CMV antigen. In certain embodiments the tag is located at the C-terminus or N-terminus of the upstream ORF encoding the CMV antigen. In certain embodiments the tag is located in the vector with the ORFs encoding two, three, four, or more CMV antigens, a 2A peptide, a furin cleavage site, or a combination thereof. In certain embodiments the tag is a peptide tag. In more specific embodiments the tag is a V5 amino acid tag.

In certain embodiments, the ORFs encoding two, three, four, or five or more CMV antigens are separated by the 2A peptide and a spacer sequence. In certain embodiments, the spacer sequence is located upstream of the 2A peptide. In certain embodiments, the spacer sequence is located between the ORFs encoding the CMV antigens. In certain embodiments, the spacer sequence is located between the upstream of the 2A peptide and the tag. In certain embodiments, the spacer sequence is located between the upstream 2A peptide and the downstream furin cleavage site. In certain embodiments the spacer sequence is located in the vector with the ORFs encoding CMV antigens, a self-cleaving peptide, a furin cleavage site, a tag or a combination thereof. In certain embodiments, the spacer sequence increases cleavage efficiency.

In certain embodiments, the ORFs encoding two, three, four, or five, or more CMV antigens are separated by a nucleotide sequence that encodes: a self-cleaving peptide, an amino acid sequence that leads to release of the upstream amino acid sequence by "ribosome skipping" or a sequence element leading to binding of the ribosome and translation of the downstream sequence such as "internal ribosome entry sites" (IRES).

In certain embodiments, any strain of human CMV or any clinical isolate of human CMV can be used with the present invention to obtain the antigens for generation of the arenaviral vectors described herein. Such CMV strains include AD-169, Merlin, C327A (GenBank M60929), C076A (GenBank M85228), and C194A (GenBank 60926). Other human CMV strains and human CMV antigenic sequences that can be used with the presently disclosed compositions and methods are listed in Meyer-Koenig et al. 1998, J Infect Dis 177:1162-1169; Shedlock et al. 2012, Human Vaccines & Immunotherapuetics 8:1-14; and Chou and Dennison 1991, J Infect Dis 163:1229-34. The sequences and strains listed in Meyer-Koenig et al. 1998, J Infect Dis 177:1162-1169; Shedlock et al. 2012, Human Vaccines & Immunotherapuetics 8:1-14; and Chou and Dennison 1991, J Infect Dis 163:1229-34 are incorporated herein by reference.

In certain embodiments, the CMV antigen can be a CMV antigen ortholog, e.g., a mammalian (i.e., non-human primate, pig, dog, cat, or horse) CMV antigen.

(a) gB Antigens

In certain embodiments, the antigen is the CMV major envelope glycoprotein gB or a fragment thereof. In certain embodiments, the antigen is a fragment of at least at least 10, 15, 20, 25, 50, 75, 100, 150, 200, 250, 300, 350, 400, 500, 600, 700 or more amino acids of CMV major envelope glycoprotein gB. In certain embodiments, the transmembrane domain of gB has been deleted. In some embodiments, the cytoplasmic domain of gB has been deleted. In certain embodiments, the antigen is an antigenic fragment of gB. In certain embodiments, the cytoplasmic and transmembrane domains of the glycoprotein gB have been deleted.

In specific embodiments, the antigen comprises the gB antigenic sites AS-2, AS-5 and AS-4. (See FIG. 2). In certain embodiments, the gB antigen comprises the antigenic sites AS-2, AS-5, AS-4, and AS-1. In certain embodiments, the antigen comprises the gB antigenic sites AS-2, AS-5, AS-4, AS-1, and AS-3. In certain embodiments, the antigen comprises the gB transmembrane domain. In certain embodiments, the antigen comprises the gB cytoplasmic domain. In certain embodiments, the antigen comprises gB antigenic sites AS-2, AS-5, AS-4, and AS-1, as well as the gB transmembrane domain. In certain embodiments, the antigen comprises the gB antigenic sites AS-2, AS-5, AS-4, AS-1, and AS-3, as well as the gB transmembrane domain. In certain embodiments, the antigen comprises the gB ectodomain.

In certain embodiments, the antigen is a fusion protein between CMV glycoprotein gB or a fragment thereof and a heterologous polypeptide. In certain embodiments, the antigen is at least 10, 20, 30, 40, 50, 75, 100, 150, 200, 250, 300, 350, 400, 450, 500, 600, 700, 800, or at least 900 amino acids long. In certain embodiments, one or more domains of gB has/have been substituted by one or more domains of a heterologous protein. In certain embodiments, the cytoplasmic domain of gB has been substituted with the cytoplasmic domain of a heterologous protein. In certain embodiments, the cytoplasmic domain and transmembrane domains of gB have been substituted by the cytoplasmic domain of a heterologous protein. In certain embodiments, the cytoplasmic and transmembrane domains of gB have been substituted by the cytoplasmic and transmembrane domains of a heterologous protein. In certain embodiments, the cytoplasmic domain of gB has been substituted by the cytoplasmic and transmembrane domains of a heterologous protein. In certain embodiments, the heterologous protein is a glycoprotein from an RNA virus. In certain embodiments, the heterologous protein is a glycoprotein from VSV. In specific embodiments, the heterologous protein is VSV-G. In more specific embodiments, the heterologous protein is the VSV-G protein of wildtype VSV. In other specific embodiments, the heterologous protein is the VSV-G protein of VSV strain AV1 or AV2. In other specific embodiments, the heterologous protein is the VSV-G protein of VSV Serotype Indiana. In other specific embodiments, the heterologous protein is the VSV-G protein of VSV strain MARM U, MARM M, MRr or MRb. In certain embodiments, the antigen is encoded by a nucleic acid sequence that is 90%, 91%, 92%, 93%, 94%, 95%, 96%, 97%, 98%, 99%, or 100% identical to SEQ ID NO: 20 or SEQ ID NO: 23. In certain embodiments, the antigen comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 21 or SEQ ID NO: 24.

In specific embodiments, the antigen comprises the gB antigenic sites AS-2, AS-5 and AS-4 and a heterologous transmembrane and cytoplasmic region derived from VSV-G. In certain embodiments, the antigen comprises the gB antigenic sites AS-2, AS-5, AS-4, and AS-1 and a heterologous transmembrane and cytoplasmic region derived from VSV-G. In certain embodiments, the antigen comprises the gB antigenic sites AS-2, AS-5, AS-4, AS-1, and AS-3 and a heterologous transmembrane and cytoplasmic region derived from VSV-G. In certain embodiments, the antigen comprises the gB transmembrane domain and a heterologous transmembrane and cytoplasmic region derived from VSV-G. In certain embodiments, the antigen comprises the gB cytoplasmic domain and a heterologous transmembrane and cytoplasmic region derived from VSV-G. In certain embodiments, the antigen comprises gB antigenic sites AS-2, AS-5, AS-4, and AS-1, as well as the gB transmembrane domain and a heterologous transmembrane and cytoplasmic region derived from VSV-G. In certain embodiments, the antigen comprises the gB antigenic sites AS-2, AS-5, AS-4, AS-1, and AS-3, as well as the gB transmembrane domain and a heterologous transmembrane and cytoplasmic region derived from VSV-G. In certain embodiments, the antigen comprises the gB ectodomain and a heterologous transmembrane and cytoplasmic region derived from VSV-G.

In certain embodiments, the antigen is a fusion protein between CMV glycoprotein gB or a fragment thereof and a heterologous polypeptide. In certain embodiments, the antigen is at least 10, 20, 30, 40, 50, 75, 100, 150, 200, 250, 300, 350, 400, 450, 500, 600, 700, 800, or at least 900 amino acids long. In certain embodiments, one or more domains of gB has/have been substituted by one or more domains of a heterologous protein. In certain embodiments, the heterologous protein is a glycoprotein of influenza virus. In specific embodiments, the heterologous protein is the hemagglutinin protein of influenza virus (Flu-HA). In more specific embodiments, the heterologous protein is the hemagglutinin protein of influenza A virus. In other specific embodiments, the heterologous protein is the hemagglutinin protein of influenza B virus. In other specific embodiments, the heterologous protein is the hemagglutinin protein of influenza C virus. In certain embodiments, the antigen is encoded by a nucleic acid sequence that is 90%, 91%, 92%, 93%, 94%, 95%, 96%, 97%, 98%, 99%, or 100% identical to SEQ ID NO: 26 or SEQ ID NO: 29. In certain embodiments, the antigen comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 27 or SEQ ID NO: 30.

In specific embodiments, the antigen comprises the gB antigenic sites AS-2, AS-5 and AS-4 and a heterologous transmembrane and cytoplasmic region derived from Flu-HA. In certain embodiments, the antigen comprises the gB antigenic sites AS-2, AS-5, AS-4, and AS-1 and a heterologous transmembrane and cytoplasmic region derived from Flu-HA. In certain embodiments, the antigen comprises the gB antigenic sites AS-2, AS-5, AS-4, AS-1, and AS-3 and a heterologous transmembrane and cytoplasmic region derived from Flu-HA. In certain embodiments, the antigen comprises the gB transmembrane domain and a heterologous transmembrane and cytoplasmic region derived from Flu-HA. In certain embodiments, the antigen comprises the gB cytoplasmic domain and a heterologous transmembrane and cytoplasmic region derived from Flu-HA. In certain embodiments, the antigen comprises gB antigenic sites AS-2, AS-5, AS-4, and AS-1, as well as the gB transmembrane domain and a heterologous transmembrane and cytoplasmic region derived from Flu-HA. In certain embodiments, the antigen comprises the gB antigenic sites AS-2, AS-5, AS-4, AS-1, and AS-3, as well as the gB transmembrane domain and a heterologous transmembrane and cytoplasmic region derived from Flu-HA. In certain embodiments, the antigen comprises the gB ectodomain and a heterologous transmembrane and cytoplasmic region derived from Flu-HA.

In certain embodiments, the gB protein is from CMV strain Merlin. Illustrative sequences that can be used with the viral vector compositions and uses thereof as described herein are set forth in SEQ ID NO: 58 to 63. In certain embodiments, the antigen comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 60 or SEQ ID NO: 63.

(b) Truncated gB Antigens

In certain embodiments, the carboxy terminus of the gB protein is truncated. In certain embodiments, the truncation of the carboxy terminus of the gB protein can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 29, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or 134 amino acids long. In another embodiment, the truncation of the carboxy terminus of the gB protein can be 1-10, 10-20, 25-30, 30-40, 40-50, 50-60, 60-70, 70-80, 80-90, 90-100, 100-110, 110-120, 120-130, or 120-134 amino acids long. In other embodiments, the truncation of the carboxy terminus of the gB protein can be 10-134, 20-134, 30-134, 40-134, 50-134, 60-134, 70-134, 80-134, 90-134, 100-134, 110-134, or 120-134 amino acids long.

In certain embodiments, the gB protein with a truncation of the carboxy-terminus comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 3 over the entire length of the truncated gB protein. In more specific embodiments, the gB protein has a truncation between amino acids 772 to 906, and comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 3 over the entire length of the truncated gB protein. In other embodiments, the gB protein with a truncation of the carboxy-terminus comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 18.

In certain embodiments, the gB protein has a deletion in the carboxy-terminus. In certain embodiments the deletion in the carboxy-terminus can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 29, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, or 133 amino acids long. In another embodiment, the deletion in the carboxy terminus of the gB protein can be 1-10, 10-20, 20-30, 30-40, 40-50, 50-60, 60-70, 70-80, 80-90, 90-100, 100-110, 110-120, 120-130, or 130-133 amino acids long. In other embodiments, the deletion in the carboxy terminus of the gB protein can be 10-133, 20-133, 30-133, 40-133, 50-133, 60-133, 70-133, 80-133, 90-133, 100-133, 110-133, or 120-133 amino acids long.

In other embodiments, the gB protein with a truncation of the carboxy-terminus is still anchored in the membrane of the CMV viron.

(c) pp65 Antigens

In certain embodiments, the antigen is the CMV tegument protein pp65 or a fragment thereof. In certain embodiments, the antigen is a fragment of at least at least 10, 15, 20, 25, 50, 75, 100, 150, 200, 250, 300, 350, 400, 500 or more amino acids of the CMV tegument protein pp65 or a fragment thereof. In certain embodiments, the antigen is an antigenic fragment of pp65. In certain embodiments, the antigen is encoded by a nucleic acid sequence that is 80%, 81%, 82%, 83%, 84%, 85%, 86%, 87%, 88%, 89%, 90%, 90%, 91%, 92%, 93%, 94%, 95%, 96%, 97%, 98%, 99%, or 100% identical to SEQ ID NO: 35. In certain embodiments, the antigen comprises an amino acid sequence that is 80%, 81%, 82%, 83%, 84%, 85%, 86%, 87%, 88%, 89%, 90%, 90%, 91%, 92%, 93%, 94%, 95%, 96%, 97%, 98%, 99%, or 100% identical to SEQ ID NO: 36.

(d) Pentameric Complex Antigens

In certain embodiments, the antigen is the CMV glycoprotein gH or a fragment thereof. In certain embodiments, the antigen is a fragment of at least 10, 15, 20, 25, 50, 75, 100, 150, 200, 250, 300, 350, 400, 500, 600, 700 or more amino acids of CMV glycoprotein gH or a fragment thereof. In certain embodiments, gH is lacking a transmembrane domain. In certain embodiments, the antigen contains only the gH ectodomain. In certain embodiments, the antigen is an antigenic fragment of gH. In certain embodiments, the antigen is encoded by a nucleic acid sequence that is 80%, 81%, 82%, 83%, 84%, 85%, 86%, 8'7%, 88%, 89%, 90%, 90%, 90%, 91%, 92%, 93%, 94%, 95%, 96%, 97%, 98%, 99%, or 100% identical to SEQ ID NO: 38. In certain embodiments, the antigen is encoded by a nucleic acid sequence that is 80%, 81%, 82%, 83%, 84%, 85%, 86%, 87%, 88%, 89%, 90%, 90%, 90%, 91%, 92%, 93%, 94%, 95%, 96%, 97%, 98%, 99%, or 100% identical to SEQ ID NO: 51.

In certain embodiments, the antigen is a derivative of the glycoprotein gH fragment. In certain embodiments the antigen is an antigenic fragment of gH with the C-terminal membrane anchor sequence deleted, gH(dTM).

In certain embodiments, the antigen is the CMV glycoprotein gL or a fragment thereof. In certain embodiments, the antigen is a fragment of at least 10, 15, 20, 25, 50, 75, 100, 150, 200, 250 or more amino acids of CMV glycoprotein gL or a fragment thereof. In certain embodiments, the antigen is an antigenic fragment of gL. In certain embodiments, the antigen is encoded by a nucleic acid sequence that is 80%, 81%, 82%, 83%, 84%, 85%, 86%, 87%, 88%, 89%, 90%, 90%, 90%, 91%, 92%, 93%, 94%, 95%, 96%, 97%, 98%, 99%, or 100% identical to SEQ ID NO: 40.

In certain embodiments, the antigen is a pentameric complex protein or a fragment thereof. In certain embodiments, the antigen is a fragment of at least at least 10, 15, 20, 25, 50, 75, 100, 150 or more amino acids of a gene product of a gene of a pentameric complex protein of CMV or a fragment thereof. In certain more specific embodiments, the pentameric complex protein is CMV UL128 or a fragment thereof. In certain embodiments, the antigen is an antigenic fragment of UL128. In certain more specific embodiments, the pentameric complex protein is CMV UL130 or a fragment thereof. In certain embodiments, the antigen is an antigenic fragment of UL130. In certain more specific embodiments, the pentameric complex protein is CMV UL131A or a fragment thereof. In certain embodiments, the antigen is an antigenic fragment of UL131A. In certain embodiments, the antigen is encoded by a nucleic acid sequence that is 80%, 81%, 82%, 83%, 84%, 85%, 86%, 87%, 88%, 89%, 90%, 90%, 90%, 91%, 92%, 93%, 94%, 95%, 96%, 97%, 98%, 99%, or 100% identical to SEQ ID NO: 42. In certain embodiments, the antigen is encoded by a nucleic acid sequence that is 80%, 81%, 82%, 83%, 84%, 85%, 86%, 87%, 88%, 89%, 90%, 90%, 90%, 91%, 92%, 93%, 94%, 95%, 96%, 97%, 98%, 99%, or 100% identical to SEQ ID NO: 45. In certain embodiments, the antigen is encoded by a nucleic acid sequence that is 80%, 81%, 82%, 83%, 84%, 85%, 86%, 87%, 88%, 89%, 90%, 90%, 90%, 91%, 92%, 93%, 94%, 95%, 96%, 97%, 98%, 99%, or 100% identical to SEQ ID NO: 47.

Nucleic acid sequences encoding a CMV antigen can be introduced in the genome of an infectious, replication-deficient arenavirus by substitution of the nucleic acid sequence of the ORF (ORF) of glycoprotein GP, the matrix protein Z, the nucleoprotein NP, or the polymerase protein L. In other embodiments, the nucleic acid sequence encoding the CMV antigen is fused to the ORF (ORF) of glycoprotein GP, the matrix protein Z, the nucleoprotein NP, or the polymerase protein L. The nucleotide sequence encoding the CMV antigen, once inserted into the genome of an infectious, replication-deficient arenavirus, can be transcribed and/or expressed under control of the four arenavirus promoters (5' UTR and 3' UTR of the S segment, and 5' UTR and 3' UTR of the L segment), as well as ribonucleic acids that can be inserted with regulatory elements that can be read by the viral RNA-dependent RNA polymerase, cellular RNA polymerase I, RNA polymerase II or RNA polymerase III, such as duplications of viral promoter sequences that are naturally found in the viral UTRs, the 28S ribosomal RNA promoter, the beta-actin promoter or the 5S ribosomal RNA promoter, respectively. The nucleic acids encoding the CMV antigen can be transcribed and/or expressed either by themselves or as read-through by fusion to arenavirus ORFs and genes, respectively, and/or in combination with one or more, e.g., two, three or four, internal ribosome entry sites.

In one embodiment, the antigen is one that is useful for the prevention of infectious disease. In a specific embodiment, the antigen is derived from CMV. In certain embodiments, the ORF that encodes the glycoprotein of the arenavirus is substituted by a nucleic acid sequence encoding gH or gL. In more specific embodiments, the nucleic acid sequence encoding the gH and gL are separated by a nucleic acid sequence encoding a 2A peptide. In other embodiments, the nucleic acid sequence encoding the gH and gL are separated by a nucleic acid sequence encoding a 2A peptide and a spacer. In more specific embodiments, the nucleic acid sequences encoding gH and gL are separated by a nucleic acid sequence encoding a 2A peptide and a furin cleavage site. In certain embodiments, the nucleic acid sequence encoding gH and gL are separated by a 2A peptide fused to a tag, such as, a V5 amino acid tag and a furin cleavage located upstream of the 2A peptide. In certain embodiments, the nucleic acid sequence encoding gH and gL is separated by a 2A peptide, a furin cleavage site fused to a tag, such as, a V5 amino acid tag, and a spacer. In specific embodiments the spacer is upstream of the 2A peptide. In yet more specific embodiments the spacer is upstream of the 2A peptide between the 2A peptide and the tag.

In certain embodiments, the nucleic acid sequences encoding glycoprotein gH (dTM) and glycoprotein gL are separated by a nucleic acid sequence encoding a self-cleaving peptide. In certain embodiments, the nucleic acid sequences that encode glycoprotein gH (dTM) and glycoprotein gL are separated by a 2A peptide. In certain embodiments the nucleic acid sequence encoding glycoprotein gH (dTM) and glycoprotein gL are connected by a 2A peptide that is fused to a tag, such as V5.

In certain embodiments, the nucleic acid sequences encoding two, three, four, or five or more CMV pentameric complex proteins are separated by a self-cleaving peptide. In certain embodiments, the nucleic acid sequences encoding CMV pentameric complex proteins are connected by a 2A peptide. In certain embodiments, nucleic acid sequences encoding CMV pentameric complex proteins are connected by a 2A peptide fused to a tag. In certain embodiments, nucleic acid sequences encoding CMV pentameric complex proteins are connected by a 2A peptide fused to a V5 amino acid tag.

In certain embodiments, the nucleic acid sequences encoding two, three, four, or five or more CMV pentameric complex proteins are separated by a self-cleaving peptide, an amino acid sequence that leads to release of upstream amino acid sequence by "ribosome skipping", or a sequence element leading to binding of the ribosome and translation of the downstream sequence such as "internal ribosome entry sites" (IRES). In certain embodiments, the nucleic acid sequences encoding two, three, four, or five or more CMV pentameric complex proteins are separated by a self-cleaving peptide, an amino acid sequence that leads to release of upstream amino acid sequence by "ribosome skipping", or a sequence element leading to binding of the ribosome and translation of the downstream sequence such as "internal ribosome entry sites" (IRES).

In certain embodiments, the nucleic acid sequences encoding two, three, four, or five or more CMV pentameric complex proteins are separated by a self-cleaving peptide and a furin cleavage site. In certain embodiments, the nucleic acid sequences encoding two, three, four, or five or more CMV pentameric complex proteins are separated by a self-cleaving peptide fused to a tag, such as, a V5 amino acid tag, and a furin cleavage site. In certain embodiments, the nucleic acid sequences encoding the CMV pentameric complex proteins are separated by a self-cleaving peptide fused to a tag, such as, a V5 amino acid tag, a furin cleavage site, and a spacer. In specific embodiments the spacer is upstream of the self-cleaving peptide.

(e) Substitution of the ORF Encoding the Glycoprotein of the Arenavirus

In certain embodiments, the ORF that encodes the glycoprotein of the arenavirus is substituted by a nucleic acid sequence encoding one, two, three, four, or five or more CMV antigens described herein. In certain embodiments, the ORF that encodes the glycoprotein of the arenavirus is substituted by a nucleic acid sequence encoding two, three, four, or five or more CMV antigens described herein, separated by self-cleaving peptides or ribosome-skipping sequences. In certain embodiments, the self-cleaving peptide (or the ribosome-skipping sequence) can be obtained from a 2A protein from a member of the virus family Picornaviridae. In certain specific embodiments, the self-cleaving peptide (or the ribosome-skipping sequence) is obtained from (or derived from) Porcine teschovirus-1 2A, Thoseaasignavirus 2A, or Foot-and-mouth disease virus 2A peptide.

In one embodiment, the ORF that encodes the glycoprotein of the arenavirus is substituted by nucleic acid sequences encoding a CMV antigen. In certain embodiments, the ORF that encodes the glycoprotein of the arenavirus is substituted by nucleic acid sequences encoding antigen that is a fragment of at least at least 10, 15, 20, 25, 50, 75, 100, 150, 200, 250, 300, 350, 400, 500, 600, 700 or more amino acids of a gene product of a gene of the major envelope glycoprotein gB of CMV or a fragment thereof. In certain embodiments, the ORF that encodes the glycoprotein of the arenavirus is substituted by nucleic acid sequences encoding an antigenic fragment of gB. In certain embodiments, the ORF that encodes the glycoprotein of the arenavirus is substituted by nucleic acid sequences encoding antigens including, but not limited to the major envelope glycoprotein gB or a fragment of gB.

In certain embodiments, the ORF that encodes the glycoprotein of the arenavirus is substituted by nucleic acid sequences encoding an antigen that is a fusion protein between gB and VSV-G. In certain embodiments, the ORF that encodes the glycoprotein of the arenavirus is substituted by nucleic acid sequences encoding an antigen that is at least 10, 15, 20, 25, 50, 75, 100, 150, 200, 250, 300, 350, 400, 500, 600, or at least 700 amino acids long. In certain embodiments, the ORF that encodes the glycoprotein of the arenavirus is substituted by nucleic acid sequence that is 80%, 81%, 82%, 83%, 84%, 85%, 86%, 87%, 88%, 89%, 90%, 90%, 90%, 91%, 92%, 93%, 94%, 95%, 96%, 97%, 98%, 99%, or 100% identical to SEQ ID NO: 20 or SEQ ID NO: 23. In certain embodiments, the ORF that encodes the glycoprotein of the arenavirus is substituted by nucleic acid sequence that encodes for an amino acid that is 80%, 81%, 82%, 83%, 84%, 85%, 86%, 87%, 88%, 89%, 90%, 90%, 90%, 91%, 92%, 93%, 94%, 95%, 96%, 97%, 98%, 99%, or 100% identical to SEQ ID NO: 21 or 24.

In certain embodiments, the ORF that encodes the glycoprotein of the arenavirus is substituted by nucleic acid sequences encoding an antigen that is a fusion protein between gB and influenza virus hemagglutinin. In certain embodiments, the ORF that encodes the glycoprotein of the arenavirus is substituted by nucleic acid sequences encoding an antigen that is at least 10, 15, 20, 25, 50, 75, 100, 150, 200, 250, 300, 350, 400, 500, 600, or at least 700 amino acids long. In certain embodiments, the ORF that encodes the glycoprotein of the arenavirus is substituted by nucleic acid sequence that is 80%, 81%, 82%, 83%, 84%, 85%, 86%, 87%, 88%, 89%, 90%, 90%, 90%, 91%, 92%, 93%, 94%, 95%, 96%, 97%, 98%, 99%, or 100% identical to SEQ ID NO: 26 or 29. In certain embodiments, the ORF that encodes the glycoprotein of the arenavirus is substituted by nucleic acid sequence that encodes for an amino acid that is 80%, 81%, 82%, 83%, 84%, 85%, 86%, 87%, 88%, 89%, 90%, 90%, 90%, 91%, 92%, 93%, 94%, 95%, 96%, 97%, 98%, 99%, or 100% identical to SEQ ID NO: 27 or 30.

In certain embodiments, the ORF that encodes the glycoprotein of the arenavirus is substituted by nucleic acid sequences encoding antigen that is a fragment of at least 10, 15, 20, 25, 50, 75, 100, 150, 200, 250, 300, 350, 400, 500 or more amino acids of a gene product of a gene of the tegument protein pp65 of CMV or a fragment thereof. In certain embodiments, the ORF that encodes the glycoprotein of the arenavirus is substituted by nucleic acid sequences encoding an antigenic fragment of pp65. In certain embodiments, the ORF that encodes the glycoprotein of the arenavirus is substituted by nucleic acid sequences encoding antigens including, but not limited to the pp65 or a fragment of pp65.

In certain embodiments, the ORF that encodes the glycoprotein of the arenavirus is substituted by nucleic acid sequences encoding antigen that is a fragment of at least at least 10, 15, 20, 25, 50, 75, 100, 150, 200, 250, 300, 350, 400, 500, 600, 700 or more amino acids of a gene product of a gene of the glycoprotein gH of CMV or a fragment thereof. In certain embodiments, the ORF that encodes the glycoprotein of the arenavirus is substituted by nucleic acid sequences encoding an antigenic fragment of gH. In certain embodiments, the ORF that encodes the glycoprotein of the arenavirus is substituted by nucleic acid sequences encoding antigens including, but not limited to gH or a fragment of gH.

In certain embodiments, the ORF that encodes the glycoprotein of the arenavirus is substituted by nucleic acid sequences encoding antigen that is a fragment of at least at least 10, 15, 20, 25, 50, 75, 100, 150, 200, 250 or more amino acids of a gene product of a gene of the glycoprotein gL of CMV or a fragment thereof. In certain embodiments, the ORF that encodes the glycoprotein of the arenavirus is substituted by nucleic acid sequences encoding an antigenic fragment of gL. In certain embodiments, the ORF that encodes the glycoprotein of the arenavirus is substituted by nucleic acid sequences encoding antigens including, but not limited to gL or a fragment of gL.

In certain embodiments, the ORF that encodes the glycoprotein of the arenavirus is substituted by nucleic acid sequences encoding antigen that is a fragment of at least at least 10, 15, 20, 25, 50, 75, 100, 150, 200, 250 or more amino acids of a gene product of a gene of the pentameric complex protein UL128 of CMV or a fragment thereof. In certain embodiments, the ORF that encodes the glycoprotein of the arenavirus is substituted by nucleic acid sequences encoding an antigenic fragment of UL128. In certain embodiments, the ORF that encodes the glycoprotein of the arenavirus is substituted by nucleic acid sequences encoding antigens including, but not limited to UL128 or a fragment of UL128.

In certain embodiments, the ORF that encodes the glycoprotein of the arenavirus is substituted by nucleic acid sequences encoding antigen that is a fragment of at least at least 10, 15, 20, 25, 50, 75, 100, 150, 200 or more amino acids of a gene product of a gene of the pentameric complex protein UL130 of CMV or a fragment thereof. In certain embodiments, the ORF that encodes the glycoprotein of the arenavirus is substituted by nucleic acid sequences encoding an antigenic fragment of UL130. In certain embodiments, the ORF that encodes the glycoprotein of the arenavirus is substituted by nucleic acid sequences encoding antigens including, but not limited to UL130 or a fragment of UL130.

In certain embodiments, the ORF that encodes the glycoprotein of the arenavirus is substituted by nucleic acid sequences encoding antigen that is a fragment of at least at least 10, 15, 20, 25, 50, 75, 100, 150 or more amino acids of a gene product of a gene of the pentameric complex protein UL131A of CMV or a fragment thereof. In certain embodiments, the ORF that encodes the glycoprotein of the arenavirus is substituted by nucleic acid sequences encoding an antigenic fragment of UL131A. In certain embodiments, the ORF that encodes the glycoprotein of the arenavirus is substituted by nucleic acid sequences encoding antigens including, but not limited to UL or a fragment of UL131A.

In certain embodiments, the ORF that encodes the glycoprotein of the arenavirus is substituted by a nucleic acid sequence encoding two, three, four, or five pentameric complex proteins or fragments of at least 10, 15, 20, 25, 50, 75, 100, 150 or more amino acids thereof, separated by self-cleaving peptides or ribosome-skipping sequences or a sequence element leading to binding of the ribosome and translation of the downstream sequence such as IRES. In specific embodiments, the self-cleaving peptides or ribosome-skipping sequences are Teschovirus 2A (T2A) peptides.

In certain embodiments, the ORF that encodes the glycoprotein of the arenavirus is substituted by a nucleic acid sequence encoding gH, gL, UL128, UL130, and UL131A. In certain embodiments, the ORF that encodes the glycoprotein of the arenavirus is substituted by a nucleic acid sequence encoding gH and gL. In certain embodiments, the ORF that encodes the glycoprotein of the arenavirus is substituted by a nucleic acid sequence encoding gH, gL, UL128, UL130, and UL131A, separated by a self-cleaving peptide or a ribosome-skipping sequence or a sequence element leading to binding of the ribosome and translation of the downstream sequence such as IRES. In certain embodiments, the ORF that encodes the glycoprotein of the arenavirus is substituted by a nucleic acid sequence encoding gH, gL, UL128, UL130, and UL131A, separated by T2A. In certain embodiments, the open reading frame that encodes the glycoprotein of the arenavirus is substituted by a nucleic acid sequence encoding gH and gL by T2A.

In certain embodiments, the ORF that encodes the glycoprotein of the arenavirus is substituted by a nucleic acid sequence encoding the ectodomain of gH, gL, UL128, UL130, and UL131A. In certain embodiments, the ORF that encodes the glycoprotein of the arenavirus is substituted by a nucleic acid sequence encoding the ectodomain of gH and gL. In certain embodiments, the ORF that encodes the glycoprotein of the arenavirus is substituted by a nucleic acid sequence encoding the ectodomain of gH, gL, UL128, UL130, and UL131A, separated by a self-cleaving peptide or a ribosome-skipping sequence or a sequence element leading to binding of the ribosome and translation of the downstream sequence such as IRES. In certain embodiments, the ORF that encodes the glycoprotein of the arenavirus is substituted by a nucleic acid sequence encoding gH and gL, separated by T2A. In certain embodiments the ORF that encodes the glycoprotein of the arenavirus is substituted by a nucleic acid sequence encoding the ectodomain of gH and gL, separated by a T2A.

In certain other embodiments, the ORF that encodes the glycoprotein of the arenavirus is substituted by a nucleic acid sequence encoding two, three, four, five, six, or seven CMV antigens, fusion proteins of CMV antigens with heterologous sequences, or fragments of at least 10, 15, 20, 25, 50, 75, 100, 150 or more amino acids thereof, separated by self-cleaving peptides or ribosome-skipping sequences or a sequence element leading to binding of the ribosome and translation of the downstream sequence such as IRES. In specific embodiments, the self-cleaving peptides are Teschovirus 2A (T2A) peptides.

In certain embodiments, the ORF that encodes the glycoprotein of the arenavirus is substituted by a nucleic acid sequence encoding one or more of gB or an antigenic fragment thereof, pp65 or an antigenic fragment thereof, gH or an antigenic fragment thereof, gL or an antigenic fragment thereof, UL128 or an antigenic fragment thereof, UL130 or an antigenic fragment thereof, and UL131A or an antigenic fragment thereof. In certain embodiments, the ORF that encodes the glycoprotein of the arenavirus is substituted by a nucleic acid sequence encoding one or more of gB or an antigenic fragment thereof, pp65 or an antigenic fragment thereof, gH or an antigenic fragment thereof, gL or an antigenic fragment thereof, UL128 or an antigenic fragment thereof, UL130 or an antigenic fragment thereof, and UL131A or an antigenic fragment thereof, separated by a self-cleaving peptide or a ribosome-skipping sequence or a sequence element leading to binding of the ribosome and translation of the downstream sequence such as IRES. In certain embodiments, the ORF that encodes the glycoprotein of the arenavirus is substituted by a nucleic acid sequence encoding one or more of gB or an antigenic fragment thereof, pp65 or an antigenic fragment thereof, gH or an antigenic fragment thereof, gL or an antigenic fragment thereof, UL128 or an antigenic fragment thereof, UL130 or an antigenic fragment thereof, and UL131A or an antigenic fragment thereof, separated by T2A. In certain embodiments, the ORF that encodes the glycoprotein of the arenavirus is substituted by a nucleic acid sequence encoding more than one copy of the CMV antigens herein. In certain embodiments, the ORF that encodes the glycoprotein of the arenavirus is substituted by a nucleic acid sequence encoding more than one copy of the CMV antigens herein, separated by a self-cleaving peptide or a ribosome-skipping sequence or a sequence element leading to binding of the ribosome and translation of the downstream sequence such as IRES. In certain embodiments, the ORF that encodes the glycoprotein of the arenavirus is substituted by a nucleic acid sequence encoding more than one copy of the CMV antigens herein, separated by T2A.

6.3 Generation of Infectious, Replication-Deficient Arenavirus Expressing a CMV Antigen Generally, arenavirus particles can be recombinantly produced by standard reverse genetic techniques as described for LCMV (L. Flatz, A. Bergthaler, J. C. de la Torre, and D. D. Pinschewer, Proc Natl Acad Sci USA 103:4663-4668, 2006; A. B. Sanchez and J. C. de la Torre, Virology 350:370, 2006; E. Ortiz-Riano, B. Y. Cheng, J. C. de la Torre, L. Martinez-Sobrido. J Gen Virol. 94:1175-88, 2013). To generate infectious, replication-deficient arenaviruses for use with the present invention these techniques can be used, however, the genome of the rescued virus is modified as described in Section 6.1. These modifications can be: i) one or more, e.g., two, three or four, of the four arenavirus ORFs (glycoprotein (GP); nucleoprotein (NP); the matrix protein Z; the RNA-dependent RNA polymerase L) are removed or is functionally inactivated to prevent formation of infectious particles in normal cells albeit still allowing gene expression in arenavirus vector-infected host cells; and ii) nucleic acids coding for CMV antigens can be introduced. Infectious, replication-deficient viruses as described herein can be produced as described in International Patent Application Publication No. WO 2009/083210 (application number PCT/EP2008/010994), which is incorporated by reference herein in its entirety.

Once generated from cDNA, the infectious, replication-deficient arenaviruses provided herein can be propagated in complementing cells. Complementing cells are cells that provide the functionality that has been eliminated from the replication-deficient arenavirus by modification of its genome (e.g., if the ORF encoding the GP protein is deleted or functionally inactivated, a complementing cell does provide the GP protein).

Owing to the removal or functional inactivation of one or more of the viral genes in arenavirus vectors (here deletion of the glycoprotein, GP, will be taken as an example), arenavirus vectors can be generated and expanded in cells providing in trans the deleted viral gene(s), e.g., the GP in the present example. Such a complementing cell line, henceforth referred to as C-cells, is generated by transfecting a mammalian cell line such as BHK-21, HEK 293, VERO or other (here BHK-21 will be taken as an example) with one or more plasmid(s) for expression of the viral gene(s) of interest (complementation plasmid, referred to as C-plasmid). The C-plasmid(s) express the viral gene(s) deleted in the arenavirus vector to be generated under control of one or more expression cassettes suitable for expression in mammalian cells, e.g., a mammalian polymerase II promoter such as the CMV or EF1alpha promoter with a polyadenylation signal. In addition, the complementation plasmid features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in E. coli, the plasmid additionally features a bacterial selection marker, such as an ampicillin resistance cassette.

Cells that can be used, e.g., BHK-21, HEK 293, MC57G or other, are kept in culture and are transfected with the complementation plasmid(s) using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing C-cell clones are identified using Western blot or flow cytometry procedures with antibodies directed against the viral protein(s) of interest. As an alternative to the use of stably transfected C-cells transient transfection of normal cells can complement the missing viral gene(s) in each of the steps where C-cells will be used below. In addition, a helper virus can be used to provide the missing functionality in trans.

Plasmids that can be used can be of two types: i) Two plasmids, referred to as TF-plasmids for expressing intracellularly in C-cells the minimal transacting factors of the arenavirus, is derived from e.g., NP and L proteins of LCMV in the present example; and ii) Plasmids, referred to as GS-plasmids, for expressing intracellularly in C-cells the arenavirus vector genome segments, e.g., the segments with designed modifications. TF-plasmids express the NP and L proteins of the respective arenavirus vector under control of an expression cassette suitable for protein expression in mammalian cells, typically e.g., a mammalian polymerase II promoter such as the CMV or EF1alpha promoter, either one of them preferentially in combination with a polyadenylation signal. GS-plasmids express the small (S) and the large (L) genome segments of the vector. Typically, polymerase I-driven expression cassettes or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing T7, or C-cells are constructed to additionally express T7 in a stable manner. In certain embodiments, TF and GS plasmids can be the same, i.e. the genome sequence and transacting factors can be transcribed by T7, polI and polII promoters from one plasmid.

For recovering of the arenavirus vector, the following procedures can be used. First day: C-cells, typically 80% confluent in M6-well plates, are transfected with a mixture of the two TF-plasmids plus the two GS-plasmids. In certain embodiments, the TF and GS plasmids can be the same, i.e. the genome sequence and transacting factors can be transcribed by T7, polI and polII promoters from one plasmid. For this one can exploit any of the commonly used strategies such as calcium-phosphate, liposome-based protocols or electroporation.

3-5 days later: The culture supernatant (arenavirus vector preparation) is harvested, aliquoted and stored at 4° C., −20° C. or −80° C. depending on how long the arenavirus vector should be stored prior to use. Then the arenavirus vector preparation's infectious titer is assessed by an immunofocus assay on C-cells.

The invention furthermore relates to expression of a CMV antigen in a cell culture wherein the cell culture is infected with an infectious, replication-deficient arenavirus expressing a CMV antigen. When used for expression of a CMV antigen in cultured cells, the following two procedures can be used:

i) The cell type of interest is infected with the arenavirus vector preparation described herein at a multiplicity of infection (MOI) of one or more, e.g., two, three or four, resulting in production of the CMV antigen in all cells already shortly after infection.

ii) Alternatively, a lower MOI can be used and individual cell clones can be selected for their level of virally driven CMV antigen expression. Subsequently individual clones can be expanded infinitely owing to the non-cytolytic nature of arenavirus vectors. Irrespective of the approach, the CMV antigen can subsequently be collected (and purified) either from the culture supernatant or from the cells themselves, depending on the properties of the CMV antigen produced. However, the invention is not limited to these two strategies, and other ways of driving expression of CMV antigen using infectious, replication-deficient arenaviruses as vectors may be considered.

6.4 Nucleic Acids, Vector Systems and Cell Lines

In one embodiment, described herein is a nucleic acid sequence encoding the large genomic segment (L segment) of an infectious, replication-deficient arenavirus described herein, in which one ORF of the genomic segment is deleted or functionally inactivated, and the genomic segment comprises a nucleotide sequence encoding a CMV antigen.

In one embodiment, described herein is a nucleic acid sequence that encodes the short genomic segment (S segment) of an infectious, replication-deficient arenavirus described herein, in which one ORF of the genomic segment is deleted or functionally inactivated and wherein the short genomic segment comprises a nucleotide sequence encoding a CMV antigen. In another embodiment, described herein is a nucleic acid sequence that encodes the short genomic segment (S segment) of an infectious, replication-deficient arenavirus described herein, in which the ORF of the glycoprotein gene is deleted or functionally inactivated and wherein the short genomic segment comprises a nucleotide sequence encoding a CMV antigen. In certain, more specific embodiments, the CMV antigen is an antigen described in Section 6.2.

In certain embodiments, the nucleic acid sequences provided herein can be derived from a particular strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In specific embodiments, the nucleic acid is derived from LCMV Clone 13. In other specific embodiments, the nucleic acid is derived from LCMV MP strain.

In a more specific embodiment, provided herein is a nucleic acid encoding an arenavirus genomic segment comprising a sequence that is at least 90%, 91%, 92%, 93%, 94%, 95%, 96%, 97%, 98%, at least 99%, or 100% identical to the sequence of SEQ ID NO: 1, SEQ ID NO: 4, SEQ ID NO: 7, SEQ ID NO: 10, SEQ ID NO: 13, SEQ ID NO:16, SEQ ID NO: 19, SEQ ID NO: 22, SEQ ID NO: 25, OR SEQ ID NO: 28, SEQ ID NO: 34, SEQ ID NO: 37, SEQ ID NO: 44, or SEQ ID NO: 50. In another embodiment, provided herein is a nucleic acid that encodes an arenavirus genomic segment comprising (i) a nucleotide sequence that is at least 90%, 91%, 92%, 93%, 94%, 95%, 96%, 97%, 98%, at least 99%, or 100% identical to the sequence of nucleotide 1639 to 3315 of SEQ ID NO: 31; and (ii) a nucleotide sequence encoding a CMV antigen.

In another embodiment, provided herein is a nucleic acid that encodes an arenavirus genomic segment comprising (i) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1639 to 3315 of SEQ ID NO: 31; and (ii) a nucleotide sequence encoding a CMV antigen.

In another embodiment, provided herein is a nucleic acid that encodes an arenavirus genomic segment comprising (i) a nucleotide sequence that is at least 90%, 91%, 92%, 93%, 94%, 95%, 96%, 97%, 98%, at least 99%, or 100% identical to the sequence of nucleotide 1640 to 3316 of SEQ ID NO: 32; and (ii) a nucleotide sequence encoding a CMV antigen.

In another embodiment, provided herein is a nucleic acid that encodes an arenavirus genomic segment comprising (i) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1640 to 3316 of SEQ ID NO: 32; and (ii) a nucleotide sequence encoding a CMV antigen In another embodiment, provided herein are nucleic acids that encode an arenavirus genomic segment comprising (i) a nucleotide sequence encoding at least one self-cleaving peptide (or ribosome-skipping sequence); and (ii) a nucleotide sequence encoding two, three, four, five, or more CMV antigens. In specific embodiments, the nucleotide sequence encoding a self-cleaving peptide encodes Teschovirus 2A. In certain embodiments, provided herein are nucleic acids that encode two, three, four, or five pentameric complex proteins separated by one or more nucleotide sequences encoding self-cleaving peptides (or ribosome-skipping sequences) (e.g., T2A). In certain other embodiments, provided herein are nucleic acids that encode one or more gB proteins or fragments thereof and one or more other CMV antigens, separated by one or more nucleotide sequences encoding self-cleaving peptides (or ribosome-skipping sequences). In other embodiments, provided herein are nucleic acids that encode one or more pp65 proteins or fragments thereof and one or more other CMV antigens, separated by one or more nucleotide sequences encoding self-cleaving peptides (or ribosome-skipping sequences). In specific embodiments, provided herein are nucleic acids that encode one or more pentameric proteins or fragments thereof and one or more other CMV antigens, separated by one or more nucleotide sequences encoding self-cleaving peptides (or ribosome-skipping sequences).

In one embodiment, described herein is a vector system comprising one or more vectors that together encode the genome of an infectious, replication-deficient arenavirus particle described herein. Specifically, provided herein is a vector system wherein the one or more vectors encode two arenavirus genomic segments, namely an L segment and an S segment, of an infectious, replication-deficient arenavirus described herein. Such a vector system can encode (on one or more separate DNA molecules):

An arenavirus S genomic segment that is modified such that an arenavirus particle carrying this modified S genomic segment cannot produce infectious progeny virus particles and an arenavirus L genomic segment that comprises a nucleotide sequence encoding (in sense or antisense) a CMV antigen;

An arenavirus L genomic segment that is modified such that an arenavirus particle carrying this modified L genomic segment cannot produce infectious progeny virus particles and an arenavirus S genomic segment that comprises a nucleotide sequence encoding (in sense or antisense) a CMV antigen;

An arenavirus S genomic segment that is modified such that an arenavirus particle carrying this modified S genomic segment cannot produce infectious progeny virus particles and wherein the arenavirus S genomic segment comprises a nucleotide sequence encoding (in sense or antisense) a CMV antigen and a wild type arenavirus L genomic segment; or An arenavirus L genomic segment that is modified such that an arenavirus particle carrying this modified L genomic segment cannot produce infectious progeny virus particles and wherein the arenavirus L genomic segment comprises a nucleotide sequence encoding (in sense or antisense) a CMV antigen and a wild type arenavirus S genomic segment.

In certain embodiments, described herein is a nucleic acid sequence encoding an arenavirus (e.g., LCMV) genomic segment in which the ORF encoding the GP of the S genomic segment is substituted with a nucleotide sequence encoding:

a nucleotide sequence encoding a cytomegalovirus glycoprotein gB or an antigenic fragment thereof;
a nucleotide sequence encoding a cytomegalovirus tegument protein pp65 or an antigenic fragment thereof;
a nucleotide sequence encoding a cytomegalovirus glycoprotein gH or an antigenic fragment thereof;
a nucleotide sequence encoding a cytomegalovirus glycoprotein gL or an antigenic fragment thereof;
a nucleotide sequence encoding a cytomegalovirus UL128 protein or an antigenic fragment thereof;
a nucleotide sequence encoding a cytomegalovirus UL130 protein or an antigenic fragment thereof; and
a nucleotide sequence encoding a cytomegalovirus UL131A protein or an antigenic fragment thereof.

In certain embodiments, described herein is a nucleic acid sequence encoding an arenavirus (e.g., LCMV) genomic segment in which the ORF encoding the GP of the S genomic segment is substituted with a nucleotide sequence encoding one or more CMV antigen sequences (e.g., one or more of those listed in the above paragraph), separated by nucleotide sequences encoding a self-cleaving peptide (or ribosome-skipping sequences). In specific embodiments, the nucleotide sequences encoding a self-cleaving peptide encode Teschovirus 2A.

In another embodiment, provided herein is a cell wherein the cell comprises a nucleic acid or a vector system described above in this section. Cell lines derived from such cells, cultures comprising such cells, and methods of culturing such cells infected are also provided herein. In certain embodiments, provided herein is a cell wherein the cell comprises a nucleic acid encoding the large genomic segment (L segment) of an infectious, replication-deficient arenavirus described herein, in which one ORF of the genomic segment is deleted or functionally inactivated, and the genomic segment comprises a nucleotide sequence encoding a CMV antigen.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a nucleotide sequence encoding CMV antigen gB or an antigenic fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a nucleotide sequence encoding a fusion protein comprising at least one domain from CMV antigen gB and a heterologous domain from VSV-G.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a nucleotide sequence encoding a fusion protein comprising at least one domain from CMV antigen gB and a heterologous domain from Flu-HA.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a nucleotide sequence encoding CMV antigen pp65 or an antigenic fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a nucleotide sequence encoding one or more of CMV antigens gH, gL, UL128, UL130, UL131A, or an antigenic fragments thereof. In specific embodiments, the genomic segment comprises a nucleotide sequence encoding one or more of the group of CMV antigens comprising gH, gL, UL128, UL130, UL131A, or antigenic fragments thereof, separated by one or more self-cleaving peptides (or ribosome-skipping sequences). In more specific embodiments, the one or more self-cleaving peptides are T2A peptides.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a nucleotide sequence encoding one or more of CMV antigens separated by one or more self-cleaving peptides (or ribosome-skipping sequences). In specific embodiments, the one or more self-cleaving peptides are T2A peptides.

In another embodiment, provided herein is a cell wherein the cell comprises two nucleic acids or a vector systems described herein. Cell lines derived from such cells, cultures comprising such cells, and methods of culturing such cells infected are also provided herein.

In certain embodiments, provided herein is a nucleic acid comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 49 or SEQ ID NO: 53. In certain embodiments, provided herein is an expression vector comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 49 or SEQ ID NO: 53. In certain embodiments, provided herein is a host cell comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 49 or SEQ ID NO: 53.

In certain embodiments, provided herein is a nucleic acid comprising a nucleotide sequence encoding an amino acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 54, 55, 56, or 57. In certain embodiments, provided herein is an expression vector comprising a nucleotide sequence encoding an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 54, 55, 56, or 57. In certain embodiments, provided herein is a host cell comprising a nucleotide sequence that encodes an amino acid sequence that is at least 80%, 81%, 82%, 83%, 84%, 85%, 86%, 8'7%, 88%, 89%, 90%, 91%, 92%, 93%, 94%, 95%, 96%, 97%, 98%, 99%, or 100% identical to SEQ ID NO: 54, 55, 56, or 57.

In certain embodiments, provided herein is an isolated protein comprising an amino acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 54, 55, 56, or 57. In certain embodiments, provided herein is a host cell that expresses a protein comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 54, 55, 56, or 57. In certain embodiments, the host cell is cultured in cell culture medium.

In certain embodiments, provided herein is a nucleic acid comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 32 or SEQ ID NO: 33. In certain embodiments, provided herein is an expression vector comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 32 or SEQ ID NO: 33. In certain embodiments, provided herein is a host cell comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 32 or SEQ ID NO: 33.

6.5 Methods of Use

In one embodiment, provided herein are methods of treating an infection in a subject comprising administering to the subject one or more infectious, replication-deficient arenaviruses expressing a CMV antigen as described herein or a composition thereof. In a specific embodiment, a method for treating an infection described herein comprises administering to a subject in need thereof an effective amount of one or more infectious, replication-deficient arenaviruses expressing a CMV antigen described herein or a composition thereof. The subject can be a mammal, such as but not limited to a human being, a mouse, a rat, a guinea pig, a domesticated animal, such as, but not limited to, a cow, a horse, a sheep, a pig, a goat, a cat, a dog, a hamster, a donkey. In a specific embodiment, the subject is a human.

In another embodiment, provided herein are methods for inducing an immune response against CMV in a subject comprising administering to the subject an infectious, replication-deficient arenavirus expressing a CMV antigen or a composition thereof.

In another embodiment, the subjects to whom an infectious, replication-deficient arenavirus expressing a CMV antigen described herein or a composition thereof is administered have, are susceptible to, or are at risk for a CMV infection or reactivation. In another specific embodiment, the subjects to whom an infectious, replication-deficient arenavirus expressing a CMV antigen described herein or a composition thereof is administered are infected with, are susceptible to, or are at risk for, an infection with CMV or reactivation with CMV.

In another embodiment, the subjects to whom an infectious, replication-deficient arenavirus expressing a CMV antigen described herein or a composition thereof is administered are suffering from, are susceptible to, or are at risk for, an infection with CMV in the pulmonary system, central nervous system, lymphatic system, gastrointestinal system, or circulatory system among others. In a specific embodiment, the subjects to whom an infectious, replication-deficient arenavirus expressing a CMV antigen described herein or a composition thereof is administered are suffering from, are susceptible to, or are at risk for, an infection with CMV in one or more organs of the body, including but not limited to the brain, liver, lungs, eyes, ears, intestines, esophagus, or salivary glands.

In another embodiment, the subjects to whom an infectious, replication-deficient arenavirus expressing a CMV antigen described herein or a composition thereof is administered to a subject suffering from symptoms including but not limited to fever, night sweats, tiredness, malaise, uneasiness, sore throat, swollen glands, joint pain, muscle pain, loss of appetite, weight loss, diarrhea, gastrointestinal ulcerations, gastrointestinal bleeding, shortness of breath, pneumonia, mouth ulcers, vision problems, hepatitis, jaundice, encephalitis, seizures, coma, or hearing loss.

In another embodiment, an infectious, replication-deficient arenavirus expressing a CMV antigen as described herein or a composition thereof is administered to a subject of any age group suffering from, are susceptible to, or are at risk for, an infection with CMV. In a specific embodiment, an infectious, replication-deficient arenavirus expressing a CMV antigen as described herein or a composition thereof is administered to a subject with a compromised immune system, a pregnant subject, a subject undergoing an organ or bone marrow transplant, a subject taking immunosuppressive drugs, a subject undergoing hemodialysis, a subject who has cancer, or a subject who is suffering from, are susceptible to, or are at risk for, an infection with CMV or reactivation of CMV. In a more specific embodiment, an infectious, replication-deficient arenavirus expressing a CMV antigen as described herein or a composition thereof is administered to a subject with a compromised immune system due to HIV infection, who is suffering from, is susceptible to, or is at risk for, an infection with CMV or reactivation of CMV. In yet another specific embodiment, an infectious, replication-deficient arenavirus expressing a CMV antigen as described herein or a composition thereof is administered to a subject who is a child of 0, 1, 2, 3, 4, 5, 6, 7, 8, 9, 10, 11, 12, 13, 14, 15, 16, or 17 years of age suffering from, are susceptible to, or are at risk for, an infection with CMV or reactivation of CMV. In yet another specific embodiment, an infectious, replication-deficient arenavirus expressing a CMV antigen described herein or a composition thereof is administered to a subject who is an infant suffering from, is susceptible to, or is at risk for, an infection with CMV or reactivation of CMV. In yet another specific embodiment, an infectious, replication-deficient arenavirus expressing a CMV antigen described herein or a composition thereof is administered to a subject who is an infant of 0, 1, 2, 3, 4, 5, 6, 7, 8, 9, 10, 11, or 12 months of age suffering from, is susceptible to, or is at risk for, an infection with CMV or reactivation of CMV. In yet another specific embodiment, an infectious, replication-deficient arenavirus expressing a CMV antigen described herein or a composition thereof is administered to an elderly subject who is suffering from, is susceptible to, or is at risk for, an infection with CMV or reactivation of CMV.

In another embodiment, an infectious, replication-deficient arenavirus expressing a CMV antigen described herein or a composition thereof is administered to subjects with a heightened risk of disseminated CMV infection. In a specific embodiment, an infectious, replication-deficient arenavirus expressing a CMV antigen described herein or a composition thereof is administered to subjects in neonatal period with immature neonatal immune system.

In another embodiment, an infectious, replication-deficient arenavirus expressing a CMV antigen as described herein or a composition thereof is administered to a subject having a dormant infection with CMV. In a specific embodiment, an infectious, replication-deficient arenavirus expressing a CMV antigen described herein or a composition thereof is administered to a subject having a dormant infection with CMV, which can reactivate upon immune system compromise. Thus, provided herein is a method for preventing reactivation of CMV.

In another embodiment, an infectious, replication-deficient arenavirus expressing a CMV antigen described herein or a composition thereof is administered to subjects infected with one or more strains of CMV. In certain embodiments, one or more of those strains include AD169, Towne, Merlin, Toledo, FIX, PH, TR, Davis, TB40/E, 3157, 6397, 711, 5234, or other strains.

In another embodiment, administering an infectious, replication-deficient arenavirus expressing a CMV antigen as described herein or a composition thereof to subjects confer cell-mediated immunity (CMI) against an infection with CMV or reactivation of CMV. Without being bound by theory, in another embodiment, an infectious, replication-deficient arenavirus expressing a CMV antigen as described herein or a composition thereof infects and expresses antigens of interest in antigen presenting cells (APC) of the host (e.g., macrophages) for direct presentation of antigens on Major Histocompatibility Complex (MHC) class I and II. In another embodiment, administering an infectious, replication-deficient arenavirus expressing a CMV antigen as described herein or a composition thereof to subjects induce plurifunctional IFN-γ and TNF-α co-producing CMV-specific CD4+ and CD8+ T cell responses (IFN-γ is produced by CD4+ and CD8+ T cells and TNF-α is produced by CD4+ T cells) of high magnitude to treat or prevent an infection with CMV or reactivation of CMV.

In another embodiment, administering an infectious, replication-deficient arenavirus expressing a CMV antigen or a composition thereof reduces the risk that an individual will develop an infection with CMV or reactivation of CMV by at least about 10%, at least about 20%, at least about 25%, at least about 30%, at least about 35%, at least about 40%, at least about 50%, at least about 60%, at least about 70%, at least about 80%, at least about 90%, or more, compared to the risk of developing an infection with CMV or reactivation of CMV in the absence of such treatment.

In another embodiment, administering an infectious, replication-deficient arenavirus expressing a CMV antigen or a composition thereof reduces the symptoms of an infection with CMV or reactivation of CMV by at least about 10%, at least about 20%, at least about 25%, at least about 30%, at least about 35%, at least about 40%, at least about 50%, at least about 60%, at least about 70%, at least about 80%, at least about 90%, or more, compared to the manifestation of the symptoms of an infection CMV or reactivation of CMV in the absence of such treatment.

In another embodiment, administering an infectious, replication-deficient arenavirus expressing a CMV antigen or a composition thereof in subjects with immature neonatal immune system induces cell-mediated immunity (CMI) response against an infection with CMV or reactivation of CMV by at least about 10%, at least about 20%, at least about 25%, at least about 30%, at least about 35%, at least about 40%, at least about 50%, at least about 60%, at least about 70%, at least about 80%, at least about 90%, or more, compared to cell-mediated immunity (CMI) response against an infection with CMV or reactivation of CMV in the absence of such a treatment.

In certain embodiments, administering an infectious, replication-deficient arenavirus expressing a CMV antigen or a composition thereof reduces the number of inclusion bodies detected in salivary glands or another histological sample. In certain embodiments, administering an infectious, replication-deficient arenavirus expressing a CMV antigen or a composition thereof reduces the number of anti-CMV antibodies detected in a patient blood sample. In certain embodiments, administering an infectious, replication-deficient arenavirus expressing a CMV antigen or a composition thereof reduces the amount of CMV pp65 detected in peripheral blood leukocytes via a CMV pp65 antigenemia test. In certain embodiments, administering an infectious, replication-deficient arenavirus expressing a CMV antigen or a composition thereof reduces the amount of CMV detected in urine, saliva, blood, tears, semen, or breast milk. In certain embodiments, administering an infectious, replication-deficient arenavirus expressing a CMV antigen or a composition thereof reduces the level of virus cultured from a urine, throat swab, bronchial lavage, or tissue sample. In certain embodiments, administering an infectious, replication-deficient arenavirus expressing a CMV antigen or a composition thereof reduces the level of virus detected through quantitative or qualitative PCR tests.

Changes in cell-mediated immunity (CMI) response function against an infection with CMV or reactivation of CMV induced by administering an infectious, replication-deficient arenavirus expressing a CMV antigen or a composition thereof in subjects can be measured by any assay known to the skilled artisan including, but not limited to flow cytometry (see, e.g., Perfetto S. P. et al., Nat Rev Immun. 2004; 4(8):648-55), lymphocyte proliferation assays (see, e.g., Bonilla F. A. et al., Ann Allergy Asthma Immunol. 2008; 101:101-4; and Hicks M. J. et al., Am J Clin Pathol. 1983; 80:159-63), assays to measure lymphocyte activation including determining changes in surface marker expression following activation of measurement of cytokines of T lymphocytes (see, e.g., Caruso A. et al., Cytometry. 1997; 27:71-6), ELISPOT assays (see, e.g., Czerkinsky C. C. et al., J Immunol Methods. 1983; 65:109-121; and Hutchings P. R. Et al., J Immunol Methods. 1989; 120:1-8), or Natural killer cell cytotoxicity assays (see, e.g., Bonilla F. A. et al., Ann Allergy Asthma Immunol. 2005 May; 94(5 Suppl 1):S1-63).

In another embodiment, described herein is a method of use with an infectious, replication-deficient arenavirus (e.g., LCMV) expressing a CMV antigen as described herein in which the ORF encoding the GP of the S genomic segment is substituted with a nucleotide sequence encoding:

a. a nucleotide sequence encoding a CMV glycoprotein gB or an antigenic fragment thereof;
b. a nucleotide sequence encoding a CMV tegument protein pp65 or an antigenic fragment thereof;
c. a nucleotide sequence encoding a CMV glycoprotein gH or an antigenic fragment thereof;
d. a nucleotide sequence encoding a CMV glycoprotein gL or an antigenic fragment thereof;
e. a nucleotide sequence encoding a CMV UL128 protein or an antigenic fragment thereof;
f. a nucleotide sequence encoding a CMV UL130 protein or an antigenic fragment thereof; or
g. a nucleotide sequence encoding a CMV UL131A protein or an antigenic fragment thereof.

In another embodiment, provided herein are methods of preventing transmission and/or infection of CMV from a mother to an unborn child comprising administering to a subject of child-bearing age an infectious, replication-deficient arenavirus expressing a CMV antigen as described herein. See section 6.2. In specific embodiments, provided herein are methods of preventing transmission and/or infection of CMV from a mother to an unborn child comprising administering to a seronegative subject of child-bearing age an infectious, replication-deficient arenavirus expressing a CMV antigen as described herein. In yet another embodiment provided herein are methods of preventing transmission and/or infection of CMV from a mother to an unborn child comprising administering to a subject of child-bearing age with the intention to procreate an infectious, replication-deficient arenavirus expressing a CMV antigen as described herein.

In another embodiment, provided herein are methods of preventing transmission and/or infection of CMV from a mother to an unborn child comprising administering to a subject of child-bearing age one or more infectious, replication-deficient arenaviruses expressing a CMV antigen as described herein. See section 6.2. In specific embodiments, provided herein are methods of preventing transmission and/or infection of CMV from a mother to an unborn child comprising administering to a seronegative subject of child-bearing age one or more infectious, replication-deficient arenaviruses expressing a CMV antigen as described herein. In yet another embodiment, provided herein are methods of preventing transmission and/or infection of CMV from a mother to an unborn child comprising administering to a subject of child-bearing age with the intention to procreate one or more infectious, replication-deficient arenaviruses expressing a CMV antigen as described herein.

In another embodiment, provided herein are methods of preventing transmission and/or infection of CMV from a mother to an unborn child comprising administering to a pregnant subject an infectious, replication-deficient arenavirus expressing a CMV antigen as described herein. In specific embodiments, provided herein are methods of preventing transmission and/or infection of CMV from a mother to an unborn child comprising administering to a pregnant subject an effective amount of an infectious, replication-deficient arenavirus expressing a CMV antigen described herein.

In another embodiment, provided herein are methods of preventing transmission and/or infection of CMV from a mother to an unborn child comprising administering to a pregnant subject one or more infectious, replication-deficient arenaviruses expressing a CMV antigen as described herein. In specific embodiments, provided herein are methods of preventing transmission and/or infection of CMV from a mother to an unborn child comprising administering to a pregnant subject an effective amount of one or more infectious, replication-deficient arenaviruses expressing a CMV antigen described herein.

In another embodiment, administering an infectious, replication-deficient arenavirus expressing a CMV antigen reduces symptomatic congenital CMV infection. In another embodiment, administering an infectious, replication-deficient arenavirus expressing a CMV antigen reduces asymptomatic congenital CMV infection.

In another embodiment, administering one or more infectious, replication-deficient arenaviruses expressing a CMV antigen reduces symptomatic congenital CMV infection. In another embodiment, administering one or more infectious, replication-deficient arenaviruses expressing a CMV antigen reduces asymptomatic congenital CMV infection.

In another embodiment, administering an infectious, replication-deficient arenavirus expressing a CMV antigen reduces manifestations of congenital CMV infection by at least about 10%, at least about 20%, at least 25%, at least about 30%, at least about 35%, at least about 40%, at least about 50%, at least about 60%, at least about 70%, at least 80%, at least 90%, or more. In another specific embodiment, administering an infectious, replication-deficient arenavirus expressing a CMV antigen reduces mortality of newborn infants with congenital CMV infection.

In another embodiment, administering one or more infectious, replication-deficient arenaviruses expressing a CMV antigen reduces manifestations of congenital CMV infection by at least about 10%, at least about 20%, at least 25%, at least about 30%, at least about 35%, at least about 40%, at least about 50%, at least about 60%, at least about 70%, at least 80%, at least 90%, or more. In another specific embodiment, administering one or more infectious, replication-deficient arenaviruses expressing a CMV antigen reduces mortality of newborn infants with congenital CMV infection.

Such manifestations of congenital CMV include but are not limited to mental retardation, blindness and sensorineural deafness, microcephaly, chorioretinitis, intracranial calcifications, hepatosplenomegaly, hepatitis, jaundice, direct hyperbilirubinemia, thrombocytopenia, petechiae, oligohydramnios, polyhydramnios, prematurity, intrauterine growth retardation, nonimmune hydrops, fetal ascites, hyptonia, and anemia.

6.6 Compositions, Administration and Dosage

The invention furthermore relates to vaccines, immunogenic compositions, and pharmaceutical compositions comprising a genetically engineered arenavirus as described herein. Such vaccines and pharmaceutical compositions can be formulated according to standard procedures in the art.

In another embodiment, provided herein are compositions comprising an infectious, replication-deficient arenaviruses described herein. Such compositions can be used in methods of treatment and prevention of disease. In a specific embodiment, the compositions described herein are used in the treatment of subjects infected with, or susceptible to, an infection with CMV or reactivation of CMV. In another specific embodiment, the immunogenic compositions provided herein can be used to induce an immune response in a host to whom the composition is administered. The immunogenic compositions described herein can be used as vaccines and can accordingly be formulated as pharmaceutical compositions. In a specific embodiment, the immunogenic compositions described herein are used in the prevention of infection of subjects (e.g., human subjects) by CMV or reactivation of CMV in subjects (e.g., human subjects).

In certain embodiments, provided herein are immunogenic compositions comprising an arenavirus vector (or a combination of different arenavirus vectors) as described herein. In certain embodiments, such an immunogenic composition further comprises a pharmaceutically acceptable excipient. In certain embodiments, such an immunogenic composition further comprises an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a infectious, replication-deficient arenavirus particle, but when the compound is administered alone does not generate an immune response to the infectious, replication-deficient arenavirus particle. In some embodiments, the adjuvant generates an immune response to the infectious, replication-deficient arenavirus particle and does not produce an allergy or other adverse reaction. Adjuvants can enhance an immune response by several mechanisms including, e.g., lymphocyte recruitment, stimulation of B and/or T cells, and stimulation of macrophages. When a vaccine or immunogenic composition of the invention comprises adjuvants or is administered together with one or more adjuvants, the adjuvants that can be used include, but are not limited to, mineral salt adjuvants or mineral salt gel adjuvants, particulate adjuvants, microparticulate adjuvants, mucosal adjuvants, and immunostimulatory adjuvants. Examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)).

The compositions comprise the infectious, replication-deficient arenaviruses described herein alone or together with a pharmaceutically acceptable carrier. Suspensions or dispersions of genetically engineered arenaviruses, especially isotonic aqueous suspensions or dispersions, can be used. The pharmaceutical compositions may be sterilized and/or may comprise excipients, e.g., preservatives, stabilizers, wetting agents and/or emulsifiers, solubilizers, salts for regulating osmotic pressure and/or buffers and are prepared in a manner known per se, for example by means of conventional dispersing and suspending processes. In certain embodiments, such dispersions or suspensions may comprise viscosity-regulating agents. The suspensions or dispersions are kept at temperatures around 2-8° C., or preferentially for longer storage may be frozen and then thawed shortly before use. For injection, the vaccine or immunogenic preparations may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

In certain embodiments, the compositions described herein additionally comprise a preservative, e.g., the mercury derivative thimerosal. In a specific embodiment, the pharmaceutical compositions described herein comprise 0.001% to 0.01% thimerosal. In other embodiments, the pharmaceutical compositions described herein do not comprise a preservative.

The pharmaceutical compositions comprise from about $10^3$ to about $10^{11}$ focus forming units of the genetically engineered arenaviruses. Unit dose forms for parenteral administration are, for example, ampoules or vials, e.g., vials containing from about $10^3$ to $10^{10}$ focus forming units or $10^5$ to $10^{15}$ physical particles of genetically engineered arenaviruses.

In another embodiment, a vaccine or immunogenic composition provided herein is administered to a subject by, including but not limited to, oral, intradermal, intramuscular, intraperitoneal, intravenous, topical, subcutaneous, percutaneous, intranasal and inhalation routes, and via scarification (scratching through the top layers of skin, e.g., using a bifurcated needle). Specifically, subcutaneous or intravenous routes can be used.

For administration intranasally or by inhalation, the preparation for use according to the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflators may be formulated containing a powder mix of the compound and a suitable powder base such as lactose or starch.

The dosage of the active ingredient depends upon the type of vaccination and upon the subject, and their age, weight, individual condition, the individual pharmacokinetic data, and the mode of administration.

The invention relates also to processes and to the use of genetically engineered arenaviruses for the manufacture of vaccines in the form of pharmaceutical preparations, which comprise genetically engineered arenaviruses as active ingredient. The pharmaceutical compositions of the present invention are prepared in a manner known per se, for example by means of conventional mixing and/or dispersing processes.

6.7 Optimized Generation of LCMV Vectors

Owing to the removal or functional inactivation of one or more of the viral genes in arenavirus vectors (here deletion of the glycoprotein, GP, will be taken as an example) arenavirus vectors can be generated and expanded in cells that provide the deleted or functionally inactivated viral gene(s) (e.g., the GP) "in trans." The resulting virus itself is infectious but is unable to produce further infectious progeny particles in non-complementing cells due to the lack of the deleted or functionally inactivated viral gene(s) (e.g., the GP). The complementing cell can provide the missing functionality either by stable transfection, transient transfection, or by infection with a helper virus that expresses the missing functionality.

In certain embodiments, the complementing cell provides the viral gene that has been deleted or functionally inactivated from the arenavirus vector genome. In a specific embodiment, the complementing cell provides the viral gene from a viral strain that is the same as the viral strain that was used to generate the genome of the arenavirus vector. In another embodiment, the complementing cell provides the viral gene from a viral strain that is different from the viral strain that was used to generate the genome of the arenavirus vector. For example, the viral gene provided in the complementing cell is obtained from the MP strain of LCMV and encodes a protein having the amino acid sequence of SEQ ID NO: 54, 55, 56, or 57.

In a specific embodiment, the complementing cell provides the GP of the MP strain of LCMV and the arenavirus vector comprises an ORF of a human CMV antigen as described herein in place of the ORF encoding the GP protein. In an even more specific embodiment, the complementing cell provides the GP of the MP strain of LCMV and the arenavirus vector is obtained from LCMV Clone 13 and comprises an ORF of a human CMV antigen as described herein in place of the ORF encoding the GP protein. In an even more specific embodiment, the GP protein is at least 90%, 91%, 92%, 93%, 94%, 95%, 96%, 97%, 98%, at least 99%, or 100% identical to the amino acid sequence of SEQ ID NO: 55.

6.8 Combination Therapy

6.8 (a) Methods

In one embodiment, provided herein are methods of treating and/or preventing a CMV infection in a subject comprising administering to the subject two or more infectious, replication-deficient arenaviruses expressing a CMV antigen as described herein. See, e.g., Section 6.2. In specific embodiments, a method for treating and/or preventing a CMV infection comprises administering a first infectious, replication-deficient arenavirus expressing a CMV antigen as described herein, e.g., in which the ORF encoding the GP of the S genomic segment is substituted with a nucleotide sequence encoding the CMV antigen, wherein the CMV antigen can be but is not limited to:

a) a nucleotide sequence encoding a CMV glycoprotein gB or an antigenic fragment thereof;
b) a nucleotide sequence encoding a CMV tegument protein pp65 or an antigenic fragment thereof;
c) a nucleotide sequence encoding a CMV glycoprotein gH or an antigenic fragment thereof;
d) a nucleotide sequence encoding a CMV glycoprotein gL or an antigenic fragment thereof;
e) a nucleotide sequence encoding a CMV glycoprotein UL128 or an antigenic fragment thereof;
f) a nucleotide sequence encoding a CMV glycoprotein UL130 or an antigenic fragment thereof;
g) a nucleotide sequence encoding a CMV glycoprotein UL131A or an antigenic fragment thereof.

and a second infectious, replication-deficient arenavirus expressing a CMV antigen as described herein, e.g., in which the ORF encoding the GP of the S genomic segment is substituted with a nucleotide sequence encoding the CMV antigen, wherein the CMV antigen can be but is not limited to:

a) a nucleotide sequence encoding a CMV glycoprotein gB or an antigenic fragment thereof;
b) a nucleotide sequence encoding a CMV tegument protein pp65 or an antigenic fragment thereof;
c) a nucleotide sequence encoding a CMV glycoprotein gH or an antigenic fragment thereof;
d) a nucleotide sequence encoding a CMV glycoprotein gL or an antigenic fragment thereof;
e) a nucleotide sequence encoding a CMV glycoprotein UL128 or an antigenic fragment thereof;
f) a nucleotide sequence encoding a CMV glycoprotein UL130 or an antigenic fragment thereof;
g) a nucleotide sequence encoding a CMV glycoprotein UL131A or an antigenic fragment thereof.

In specific embodiments, provided herein are methods for treating and/or preventing a CMV infection comprising administering a first infectious, replication-deficient arenavirus expressing a first CMV antigen, selected from: a CMV tegument protein pp65 or an antigenic fragment thereof; a CMV glycoprotein gH or an antigenic fragment thereof; a CMV glycoprotein gL; a CMV glycoprotein UL128 or an antigenic fragment thereof; or an antigenic fragment thereof; a CMV glycoprotein UL130 or an antigenic fragment thereof; or a CMV glycoprotein UL131A or an antigenic fragment thereof, as described herein and a second infectious, replication-deficient arenavirus expressing a second CMV antigen, selected from: a nucleotide sequence encoding a CMV glycoprotein gB or an antigenic fragment thereof; a CMV tegument protein pp65 or an antigenic fragment thereof; a CMV glycoprotein gH or an antigenic fragment thereof; a CMV glycoprotein gL; a CMV glycoprotein UL128 or an antigenic fragment thereof; or an antigenic fragment thereof; a CMV glycoprotein UL130 or an antigenic fragment thereof; or a CMV glycoprotein UL131A or an antigenic fragment thereof.

In certain embodiments, provided herein are methods for treating and/or preventing an infection comprising administering two arenavirus vector constructs expressing a CMV antigen as described herein. In a specific embodiment, the two arenavirus vector constructs express a different CMV antigen.

In certain embodiments, provided herein are methods for treating and/or preventing an infection comprising administering two or more arenavirus vector constructs expressing a CMV antigen as described herein. In a specific embodiment, provided herein are methods for treating and/or preventing an infection comprising administering three or more arenavirus vector constructs expressing a CMV antigen as described herein. In another embodiment, provided herein are methods for treating/and or preventing an infection comprising administering four or more arenavirus vector constructs, five or more arenavirus vector constructs, six or more arenavirus vector constructs or 7 arenavirus vector constructs each expressing a CMV antigen as described herein. In certain embodiments, the arenavirus vector construct can be LCMV.

In certain embodiments, provided herein are methods for treating and/or preventing an infection comprising administering two or more arenavirus vector constructs each expressing a different CMV antigen as described herein. In a specific embodiment, provided herein are methods for treating and/or preventing an infection comprising administering three or more arenavirus vector constructs, each expressing a different CMV antigen as described herein. In another embodiment, provided herein are methods for treating/and or preventing an infection comprising administering four or more arenavirus vector constructs, five or more arenavirus vector constructs, six or more arenavirus vector constructs, or 7 arenavirus vector constructs each expressing a different CMV antigen as described herein. In certain embodiments, the arenavirus vector construct can be LCMV.

In specific embodiments, the antigen is the CMV envelope glycoprotein gB or a fragment thereof (See, e.g., Section 6.2(a)). In more specific embodiments, the antigen is the CMV envelope glycoprotein gB with a truncation of the carboxy-terminus. (See, e.g., Section 6.2(b)).

In certain embodiments, the antigen is the CMV tegument protein pp65 or a fragment thereof. (See, e.g., Section 6.2(c)).

In certain embodiments, the antigen is a CMV pentameric complex protein. In another embodiment the CMV pentameric complex antigen is gH, gH (dTM), gL, UL128, UL131A, or UL130 or combinations thereof. (See, e.g., Section 6.2(d)).

In certain embodiments, the vector generated to encode one or more CMV antigens as described herein comprises one or more nucleic acids encoding a CMV antigen and combinations thereof as described. In specific embodiments the CMV antigens as described herein are separated by various linkers, spacers, and cleavage sites as described herein.

In another embodiment, the vector generated to encode one or more CMV antigens as described herein of the first infectious, replication-deficient arenavirus may be based on LCMV Clone 13 or LCMV MP strain. (See, e.g., Section 7.1).

In another embodiment, the vector generated to encode one or more CMV antigens as described herein of the second infectious, replication-deficient arenavirus may be based on LCMV Clone 13 or LCMV MP strain. (See, e.g., Section 7.1).

In a specific embodiment, provided herein are methods of treating and/or preventing an infection in a subject comprising administering to the subject a first infectious, replication-deficient arenavirus expressing a CMV tegument protein pp65 or an antigenic fragment thereof and a second infectious, replication-deficient arenavirus expressing a CMV glycoprotein gB or an antigenic fragment thereof.

In a specific embodiment, provided herein are methods of treating and/or preventing an infection in a subject comprising administering sequentially to the subject a first infectious, replication-deficient arenavirus expressing a CMV tegument protein pp65 or an antigenic fragment thereof and a second infectious, replication-deficient arenavirus expressing a CMV glycoprotein gB or an antigenic fragment thereof.

In a specific embodiment, provided herein are methods of treating and/or preventing an infection in a subject comprising administering simultaneously to the subject a first infectious, replication-deficient arenavirus expressing a CMV tegument protein pp65 or an antigenic fragment thereof and a second infectious, replication-deficient arenavirus expressing a CMV glycoprotein gB or an antigenic fragment thereof.

In another embodiment, the first infectious, replication-deficient arenavirus expressing a CMV tegument protein pp65 or an antigenic fragment thereof is a primary vaccine antigen and the second infectious, replication-deficient arenavirus expressing a CMV glycoprotein gB or an antigenic fragment thereof is a secondary vaccine antigen.

In a specific embodiment, provided herein are methods of treating and/or preventing an infection with CMV in a subject comprising administering to the subject a first infectious, replication-deficient arenavirus expressing a CMV tegument protein pp65 or an antigenic fragment thereof and a second infectious, replication-deficient arenavirus expressing a CMV glycoprotein gB with a truncation of the carboxy-terminus. (See, e.g., Section 6.2(b) for truncated gB proteins).

In a specific embodiment, provided herein are methods of treating and/or preventing an infection with CMV in a subject comprising administering sequentially to the subject a first infectious, replication-deficient arenavirus expressing a CMV tegument protein pp65 or an antigenic fragment thereof and a second infectious, replication-deficient arenavirus expressing a CMV glycoprotein gB with a truncation of the carboxy-terminus. (See, e.g., Section 6.2(b) for truncated gB proteins).

In a specific embodiment, provided herein are methods of treating and/or preventing an infection with CMV in a subject comprising administering simultaneously to the subject a first infectious, replication-deficient arenavirus expressing a CMV tegument protein pp65 or an antigenic fragment thereof and a second infectious, replication-deficient arenavirus expressing a CMV glycoprotein gB with a truncation of the carboxy-terminus. (See, e.g., Section 6.2(b) for truncated gB proteins).

In another embodiment, the first infectious, replication-deficient arenavirus expressing a CMV tegument protein pp65 or an antigenic fragment thereof is a primary vaccine antigen and the second infectious, replication-deficient arenavirus expressing a CMV glycoprotein gB with a truncation of the carboxy-terminus is a secondary vaccine antigen.

In certain embodiments, administering a first infectious, replication-deficient arenavirus expressing a CMV glycoprotein gB or a fragment thereof or a CMV tegument protein pp65 and a second infectious, replication-deficient arenavirus expressing a CMV glycoprotein gB or a fragment thereof or a CMV tegument protein pp65 provides a better protective effect to CMV after vaccination than administering a single infectious, replication-deficient arenavirus expressing a CMV antigen, e.g., expressing only the glycoprotein gB (or a fragment thereof) or only the tegument protein pp65. In other embodiments, administering a first infectious, replication-deficient arenavirus expressing a CMV glycoprotein gB or a fragment thereof or a CMV tegument protein pp65 and a second infectious, replication-deficient arenavirus expressing a CMV glycoprotein gB or a fragment thereof or a CMV tegument protein pp65 elicits a greater immune response than administering a single infectious, replication-deficient arenavirus expressing a CMV antigen e.g., expressing only the glycoprotein gB (or a fragment thereof) or only the tegument protein pp65. In another embodiment, administering a first infectious, replication-deficient arenavirus expressing a CMV glycoprotein gB or a fragment thereof or a CMV tegument protein pp65 and a second infectious, replication-deficient arenavirus expressing a CMV glycoprotein gB or a fragment thereof, or a CMV tegument protein pp65 elicits a larger CD8+ T cell response than administering a single infectious, replication-deficient arenavirus expressing a CMV antigen e.g., expressing only the glycoprotein gB (or a fragment thereof) or only the tegument protein pp65. In other embodiments, administering a first infectious, replication-deficient arenavirus expressing a CMV glycoprotein gB or a fragment thereof or a CMV tegument protein pp65 and a second infectious, replication-deficient arenavirus expressing a CMV glycoprotein gB or a fragment thereof or a CMV tegument protein pp65 elicits higher titers of neutralizing antibodies than administering a single infectious, replication-deficient arenavirus expressing a CMV antigen e.g., expressing only the glycoprotein gB (or a fragment thereof) or only the tegument protein pp65.

In certain embodiments, the infectious replication-deficient arenavirus expressing a CMV glycoprotein gB with a truncation of the carboxy-terminus (see Section 6.2(b)) provides a better protective effect to CMV after vaccination than an infectious, replication-deficient arenavirus expressing a CMV glycoprotein gB, wherein the transmembrane domain of gB has been deleted, as tested by ELISA, neutralizing antibody assay, and animal models. See Section 6.9. In other embodiments, the infectious, replication-deficient arenavirus expressing a CMV glycoprotein gB with a truncation of the carboxy-terminus elicits a greater immune response than an infectious, replication-deficient arenavirus expressing a CMV glycoprotein gB, wherein the transmembrane domain of gB has been deleted. In certain embodiments, the infectious, replication-deficient arenavirus expressing a CMV glycoprotein gB with a truncation of the carboxy-terminus elicits a larger CD8+ T cell response than the infectious, replication-deficient arenavirus expressing a CMV glycoprotein gB, wherein the transmembrane domain of gB has been deleted. In other embodiments the replication-deficient arenavirus expressing a CMV glycoprotein gB with a truncation of the carboxy-terminus elicits higher titers of neutralizing antibodies than the infectious, replication-deficient arenavirus expressing a CMV glycoprotein gB, wherein the transmembrane domain of gB has been deleted. (See e.g., FIGS. 12, 13 and 25, 26).

In yet another embodiment, provided herein is the combined use of the replication-deficient arenavirus expressing a CMV antigen described herein and one or more replication-defective virus vectors. In a more specific embodiment the replication-defective virus vector is selected from the group comprising of poxviruses, adenoviruses, alphaviruses, herpes simplex viruses, paramyxoviruses, rhabdoviruses, poliovirus, adeno-associated virus, and sendai virus, and mixtures thereof. In a specific embodiment, the poxvirus is a modified vaccine Ankara.

In yet another embodiment, provided herein is the combined use of the replication-deficient arenavirus expressing a CMV antigen described herein and one or more replication-defective virus vectors expressing a CMV antigen. In a more specific embodiment the replication-defective virus vector is selected from the group comprising of poxviruses, adenoviruses, alphaviruses, herpes simplex viruses, paramyxoviruses, rhabdoviruses, poliovirus, adeno-associated virus, and sendai virus, and mixtures thereof. In a specific embodiment, the poxvirus is a modified vaccine Ankara.

In another embodiment, the first infectious, replication-deficient arenavirus expressing a CMV antigen as described herein is administered before or after the second infectious, replication-deficient arenavirus expressing a CMV antigen as described herein. For example the first infectious, replication-deficient arenavirus expressing a CMV antigen is administered around 30-60 minutes before or after the first administration of the second infectious, replication-deficient arenavirus.

In another embodiment, the first infectious, replication-deficient arenavirus expressing a vaccine antigen is administered before the second infectious, replication-deficient arenavirus expressing a vaccine antigen. In certain embodiments there is a period of about 1 hour, 2 hours, 3 hours, 6 hours, 12 hours, 1 day, 2 days, 3 days, 5 days, 1 week, 2 weeks, 1 month, 2 months, 3 months, 4 months, 5 months, 6 months, 7 months, 8 months, 9 months, 10 months, 11 months, 1 year between the administration of the first infectious, replication-deficient arenavirus and the second infectious, replication-deficient arenavirus.

In another embodiment, two infectious, replication-deficient arenaviruses are administered in a treatment regime at molar ratios ranging from about 1:1 to 1:1000, in particular including: 1:1 ratio, 1:2 ratio, 1:5 ratio, 1:10 ratio, 1:20 ratio, 1:50 ratio, 1:100 ratio, 1:200 ratio, 1:300 ratio, 1:400 ratio, 1:500 ratio, 1:600 ratio, 1:700 ratio, 1:800 ratio, 1:900 ratio, 1:1000 ratio.

In another embodiment, the subjects whom two or more infectious, replication-deficient arenavirus expressing a CMV antigen described herein is administered have, are susceptible to, or are at risk for a CMV infection or reactivation. In another embodiment, the subjects whom two or more infections, replication-deficient arenaviruses expressing a CMV antigen described herein is administered are infected with, are susceptible to, or are at risk for, an infection with CMV or reactivation with CMV.

In another embodiment, the subjects whom two or more infectious, replication-deficient arenaviruses expressing a CMV antigen described herein, are administered simultaneously have, are susceptible to, or are at risk for a CMV infection or reactivation. In another embodiment, the subjects whom two or more infections, replication-deficient arenaviruses expressing a CMV antigen described herein are administered simultaneously are infected with, are susceptible to, or are at risk for, an infection with CMV or reactivation with CMV.

In another embodiment, the subjects whom two or more infectious, replication-deficient arenaviruses expressing a CMV antigen described herein, are administered sequentially have, are susceptible to, or are at risk for a CMV infection or reactivation. In another embodiment, the subjects whom two or more infections, replication-deficient arenaviruses expressing a CMV antigen described herein are administered sequentially are infected with, are susceptible to, or are at risk for, an infection with CMV or reactivation with CMV.

In another embodiment, said two or more infectious, replication-deficient arenaviruses expressing a CMV antigen as described herein are further administered in combination with at least one other medicament for treating and/or preventing CMV. Therapeutic medicaments for treating and/or preventing CMV include, but are not limited to Valganciclovir, Ganciclovir, Foscarnet, Cidofovir, or Maribavir.

In another embodiment, said two or more infectious, replication-deficient arenaviruses expressing a CMV antigen as described herein are further administered in a combination with at least one other immunomodulator. In a more specific embodiment, said two or more infectious, replication-deficient arenaviruses expressing a CMV antigen as described herein are further administered in a combination with at least one Th1-specific adjuvant. In a more specific embodiment the Th-1 specific adjuvant is Bacillus Calmette-Guerin (BCG).

In another embodiment, the administration regime can involve administering to a symptomatic subject a second infectious, replication-deficient arenavirus expressing a CMV antigen as described herein. In yet another embodiment, the administration regime can involve administering to an subject with a compromised immune system, especially transplant recipients, HIV-infected persons, a pregnant subject, a subject who has cancer, or a second infectious, replication-deficient arenavirus expressing a CMV antigen as described herein. In another embodiment, two or more infectious, replication-deficient arenaviruses expressing a CMV antigen as described herein are administered to a subject who is a child of 0, 1, 2, 3, 4, 5, 6, 7, 8, 9, 10, 11, 12, 13, 14, 15, 16, or 17 years of age suffering from or susceptible to, or are at risk for, an infection with CMV or reactivation of CMV.

In another embodiment, the administration regime can involve administering to a subject who is a child, a first replication deficient arenavirus expressing a CMV antigen, and administering to the same subject who is an adolescent a second replication deficient arenavirus expressing a CMV antigen. In a specific embodiment, the administration regime can involve administering to a subject who is 0, 1, 2, 3, 4, 5, 6, 7, 8, 9, 10, 11, 12, 13, 14, 15, 16, or 17 years of age a first, replication-deficient arenavirus expressing a CMV antigen as described herein, and to the same subject who is 12, 13, 14, 15, 16, 17, 18, 19, 20, 21, 22, 23, 24, 25 years of age a second infectious replication-deficient arenavirus expressing a CMV antigen.

In another embodiment, the administration regime can involve administering to a prepubescent subject a second infectious, replication-deficient arenavirus expressing a CMV antigen. In another embodiment, the administration regime can involve administering to an adolescent male, aged 12 to 18 years a second infectious, replication-deficient arenavirus expressing a CMV antigen as described herein. In another embodiment, the administration regime can involve administering to a female, aged 12 to 18 years a second infectious, replication-deficient arenavirus expressing a CMV antigen.

In another embodiment, administering two or more infectious, replication-deficient arenaviruses expressing a CMV antigen reduces the risk that an individual will develop an infection with CMV or reactivation of CMV by at least 10%, at least about 20%, at least about 25%, at least about 30%, at least about 40%, at least about 50%, at least about 60%, at least about 70%, at least about 80%, at least about 90%, or more, compared with the manifestation of the symptoms of an infection CMV or reactivation of CMV in the absence of such treatment.

In another embodiment, administering two or more infectious, replication-deficient arenaviruses expressing a CMV antigen, administered separately, reduces the risk that an individual will develop an infection with CMV or reactivation of CMV by at least 10%, at least about 20%, at least about 25%, at least about 30%, at least about 40%, at least about 50%, at least about 60%, at least about 70%, at least about 80%, at least about 90%, or more, compared with the manifestation of the symptoms of an infection CMV or reactivation of CMV in the absence of such treatment.

In another embodiment, administering two or more infectious, replication-deficient arenaviruses expressing a CMV antigen, administered sequentially, reduces the risk that an individual will develop an infection with CMV or reactivation of CMV by at least 10%, at least about 20%, at least about 25%, at least about 30%, at least about 40%, at least about 50%, at least about 60%, at least about 70%, at least about 80%, at least about 90%, or more, compared with the manifestation of the symptoms of an infection CMV or reactivation of CMV in the absence of such treatment.

6.8 (b) Compositions

The invention furthermore relates to vaccines, immunogenic compositions, and pharmaceutical compositions comprising a genetically engineered arenavirus as described herein. Such vaccines and pharmaceutical compositions can be formulated according to standard procedures in the art.

In one embodiment, provided herein are compositions comprising two or more infectious, replication-deficient arenaviruses expressing a CMV antigen as described herein.

See, e.g., Section 6.2. In a specific embodiments, the compositions described herein comprises administering to a subject a first infectious, replication-deficient arenavirus expressing a CMV antigen as described herein, e.g., in which the ORF encoding the GP of the S genomic segment is substituted with a nucleotide sequence encoding the CMV antigen. The CMV antigen can be but is not limited to:

a) a nucleotide sequence encoding a CMV glycoprotein gB or an antigenic fragment thereof;
b) a nucleotide sequence encoding a CMV tegument protein pp65 or an antigenic fragment thereof;
c) a nucleotide sequence encoding a CMV glycoprotein gH or an antigenic fragment thereof;
d) a nucleotide sequence encoding a CMV glycoprotein gL or an antigenic fragment thereof;
e) a nucleotide sequence encoding a CMV glycoprotein UL128 or an antigenic fragment thereof;
f) a nucleotide sequence encoding a CMV glycoprotein UL130 or an antigenic fragment thereof;
g) a nucleotide sequence encoding a CMV glycoprotein UL131A or an antigenic fragment thereof;

and a second infectious, replication-deficient arenavirus composition expressing a CMV antigen as described herein, e.g., in which the ORF encoding the GP of the S genomic segment is substituted with a nucleotide sequence encoding the CMV antigen. The CMV antigen can be but is not limited to:

a) a nucleotide sequence encoding a CMV glycoprotein gB or an antigenic fragment thereof;
b) a nucleotide sequence encoding a CMV tegument protein pp65 or an antigenic fragment thereof;
c) a nucleotide sequence encoding a CMV glycoprotein gH or an antigenic fragment thereof;
d) a nucleotide sequence encoding a CMV glycoprotein gL or an antigenic fragment thereof;
e) a nucleotide sequence encoding a CMV glycoprotein UL128 or an antigenic fragment thereof;
f) a nucleotide sequence encoding a CMV glycoprotein UL130 or an antigenic fragment thereof;
g) a nucleotide sequence encoding a CMV glycoprotein UL131A or an antigenic fragment thereof.

In specific embodiments, provided herein are methods for treating and/or preventing a CMV infection comprising administering a first infectious, replication-deficient arenavirus expressing a first CMV antigen, selected from: a CMV tegument protein pp65 or an antigenic fragment thereof; a CMV glycoprotein gH or an antigenic fragment thereof; a CMV glycoprotein gL; a CMV glycoprotein UL128 or an antigenic fragment thereof; or an antigenic fragment thereof; a CMV glycoprotein UL130 or an antigenic fragment thereof; or a CMV glycoprotein UL131A or an antigenic fragment thereof, as described herein and a second infectious, replication-deficient arenavirus expressing a second CMV antigen, selected from: a nucleotide sequence encoding a CMV glycoprotein gB or an antigenic fragment thereof; a CMV tegument protein pp65 or an antigenic fragment thereof; a CMV glycoprotein gH or an antigenic fragment thereof; a CMV glycoprotein gL; a CMV glycoprotein UL128 or an antigenic fragment thereof; or an antigenic fragment thereof; a CMV glycoprotein UL130 or an antigenic fragment thereof; or a CMV glycoprotein UL131A or an antigenic fragment thereof.

In certain embodiments, provided herein are compositions suitable for a method of treating and/or preventing a CMV infection comprising administering two arenavirus construct expressing a CMV antigen as described herein. In a specific embodiment, the two arenavirus vector constructs express a CMV antigen.

In certain embodiments, provided herein are compositions comprising two or more arenavirus vector constructs expressing a CMV antigen as described herein. In specific embodiments, provided herein are compositions comprising three or more arenavirus vector constructs expressing a CMV antigen as described herein. In another embodiment, provided herein are compositions comprising four or more arenavirus vector constructs expressing a CMV antigen, five or more arenavirus vector constructs expressing a CMV antigen, six or more arenavirus vector constructs expressing a CMV antigen or 7 arenavirus vector constructs each expressing a CMV antigen as described herein or a combination thereof. In certain embodiments, the arenavirus can be LCMV.

In specific embodiments, the antigen is the CMV major envelope glycoprotein gB or a fragment thereof. (See, e.g., Section 6.2(a)). In more specific embodiments, the antigen is the CMV major envelope glycoprotein gB with a truncation of the carboxy-terminus. (See, e.g., Section 6.2(b) for truncated gB proteins).

In certain embodiments, the antigen is the CMV tegument protein pp65 or a fragment thereof. (See, e.g., Section 6.2(c)).

In certain embodiments, the antigen is a CMV pentameric complex protein. In another embodiment the CMV pentameric complex antigen is gH, gH (dTM), gL, UL128, UL131A, or UL130 or combinations thereof. (See, e.g., Section 6.2(d)).

In certain embodiments, the vector generated to encode one or more CMV antigens as described herein comprises one or more nucleic acids encoding a CMV antigen and combinations thereof as described. In specific embodiments the CMV antigens as described herein are separated by various linkers, spacers, and cleavage sites as described herein.

In another embodiment, the vector generated to encode one or more CMV antigens as described herein of the first infectious, replication-deficient arenavirus may be based on LCMV Clone 13 or LCMV MP strain. (See, e.g., Section 7.1).

In another embodiment, the vector generated to encode one or more CMV antigens as described herein of the second infectious, replication-deficient arenavirus may be based on LCMV Clone 13 or LCMV MP strain. (See, e.g., Section 7.1).

In a specific embodiment, provided herein are compositions suitable for a method of treating and/or preventing a CMV infection in a subject comprising administering to the subject a first infectious, replication-deficient arenavirus composition expressing a CMV tegument protein pp65 or an antigenic fragment thereof and a second infectious, replication-deficient arenavirus composition expressing a CMV glycoprotein gB or an antigenic fragment thereof.

In a specific embodiment, provided herein are compositions suitable for a method of treating and/or preventing an infection in a subject comprising administering sequentially to the subject a first infectious, replication-deficient arenavirus expressing a CMV tegument protein pp65 or an antigenic fragment thereof and a second infectious, replication-deficient arenavirus expressing a CMV glycoprotein gB or an antigenic fragment thereof.

In a specific embodiment, provided herein are compositions suitable for a an infection in a subject comprising administering simultaneously to the subject a first infectious, replication-deficient arenavirus expressing a CMV tegument protein pp65 or an antigenic fragment thereof and a second infectious, replication-deficient arenavirus expressing a CMV glycoprotein gB or an antigenic fragment thereof.

In another embodiment, the first infectious, replication-deficient arenavirus composition expressing a CMV tegument protein pp65 or an antigenic fragment thereof is a primary vaccine antigen and the second infectious, replication-deficient arenavirus expressing a CMV glycoprotein gB or an antigenic fragment thereof is a secondary vaccine antigen.

In a specific embodiment, provided herein is a composition comprising a first infectious, replication-deficient arenavirus composition expressing a CMV tegument protein pp65 or an antigenic fragment thereof and a second infectious, replication-deficient arenavirus composition expressing a CMV glycoprotein with a truncation of the carboxy-terminus. (See, e.g., Section 6.2(b) for truncated gB proteins).

In yet another embodiment, provided herein is the combined use of the replication-deficient arenaviruses compositions expressing a CMV antigen as described herein and one or more replication-defective virus vector compositions. In a more specific embodiment the replication-defective virus vector composition can be but is not limited to: poxviruses, adenoviruses, alphaviruses, herpes simplex viruses, paramyxoviruses, rhabdoviruses, poliovirus, adeno-associated virus, and Sendai virus, and mixtures thereof. In a specific embodiment, the poxvirus is a modified vaccine Ankara.

In another embodiment, two infectious, replication-deficient arenaviruses compositions have molar ratios ranging from about 1:1 to 1:1000, in particular including: 1:1 ratio, 1:2 ratio, 1:5 ratio, 1:10 ratio, 1:20 ratio, 1:50 ratio, 1:100 ratio, 1:200 ratio, 1:300 ratio, 1:400 ratio, 1:500 ratio, 1:600 ratio, 1:700 ratio, 1:800 ratio, 1:900 ratio, 1:1000 ratio.

In another embodiment, compositions are suitable for administration to the subjects in which two or more infectious, replication-deficient arenavirus compositions expressing a CMV antigen described herein is administered have, are susceptible to, or are at risk for a CMV infection or reactivation. In another embodiment, the subjects whom two or more infections, replication-deficient arenaviruses compositions expressing a CMV antigen described herein or a composition thereof is administered are infected with, are susceptible to, or are at risk for, an infection with CMV or reactivation with CMV.

In another embodiment, said two or more infectious, replication-deficient arenavirus compositions further comprise at least one other medicament for treating and/or preventing CMV infection or reactivation of CMV. Therapeutic medicaments include, but are not limited to, Valganciclovir, Ganciclovir, Foscarnet, Cidofovir, or Maribavir.

In another embodiment, compositions are suitable for administrating to a symptomatic subject a second infectious, replication-deficient arenavirus composition expressing a CMV antigen or a fragment thereof as described herein. In yet another embodiment, the compositions are suitable for administration to a subject with a compromised immune system, especially transplant recipients, HIV-infected persons, a pregnant subject, or a subject who has cancer, a second infectious, replication-deficient arenavirus composition expressing a CMV antigen described herein or a fragment thereof. In another embodiment, two or more infectious, replication-deficient arenavirus compositions expressing a CMV antigen as described herein or a fragment thereof are suitable for administrating to a subject who is a child of 0, 1, 2, 3, 4, 5, 6, 7, 8, 9, 10, 11, 12, 13, 14, 15, 16, or 17 years of age suffering from or susceptible to, or are at risk for, an infection with CMV or reactivation of CMV.

In another embodiment, compositions are suitable for administrating to a subject who is a child, a first replication deficient arenavirus expressing a CMV antigen, and administering to the same subject who is an adolescent a second replication deficient arenavirus expressing a CMV antigen. In a specific embodiment, the administration regime can involve administering to a subject who is 0, 1, 2, 3, 4, 5, 6, 7, 8, 9, 10, 11, 12, 13, 14, 15, 16, or 17 years of age a first, replication-deficient arenavirus expressing a CMV antigen as described herein, and to the same subject who is 12, 13, 14, 15, 16, 17, 18, 19, 20, 21, 22, 23, 24, 25 years of age a second infectious replication-deficient arenavirus expressing a CMV antigen.

In another embodiment, compositions are suitable for administering to a prepubescent subject a second infectious, replication-deficient arenavirus expressing a CMV antigen. In another embodiment, the administration regime can involve administering to an adolescent male, aged 12 to 18 years a second infectious, replication-deficient arenavirus expressing a CMV antigen as described herein. In another embodiment, the administration regime can involve administering to a female, aged 12 to 18 years a second infectious, replication-deficient arenavirus expressing a CMV antigen.

In another embodiment, two or more infectious, replication-deficient arenavirus compositions expressing a CMV antigen or a fragment thereof, as described herein reduce the risk that an individual will develop an infection with CMV or reactivation of CMV by at least 10%, at least about 20%, at least about 25%, at least about 30%, at least about 40%, at least about 50%, at least about 60%, at least about 70%, at least about 80%, at least about 90%, or more, compared with the manifestation of the symptoms of an infection CMV or reactivation of CMV in the absence of such treatment.

In another embodiment, two or more infectious, replication-deficient arenavirus compositions expressing a CMV antigen or a fragment thereof, as described herein, administered separately, reduce the risk that an individual will develop an infection with CMV or reactivation of CMV by at least 10%, at least about 20%, at least about 25%, at least about 30%, at least about 40%, at least about 50%, at least about 60%, at least about 70%, at least about 80%, at least about 90%, or more, compared with the manifestation of the symptoms of an infection CMV or reactivation of CMV in the absence of such treatment.

In another embodiment, two or more infectious, replication-deficient arenavirus compositions expressing a CMV antigen or a fragment thereof, as described herein, administered sequentially, reduce the risk that an individual will develop an infection with CMV or reactivation of CMV by at least 10%, at least about 20%, at least about 25%, at least about 30%, at least about 40%, at least about 50%, at least about 60%, at least about 70%, at least about 80%, at least about 90%, or more, compared with the manifestation of the symptoms of an infection CMV or reactivation of CMV in the absence of such treatment.

In another embodiment, provided herein the invention provides a vaccine composition comprising a synergistic combination of two or more infectious replication-deficient arenaviruses expressing a CMV antigen.

In specific embodiments, provided herein is a pharmaceutical composition comprising an infectious, replication-deficient arenavirus expressing a CMV glycoprotein gB with a truncation of the carboxy-terminus See, e.g., Section 6.2(b) for truncated gB proteins). In another embodiment, provided herein is a pharmaceutical composition comprising a first infectious, replication deficient arenavirus expressing a CMV glycoprotein gB with a truncation of the carboxy-terminus or a CMV tegument protein pp65 and a second infectious, replication deficient arenavirus expressing a CMV glycoprotein gB with a truncation of the carboxy-terminus or a CMV tegument protein pp65.

In other embodiments, the pharmaceutical composition comprises an infectious, replication-deficient arenavirus expressing a CMV glycoprotein gB with a truncation of the carboxy-terminus that can be 80%, 81%, 82%, 83%, 84%, 85%, 86%, 87%, 88%, 89%, 90%, 91%, 92%, 93%, 94% 95%, 96%, 97%, 98%, 99% or 100% identical to the amino acid sequence of SEQ ID NO: 3 over the entire length of the truncated gB protein. In more specific embodiments, the CMV glycoprotein gB has a truncation in the region of amino acids 773-906 of SEQ ID NO: 3. In a specific embodiment, the truncated gB protein consists of the amino acid sequence of SEQ ID NO: 18.

In certain embodiments, the truncation can of the glycoprotein gB can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 29, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or 134 amino acids long. See section 6.2(b) for truncated gB proteins.

In certain embodiments, provided herein is an immunogenic composition comprising an infectious, replication-deficient arenavirus expressing a CMV glycoprotein gB with a truncation of the carboxy-terminus (See, e.g., Section 6.2(b) for truncated gB proteins). In another embodiment, provided herein is an immunogenic composition comprising a first infectious, replication deficient arenavirus expressing a CMV glycoprotein gB with a truncation of the carboxy-terminus or a CMV tegument protein pp65 and a second infectious, replication deficient arenavirus expressing a CMV glycoprotein gB with a truncation of the carboxy-terminus or a CMV tegument protein pp65.

In other embodiments, the immunogenic composition comprises a polypeptide that can be 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequence of SEQ ID NO: 3 over the entire length of the other gB. In more specific embodiments, the immunogenic composition has a truncation or deletion in the region of amino acids 773-906 of SEQ ID NO: 3. In yet other specific embodiments, the truncation or deletion 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 29, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or 134 amino acids long. In certain embodiments, the immunogenic composition further comprises a pharmaceutically acceptable carrier.

6.9 Assays

Assay for Measuring Arenavirus Vector Infectivity

Any assay known to the skilled artisan can be used for measuring the infectivity of an arenavirus vector preparation. For example, determination of the virus/vector titer can be done by a "focus forming unit assay" (FFU assay). In brief, complementing cells, e.g. HEK 293 cells expressing LCMV GP protein, are plated and inoculated with different dilutions of a virus/vector sample. After an incubation period, to allow cells to form a monolayer and virus to attach to cells, the monolayer is covered with Methylcellulose. When the plates are further incubated, the original infected cells release viral progeny. Due to the Methylcellulose overlay the spread of the new viruses is restricted to neighboring cells. Consequently, each infectious particle produces a circular zone of infected cells called a Focus. Such Foci can be made visible and by that countable using antibodies against LCMV-NP and a HRP-based color reaction. The titer of a virus/vector can be calculated in focus-forming units per milliliter (FFU/mL).

To determine the infectious titer (FFU/mL) of transgene-carrying vectors this assay is modified by the use of the respective transgene-specific antibody instead of anti-LCMV-NP antibody.

Serum ELISA Determination of the humoral immune response upon vaccination of animals (e.g. mice, guinea pigs) can be done by antigen-specific serum ELISA's (enzyme-linked immunosorbent assays). In brief, plates are coated with antigen (e.g. recombinant protein), blocked to avoid unspecific binding of antibodies and incubated with serial dilutions of sera. After incubation, bound serum-antibodies can be detected, e.g., using an enzyme-coupled anti-species (e.g. mouse, guinea pig)-specific antibody (detecting total IgG or IgG subclasses) and subsequent color reaction. Antibody titers can be determined as, e.g., endpoint geometric mean titer.

Neutralizing Assay in ARPE-19 cells. Determination of the neutralizing activity of induced antibodies in sera is performed with the following cell assay using ARPE-19 cells from ATCC and a GFP-tagged virus. In addition supplemental guinea pig serum as a source of exogenous complement is used. The assay is started with seeding of $6.5 \times 10^3$ cells/well (50 μl/well) in a 384 well plate one or two days before using for neutralization. The neutralization is done in 96-well sterile tissue culture plates without cells for 1 h at 37° C. After the neutralization incubation step the mixture is added to the cells and incubated for additional 4 days for GFP-detection with a plate reader. A positive neutralizing human sera is used as assay positive control on each plate to check the reliability of all results. Titers (EC50) are determined using a 4 parameter logistic curve fitting. As additional testing the wells are checked with a fluorescence microscope.

Plaque Reduction Assay In brief, plaque reduction (neutralization) assays for guinea pig cytomegalovirus are performed by use of an isolate of GPCMV tagged with green fluorescent protein, 5% rabbit serum was used as a source of exogenous complement, and plaques were enumerated by fluorescence microscopy. Neutralization titers were defined as the highest dilution of serum that resulted in a 50% reduction in plaques, compared with that in control (pre-immune) serum samples.

Neutralization Assay in guinea pig lung fibroblast (GPL) cells In brief, serial dilutions of test and control (pre-vaccination) sera were prepared in GPL complete media with supplemental rabbit serum (1%) as a source of exogenous complement. The dilution series spanned 1:40 through 1:5120. Serum dilutions were incubated with eGFP tagged virus (100-200 pfu per well) for 30 min at 37° C., and then transferred to 12-well plates containing confluent GPL cells. Samples were processed in triplicate. After 2 hours incubation at 37° C. the cells were washed with PBS, re-fed with GPL complete media and incubated at 37° C./5% $CO_2$ for 5 days. Plaques were visualized by fluorescence microscopy, counted, and compared to control wells. That serum dilution resulting in a 50% reduction in plaque number compared to controls was designated as the neutralizing titer.

qPCR LCMV RNA genomes are isolated using QIAamp Viral RNA mini Kit (QIAGEN), according to the protocol provided by the manufacturer. LCMV RNA genome equivalents are detected by quantitative PCR carried out on an StepOnePlus Real Time PCR System (Applied Biosystems) with SuperScript® III Platinum® One-Step qRT-PCR Kit (Invitrogen) and primers and probes (FAM reporter and NFQ-MGB Quencher) specific for part of the LCMV NP coding region. The temperature profile of the reaction is: 30 min at 60° C., 2 min at 95° C., followed by 45 cycles of 15 s at 95° C., 30 s at 56° C. RNA is quantified by comparison of the sample results to a standard curve prepared from a log 10 dilution series of a spectrophotometrically quantified, in vitro-transcribed RNA fragment, corresponding to a fragment of the LCMV NP coding sequence containing the primer and probe binding sites.

Western Blotting Infected cells grown in tissue culture flasks or in suspension are lysed at indicated timepoints post infection using RIPA buffer (Thermo Scientific) or used directly without cell-lysis. Samples are heated to 99° C. for 10 minutes with reducing agent and NuPage LDS Sample buffer (NOVEX) and chilled to room temperature before loading on 4-12% SDS-gels for electrophoresis. Proteins are blotted onto membranes using Invitrogens iBlot Gel transfer Device and visualized by Ponceau staining. Finally, the preparations are probed with an primary antibodies directed against proteins of interest and alkaline phosphatase conjugated secondary antibodies followed by staining with 1-Step NBT/BCIP solution (INVITROGEN).

MHC-Peptide Multimer Staining Assay for Detection of Antigen-Specific CD8+ T-cell proliferation Any assay known to the skilled artisan can be used to test antigen-specific CD8+ T-cell responses. For example, the MHC-peptide tetramer staining assay can be used (see, e.g., Altman J. D. et al., Science. 1996; 274:94-96; and Murali-Krishna K. et al., Immunity. 1998; 8:177-187). Briefly, the assay comprises the following steps, a tetramer assay is used to detect the presence of antigen specific T-cells. In order for a T-cell to detect the peptide to which it is specific, it must both recognize the peptide and the tetramer of MHC molecules custom made for an antigen specific T-cell (typically fluorescently labeled). The tetramer is then detected by flow cytometry via the fluorescent label.

ELISPOT Assay for Detection of Antigen-Specific CD4+ T-cell Proliferation Any assay known to the skilled artisan can be used to test antigen-specific CD4+ T-cell responses. For example, the ELISPOT assay can be used (see, e.g., Czerkinsky C. C. et al., J Immunol Methods. 1983; 65:109-121; and Hutchings P. R. Et al., J Immunol Methods. 1989; 120:1-8). Briefly, the assay comprises the following steps: An immunospot plate is coated with an anti-cytokine antibody. Cells are incubated in the immunospot plate. Cells secrete cytokines and are then washed off. Plates are then coated with a second biotyinlated-anticytokine antibody and visualized with an avidin-HRP system.

Intracellular Cytokine Assay for Detection of Functionality of CD8+ and CD4+ T-cell Responses Any assay known to the skilled artisan can be used to test the functionality of CD8+ and CD4+ T cell responses. For example, the intracellular cytokine assay combined with flow cytometry can be used (see, e.g., Suni M. A. et al., J Immunol Methods. 1998; 212:89-98; Nomura L. E. et al., Cytometry. 2000; 40:60-68; and Ghanekar S. A. et al., Clinical and Diagnostic Laboratory Immunology. 2001; 8:628-63). Briefly, the assay comprises the following steps: activation of cells via specific peptides or protein, an inhibition of protein transport (e.g., brefeldin A) is added to retain the cytokines within the cell. After washing, antibodies to other cellular markers can be added to the cells. Cells are then fixed and permeabilized. The anti-cytokine antibody is added and the cells can be analyzed by flow cytometry.

Assay for Confirming Replication-Deficiency of Viral Vectors Any assay known to the skilled artisan that determines concentration of infectious and replication-competent virus particles can also be used as a to measure replication-deficient viral particles in a sample. For example, FFU assays (as described in [00225]) with non-complementing cells can be used for this purpose.

Furthermore, plaque-based assays are the standard method used to determine virus concentration in terms of plaque forming units (PFU) in a virus sample. Specifically, a confluent monolayer of non-complementing host cells is infected with the virus at varying dilutions and covered with a semi-solid medium, such as agar to prevent the virus infection from spreading indiscriminately. A viral plaque is formed when a virus successfully infects and replicates itself in a cell within the fixed cell monolayer (see, e.g., Kaufmann, S. H.; Kabelitz, D. (2002). Methods in Microbiology Vol. 32:Immunology of Infection. Academic Press. ISBN 0-12-521532-0). Plaque formation can take 3-14 days, depending on the virus being analyzed. Plaques are generally counted manually and the results, in combination with the dilution factor used to prepare the plate, are used to calculate the number of plaque forming units per sample unit volume (PFU/mL). The PFU/mL result represents the number of infective replication-competent particles within the sample.

Assay for Expression of Viral Antigen Any assay known to the skilled artisan can be used for measuring expression of viral antigens. For example, FFU assays (as described in [00225]) can be performed. For detection, mono- or polyclonal antibody preparation(s) against respective viral antigens are used (transgene-specific FFU).

Furthermore, Western Blotting (as described in [00231]) can be performed.

Animal Models The safety, tolerance and immunogenic effectiveness of vaccines comprising of an infectious, replication-deficient arenavirus expressing a CMV antigen described herein or a composition thereof can be tested in animals models. In certain embodiments, the animal models that can be used to test the safety, tolerance and immunogenic effectiveness of the vaccines and compositions thereof used herein include mouse, guinea pig, rat, and monkey. In a preferred embodiment, the animal models that can be used to test the safety, tolerance and immunogenic effectiveness of the vaccines and compositions thereof used herein include mouse.

Guinea pig model The preclinical evaluation of the immunogenicity and efficacy of HCMV vaccines is made difficult by the species specificity of CMV. However, in guinea pigs, guinea pig CMV (GPCMV) does cross the placenta to cause a congenital infection similar to human infection (Bourne N et al, JID 1996; Schleiss M et al, JID 2003). Furthermore, the structure of the placenta as well as the trimester-like pregnancy period of guinea pigs is similar to that in humans. In addition, as in humans, transplacental passage of maternal antibodies occurs. Based on these features the guinea pig model is been commonly used for the evaluation of vaccine strategies.

To investigate protective efficacy against congenital CMV infection Hartley guinea pigs can be immunized with test vaccine candidates and immunized guinea pigs can subsequently be allowed to breed. Pregnancies in guinea pig dams can be confirmed and monitored by palpitation. Pregnant dams can be challenged with GPCMV and pup mortality can be measured and protection rates be determined at parturition.

In certain embodiments, inclusion of heterologous domains from other viruses into the human CMV antigen results in induction of higher antibody levels. To test the generation of neutralizing antibodies, an assay can be conducted as follows: female guinea pigs are immunized three times on days 0, 21 and 42. Two weeks after the last vaccine dose, the immunized guinea pigs are allowed to breed. Pregnant guinea pigs are challenged at 40-50 days of gestation with GPCMV. Sera of vaccinated animals will be analyzed by ELISA and neutralization assays and blood samples will be obtained after challenge for detection of viremia by Real-Time PCR. Dams will be monitored until delivery, and survival and condition of the offspring will be analyzed in detail.

In certain embodiments, inclusion of heterologous domains from other viruses into the human CMV antigen results in induction of higher antibody levels.

7. EXAMPLES

7.1 Design of Arenavirus Vector Genome/Vector Construction

Following established approaches (U.S. Patent Application Publication No. US 2010/0297172 A1; and Flatz L. et al., Nat Med. 2010 March; 16(3): 339-345), rLCMV vaccine vectors expressing the respective CMV antigens or certain domains thereof were designed (FIG. 1).

Design of rLCMV vectors expressing CMV gB For generation of rLCMV vaccine vectors expressing the gB antigen of CMV various rLCMV-gB vector constructs (FIG. 2) were designed encoding selected parts of the gB protein. Respective constructs included rLCMV vectors encoding:
- full-length wildtype gB (HK1-HgB(FL), SEQ ID NO: 1),
- transmembrane region deleted (dTM) gB in which the amino acids 1-698 were fused to amino acids 775-906 (HK1-HgB(dTM), SEQ ID NO: 4),
- a C-terminally truncated gB consisting of the N-terminal 706 amino acids of gB (HK1-HgB(1-706), SEQ ID NO: 7),
- a C-terminally truncated gB consisting of the N-terminal 691 amino acids of gB (HK1-HgB(1-691), SEQ ID NO: 10)
- a C-terminally truncated gB consisting of the N-terminal 447 amino acids of gB (HK1-HgB(1-447), SEQ ID NO: 13),
- a C-terminally truncated gB consisting of the N-terminal 772 amino acids of gB, encoding the ectodomain and the transmembrane region of gB, followed by an artificial Arginine residue at position 773 (HK1-HgB(dCt), SEQ ID NO: 16),
- a gB construct consisting of the N-terminal 751 amino acids of gB followed by the C-terminal 49 amino acids of Vesicular Stromatitis Virus Protein G (HK1-HgB (VSVG-1), SEQ ID NO: 19),
- a gB construct consisting of the N-terminal 706 amino acids of gB followed by the C-terminal 49 amino acids of Vesicular Stromatitis Virus Protein G (HK1-HgB (VSVG-2), SEQ ID NO: 22),
- a C-terminally truncated gB consisting of the N-terminal 751 amino acids of gB followed by the C-terminal 37 amino acids of Influenza hemagglutinin H3 (HK1-HgB (H3-1), SEQ ID NO: 25),
- a C-terminally truncated gB consisting of the N-terminal 706 amino acids of gB followed by the C-terminal 37 amino acids of Influenza hemagglutinin H3 (HK1-HgB (H3-2), SEQ ID NO: 28).

As the species specificity of CMV precludes animal efficacy studies of vaccines expressing human CMV antigens, not only rLCMV vectors encoding the gB sequence of human CMV (HCMV) have been generated, but also corresponding vectors expressing analogous sequences of guinea pig CMV (GPCMV) for some constructs, e.g. HK1-GPgB(FL), HK1-GPgB(FLuc), HK1-GPgB(dTM), HK1-GPgB(dTMuc), HK1-GPgB(1-706), HK1-GPgB(1-691), HK1-GPgB(1-447), HK1-GPgB(dCt). HK1-GPgB(FLuc) has been designed analogously to HK1-GPgB(FL) except that the furin-cleavage site located in the ectodomain of gB has been inactivated by mutation. HK1-GPgB(dTMuc) has been designed analogously to HK1-GPgB(dTM) except that the furin-cleavage site located in the ectodomain of gB has been inactivated by mutation. Vector constructs encoding GPCMV antigens enable pre-clinical immunogenicity and efficacy studies in the guinea pig model which presents the gold standard for CMV vaccine development. Similarly, constructs expressing the analogous sequences of mouse CMV gB were generated allowing for rapid and cost effective pre-screening of the individual vector design.

Analogously, an rLCMV vector has been constructed that expresses the full-length T-cell antigen pp65 from human CMV (HK1-Hpp65, SEQ ID NO: 34). In addition, a corresponding vector expressing the analogous sequences of guinea pig CMV (GPCMV) has been generated (HK1-GPpp65).

In addition, rLCMV vectors for expression of different parts of the pentameric complex (PC) of CMV, formed by the glycoproteins gH/gL, UL128, UL130, and UL131A, have been designed. In order to generate an rLCMV vector expressing the full complex, a polyprotein vector encoding the five proteins separated by Teschovirus 2A peptide (T2A) sequences (FIG. 3) has been designed (Donnelly M L L et al 2001, Gao S Y et al 2012, Kim J H et al 2011). Self-cleaving 2A peptides have been chosen as they are relatively small in size and show high cleavage efficiency between genes upstream and downstream of the 2A peptide (Donnelly M L L et al 2001, Gao S Y et al 2012, Kim J H et al 2011).

Respective constructs comprised
- a vector encoding glycoprotein gH only (HK1-HgH, SEQ ID NO: 37)

a vector encoding a transmembrane domain deleted version of glycoprotein gH (HK1-HgH(dTM), SEQ ID NO: 50).

Derivation of rLCMV vector constructs rLCMV vectors may differ in the LCMV strain from which the cDNA sequences are derived and the plasmid system used for their rescue. Clone 13 or MP strain LCMV are two possible strains used for the derivation of vectors. Studies comparing the effect of the rLCMV vector backbone, Clone 13 and MP, on the induction of immune responses has been evaluated using Hpp65, HgBdTM and GPgBdTM as transgenes as shown in FIG. 16-18. Four different approaches/plasmid systems may be used for vector rescue. In one approach, transcription of the short (S) and long (L) genomic segments of the viral vector is controlled by a murine-specific RNA polymerase I promoter and terminator. The polymerase and NP proteins are expressed from individual constructs under control of a polymerase II promoter. Substitution of GP by a CMV antigen in the cDNA system followed by transfection of the four plasmids in murine cells which provide the LCMV GP protein in trans leads to formation of vector particles which can be harvested from the supernatant of transfected cells. This approach is used in Flatz, et al., Proc. Natl. Acad. Sci. USA 2006, 103:4663.

In the second system, transcription of the S (including CMV antigen) and the L segment are under control of a T7 promoter, which necessitates the introduction of a fifth plasmid encoding T7 polymerase to drive expression from T7 promoters. The viral trans-acting factors (NP and L) are again co-expressed from different plasmids using an RNA polymerase II promoter. This system is adapted from Sanchez & de la Torre, Virology 2006 July, 350(2):370.

In the third system, transcription of the short (S) and long (L) genomic segments of the viral vector is controlled by a human RNA polymerase I promoter and appropriate terminator. The viral trans-acting factors (NP and L) are again co-expressed from different plasmids using an RNA polymerase II promoter.

In the fourth system, transcription of the short (S) and long (L) genomic segments of the viral vector is controlled by a human RNA polymerase I promoter and appropriate terminator. On the same plasmid, transcription of the viral trans-acting factors is driven by a polymerase II promoter which is designed to be directed in the opposite direction to drive transcription of positive strand RNA from the NP and L ORFs from the same template. Such an approach was used before to generate recombinant Influenza viruses and is described in Hoffmann E et al 2000. All rLCMV vectors described above can be produced according to established methodology (U.S. Patent Application Publication No. US 2010/0297172 A1; and Flatz L. et al., Nat Med. 2010 March; 16(3): 339-345). Other methods can also be used; e.g., different plasmid systems, different cells and different transfection methods can be used to generate the arenavirus vectors provided herein.

7.2 Vector Characterization

Characterization of rLCMV vectors expressing CMV gB Characterization of the generated vector constructs included analysis of viral replication and specific infectivity of host cells (FIG. 4).

FIG. 4 shows viral titers and infectivity of vector constructs HK1-HgB(FL), HK1-HgB(dTM), HK1-HgB(706), HK1-HgB(691), HK1-HgB(dCt), HK1-HgB(VSVG-1), HK1-HgB(VSVG-2), HK1-HgB(H3-1) and HK1-HgB(H3-2). The respective vector constructs showed similar peak titers and infectivity comparable to a control LCMV vector expressing the green-fluorescent-protein (HK1-GFP), indicating that there was no negative impact on vector production due to the size and nature of the transgenes.

In order to analyze vector replication, growth curves were performed using suspension HEK 293 cells expressing LCMV GP. Respective cells were seeded with cell density of $3 \times 10^5$ cells/ml and infected with individual vectors (HK1-HgB(dTM), HK1-HgB(dCt), HK1-HgB(VSVG-1), HK1-HgB(H3-2) and HK1-HgB(691)) at MOI of 0.001. Samples were drawn every 24 hours and analysed by FFU assay (FIG. 5). All tested vectors exhibited similar growth kinetics and peak titers compared to HK1-GFP indicating that the individual gB transgenes did not interfere with vector replication to a greater extent than the small reportergene GFP.

Western blot experiments were used to confirm presence of the gB antigen for all tested constructs, exemplary data are shown in FIG. 6. Uncleaved precursors of full length gB are expected to band at ~160 kDa whereas cleaved gB consists of a surface component with an estimated molecular mass of 116 kDa that is linked by disulfide bonds to a transmembrane component with an estimated molecular mass of 55 kDa. However, due to use of a monoclonal primary antibody only two bands representing the uncleaved gB protein and the smaller cleavage product of gB are expected to be visible on the blot. Full length gB (lane 7) banded at the expected range of ~160 kDa, whereas all remaining constructs showed bands of lower size which can be explained by the deletion or exchange of at least part of the gB cytoplasmic domain. Analogously, the transmembrane part of full length gB (lane 7) bands at ~60 kDa (slightly higher than expected) and all gB derivates exhibit cleavage products of lower size. In general HK1-gB(FL) and HK1-gB(dTM) exhibited weaker gB bands compared to all other vectors.

Comparison of immunogenicity of HK1-GPgB(FL), HK1-GPgB(dTM) and HK1-GPgB(dTMuc) Next, the immunogenicity of HK1-GPgB(FL), HK1-GPgB(dTM) and HK1-GPgB(dTMuc) were analyzed and compared in mice (FIG. 7). C57BL/6 mice were immunized subcutaneously with $6.7 \times 10^4$ FFU/dose of the respective vectors on days 0, 21 and 42 of the experiment. Sera of immunized mice were collected on days 21, 42 and 63 of the experiment and anti-gB antibody titers were measured by ELISA. An analogous rLCMV vector expressing the green fluorescent protein (HK1-GFP) was used as a control. The control vector was used at a concentration of $9.2 \times 10^5$ FFU per injection.

HK1-GPgB(dTM) and HK1-GPgB(dTMuc) induced significantly higher antibody titers than HK1-GPgB(FL) after subcutaneous injection in mice.

Comparison of immunogenicity of HK1-GPgB(dTM) vaccine vector administered by intramuscular or subcutaneous route at different concentrations Next, the immunogenicity of HK1-GPgB-dTM, when administered at different doses and different injection routes, was analyzed systematically (FIGS. 8A and B).

These analyses demonstrated that HK1-GPgB-dTM induced higher antibody responses following intramuscular injection (FIG. 8A) compared to subcutaneous administration. Among the tested immunization doses, vaccine doses of $2 \times 10^6$ and $6.7 \times 10^4$ FFU/dose resulted in comparably high antibody titers.

Comparison of the intramuscular and intradermal route of immunization. The induction of humoral as well as CD8+ T cell responses was analyzed after immunization with different concentrations of either HK1-HgB(dCt) (FIG. 8C) or HK1-Hpp65 (FIG. 8D) using the intramuscular and the intradermal route. Respective results demonstrate that significantly higher titers of antigen-specific antibodies were elicited by the intramuscular compared to the intradermal route at a dose of $5.6 \times 10^5$ FFU (FIG. 8C, groups 1 and 3) indicating that no dose sparing effect could be achieved when the vaccine was administered via the intradermal route. Similarly, higher CD8+ T cell responses were observed after intramuscular injection compared to intradermal immunization at a dose of $6.7 \times 10^5$ FFU (FIG. 8D groups 1 and 3).

Comparison of the immunogenicity of HK1-HgB(dTM), HK1-HgB(1-706), HK1-HgB(1-691), HK1-HgB(dCt), HK1-HgB(H3-1), HK1-HgB(H3-2), HK1-HgB(VSVG-1), HK1-HgB(VSVG-2) and a recombinant gB protein mixed with adjuvant The immunogenicity of HK1-HgB(dTM), HK1-HgB(1-706), HK1-HgB(1-691), HK1-HgB(dCt), HK1-HgB(H3-1), HK1-HgB(H3-2), HK1-HgB(VSVG-1), HK1-HgB(VSVG-2) and a recombinant gB protein mixed with adjuvant was analyzed in mice. C57BL/6 mice were immunized intramuscularly with $1 \times 10^5$ FFU/dose of the respective vectors or 5 µg of a recombinant gB protein mixed 1:1 with adjuvant on days 0 and 21 of the experiment. Sera of immunized mice were collected prior to each vaccine dose on days 0, 21 as well as in intervals of three weeks on days 42, 63, 84 and 105 of the experiment. Generated sera were tested for the level of anti-HCMVgB IgG antibodies by ELISA and for the presence of neutralizing antibodies by Neutralization Assay in ARPE-19 cells.

Statistical analysis of the respective ELISA data (FIG. 9) revealed comparable antibody induction of the recombinant gB protein (mixed with adjuvant) and all tested rLCMV-gB constructs. In addition, generated results indicate that very long-lasting immune responses can already be achieved after two immunizations as antibody levels reach a plateau after the second immunization.

Functionality of the induced antibodies In order to test the functionality of the induced antibodies, the sera of vaccinated animals were further analyzed by Neutralization Assay in ARPE-19 cells. The neutralizing activity of the induced antibodies, present in the sera of immunized mice, collected on day 42, was measured in epithelial ARPE-19 cells (FIG. 10). Respective results indicate that all tested rLCMV-gB constructs induced higher HCMV neutralizing antibody levels than the recombinant subunit gB protein mixed with adjuvant. However, HgB(dTM) induced significantly lower levels of HCMV neutralizing antibodies than all other tested rLCMV-gB vectors.

Analysis of individual IgG subclasses The sera of selected experimental groups (vaccinated with HK1-HgB(dTM), HK1-HgB(1-706), HK1-HgB(1-691), HK1-HgB(H3-2), HK1-HgB(VSVG-1), and recombinant gB protein mixed with adjuvant), collected on day 42, were analyzed by HCMVgB-specific IgG subclass ELISA (FIG. 11). The respective analysis revealed predominant induction of IgG2c by rLCMV-gB constructs whereas the recombinant gB protein mixed with adjuvant induced mainly IgG1. This data point to a type 1 biased immune response induction by rLCMV-gB vectors which seems to be significantly different from the type 2 biased response induced by the gB subunit protein.

Immunogenicity of HK1-GPgB(dTM) in guinea pigs Hartley guinea pigs were immunized by intramuscular injection with different concentrations ($1.54 \times 10^7$, $1.54 \times 10^6$, $1.54 \times 10^5$ and $1.54 \times 10^4$ FFU/dose) of HK1-GPgB-dTM on days 0, 21 and 42 of the experiment. For control purposes one animal received no vaccine or buffer. Sera of immunized animals were collected on days 0, 21, 42 and 63 of the experiment and anti-GPgB antibody titers were analyzed by GPgB-specific IgG ELISA. A GPCMV positive serum was used as control.

ELISA data show that already after single intramuscular immunization (prime), HK1-GPgB(dTM) induced anti-GPgB antibody responses of considerable magnitude in a dose-dependent manner (FIG. 12). These responses could efficiently be augmented when the same vector was re-administered three weeks after prime and reached a plateau of IgG response after two injections for the three highest doses ($1.54 \times 10^7$, $1.54 \times 10^6$, $1.54 \times 10^5$) of HK1-GPgB(dTM). The values reached are similar to a control serum used (generated 30 dpi with $1 \times 10^5$ pfu GPCMV. A significant lower response was induced by the lowest dose group ($1.54 \times 10^4$).

Respective sera were further analyzed for the presence of virus neutralizing antibodies by plaque reduction assay (FIG. 13). Results showed the induction of neutralizing antibodies in guinea pigs upon immunization with HK1-GPgB(dTM). Respective data point to a minimum dose in the range of $\geq 1.54 \times 10^5$ of HK1-GpgB(dTM) required to elicit robust neutralizing antibodies. Based on the available data a dose of $1.54 \times 10^6$ FFU has been selected to study the protective effect of HK1-GpgB(dTM) in the congenital model of GPCMV infection (compare FIG. 23).

Characterization of rLCMV vectors expressing CMV pp65 In order to characterize the growth kinetics and the infectivity of the generated HK1-Hpp65 vector, LCMV GP expressing HEK 293 suspension cells were infected with HK1-Hpp65 at MOI=0.001. At defined timepoints (2 h, 24 h, 48 h, 72 h and 96 h) after infection samples of cell supernatant were drawn and analyzed by FFU assay and qPCR (FIG. 14).

Data in FIG. 14 show comparable replication kinetics, peak titers and infectivity of vector construct HK1-Hpp65 and control vector HK1-GFP, indicating that the pp65 antigen does not negatively influence vector growth or infectivity. Lower particle infectivity ratios were observed at later timepoints.

To confirm the expression of the pp65 antigen, LCMV GP expressing HEK 293 suspension cells were infected with HK1-Hpp65 or a negative control vector HK1-GFP and were harvested and lysed 96 h post infection and subsequently analyzed by Western Blotting using a monoclonal anti HCMV pp65 primary antibody and an appropriate alkaline phosphatase conjugated secondary antibody (FIG. 15).

Next the immunogenicity of HK1-Hpp65 and HK3-Hpp65 was analyzed in C57BL/6 mice to examine the effect of different LCMV vector backbones (HK1 (clone13), HK3 (MP)). C57BL/6 mice were vaccinated i.m. (50 µL/thigh; total 100 µL/mouse) with a target dose of $1 \times 10^4$ FFU of HK1-Hpp65 (Group 1) or HK3-Hpp65 (Group 2). Non-vaccinated mice were used as a control (Group 7). The induction of cellular immune responses was determined by flow cytometry on day 10 after injection, analysing cytokine production (IL-2, IFN-g, TNF-a) of CD4+ and CD8+ T cells. A Hpp65 peptide pool (based on Shedlock D. J. et al; Human Vaccines & Immunotherapeutics 2012) was used for the re-stimulation of splenocytes.

After single intramuscular injection HK1-Hpp65 and HK3-Hpp65 induced HCMV-specific CD8+ (and CD4+) T cell responses of considerable magnitude. The frequency of CD8+ T cell responses, analyzed 10 days after single injection, was higher than observed for CD4+ T cell responses (FIGS. 16 A and B, respectively). Based on the vector backbone (HK1 or HK3) there was no difference in the induction of CD4+ T cells observed. In contrast, higher CD8+ T cells responses were induced by HK1-pp65 compared to HK3-Hpp65. (C) HCMV-specific CD8+ T cell responses of similar magnitude were observed 10 days (day 66 of experiment) after single intramuscular injection (day 56 of experiment) with HK1-Hpp65 (Group 3) and HK3-Hpp65 (Group 4) in mice that had previously been immunized twice (8 and 4 weeks before; i.e. days 0 and 28 of experiment) with HK1-HgB(dTM). Respective results indicate that the induction of antigen-specific CD8+ T cell responses had not been impaired by vector-immunity due to prior immunization with the same vector backbone.

The effect of the rLCMV vector backbone, HK1 (Clone 13) or HK3 (MP), on the induction of an immune response was also evaluated using GPgBdTM (FIG. 17) and HgBdTM (FIG. 18) as transgenes.

To examine the effect of different vector backbones on the immunogenicity of GPgB-dTM construct, C57BL/6 mice were vaccinated i.m. on days 0 and 28 with a target dose of $1 \times 10^4$ FFU of respective vectors. Sera from individual animals were generated prior to each vaccine dose (days 0, 28) as well as four weeks (day 56) after the last (second) injection. All sera were tested for the level of GPgB-specific IgG antibodies by ELISA; ELISA data are expressed as geometric mean GPgB-specific IgG endpoint titer. Statistical analysis of data presented in FIG. 17 indicate that the response induced by HK1-GPgB(dTM) is superior to HK3-GPgB(dTM).

To examine the effect of different vector backbones on the immunogenicity of HgB-dTM construct, C57BL/6 mice were vaccinated i.m. on days 0 and 28 with a target dose of $1 \times 10^4$ FFU of respective vectors. Sera from individual animals were generated prior to each vaccine dose (days 0, 28) as well as four weeks (day 56) after the last (second) injection. All sera were tested for the level of HgB-specific IgG antibodies by ELISA; ELISA data are expressed as geometric mean HgB-specific IgG endpoint titer. Statistical analysis of data presented in FIG. 18 indicate that the response induced by HK1-HgB(dTM) and HK3-HgB(dTM) are not significantly different.

To determine the optimal LCMV strain to use with HEK 293 T cells, as shown in FIG. 19, HEK 293T cells were seeded in M6 well culture wells at a density of 500,000 cells per well. The next day, they were infected at a multiplicity of infection of 0.05 by MP, Pasteur, Clone 13 and WE54 strains. Supernatant was harvested at the indicated time point and viral titres were determined by immunofocus assay. Symbols represent the mean of two wells.

Immunogenicity of HK1-HgB(dCt) in rabbits New Zealand white rabbits were immunized by intramuscular injection with different concentrations ($2.0 \times 10^2$, $4.4 \times 10^4$ and $4.5 \times 10^6$ FFU/dose) of HK1-HgB(dCt) on days 0 and 28 of the experiment. Sera of immunized animals were collected on days 0, 28 and 42 of the experiment and anti-HgB antibody titers were analyzed by HgB-specific IgG ELISA.

ELISA data show that already after single intramuscular immunization (prime) higher doses ($4.4 \times 10^4$ and $4.5 \times 10^6$ FFU/dose) of HK1-HgB(dCt) induced anti-HgB antibody responses of considerable magnitude in a dose-dependent manner (FIG. 20). These responses could efficiently be augmented when the same vector was re-administered four weeks after prime. Injection of $4.5 \times 10^6$ FFU/dose of HK1-HgB(dCt) induced statistically significant higher antibody responses than a $4.4 \times 10^4$ FFU/dose at days 28 and 42.

Duration of antibody responses and comparison of different immunization schedules Different injection schedules were compared in regard to the level as well as the duration of antibody responses, induced upon immunization with HK1-HgB(H3-2), HK1-HgB(VSVG-1), and a recombinant gB protein mixed with adjuvant (FIG. 21A) or HK1-HgB (H3-2), HK1-HgB(VSVG-1), HgB(dTM), HK1-HgB(dCt) and a recombinant gB protein mixed with adjuvant (FIG. 21B). C57BL/6 mice were immunized intramuscularly with $1 \times 10^5$ FFU/dose of the respective vectors or 5 μg of a recombinant gB protein mixed 1:1 with adjuvant on days 0, 21 and 42 (FIG. 21A) or on days 0, 21 and 105 (FIG. 21B) of the experiment. Sera of immunized mice were collected on days 21, 42, 63, 91, 119, 147 and 175 (FIG. 21A) or on days 21, 42, 63, 84, 105 and 126 (FIG. 21B) of the experiment. Generated sera were tested for the level of anti-HCMVgB IgG antibodies by ELISA. Respective ELISA data indicate that maximum antibody levels can be achieved by two immunizations and that induced humoral responses are very long-lasting.

No negative interference by simultaneous injection of two vectors In order to investigate a potential interference of different LCMV vector constructs, the induction of B and CD8+ T cell responses was analyzed after immunization with HK1-HgB(dCt) alone, HK1-Hpp65 alone or simultaneous injection of HK1-HgB(dCt) and HK1-Hpp65. C57BL/6 mice were immunized intramuscularly with $9 \times 10^4$ FFU/dose of HK1-HgB(dCt) alone, $9 \times 10^4$ FFU/dose of HK1-Hpp65 alone or $9 \times 10^4$ FFU/dose of each HK1-HgB (dCt) and HK1-Hpp65 together on days 0 and 28. The induction of anti-HCMVgB antibodies (FIG. 22A) or pp65-specific CD8+ T cell responses (FIG. 22B) was monitored 49 days after the first injection. No significant difference in anti-HCMVgB antibody levels (FIG. 22A) or pp65-specific CD8+ T cell responses (FIG. 22B) could be observed between the monovalent (HK1-HgB(dCt) or HK1-Hpp65 only) and the bivalent (HK1-HgB(dCt) and HK1-Hpp65) vaccine indicating a lack of negative interference when two rLCMV vectors are mixed and co-injected.

LCMV vectors protect pups against congenital CMV infection in the guinea pig model The preclinical evaluation of the protective efficacy against congenital CMV infection of HCMV vaccines is made difficult by the species specificity of CMV. However, guinea pig CMV (GPCMV) does cross the placenta to cause a congenital infection similar to human infection (Bourne N et al, JID 1996; Schleiss M et al, JID 2003). In addition, the structure of the placenta as well as the trimester-like pregnancy period and the transplacental passage of maternal antibodies are similar in guinea pigs and humans. Based on these features the guinea pig model is the best available animal model for the evaluation of CMV vaccine efficacy against congenital infection.

Hartley guinea pigs were immunized intramuscularly three times on days 0, 21 and 42 with HK1-GPgB(dTM), HK1-GPpp65 or buffer (control group). About two weeks after the last vaccine dose, the immunized guinea pigs were allowed to breed. Pregnant guinea pigs were challenged at ~45 days of gestation with GPCMV and were subsequently monitored until delivery. Analysis of the survival of offspring revealed a significant reduction in pup mortality in dams immunized with HK1-GPgB(dTM) ($p=0.026$) or HK1-GPpp65 ($p=0.032$) alone prior to breeding (FIG. 23). Higher rates of protection can be anticipated after vaccination with a combination of rLCMV vector constructs expressing gB and pp65. See e.g., FIG. 28.

To determine the safety (virulence and virus replication) of rLCMV vectors, specific mice, highly susceptible to LCMV infection, have been inoculated intracerebrally on day 0 with HK3-Hpp65 or HK3-Mpp65, a replication-deficient LCMV vector derived from the MP strain of LCMV expressing the pp65 antigen from mouse CMV. Mice have subsequently been monitored for signs of illness. The presence of replicating virus has been analyzed in brain tissues collected on day 28 or earlier in case of illness.

No signs of illness and no virus replication could be observed in AG129 mice, which are deficient in IFN α/β and γ receptors and are thus highly susceptible to LCMV infection, 28 days after intracerebral inoculation of different doses of HK3-Hpp65 or HK3-Mpp65 (FIG. 24A). In contrast, AG129 mice inoculated with wildtype LCMV showed signs of disease and thus had to be euthanized on day 7.

Similarly, no virus replication could be observed in T and B cell deficient RAG−/−mice, which are also highly susceptible to LCMV infection, 28 days after intracerebral inoculation of different doses of HK3-Hpp65 or HK3-Mpp65 (FIG. 24B). High doses of replicating virus could be observed in RAG−/− mice inoculated with wildtype LCMV.

Immunogenicity of HK1-GPgB(dCt) and HK1-GPpp65 in Guinea Pigs

Hartley guinea pigs (18 animals/group) were immunized by intramuscular injection with $8 \times 10^5$ FFU/dose of HK1-GPgB(dCt) (group 1), $8 \times 10^5$ FFU/dose of HK1-GPpp65 (group 2), or $8 \times 10^5$ FFU/dose of each HK1-GPgB(dCt) and HK1-GPpp65 (group 3) on days 0, 31 and 72 (group 1)/days 0, 31 and 70 (group 2)/days 0, 34 and 70 (group 3) of the experiment. In addition, Hartley guinea pigs (18 animals/group) were immunized by subcutaneous injection with 50 μg of subunit gB protein, formulated in Complete Freund's Adjuvant (group 4) on days 0, 46 and 76. Sera of immunized animals were collected on days 0, 28, 52, 103 and 155 of the experiment and anti-GPgB antibody titers were analyzed by GPgB-specific IgG ELISA using a sera pool with assigned anti-gB antibody titer as a reference standard.

ELISA data show that already after single immunization HK1-GPgB(dCt) induced anti-GPgB antibody responses of considerable magnitude (FIG. 25). These responses could be efficiently augmented when the same vector was re-administered one month after the first vaccination. Anti-GPgB antibody responses induced by immunization with HK1-GPgB(dCt) alone were in a similar range as those induced after vaccination with HK1-GPgB(dCt) in combination with HK1-GPpp65. Importantly, significantly higher levels of anti-GPgB antibodies were stimulated after immunization with HK1-GPgB(dCt) than after vaccination with a subunit gB protein formulated in Complete Freund's Adjuvant.

Neutralization Data

Respective sera were further analyzed for the presence of virus neutralizing antibodies by Neutralization Assay in GPL cells (FIG. 26). Results showed the induction of neutralizing antibodies in guinea pigs upon immunization with HK1-GPgB(dCt) alone (group 1) or HK1-GPgB(dCt) in combination with HK1-GPpp65 (group 3). Consistent with the ELISA data (FIG. 25) HK1-GPgB(dCt) induced significantly (P<0.0001, unpaired t test) higher levels of neutralizing antibodies than a subunit gB protein formulated in Complete Freund's Adjuvant. Unexpectedly, the combination of HK1-GPgB(dCt) with HK1-GPpp65 (Group 3) elicited significantly (P=0.0003, unpaired t test) more potently neutralizing sera than HK1-GPgB(dCt) alone (Group 1).

T Cell Data

In order to analyze the induction of pp65-specific T cell responses in vaccinated animals, splenocytes were isolated from Hartley guinea pigs immunized intramuscularly with $8 \times 10^5$ FFU/dose of HK1-GFP (group 1), $8 \times 10^5$ FFU/dose of HK1-GPpp65 (group 2) or $8 \times 10^5$ FFU/dose of each HK1-GPgB(dCt) and HK1-GPpp65 (group 3). Three animals from each vaccine group (group 1, group 2, and group 3) were sacrificed after 2 doses of vaccine (animals were sacrificed at 43, 40, and 37 days post-second dose of vaccine, respectively). Three additional animals from each vaccine group were sacrificed at 7 days post-dose 3 in order to analyze whether a third vaccine dose further augments the pp65-specific T cell response, compared to two doses of vaccine.

Isolated splenocytes were analyzed by ELISPOT assay using pools of pp65 peptides for re-stimulation. Respective peptides (Sigma-Aldrich, St. Louis, Mo.) were designed to span pp65 in 9 amino acids long fragments with 5 amino acid overlaps (140 total peptides). Peptides were allocated into pools containing 11 or 12 peptides. The magnitude of each animal's response is the cumulative difference ("area under the curve") between the peptide re-stimulated splenocytes and splenocytes restimulated with the DMSO (vehicle) control, for each peptide pool.

As shown in FIG. 27 A, pp65-specific IFN-γ producing splenocytes were induced in animals vaccinated with HK1-GPpp65 alone (group 2) as well as in animals vaccinated with HK1-GPpp65 in combination with HK1-GPgB(dCt) (group 3). In both vaccine groups, higher average numbers of pp65-specific IFN-γ producing splenocytes were observed after three vaccine doses compared to two doses.

While the small group sizes (n=3) prevent direct statistical comparison between vaccine groups after either 2 or 3 doses of vaccine, statistical comparisons can be made between combined vaccination groups, i.e., combining the data from the 2 dose group and 3 dose group together for each vaccine (group 1, group 2, and group 3) (FIG. 27 B). Respective analysis revealed that animals vaccinated with HK1-GPpp65 (group 2) had a significantly increased number of pp65-specific splenocytes per animal compared to HK1-GFP controls (group 1). Similarly, the HK1-GPgB(dCt)/HK1-GPpp65 vaccine group (group 3) also had a significantly increased number of pp65-specific splenocytes compared to HK1-GFP controls (group 1). No statistically significant difference between the vaccine groups 2 and 3 could be observed indicating that the presence of gB did not interfere with the pp65 response.

Protection Data

LCMV vectors protect pups against congenital CMV infection in the guinea pig model. The preclinical evaluation of the protective efficacy against congenital CMV infection of HCMV vaccines is made difficult by the species specificity of CMV. However, guinea pig CMV (GPCMV) does cross the placenta to cause a congenital infection similar to human infection (Bourne N et al, JID 1996; Schleiss M et al, JID 2003). In addition, the structure of the placenta as well as the trimester-like pregnancy period and the transplacental passage of maternal antibodies are similar in guinea pigs and humans. Based on these features the guinea pig model is the best available animal model for the evaluation of CMV vaccine efficacy against congenital infection.

Hartley guinea pigs (18 animals/group) were immunized intramuscularly three times (on days 0, ~30 and ~70) with $8 \times 10^5$ FFU/dose of HK1-GFP (group 1), $8 \times 10^5$ FFU/dose of HK1-GPgB(dCt) (group 2), $8 \times 10^5$ FFU/dose of HK1-GPpp65 (group 3) or $8 \times 10^5$ FFU/dose of each HK1-GPgB(dCt) and HK1-GPpp65 (group 4). Approximately one month after the last vaccine dose, the immunized guinea pigs were allowed to breed. Pregnancies in guinea pig dams were confirmed and monitored by palpitation. Pregnant dams were challenged in the third trimester of gestation with GPCMV and were subsequently monitored until delivery. Analysis of the survival of offspring (FIG. 28) revealed a reduction in pup mortality in dams immunized with HK1-GPgB(dCt) or HK1-GPpp65 alone compared to the control group. Vaccination with HK1-GPgB(dCt) conferred better protection than HK1-GPpp65. Even higher rates of protection could be observed after vaccination with a combination of HK1-GPgB(dCt) and HK1-GPpp65. A high mortality rate in the control group (group 1) indicates stringent challenge conditions.

EQUIVALENTS AND INCORPORATION BY REFERENCE

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following embodiments. All references (including patent applications, patents, and publications) cited herein are incorporated herein by reference in their entireties and for all purposes to the same extent as if each individual publication or patent or patent application was specifically and individually indicated to be incorporated by reference in its entirety for all purposes.

What is claimed:

1. A method of inducing an immune response against cytomegalovirus (CMV) infection in a patient, wherein said method comprises administering to the patient a first infectious, replication-deficient arenavirus viral vector engineered to contain a genome with the ability to amplify and express its genetic information in infected cells but unable to produce further infectious progeny particles in normal, not genetically engineered cells,
   wherein the arenavirus open reading frame encoding the glycoprotein (GP) is removed and replaced by a first nucleotide sequence encoding a cytomegalovirus glycoprotein B (gB) with a truncation of the cytoplasmic domain and/or transmembrane domain or an antigenic fragment thereof,
   wherein the first arenavirus viral vector is based on lymphocytic choriomeningitis virus.

2. The method of claim 1, further comprising administering to the patient a second infectious, replication-deficient arenavirus viral vector engineered to contain a genome with the ability to amplify and express its genetic information in infected cells but unable to produce further infectious progeny particles in normal, not genetically engineered cells,
   wherein the arenavirus open reading frame encoding the glycoprotein (GP) of the second arenavirus viral vector is removed and replaced by a second nucleotide sequence encoding a cytomegalovirus tegument protein pp65 or an antigenic fragment thereof,
   wherein the second arenavirus viral vector is based on lymphocytic choriomeningitis virus.

3. The method of claim 1, wherein the first nucleotide sequence encodes a cytomegalovirus gB with a truncation of the cytoplasmic domain and/or transmembrane domain comprising an amino acid sequence that is: (a) at least 80% identical to amino acids 1 to 771 of SEQ ID NO: 3 or amino acids 1 to 772 of SEQ ID NO: 60, and comprises a deletion of the cytoplasmic domain between amino acids 772 to 906 of SEQ ID NO: 3 or between amino acids 773 to 907 of SEQ ID NO: 60, respectively; or (b) at least 80% identical to SEQ ID NO: 6, SEQ ID NO: 9, SEQ ID NO: 12, SEQ ID NO: 15, SEQ ID NO: 18, or SEQ ID NO: 63.

4. The method of claim 1, wherein the truncation of the cytoplasmic domain is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or 134 amino acids long.

5. The method of claim 2, wherein the administration of the first arenavirus viral vector or the second arenavirus viral vector, or both, is intramuscular.

6. The method of claim 3, wherein the cytomegalovirus gB with a truncation of the cytoplasmic domain comprises an amino acid sequence that is 100% identical to SEQ ID NO: 18.

7. The method of claim 2, wherein the cytomegalovirus tegument protein pp65 comprises an amino acid sequence that is 100% identical to SEQ ID NO: 36.

8. The method of claim 3, wherein the cytomegalovirus gB with a truncation of the cytoplasmic domain comprises an amino acid sequence that is at least 80% identical to SEQ ID NO: 18.

9. The method of claim 3, wherein the cytomegalovirus gB with a truncation of the cytoplasmic domain comprises an amino acid sequence that is at least 85% identical to SEQ ID NO: 18.

10. The method of claim 3, wherein the cytomegalovirus gB with a truncation of the cytoplasmic domain comprises an amino acid sequence that is at least 90% identical to SEQ ID NO: 18.

11. The method of claim 3, wherein the cytomegalovirus gB with a truncation of the cytoplasmic domain comprises an amino acid sequence that is at least 95% identical to SEQ ID NO: 18.

12. The method of claim 3, wherein the cytomegalovirus gB with a truncation of the cytoplasmic domain comprises an amino acid sequence that is at least 98% identical to SEQ ID NO: 18.

13. The method of claim 3, wherein the cytomegalovirus gB with a truncation of the cytoplasmic domain consists of an amino acid sequence that is 100% identical to SEQ ID NO: 18.

14. The method of claim 1, wherein the first nucleotide sequence encodes a cytomegalovirus gB wherein: (i) the cytoplasmic domain of the cytomegalovirus gB has been deleted; (ii) the transmembrane domain of the cytomegalovirus gB has been deleted; or (iii) the cytoplasmic domain and transmembrane domain of the cytomegalovirus gB have been deleted.

15. The method of claim 2, wherein the cytomegalovirus tegument protein pp65 comprises an amino acid sequence that is at least 80% identical to SEQ ID NO: 36.

16. The method of claim 2, wherein the cytomegalovirus tegument protein pp65 comprises an amino acid sequence that is at least 85% identical to SEQ ID NO: 36.

17. The method of claim 2, wherein the cytomegalovirus tegument protein pp65 comprises an amino acid sequence that is at least 90% identical to SEQ ID NO: 36.

18. The method of claim 2, wherein the cytomegalovirus tegument protein pp65 comprises an amino acid sequence that is at least 95% identical to SEQ ID NO: 36.

19. The method of claim 2, wherein the cytomegalovirus tegument protein pp65 comprises an amino acid sequence that is at least 98% identical to SEQ ID NO: 36.

20. The method of claim 2, wherein the cytomegalovirus tegument protein pp65 consists of an amino acid sequence that is 100% identical to SEQ ID NO: 36.

21. The method of claim 1, wherein the first arenavirus viral vector is based on lymphocytic choriomeningitis virus Clone 13 strain.

22. The method of claim 2, wherein the second arenavirus viral vector is based on lymphocytic choriomeningitis virus Clone 13 strain.

23. The method of claim 2, wherein the first arenavirus viral vector and the second arenavirus viral vector are administered separately.

24. The method of claim 2, wherein the first arenavirus viral vector and the second arenavirus viral vector are administered simultaneously.

25. A method of inducing an immune response against CMV infection in a patient, wherein said method comprises administering to the patient:
a) a first infectious, replication-deficient arenavirus viral vector engineered to contain a genome with the ability to amplify and express its genetic information in infected cells but unable to produce further infectious progeny particles in normal, not genetically engineered cells, wherein the arenavirus open reading frame encoding the glycoprotein (GP) is removed and replaced by a nucleotide sequence encoding a cytomegalovirus glycoprotein B (gB), wherein the cytomegalovirus gB has a truncation of the cytoplasmic domain; and
b) a second infectious, replication-deficient arenavirus viral vector engineered to contain a genome with the ability to amplify and express its genetic information in infected cells but unable to produce further infectious progeny particles in normal, not genetically engineered cells, wherein the arenavirus open reading frame encoding the glycoprotein (GP) is removed and replaced by a nucleotide sequence encoding a cytomegalovirus tegument protein pp65,
wherein the first arenavirus viral vector, or the second arenavirus viral vector, or both are based on lymphocytic choriomeningitis virus.

26. The method of claim 25, wherein the administration is intramuscular.

27. The method of claim 25, wherein the cytomegalovirus gB with a truncation of the cytoplasmic domain comprises an amino acid sequence that is at least 80% identical to SEQ ID NO: 18.

28. The method of claim 25, wherein the cytomegalovirus gB with a truncation of the cytoplasmic domain comprises an amino acid sequence that is at least 85% identical to SEQ ID NO: 18.

29. The method of claim 25, wherein the cytomegalovirus gB with a truncation of the cytoplasmic domain comprises an amino acid sequence that is at least 90% identical to SEQ ID NO: 18.

30. The method of claim 25, wherein the cytomegalovirus gB with a truncation of the cytoplasmic domain comprises an amino acid sequence that is at least 95% identical to SEQ ID NO: 18.

31. The method of claim 25, wherein the cytomegalovirus gB with a truncation of the cytoplasmic domain comprises an amino acid sequence that is at least 98% identical to SEQ ID NO: 18.

32. The method of claim 25, wherein the cytomegalovirus gB with a truncation of the cytoplasmic domain consists of an amino acid sequence that is 100% identical to SEQ ID NO: 18.

33. The method of claim 25, wherein the cytomegalovirus tegument protein pp65 comprises an amino acid sequence that is at least 80% identical to SEQ ID NO: 36.

34. The method of claim 25, wherein the cytomegalovirus tegument protein pp65 comprises an amino acid sequence that is at least 85% identical to SEQ ID NO: 36.

35. The method of claim 25, wherein the cytomegalovirus tegument protein pp65 comprises an amino acid sequence that is at least 90% identical to SEQ ID NO: 36.

36. The method of claim 25, wherein the cytomegalovirus tegument protein pp65 comprises an amino acid sequence that is at least 95% identical to SEQ ID NO: 36.

37. The method of claim 25, wherein the cytomegalovirus tegument protein pp65 comprises an amino acid sequence that is at least 98% identical to SEQ ID NO: 36.

38. The method of claim 25, wherein the cytomegalovirus tegument protein pp65 consists of an amino acid sequence that is 100% identical to SEQ ID NO: 36.

39. The method of claim 25, wherein the first arenavirus viral vector, or the second arenavirus viral vector, or both are based on lymphocytic choriomeningitis virus Clone 13 strain.

40. The method of claim 25, wherein the first arenavirus viral vector and the second arenavirus viral vector are administered separately.

41. The method of claim 25, wherein the first arenavirus viral vector and the second arenavirus viral vector are administered simultaneously.

42. A method of inducing an immune response against CMV infection in a patient, wherein said method comprises administering to the patient:
   a) a first infectious, replication-deficient arenavirus viral vector engineered to contain a genome with the ability to amplify and express its genetic information in infected cells but unable to produce further infectious progeny particles in normal, not genetically engineered cells, wherein the arenavirus open reading frame encoding the glycoprotein (GP) is removed and replaced by a nucleotide sequence encoding the amino acid sequence of SEQ ID NO: 18; and
   b) a second infectious, replication-deficient arenavirus viral vector engineered to contain a genome with the ability to amplify and express its genetic information in infected cells but unable to produce further infectious progeny particles in normal, not genetically engineered cells, wherein the arenavirus open reading frame encoding the glycoprotein (GP) is removed and replaced by a nucleotide sequence encoding the amino acid sequence of SEQ ID NO: 36,
wherein the first arenavirus viral vector and the second arenavirus viral vector are administered simultaneously and the administration is intramuscular,
wherein the first arenavirus viral vector, or the second arenavirus viral vector, or both are based on lymphocytic choriomeningitis virus.

43. The method of claim 42, wherein the first arenavirus viral vector, or the second arenavirus viral vector, or both are based on lymphocytic choriomeningitis virus Clone 13 strain.

44. The method of claim 1, wherein the administration is intramuscular.

45. The method of claim 3, wherein the cytomegalovirus gB with a truncation of the cytoplasmic domain comprises a deletion of the cytoplasmic domain between amino acids 772 to 906 of SEQ ID NO: 3.

46. The method of claim 3, wherein the cytomegalovirus gB with a truncation of the cytoplasmic domain comprises a deletion of the cytoplasmic domain between amino acids 773 to 907 of SEQ ID NO: 60.

47. The method of claim 3, wherein the cytomegalovirus gB with a truncation of the cytoplasmic domain comprises an amino acid sequence consisting of the amino acid sequence of SEQ ID NO: 18.

48. The method of claim 2, wherein the cytomegalovirus tegument protein pp65 comprises an amino acid sequence consisting of the amino acid sequence of SEQ ID NO: 36.

49. The method of claim 1, wherein the method is treating a cytomegalovirus infection in the patient.

50. The method of claim 1, wherein the method is preventing a disease associated with a cytomegalovirus infection in the patient.

51. The method of claim 25, wherein the method is treating a cytomegalovirus infection in the patient.

52. The method of claim 25, wherein the method is preventing a disease associated with a cytomegalovirus infection in the patient.

53. The method of claim 42, wherein the method is treating a cytomegalovirus infection in the patient.

54. The method of claim 42, wherein the method is preventing a disease associated with a cytomegalovirus infection in the patient.

55. The method of claim 42, wherein the normal, not genetically engineered cells do not express the glycoprotein (GP) of the first and second arenavirus viral vector.

* * * * *

```
                        SEQUENCE LISTING

<160> NUMBER OF SEQ ID NOS: 63

<210> SEQ ID NO 1
<211> LENGTH: 4601
<212> TYPE: DNA
<213> ORGANISM: Artificial Sequence
<220> FEATURE:
<223> OTHER INFORMATION: HK1-HgB(FL)

<400> SEQUENCE: 1
gcgcaccggg gatcctaggc tttttggatt gcgctttcct ctagatcaac tgggtgtcag     60
gccctatcct acagaaggat ggaatccaga atctggtgcc tggtagtctg cgttaacctg    120
tgtatcgtct gtctgggtgc tgcggtttcc tcttctagta cttcccatgc aacttcttct    180
actcacaatg gaagccatac ttctcgtacg acgtctgctc aaacccggtc agtctattct    240
caacacgtaa cgtcttctga agccgtcagt catagagcca acgagactat ctacaacact    300
accctcaagt acggagatgt ggtgggagtc aacactacca agtaccccta tcgcgtgtgt    360
tctatggccc agggtacgga tcttattcgc tttgaacgta atatcatctg cacctcgatg    420
aagcctatca atgaagactt ggatgagggc atcatggtgg tctacaagcg caacatcgtg    480
gcgcacacct taaggtacg ggtctaccaa aaggttttga cgtttcgtcg tagctacgct    540
tacatctaca ccacttatct gctgggcagc aatacggaat acgtggcgcc tcctatgtgg    600
gagattcatc acatcaacaa gtttgctcaa tgctacagtt cctacagccg cgttatagga    660
ggcacggttt tcgtggcata tcatagggac agttatgaaa acaaaaccat gcaattaatt    720
cccgacgatt attccaacac ccacagtacc cgttacgtga cggtcaagga tcagtggcac    780
agccgcggca gcacctggct ctatcgtgag acctgtaatc tgaactgtat gctgaccatc    840
actactgcgc gctccaagta tccttatcat tttttgcaa cttccacggg tgatgtggtt    900
tacatttctc ctttctacaa cggaaccaat cgcaatgcca gctactttgg agaaaacgcc    960
gacaagtttt tcatttccc gaactacacc atcgtttccg actttggaag acccaacgct   1020
gcgccagaaa cccataggtt ggtggctttt ctcgaacgtg ccgactcggt gatctcttgg   1080
gatatacagg acgagaagaa tgtcacctgc cagctcacct tctgggaagc ctcggaacgt   1140
actatccgtt ccgaagccga agactcgtac cacttttctt ctgccaaaat gactgcaact   1200
tttctgtcta agaaacaaga agtgaacatg tccgactccg cgctggactg cgtacgtgat   1260
gaggctataa ataagttaca gcagatttt aatacttcat acaatcaaac atatgaaaaa   1320
tacggaaacg tgtccgtctt cgaaaccagc ggcggtctgg tggtgttctg gcaaggcatc   1380
aagcaaaaat ctttggtgga attggaacgt ttggccaatc gatccagtct gaatatcact   1440
cataggacca gaagaagtac gagtgacaat aatcaactc atttgtccag catggaatcg   1500
gtgcacaatc tggtctacgc ccagctgcag ttcacctatg acacgttgcg cggttacatc   1560
```

```
aaccgggcgc tggcgcaaat cgcagaagcc tggtgtgtgg atcaacggcg caccctagag    1620
gtcttcaagg aactcagcaa gatcaacccg tcagccattc tctcggccat ttacaacaaa    1680
ccgattgccg cgcgtttcat gggtgatgtc ttgggcctgg ccagctgcgt gaccatcaac    1740
caaaccagcg tcaaggtgct gcgtgatatg aacgtgaagg aatcgccagg acgctgctac    1800
tcacgacccg tggtcatctt taatttcgcc aacagctcgt acgtgcagta cggtcaactg    1860
ggcgaggaca acgaaatcct gttgggcaac caccgcactg aggaatgtca gcttcccagc    1920
ctcaagatct tcatcgccgg gaactcggcc tacgagtacg tggactacct cttcaaacgc    1980
atgattgacc tcagcagtat ctccaccgtc gacagcatga tcgccctgga tatcgacccg    2040
ctggaaaata ccgacttcag ggtactggaa ctttactcgc agaaagagct gcgttccagc    2100 aacgttttg acctcgaaga gatcatgcgc gaattcaact cgtacaagca gcgggtaaag    2160
tacgtggagg acaaggtagt cgacccgcta ccgccctacc tcaagggtct ggacgacctc    2220
atgagcggcc tggcgccgc gggaaaggcc gttggcgtag ccattggggc cgtgggtggc    2280
gcggtggcct ccgtggtcga aggcgttgcc accttcctca aaaaccccctt cggagccttc    2340 accatcatcc tcgtggccat agccgtagtc attatcactt atttgatcta tactcgacag    2400
cggcgtctgt gcacgcagcc gctgcagaac ctctttccct atctggtgtc cgccgacggg    2460
accaccgtga cgtcgggcag caccaaagac acgtcgttac aggctccgcc ttcctacgag    2520
gaaagtgttt ataattctgg tcgcaaagga ccgggaccac cgtcgtctga tgcatccacg    2580
gcggctccgc cttacaccaa cgagcaggct taccagatgc ttctggccct ggcccgtctg    2640
gacgcagagc agcgagcgca gcagaacggt acagattctt tggacggaca gactggcacg    2700
caggacaagg gacagaagcc taacctgcta gaccggctgc gacatcgcaa aaacggctac    2760
agacacttga agactccga cgaagaagag aacgtctgaa gaacagcgcc tccctgactc    2820
tccacctcga agaggtgga gagtcaggga ggcccagagg gtcttagagt gtcacaacat    2880
ttgggcctct aaaaattagg tcatgtggca gaatgttgtg aacagttttc agatctggga    2940
gccttgcttt ggaggcgctt tcaaaaatga tgcagtccat gagtgcacag tgcggggtga    3000
tctctttctt cttttttgtcc cttactattc cagtatgcat cttacacaac cagccatatt    3060
tgtcccacac tttatcttca tactccctcg aagcttccct ggtcatttca acatcgataa    3120
gcttaatgtc cttcctattt tgtgagtcca gaagctttct gatgtcatcg gagccttgac    3180
agcttagaac catcccctgc ggaagagcac ctataactga cgaggtcaac ccgggttgcg    3240
cattgaagag gtcggcaaga tccatgccgt gtgagtactt ggaatcttgc ttgaattgtt    3300
tttgatcaac gggttccctg taaaagtgta tgaactgccc gttctgtggt tggaaaattg    3360
ctatttccac tggatcatta aatctaccct caatgtcaat ccatgtagga gcgttggggt    3420
caattcctcc catgaggtct tttaaaagca ttgtctggct gtagcttaag cccacctgag    3480
gtggacctgc tgctccaggc gctggcctgg gtgagttgac tgcaggtttc tcgcttgtga    3540
gatcaattgt tgtgttttcc catgctctcc ccacaatcga tgttctacaa gctatgtatg    3600
gccatccttc acctgaaagg caaactttat agaggatgtt ttcataaggg ttcctgtccc    3660
caacttggtc tgaaacaaac atgttgagtt ttctcttggc cccgagaact gccttcaaga    3720
gatcctcgct gttgcttggc ttgatcaaaa ttgactctaa catgttaccc ccatccaaca    3780
gggctgcccc tgccttcacg gcagcaccaa gactaaagtt atagccagaa atgttgatgc    3840
tggactgctg ttcagtgatg acccccagaa ctgggtgctt gtctttcagc cttttcaagat    3900 cattaagatt tggatacttg actgtgtaaa gcaagccaag gtctgtgagc gcttgtacaa    3960
```

```
cgtcattgag cggagtctgt gactgtttgg ccatacaagc catagttaga cttggcattg   4020
tgccaaattg attgttcaaa agtgatgagt ctttcacatc ccaaactctt accacaccac   4080
ttgcaccctg ctgaggcttt ctcatcccaa ctatctgtag gatctgagat ctttggtcta   4140
gttgctgtgt tgttaagttc cccatatata ccctgaagc ctgggggcctt tcagacctca   4200 tgatcttggc cttcagcttc tcaaggtcag ccgcaagaga catcagttct tctgcactga   4260
gcctccccac tttcaaaaca ttcttctttg atgttgactt taaatccaca agagaatgta   4320
cagtctggtt gagacttctg agtctctgta ggtctttgtc atctctcttt tccttcctca   4380
tgatcctctg aacattgctg acctcagaga agtccaaccc attcagaagg ttggttgcat   4440
ccttaatgac agcagccttc acatctgatg tgaagctctg caattctctt ctcaatgctt   4500
gcgtccattg gaagctctta acttccttag acaaggacat cttgttgctc aatggtttct   4560
caagacaaat gcgcaatcaa atgcctagga tccactgtgc g                      4601
```

<210> SEQ ID NO 2
<211> LENGTH: 2721
<212> TYPE: DNA
<213> ORGANISM: Artificial Sequence
<220> FEATURE:
<223> OTHER INFORMATION: HgB(FL) cDNA sequence

<400> SEQUENCE: 2

```
atggaatcca gaatctggtg cctggtagtc tgcgttaacc tgtgtatcgt ctgtctgggt     60
gctgcggttt cctcttctag tacttcccat gcaacttctt ctactcacaa tggaagccat    120
acttctcgta cgacgtctgc tcaaacccgg tcagtctatt ctcaacacgt aacgtcttct    180
gaagccgtca gtcatagagc caacgagact atctacaaca ctaccctcaa gtacggagat    240
gtggtgggag tcaacactac caagtacccc tatcgcgtgt gttctatggc caggtacg     300 gatcttattc gctttgaacg taatatcatc tgcacctcga tgaagcctat caatgaagac    360
ttggatgagg gcatcatggt ggtctacaag cgcaacatcg tggcgcacac ctttaaggta    420
cgggtctacc aaaaggtttt gacgtttcgt cgtagctacg cttacatcta caccacttat    480
ctgctgggca gcaatacgga atacgtggcg cctcctatgt gggagattca tcacatcaac    540
aagtttgctc aatgctacag ttcctacagc cgcgttatag aggcacggt tttcgtggca    600 tatcataggg acagttatga aaacaaaacc atgcaattaa ttcccgacga ttattccaac    660
acccacagta cccgttacgt gacggtcaag gatcagtggc acagccgcgg cagcacctgg    720
ctctatcgtg agacctgtaa tctgaactgt atgctgacca tcactactgc gcgctccaag    780
tatccttatc atttttttgc aacttccacg ggtgatgtgg tttacatttc tccttctac    840 aacggaacca atcgcaatgc cagctacttt ggagaaaacg ccgacaagtt tttcattttc    900
ccgaactaca ccatcgtttc cgactttgga agacccaacg ctgcgccaga aacccatagg    960
ttggtggctt tctctgaacg tgccgactcg gtgatctctt gggatataca ggacgagaag   1020
aatgtcacct gccagctcac cttctgggaa gcctcggaac gtactatccg ttccgaagcc   1080
gaagactcgt accactttc ttctgccaaa atgactgcaa cttttctgtc taagaaacaa   1140
gaagtgaaca tgtccgactc cgcgctgac tgcgtacgtg atgaggctat aaataagtta   1200
cagcagattt tcaatacttc atacaatcaa acatatgaaa aatacggaaa cgtgtccgtc   1260
ttcgaaacca gcgcggtct ggtggtgttc tggcaaggca tcaagcaaaa atctttggtg   1320
gaattggaac gtttggccaa tcgatccagt ctgaatatca ctcataggac cagaagaagt   1380
```

```
acgagtgaca ataatacaac tcatttgtcc agcatggaat cggtgcacaa tctggtctac   1440
gcccagctgc agttcaccta tgacacgttg cgcggttaca tcaaccgggc gctggcgcaa   1500
atcgcagaag cctggtgtgt ggatcaacgg cgcaccctag aggtcttcaa ggaactcagc   1560
aagatcaacc cgtcagccat tctctcggcc atttacaaca aaccgattgc cgcgcgtttc   1620
atgggtgatg tcttgggcct ggccagctgc gtgaccatca accaaaccag cgtcaaggtg   1680
ctgcgtgata tgaacgtgaa ggaatcgcca ggacgctgct actcacgacc cgtggtcatc   1740
tttaatttcg ccaacagctc gtacgtgcag tacggtcaac tgggcgagga caacgaaatc   1800
ctgttgggca accaccgcac tgaggaatgt cagcttccca gcctcaagat cttcatcgcc   1860
gggaactcgg cctacgagta cgtggactac ctcttcaaac gcatgattga cctcagcagt   1920
atctccaccg tcgacagcat gatcgccctg gatatcgacc cgctggaaaa taccgacttc   1980
agggtactgg aactttactc gcagaaagag ctgcgttcca gcaacgtttt tgacctcgaa   2040
gagatcatgc gcgaattcaa ctcgtacaag cagcgggtaa agtacgtgga ggacaaggta   2100
gtcgacccgc taccgcccta cctcaagggt ctggacgacc tcatgagcgg cctgggcgcc   2160
gcgggaaagg ccgttggcgt agccattggg gccgtgggtg gcgcggtggc ctccgtggtc   2220
gaaggcgttg ccaccttcct caaaaacccc ttcggagcct tcaccatcat cctcgtggcc   2280
atagccgtag tcattatcac ttatttgatc tatactcgac agcggcgtct gtgcacgcag   2340
ccgctgcaga acctctttcc ctatctggtg tccgccgacg ggaccaccgt gacgtcgggc   2400
agcaccaaag acacgtcgtt acaggctccg ccttcctacg aggaaagtgt ttataattct   2460
ggtcgcaaag gaccgggacc accgtcgtct gatgcatcca cggcggctcc gccttacacc   2520
aacgagcagg cttaccagat gcttctggcc ctggcccgtc tggacgcaga gcagcgagcg   2580
cagcagaacg gtacagattc tttggacgga cagactggca cgcaggacaa gggacagaag   2640
cctaacctgc tagaccggct gcgacatcgc aaaaacggct acagacactt gaaagactcc   2700
gacgaagaag agaacgtctg a                                             2721
```

<210> SEQ ID NO 3
<211> LENGTH: 906
<212> TYPE: PRT
<213> ORGANISM: Artificial Sequence
<220> FEATURE:
<223> OTHER INFORMATION: HgB(FL) amino acid sequence

<400> SEQUENCE: 3

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125
```

-continued

```
Tyr Lys Arg Asn Ile Val Ala His Thr Phe Lys Val Arg Val Tyr Gln
    130                 135                 140
Lys Val Leu Thr Phe Arg Arg Ser Tyr Ala Tyr Ile Tyr Thr Thr Tyr
145                 150                 155                 160
Leu Leu Gly Ser Asn Thr Glu Tyr Val Ala Pro Pro Met Trp Glu Ile
                165                 170                 175
His His Ile Asn Lys Phe Ala Gln Cys Tyr Ser Ser Tyr Ser Arg Val
            180                 185                 190
Ile Gly Gly Thr Val Phe Val Ala Tyr His Arg Asp Ser Tyr Glu Asn
        195                 200                 205
Lys Thr Met Gln Leu Ile Pro Asp Asp Tyr Ser Asn Thr His Ser Thr
210                 215                 220
Arg Tyr Val Thr Val Lys Asp Gln Trp His Ser Arg Gly Ser Thr Trp
225                 230                 235                 240
Leu Tyr Arg Glu Thr Cys Asn Leu Asn Cys Met Leu Thr Ile Thr Thr
                245                 250                 255
Ala Arg Ser Lys Tyr Pro Tyr His Phe Phe Ala Thr Ser Thr Gly Asp
            260                 265                 270
Val Val Tyr Ile Ser Pro Phe Tyr Asn Gly Thr Asn Arg Asn Ala Ser
        275                 280                 285
Tyr Phe Gly Glu Asn Ala Asp Lys Phe Phe Ile Phe Pro Asn Tyr Thr
290                 295                 300
Ile Val Ser Asp Phe Gly Arg Pro Asn Ala Ala Pro Glu Thr His Arg
305                 310                 315                 320
Leu Val Ala Phe Leu Glu Arg Ala Asp Ser Val Ile Ser Trp Asp Ile
                325                 330                 335
Gln Asp Glu Lys Asn Val Thr Cys Gln Leu Thr Phe Trp Glu Ala Ser
            340                 345                 350
Glu Arg Thr Ile Arg Ser Glu Ala Glu Asp Ser Tyr His Phe Ser Ser
        355                 360                 365
Ala Lys Met Thr Ala Thr Phe Leu Ser Lys Lys Gln Glu Val Asn Met
370                 375                 380
Ser Asp Ser Ala Leu Asp Cys Val Arg Asp Glu Ala Ile Asn Lys Leu
385                 390                 395                 400
Gln Gln Ile Phe Asn Thr Ser Tyr Asn Gln Thr Tyr Glu Lys Tyr Gly
                405                 410                 415
Asn Val Ser Val Phe Glu Thr Ser Gly Gly Leu Val Val Phe Trp Gln
            420                 425                 430
Gly Ile Lys Gln Lys Ser Leu Val Glu Leu Glu Arg Leu Ala Asn Arg
        435                 440                 445
Ser Ser Leu Asn Ile Thr His Arg Thr Arg Ser Thr Ser Asp Asn
450                 455                 460
Asn Thr Thr His Leu Ser Ser Met Glu Ser Val His Asn Leu Val Tyr
465                 470                 475                 480
Ala Gln Leu Gln Phe Thr Tyr Asp Thr Leu Arg Gly Tyr Ile Asn Arg
                485                 490                 495
Ala Leu Ala Gln Ile Ala Glu Ala Trp Cys Val Asp Gln Arg Arg Thr
            500                 505                 510
Leu Glu Val Phe Lys Glu Leu Ser Lys Ile Asn Pro Ser Ala Ile Leu
        515                 520                 525
Ser Ala Ile Tyr Asn Lys Pro Ile Ala Ala Arg Phe Met Gly Asp Val
530                 535                 540
```

```
Leu Gly Leu Ala Ser Cys Val Thr Ile Asn Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
                580                 585                 590

Gln Leu Gly Glu Asp Asn Glu Ile Leu Leu Gly Asn His Arg Thr Glu
            595                 600                 605

Glu Cys Gln Leu Pro Ser Leu Lys Ile Phe Ile Ala Gly Asn Ser Ala
        610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
                660                 665                 670

Ser Ser Asn Val Phe Asp Leu Glu Glu Ile Met Arg Glu Phe Asn Ser
            675                 680                 685

Tyr Lys Gln Arg Val Lys Tyr Val Glu Asp Lys Val Val Asp Pro Leu
        690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
                740                 745                 750

Ala Phe Thr Ile Ile Leu Val Ala Ile Ala Val Val Ile Ile Thr Tyr
            755                 760                 765

Leu Ile Tyr Thr Arg Gln Arg Arg Leu Cys Thr Gln Pro Leu Gln Asn
        770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
                805                 810                 815

Val Tyr Asn Ser Gly Arg Lys Gly Pro Gly Pro Pro Ser Ser Asp Ala
                820                 825                 830

Ser Thr Ala Ala Pro Pro Tyr Thr Asn Glu Gln Ala Tyr Gln Met Leu
            835                 840                 845

Leu Ala Leu Ala Arg Leu Asp Ala Glu Gln Arg Ala Gln Gln Asn Gly
        850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Asn Val
                900                 905

<210> SEQ ID NO 4
<211> LENGTH: 4373
<212> TYPE: DNA
<213> ORGANISM: Artificial Sequence
<220> FEATURE:
<223> OTHER INFORMATION: HK1-HgB(dTM)

<400> SEQUENCE: 4
```

-continued

| | |
|---|---|
| gcgcaccggg gatcctaggc tttttggatt gcgctttcct ctagatcaac tgggtgtcag | 60 |
| gccctatcct acagaaggat ggaatccagg atctggtgcc tggtagtctg cgttaacctg | 120 |
| tgtatcgtct gtctgggtgc tgcggtttcc tcttctagta cttcccatgc aacttcttct | 180 |
| actcacaatg gaagccatac ttctcgtacg acgtctgctc aaacccggtc agtctattct | 240 |
| caacacgtaa cgtcttctga agccgtcagt catagagcca acgagactat ctacaacact | 300 |
| accctcaagt acgagatgt ggtgggagtc aacactacca agtacccta tcgcgtgtgt | 360 |
| tctatggccc agggtacgga tcttattcgc tttgaacgta atatcatctg caccctcgatg | 420 |
| aagcctatca tgaagactt ggatgagggc atcatggtgg tctacaagcg caacatcgtg | 480 |
| gcgcacacct ttaaggtacg ggtctaccaa aaggttttga cgtttcgtcg tagctacgct | 540 |
| tacatctaca ccacttatct gctgggcagc aatacggaat acgtggcgcc tcctatgtgg | 600 |
| gagattcatc acatcaacaa gtttgctcaa tgctacagtt cctacagccg cgttatagga | 660 |
| ggcacggttt tcgtggcata tcataggac agttatgaaa acaaaaccat gcaattaatt | 720 |
| cccgacgatt attccaacac ccacagtacc cgttacgtga cggtcaagga tcagtggcac | 780 |
| agccgcggca gcacctggct ctatcgtgag acctgtaatc tgaactgtat gctgaccatc | 840 |
| actactgcgc gctccaagta tccttatcat tttttgcaa cttccacggg tgatgtggtt | 900 |
| tacatttctc ctttctacaa cggaaccaat cgcaatgcca gctactttgg agaaaacgcc | 960 |
| gacaagtttt tcattttccc gaactacacc atcgttccg actttggaag acccaacgct | 1020 |
| gcgccagaaa cccataggtt ggtggctttt ctcgaacgtg ccgactcggt gatctcttgg | 1080 |
| gatatacagg acgagaagaa tgtcacctgc cagctcacct tctgggaagc ctcggaacgt | 1140 |
| actatccgtt ccgaagccga agactcgtac cacttttctt ctgccaaaat gactgcaact | 1200 |
| tttctgtcta agaaacaaga agtgaacatg tccgactccg cgctggactg cgtacgtgat | 1260 |
| gaggctataa ataagttaca gcagattttc aatacttcat acaatcaaac atatgaaaaa | 1320 |
| tacgaaaacg tgtccgtctt cgaaccagcc ggcggtctgg tggtgttctg gcaaggcatc | 1380 |
| aagcaaaaat ctttggtgga attggaacgt ttggccaatc gatccagtct gaatatcact | 1440 |
| cataggacca gaagaagtac gagtgacaat aatacaactc atttgtccag catggaatcg | 1500 |
| gtgcacaatc tggtctacgc ccagctgcag ttcacctatg acacgttgcg cggttacatc | 1560 |
| aaccgggcgc tggcgcaaat cgcagaagcc tggtgtgtgg atcaacggcg caccctagag | 1620 |
| gtcttcaagg aactcagcaa gatcaacccg tcagccattc tctcggccat ttacaacaaa | 1680 |
| ccgattgccg cgcgtttcat gggtgatgtc ttgggcctgg ccagctgcgt gaccatcaac | 1740 |
| caaaccagcg tcaaggtgct gcgtgatatg aacgtgaagg aatcgccagg acgctgctac | 1800 |
| tcacgacccg tggtcatctt taatttcgcc aacagctcgt acgtgcagta cggtcaactg | 1860 |
| ggcgaggaca acgaaatcct gttgggcaac caccgcactg aggaatgtca gcttcccagc | 1920 |
| ctcaagatct tcatcgccgg gaactcggcc tacgagtacg tggactacct cttcaaacgc | 1980 |
| atgattgacc tcagcagtat ctccaccgtc gacagcatga tcgccctgga tatcgacccg | 2040 |
| ctggaaaata ccgacttcag ggtactggaa ctttactcgc agaaagagct gcgttccagc | 2100 |
| aacgttttg acctcgaaga gatcatgcgc gaattcaact cgtacaagca gcgggtaaag | 2160 |
| tacgtggagg accggcgtct gtgcacgcag ccgctgcaga acctctttcc ctatctggtg | 2220 |
| tccgccgacg ggaccaccgt gacgtcgggc agcaccaaag acacgtcgtt acaggctccg | 2280 |
| ccttcctacg aggaaagtgt ttataattct ggtcgcaaag gaccgggacc accgtcgtct | 2340 |
| gatgcatcca cggcggctcc gccttacacc aacgagcagg cttaccagat gcttctggcc | 2400 |

```
ctggcccgtc tggacgcaga gcagcgagcg cagcagaacg gtacagattc tttggacgga    2460
cagactggca cgcaggacaa gggacagaag cctaacctgc tagaccggct gcgacatcgc    2520
aaaaacggct acagacactt gaaagactcc gacgaagaag agaacgtctg aagaacagcg    2580
cctccctgac tctccacctc gaaagaggtg gagagtcagg gaggcccaga gggtcttaga    2640
gtgtcacaac atttgggcct ctaaaaatta ggtcatgtgg cagaatgttg tgaacagttt    2700
tcagatctgg gagccttgct ttggaggcgc tttcaaaaat gatgcagtcc atgagtgcac    2760
agtgcggggt gatctctttc ttcttttgt cccttactat tccagtatgc atcttacaca    2820
accagccata tttgtcccac actttatctt catactccct cgaagcttcc ctggtcattt    2880
caacatcgat aagcttaatg tccttcctat tttgtgagtc cagaagcttt ctgatgtcat    2940
cggagccttg acagcttaga accatcccct gcggaagagc acctataact gacgaggtca    3000
acccgggttg cgcattgaag aggtcggcaa gatccatgcc gtgtgagtac ttggaatctt    3060
gcttgaattg ttttgatca acgggttccc tgtaaaagtg tatgaactgc ccgttctgtg     3120
gttggaaaat tgctatttcc actggatcat taaatctacc ctcaatgtca atccatgtag    3180
gagcgttggg gtcaattcct cccatgaggt cttttaaaag cattgtctgg ctgtagctta    3240
agcccacctg aggtggacct gctgctccag gcgctggcct gggtgagttg actgcaggtt    3300
tctcgcttgt gagatcaatt gttgtgtttt cccatgctct ccccacaatc gatgttctac    3360
aagctatgta tggccatcct tcacctgaaa ggcaaacttt atagaggatg ttttcataag    3420
ggttcctgtc cccaacttgg tctgaaacaa acatgttgag ttttctcttg gccccgagaa    3480
ctgccttcaa gagatcctcg ctgttgcttg gcttgatcaa aattgactct aacatgttac    3540
ccccatccaa cagggctgcc cctgccttca cggcagcacc aagactaaag ttatagccag    3600
aaatgttgat gctggactgc tgttcagtga tgaccccag aactgggtgc ttgtctttca     3660
gcctttcaag atcattaaga tttggatact tgactgtgta aagcaagcca aggtctgtga    3720
gcgcttgtac aacgtcattg agcggagtct gtgactgttt ggccatacaa gccatagtta    3780
gacttggcat tgtgccaaat tgattgttca aaagtgatga gtctttcaca tcccaaactc    3840
ttaccacacc acttgcaccc tgctgaggct ttctcatccc aactatctgt aggatctgag    3900
atctttggtc tagttgctgt gttgttaagt tccccatata taccccctgaa gcctggggcc    3960 tttcagacct catgatcttg gccttcagct tctcaaggtc agccgcaaga gacatcagtt    4020
cttctgcact gagcctcccc actttcaaaa cattcttctt tgatgttgac tttaaatcca    4080
caagagaatg tacagtctgg ttgagacttc tgagtctctg taggtctttg tcatctctct    4140
tttccttcct catgatcctc tgaacattgc tgacctcaga gaagtccaac ccattcagaa    4200
ggttggttgc atcctaatg acagcagcct tcacatctga tgtgaagctc tgcaattctc     4260
ttctcaatgc ttgcgtccat tggaagctct taacttcctt agacaaggac atcttgttgc    4320
tcaatggttt ctcaagacaa atgcgcaatc aaatgcctag gatccactgt gcg           4373
```

<210> SEQ ID NO 5
<211> LENGTH: 2493
<212> TYPE: DNA
<213> ORGANISM: Artificial Sequence
<220> FEATURE:
<223> OTHER INFORMATION: HgB(dTM) cDNA sequence

<400> SEQUENCE: 5

```
atggaatcca ggatctggtg cctggtagtc tgcgttaacc tgtgtatcgt ctgtctgggt       60
```

```
gctgcggttt cctcttctag tacttcccat gcaacttctt ctactcacaa tggaagccat    120
acttctcgta cgacgtctgc tcaaacccgg tcagtctatt ctcaacacgt aacgtcttct    180
gaagccgtca gtcatagagc caacgagact atctacaaca ctaccctcaa gtacggagat    240
gtggtgggag tcaacactac caagtacccc tatcgcgtgt gttctatggc ccagggtacg    300
gatcttattc gctttgaacg taatatcatc tgcacctcga tgaagcctat caatgaagac    360
ttggatgagg gcatcatggt ggtctacaag cgcaacatcg tggcgcacac ctttaaggta    420
cgggtctacc aaaaggtttt gacgtttcgt cgtagctacg cttacatcta caccacttat    480
ctgctgggca gcaatacgga atacgtggcg cctcctatgt gggagattca tcacatcaac    540
aagtttgctc aatgctacag ttcctacagc cgcgttatag gaggcacggt tttcgtggca    600
tatcataggg acagttatga aaacaaaacc atgcaattaa ttcccgacga ttattccaac    660
acccacagta cccgttacgt gacggtcaag gatcagtggc acagccgcgg cagcacctgg    720
ctctatcgtg agacctgtaa tctgaactgt atgctgacca tcactactgc gcgctccaag    780
tatccttatc attttttgc aacttccacg ggtgatgtgg tttacatttc tcctttctac    840
aacggaacca atcgcaatgc cagctacttt ggagaaaacg ccgacaagtt tttcattttc    900
ccgaactaca ccatcgtttc cgactttgga agacccaacg ctgcgccaga aacccatagg    960
ttggtggctt ttctcgaacg tgccgactcg gtgatctctt gggatataca ggacgagaag   1020
aatgtcacct gccagctcac cttctgggaa gcctcggaac gtactatccg ttccgaagcc   1080
gaagactcgt accactttc ttctgccaaa atgactgcaa cttttctgtc taagaaacaa   1140
gaagtgaaca tgtccgactc cgcgctggac tgcgtacgtg atgaggctat aaataagtta   1200
cagcagattt tcaatacttc atacaatcaa acatatgaaa aatacggaaa cgtgtccgtc   1260
ttcgaaacca gcggcggtct ggtggtgttc tggcaaggca tcaagcaaaa atctttggtg   1320
gaattggaac gtttggccaa tcgatccagt ctgaatatca ctcataggac cagaagaagt   1380
acgagtgaca ataatacaac tcatttgtcc agcatggaat cggtgcacaa tctggtctac   1440
gcccagctgc agttcaccta tgacacgttg cgcggttaca tcaaccgggc gctggcgcaa   1500
atcgcagaag cctggtgtgt ggatcaacgg cgcacctag aggtcttcaa ggaactcagc   1560
aagatcaacc cgtcagccat tctctcggcc atttacaaca aaccgattgc cgcgcgtttc   1620
atgggtgatg tcttgggcct ggccagctgc gtgaccatca accaaaccag cgtcaaggtg   1680
ctgcgtgata tgaacgtgaa ggaatcgcca ggacgctgct actcacgacc cgtggtcatc   1740
tttaatttcg ccaacagctc gtacgtgcag tacggtcaac tgggcgagga caacgaaatc   1800
ctgttgggca accaccgcac tgaggaatgt cagcttccca gcctcaagat cttcatcgcc   1860
gggaactcgg cctacgagta cgtggactac ctcttcaaac gcatgattga cctcagcagt   1920
atctccaccg tcgacagcat gatcgccctg gatatcgacc cgctggaaaa taccgacttc   1980
agggtactgg aacttactc gcagaaagag ctgcgttcca gcaacgtttt tgacctcgaa   2040
gagatcatgc gcgaattcaa ctcgtacaag cagcgggtaa agtacgtgga ggaccggcgt   2100
ctgtgcacgc agccgctgca gaacctcttt ccctatctgg tgtccgccga cgggaccacc   2160
gtgacgtcgg gcagcaccaa agacacgtcg ttacaggctc cgccttccta cgaggaaagt   2220
gtttataatt ctggtcgcaa aggaccggga ccaccgtcgt ctgatgcatc cacggcggct   2280
ccgccttaca ccaacgagca ggcttaccag atgcttctgg ccctggcccg tctggacgca   2340
gagcagcgag cgcagcagaa cggtacagat tctttggacg gacagactgg cacgcaggac   2400
aagggacaga agcctaacct gctagaccgg ctgcgacatc gcaaaaacgg ctacagacac   2460
```
ttgaaagact ccgacgaaga agagaacgtc tga                                      2493

<210> SEQ ID NO 6
<211> LENGTH: 830
<212> TYPE: PRT
<213> ORGANISM: Artificial Sequence
<220> FEATURE:
<223> OTHER INFORMATION: HgB(dTM) amino acid sequence

<400> SEQUENCE: 6

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
            35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Ile Phe Pro Asn Tyr Thr
    290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350
```

```
Glu Arg Thr Ile Arg Ser Glu Ala Glu Asp Ser Tyr His Phe Ser Ser
            355                 360                 365

Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
                420                 425                 430

Gly Ile Lys Gln Lys Ser Leu Val Glu Leu Glu Arg Leu Ala Asn Arg
            435                 440                 445

Ser Ser Leu Asn Ile Thr His Arg Thr Arg Arg Ser Thr Ser Asp Asn
    450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
        515                 520                 525

Ser Ala Ile Tyr Asn Lys Pro Ile Ala Ala Arg Phe Met Gly Asp Val
    530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
            580                 585                 590

Gln Leu Gly Glu Asp Asn Glu Ile Leu Leu Gly Asn His Arg Thr Glu
        595                 600                 605

Glu Cys Gln Leu Pro Ser Leu Lys Ile Phe Ile Ala Gly Asn Ser Ala
    610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
        675                 680                 685

Tyr Lys Gln Arg Val Lys Tyr Val Glu Asp Arg Arg Leu Cys Thr Gln
    690                 695                 700

Pro Leu Gln Asn Leu Phe Pro Tyr Leu Val Ser Ala Asp Gly Thr Thr
705                 710                 715                 720

Val Thr Ser Gly Ser Thr Lys Asp Thr Ser Leu Gln Ala Pro Pro Ser
                725                 730                 735

Tyr Glu Glu Ser Val Tyr Asn Ser Gly Arg Lys Gly Pro Gly Pro Pro
            740                 745                 750

Ser Ser Asp Ala Ser Thr Ala Ala Pro Pro Tyr Thr Asn Glu Gln Ala
        755                 760                 765

Tyr Gln Met Leu Leu Ala Leu Ala Arg Leu Asp Ala Glu Gln Arg Ala
```

```
                770              775              780
Gln Gln Asn Gly Thr Asp Ser Leu Asp Gly Gln Thr Gly Thr Gln Asp
785                 790                 795                 800

Lys Gly Gln Lys Pro Asn Leu Leu Asp Arg Leu Arg His Arg Lys Asn
                805                 810                 815

Gly Tyr Arg His Leu Lys Asp Ser Asp Glu Glu Glu Asn Val
            820                 825                 830

<210> SEQ ID NO 7
<211> LENGTH: 4001
<212> TYPE: DNA
<213> ORGANISM: Artificial Sequence
<220> FEATURE:
<223> OTHER INFORMATION: HK1-HgB(1-706)

<400> SEQUENCE: 7
```

| | | | | | |
|---|---|---|---|---|---|
| gcgcaccggg | gatcctaggc | tttttggatt | gcgctttcct | ctagatcaac | tgggtgtcag | 60 |
| gccctatcct | acagaaggat | ggaatccagg | atctggtgcc | tggtagtctg | cgttaacctg | 120 |
| tgtatcgtct | gtctgggtgc | tgcggtttcc | tcttctagta | cttcccatgc | aacttcttct | 180 |
| actcacaatg | gaagccatac | ttctcgtacg | acgtctgctc | aaacccggtc | agtctattct | 240 |
| caacacgtaa | cgtcttctga | agccgtcagt | catagagcca | acgagactat | ctacaacact | 300 |
| accctcaagt | acgagatgt | ggtgggagtc | aacactacca | agtaccccta | tcgcgtgtgt | 360 |
| tctatggccc | agggtacgga | tcttattcgc | tttgaacgta | atatcatctg | cacctcgatg | 420 |
| aagcctatca | atgaagactt | ggatgagggc | atcatggtgg | tctacaagcg | caacatcgtg | 480 |
| gcgcacacct | ttaaggtacg | ggtataccaa | aaggttttga | cgtttcgtcg | tagctacgct | 540 |
| tacatctaca | ccacttatct | gctgggcagc | aatacggaat | acgtggcgcc | tcctatgtgg | 600 |
| gagattcatc | acatcaacaa | gtttgctcaa | tgctacagtt | cctacagccg | cgttatagga | 660 |
| ggcacggttt | tcgtggcata | tcatagggac | agttatgaaa | acaaaaccat | gcaattaatt | 720 |
| cccgacgatt | attccaacac | ccacagtacc | cgttacgtga | cggtcaagga | tcagtggcac | 780 |
| agccgcggca | gcacctggct | ctatcgtgag | acctgtaatc | tgaactgtat | gctgaccatc | 840 |
| actactgcgc | gctccaagta | tccttatcat | tttttttgcaa | cttccacggg | tgatgtggtt | 900 |
| tacatttctc | ctttctacaa | cggaaccaat | cgcaatgcca | gctactttgg | agaaaacgcc | 960 |
| gacaagtttt | tcatttttccc | gaactacacc | atcgtttccg | actttggaag | acccaacgct | 1020 |
| gcgccagaaa | cccataggtt | ggtggctttt | ctcgaacgtg | ccgactcggt | gatctcttgg | 1080 |
| gatatacagg | acgagaagaa | tgtcacctgc | cagctcacct | tctgggaagc | ctcggaacgt | 1140 |
| actatccgtt | ccgaagccga | agactcgtac | cacttttctt | ctgccaaaat | gactgcaact | 1200 |
| tttctgtcta | agaacaaga | agtgaacatg | tccgactccg | cgctggactg | cgtacgtgat | 1260 |
| gaggctataa | ataagttaca | gcagattttc | aatacttcat | acaatcaaac | atatgaaaaa | 1320 |
| tacggaaacg | tgtccgtctt | cgaaccagc | ggcggtctgg | tggtgttctg | gcaaggcatc | 1380 |
| aagcaaaaat | ctttggtgga | attggaacgt | ttggccaatc | gatccagtct | gaatatcact | 1440 |
| cataggacca | gaagaagtac | gagtgacaat | aatacaactc | atttgtccag | catggaatcg | 1500 |
| gtgcacaatc | tggtctacgc | ccagctgcag | ttcacctatg | acacgttgcg | cggttacatc | 1560 |
| aaccgggcgc | tggcgcaaat | cgcagaagcc | tggtgtgtgg | atcaacggcg | caccctagag | 1620 |
| gtcttcaagg | aactcagcaa | gatcaaccg | tcagccattc | tctcggccat | ttacaacaaa | 1680 |
| ccgattgccg | cgcgtttcat | gggtgatgtc | ttgggcctgg | ccagctgcgt | gaccatcaac | 1740 |

```
caaaccagcg tcaaggtgct gcgtgatatg aacgtgaagg aatcgccagg acgctgctac    1800
tcacgacccg tggtcatctt taatttcgcc aacagctcgt acgtgcagta cggtcaactg    1860
ggcgaggaca acgaaatcct gttgggcaac caccgcactg aggaatgtca gcttcccagc    1920
ctcaagatct tcatcgccgg gaactcggcc tacgagtacg tggactacct cttcaaacgc    1980
atgattgacc tcagcagtat ctccaccgtc gacagcatga tcgccctgga tatcgacccg    2040
ctggaaaata ccgacttcag ggtactggaa ctttactcgc agaaagagct gcgttccagc    2100
aacgtttttg acctcgaaga gatcatgcgc gaattcaact cgtacaagca gcgggtaaag    2160
tacgtggagg acaaggtagt cgacccgcta ccgccctgaa gaacagcgcc tccctgactc    2220
tccacctcga agaggtgga gagtcaggga ggcccagagg gtcttagagt gtcacaacat    2280
ttgggcctct aaaaattagg tcatgtggca gaatgttgtg aacagttttc agatctggga    2340
gccttgcttt ggaggcgctt tcaaaaatga tgcagtccat gagtgcacag tgcggggtga    2400
tctctttctt cttttttgtcc cttactattc cagtatgcat cttacacaac cagccatatt    2460
tgtcccacac tttatcttca tactccctcg aagcttccct ggtcatttca acatcgataa    2520
gcttaatgtc cttcctattt tgtgagtcca gaagctttct gatgtcatcg gagccttgac    2580
agcttagaac catcccctgc ggaagagcac ctataactga cgaggtcaac ccgggttgcg    2640
cattgaagag gtcggcaaga tccatgccgt gtgagtactt ggaatcttgc ttgaattgtt    2700
tttgatcaac gggttccctg taaaagtgta tgaactgccc gttctgtggt tggaaaattg    2760
ctatttccac tggatcatta aatctacccct caatgtcaat ccatgtagga gcgttggggt    2820
caattcctcc catgaggtct tttaaaagca ttgtctggct gtagcttaag cccacctgag    2880
gtggacctgc tgctccaggc gctggcctgg gtgagttgac tgcaggtttc tcgcttgtga    2940
gatcaattgt tgtgttttcc catgctctcc ccacaatcga tgttctacaa gctatgtatg    3000
gccatccttc acctgaaagg caaactttat agaggatgtt ttcataaggg ttcctgtccc    3060
caacttggtc tgaaacaaac atgttgagtt ttctcttggc cccgagaact gccttcaaga    3120
gatcctcgct gttgcttggc ttgatcaaaa ttgactctaa catgttaccc ccatccaaca    3180
gggctgcccc tgccttcacg gcagcaccaa gactaaagtt atagccagaa atgttgatgc    3240
tggactgctg ttcagtgatg accccccagaa ctgggtgctt gtctttcagc cttttcaagat    3300
cattaagatt tggatacttg actgtgtaaa gcaagccaag gtctgtgagc gcttgtacaa    3360
cgtcattgag cggagtctgt gactgtttgg ccatacaagc catagttaga cttggcattg    3420
tgccaaattg attgttcaaa agtgatgagt ctttcacatc ccaaactctt accacaccac    3480
ttgcaccctg ctgaggcttt ctcatcccaa ctatctgtag gatctgagat ctttggtcta    3540
gttgctgtgt tgttaagttc cccatatata cccctgaagc ctgggggcctt tcagacctca    3600
tgatcttggc cttcagcttc tcaaggtcag ccgcaagaga catcagttct tctgcactga    3660
gcctccccac tttcaaaaca ttcttctttg atgttgactt taaatccaca agagaatgta    3720
cagtctggtt gagacttctg agtctctgta ggtctttgtc atctctcttt tccttcctca    3780
tgatcctctg aacattgctg acctcagaga agtccaaccc attcagaagg ttggttgcat    3840
ccttaatgac agcagccttc acatctgatg tgaagctctg caattctctt ctcaatgctt    3900
gcgtccattg gaagctctta acttccttag acaaggacat cttgttgctc aatggtttct    3960
caagacaaat gcgcaatcaa atgcctagga tccactgtgc g                       4001
```

<210> SEQ ID NO 8
<211> LENGTH: 2121

<212> TYPE: DNA
<213> ORGANISM: Artificial Sequence
<220> FEATURE:
<223> OTHER INFORMATION: HgB(1-706) cDNA sequence

<400> SEQUENCE: 8

| | |
|---|---|
| atggaatcca ggatctggtg cctggtagtc tgcgttaacc tgtgtatcgt ctgtctgggt | 60 |
| gctgcggttt cctcttctag tacttcccat gcaacttctt ctactcacaa tggaagccat | 120 |
| acttctcgta cgacgtctgc tcaaacccgg tcagtctatt ctcaacacgt aacgtcttct | 180 |
| gaagccgtca gtcatagagc caacgagact atctacaaca ctaccctcaa gtacggagat | 240 |
| gtggtgggag tcaacactac caagtacccc tatcgcgtgt gttctatggc ccagggtacg | 300 |
| gatcttattc gctttgaacg taatatcatc tgcacctcga tgaagcctat caatgaagac | 360 |
| ttggatgagg gcatcatggt ggtctacaag cgcaacatcg tggcgcacac ctttaaggta | 420 |
| cgggtatacc aaaaggtttt gacgtttcgt cgtagctacg cttacatcta caccacttat | 480 |
| ctgctgggca gcaatacgga atacgtggcg cctcctatgt gggagattca tcacatcaac | 540 |
| aagtttgctc aatgctacag ttcctacagc cgcgttatag gaggcacggt tttcgtggca | 600 |
| tatcataggg acagttatga aaacaaaacc atgcaattaa ttcccgacga ttattccaac | 660 |
| acccacagta cccgttacgt gacggtcaag gatcagtggc acagccgcgg cagcacctgg | 720 |
| ctctatcgtg agacctgtaa tctgaactgt atgctgacca tcactactgc gcgctccaag | 780 |
| tatccttatc attttttgc aacttccacg ggtgatgtgg tttacatttc tcctttctac | 840 |
| aacggaacca atcgcaatgc cagctacttt ggagaaaacg ccgacaagtt tttcattttc | 900 |
| ccgaactaca ccatcgtttc cgactttgga agacccaacg ctgcgccaga aacccatagg | 960 |
| ttggtggctt ttctcgaacg tgccgactcg gtgatctctt gggatataca ggacgagaag | 1020 |
| aatgtcacct gccagctcac cttctgggaa gcctcggaac gtactatccg ttccgaagcc | 1080 |
| gaagactcgt accactttc ttctgccaaa atgactgcaa cttttctgtc taagaaacaa | 1140 |
| gaagtgaaca tgtccgactc cgcgctggac tgcgtacgtg atgaggctat aaataagtta | 1200 |
| cagcagattt tcaatacttc atacaatcaa acatatgaaa aatacggaaa cgtgtccgtc | 1260 |
| ttcgaaacca gcggcggtct ggtggtgttc tggcaaggca tcaagcaaaa atctttggtg | 1320 |
| gaattggaac gtttggccaa tcgatccagt ctgaatatca ctcataggac cagaagaagt | 1380 |
| acgagtgaca ataatacaac tcatttgtcc agcatggaat cggtgcacaa tctggtctac | 1440 |
| gcccagctgc agttcaccta tgacacgttg cgcggttaca tcaaccgggc gctggcgcaa | 1500 |
| atcgcagaag cctggtgtgt ggatcaacgg cgcaccctag aggtcttcaa ggaactcagc | 1560 |
| aagatcaacc cgtcagccat tctctcggcc atttacaaca aaccgattgc cgcgcgtttc | 1620 |
| atgggtgatg tcttgggcct ggccagctgc gtgaccatca accaaaccag cgtcaaggtg | 1680 |
| ctgcgtgata tgaacgtgaa ggaatcgcca ggacgctgct actcacgacc cgtggtcatc | 1740 |
| tttaatttcg ccaacagctc gtacgtgcag tacggtcaac tgggcgagga caacgaaatc | 1800 |
| ctgttgggca ccaccgcac tgaggaatgt cagcttccca gcctcaagat cttcatcgcc | 1860 |
| gggaactcgg cctacgagta cgtggactac ctcttcaaac gcatgattga cctcagcagt | 1920 |
| atctccaccg tcgacagcat gatcgccctg gatatcgacc cgctggaaaa taccgacttc | 1980 |
| agggtactgg aactttactc gcagaaagag ctgcgttcca gcaacgtttt tgacctcgaa | 2040 |
| gagatcatgc gcgaattcaa ctcgtacaag cagcgggtaa agtacgtgga ggacaaggta | 2100 |
| gtcgacccgc taccgccctg a | 2121 |

```
<210> SEQ ID NO 9
<211> LENGTH: 706
<212> TYPE: PRT
<213> ORGANISM: Artificial Sequence
<220> FEATURE:
<223> OTHER INFORMATION: HgB(1-706) amino acid sequence

<400> SEQUENCE: 9
```

| | | | | | | | | | | | | | | | |
|---|---|---|---|---|---|---|---|---|---|---|---|---|---|---|---|
| Met | Glu | Ser | Arg | Ile | Trp | Cys | Leu | Val | Val | Cys | Val | Asn | Leu | Cys | Ile |
| 1 | | | | 5 | | | | | 10 | | | | | 15 | |
| Val | Cys | Leu | Gly | Ala | Ala | Val | Ser | Ser | Ser | Thr | Ser | His | Ala | Thr | |
| | | | 20 | | | | | 25 | | | | | 30 | | |
| Ser | Ser | Thr | His | Asn | Gly | Ser | His | Thr | Ser | Arg | Thr | Thr | Ser | Ala | Gln |
| | | 35 | | | | | 40 | | | | | 45 | | | |
| Thr | Arg | Ser | Val | Tyr | Ser | Gln | His | Val | Thr | Ser | Ser | Glu | Ala | Val | Ser |
| | 50 | | | | | 55 | | | | | 60 | | | | |
| His | Arg | Ala | Asn | Glu | Thr | Ile | Tyr | Asn | Thr | Thr | Leu | Lys | Tyr | Gly | Asp |
| 65 | | | | | 70 | | | | | 75 | | | | | 80 |
| Val | Val | Gly | Val | Asn | Thr | Thr | Lys | Tyr | Pro | Tyr | Arg | Val | Cys | Ser | Met |
| | | | | 85 | | | | | 90 | | | | | 95 | |
| Ala | Gln | Gly | Thr | Asp | Leu | Ile | Arg | Phe | Glu | Arg | Asn | Ile | Ile | Cys | Thr |
| | | | 100 | | | | | 105 | | | | | 110 | | |
| Ser | Met | Lys | Pro | Ile | Asn | Glu | Asp | Leu | Asp | Glu | Gly | Ile | Met | Val | Val |
| | | 115 | | | | | 120 | | | | | 125 | | | |
| Tyr | Lys | Arg | Asn | Ile | Val | Ala | His | Thr | Phe | Lys | Val | Arg | Val | Tyr | Gln |
| | 130 | | | | | 135 | | | | | 140 | | | | |
| Lys | Val | Leu | Thr | Phe | Arg | Arg | Ser | Tyr | Ala | Tyr | Ile | Tyr | Thr | Thr | Tyr |
| 145 | | | | | 150 | | | | | 155 | | | | | 160 |
| Leu | Leu | Gly | Ser | Asn | Thr | Glu | Tyr | Val | Ala | Pro | Pro | Met | Trp | Glu | Ile |
| | | | | 165 | | | | | 170 | | | | | 175 | |
| His | His | Ile | Asn | Lys | Phe | Ala | Gln | Cys | Tyr | Ser | Ser | Tyr | Ser | Arg | Val |
| | | | 180 | | | | | 185 | | | | | 190 | | |
| Ile | Gly | Gly | Thr | Val | Phe | Val | Ala | Tyr | His | Arg | Asp | Ser | Tyr | Glu | Asn |
| | | 195 | | | | | 200 | | | | | 205 | | | |
| Lys | Thr | Met | Gln | Leu | Ile | Pro | Asp | Asp | Tyr | Ser | Asn | Thr | His | Ser | Thr |
| | 210 | | | | | 215 | | | | | 220 | | | | |
| Arg | Tyr | Val | Thr | Val | Lys | Asp | Gln | Trp | His | Ser | Arg | Gly | Ser | Thr | Trp |
| 225 | | | | | 230 | | | | | 235 | | | | | 240 |
| Leu | Tyr | Arg | Glu | Thr | Cys | Asn | Leu | Asn | Cys | Met | Leu | Thr | Ile | Thr | Thr |
| | | | | 245 | | | | | 250 | | | | | 255 | |
| Ala | Arg | Ser | Lys | Tyr | Pro | Tyr | His | Phe | Phe | Ala | Thr | Ser | Thr | Gly | Asp |
| | | | 260 | | | | | 265 | | | | | 270 | | |
| Val | Val | Tyr | Ile | Ser | Pro | Phe | Tyr | Asn | Gly | Thr | Asn | Arg | Asn | Ala | Ser |
| | | 275 | | | | | 280 | | | | | 285 | | | |
| Tyr | Phe | Gly | Glu | Asn | Ala | Asp | Lys | Phe | Phe | Ile | Phe | Pro | Asn | Tyr | Thr |
| | 290 | | | | | 295 | | | | | 300 | | | | |
| Ile | Val | Ser | Asp | Phe | Gly | Arg | Pro | Asn | Ala | Ala | Pro | Glu | Thr | His | Arg |
| 305 | | | | | 310 | | | | | 315 | | | | | 320 |
| Leu | Val | Ala | Phe | Leu | Glu | Arg | Ala | Asp | Ser | Val | Ile | Ser | Trp | Asp | Ile |
| | | | | 325 | | | | | 330 | | | | | 335 | |
| Gln | Asp | Glu | Lys | Asn | Val | Thr | Cys | Gln | Leu | Thr | Phe | Trp | Glu | Ala | Ser |
| | | | 340 | | | | | 345 | | | | | 350 | | |
| Glu | Arg | Thr | Ile | Arg | Ser | Glu | Ala | Glu | Asp | Ser | Tyr | His | Phe | Ser | Ser |
| | | 355 | | | | | 360 | | | | | 365 | | | |

Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
                420                 425                 430

Gly Ile Lys Gln Lys Ser Leu Val Glu Leu Glu Arg Leu Ala Asn Arg
                435                 440                 445

Ser Ser Leu Asn Ile Thr His Arg Thr Arg Arg Ser Thr Ser Asp Asn
450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
                500                 505                 510

Leu Glu Val Phe Lys Glu Leu Ser Lys Ile Asn Pro Ser Ala Ile Leu
                515                 520                 525

Ser Ala Ile Tyr Asn Lys Pro Ile Ala Ala Arg Phe Met Gly Asp Val
530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
                580                 585                 590

Gln Leu Gly Glu Asp Asn Glu Ile Leu Leu Gly Asn His Arg Thr Glu
                595                 600                 605

Glu Cys Gln Leu Pro Ser Leu Lys Ile Phe Ile Ala Gly Asn Ser Ala
610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
                660                 665                 670

Ser Ser Asn Val Phe Asp Leu Glu Glu Ile Met Arg Glu Phe Asn Ser
                675                 680                 685

Tyr Lys Gln Arg Val Lys Tyr Val Glu Asp Lys Val Val Asp Pro Leu
690                 695                 700

Pro Pro
705

<210> SEQ ID NO 10
<211> LENGTH: 3956
<212> TYPE: DNA
<213> ORGANISM: Artificial Sequence
<220> FEATURE:
<223> OTHER INFORMATION: HK1-HgB(1-691)

<400> SEQUENCE: 10
gcgcaccggg gatcctaggc ttttggatt gcgctttcct ctagatcaac tgggtgtcag    60
gccctatcct acagaaggat ggaatccagg atctggtgcc tggtagtctg cgttaacctg   120

```
tgtatcgtct gtctgggtgc tgcggtttcc tcttctagta cttcccatgc aacttcttct    180
actcacaatg gaagccatac ttctcgtacg acgtctgctc aaacccggtc agtctattct    240
caacacgtaa cgtcttctga agccgtcagt catagagcca acgagactat ctacaacact    300
accctcaagt acggagatgt ggtgggagtc aacactacca agtaccccta tcgcgtgtgt    360
tctatggccc agggtacgga tcttattcgc tttgaacgta atatcatctg cacctcgatg    420
aagcctatca atgaagactt ggatgagggc atcatggtgg tctacaagcg caacatcgtg    480
gcgcacacct ttaaggtacg ggtctaccaa aaggttttga cgtttcgtcg tagctacgct    540
tacatctaca ccacttatct gctgggcagc aatacggaat acgtggcgcc tcctatgtgg    600
gagattcatc acatcaacaa gtttgctcaa tgctacagtt cctacagccg cgttatagga    660
ggcacggttt tcgtggcata tcatagggac agttatgaaa acaaaaccat gcaattaatt    720
cccgacgatt attccaacac ccacagtacc cgttacgtga cggtcaagga tcagtggcac    780
agccgcggca gcacctggct ctatcgtgag acctgtaatc tgaactgtat gctgaccatc    840
actactgcgc gctccaagta tccttatcat ttttttgcaa cttccacggg tgatgtggtt    900
tacatttctc ctttctacaa cggaaccaat cgcaatgcca gctactttgg agaaaacgcc    960
gacaagtttt tcatttttccc gaactacacc atcgtttccg actttggaag acccaacgct   1020
gcgccagaaa cccataggtt ggtggctttt ctcgaacgtg ccgactcggt gatctcttgg   1080
gatatacagg acgagaagaa tgtcacctgc cagctcacct tctgggaagc ctcggaacgt   1140
actatccgtt ccgaagccga agactcgtac cacttttctt ctgccaaaat gactgcaact   1200
tttctgtcta agaaacaaga agtgaacatg tccgactccg cgctggactg cgtacgtgat   1260
gaggctataa ataagttaca gcagattttc aatacttcat acaatcaaac atatgaaaaa   1320
tacggaaacg tgtccgtctt cgaaaccagc ggcggtctgg tggtgttctg gcaaggcatc   1380
aagcaaaaat ctttggtgga attggaacgt ttggccaatc gatccagtct gaatatcact   1440
cataggacca gaagaagtac gagtgacaat aatacaactc atttgtccag catggaatcg   1500
gtgcacaatc tggtctacgc ccagctgcag ttcacctatg acacgttgcg cggttacatc   1560
aaccgggcgc tggcgcaaat cgcagaagcc tggtgtgtgg atcaacggcg caccctagag   1620
gtcttcaagg aactcagcaa gatcaacccg tcagccattc tctcggccat ttacaacaaa   1680
ccgattgccg cgcgtttcat gggtgatgtc ttgggcctgg ccagctgcgt gaccatcaac   1740
caaaccagcg tcaaggtgct gcgtgatatg aacgtgaagg aatcgccagg acgctgctac   1800
tcacgacccg tggtcatctt taatttcgcc aacagctcgt acgtgcagta cggtcaactg   1860
ggcgaggaca acgaaatcct gttgggcaac caccgcactg aggaatgtca gcttcccagc   1920
ctcaagatct tcatcgccgg gaactcggcc tacgagtacg tggactacct cttcaaacgc   1980
atgattgacc tcagcagtat ctccaccgtc gacagcatga tcgccctgga tatcgacccg   2040
ctggaaaata ccgacttcag ggtactggaa ctttactcgc agaaagagct gcgttccagc   2100 aacgttttg acctcgaaga gatcatgcgc gaattcaact cgtacaagca gtgaagaaca   2160
gcgcctccct gactctccac ctcgaaagag gtggagagtc agggaggccc agagggtctt   2220
agagtgtcac aacatttggg cctctaaaaa ttaggtcatg tggcagaatg ttgtgaacag   2280
ttttcagatc tgggagcctt gctttggagg cgctttcaaa aatgatgcag tccatgagtg   2340
cacagtgcgg ggtgatctct ttcttctttt tgtcccttac tattccagta tgcatcttac   2400
acaaccagcc atatttgtcc cacactttat cttcatactc cctcgaagct tccctggtca   2460
```

```
tttcaacatc gataagctta atgtccttcc tattttgtga gtccagaagc tttctgatgt    2520
catcggagcc ttgacagctt agaaccatcc cctgcggaag agcacctata actgacgagg    2580
tcaacccggg ttgcgcattg aagaggtcgg caagatccat gccgtgtgag tacttggaat    2640
cttgcttgaa ttgtttttga tcaacggggtt ccctgtaaaa gtgtatgaac tgcccgttct    2700
gtggttggaa aattgctatt tccactggat cattaaatct accctcaatg tcaatccatg    2760
taggagcgtt ggggtcaatt cctcccatga ggtcttttaa aagcattgtc tggctgtagc    2820
ttaagcccac ctgaggtgga cctgctgctc caggcgctgg cctgggtgag ttgactgcag    2880
gtttctcgct tgtgagatca attgttgtgt tttcccatgc tctccccaca atcgatgttc    2940
tacaagctat gtatggccat ccttcacctg aaaggcaaac tttatagagg atgttttcat    3000
aagggttcct gtccccaact tggtctgaaa caaacatgtt gagttttctc ttggccccga    3060
gaactgcctt caagagatcc tcgctgttgc ttggcttgat caaaattgac tctaacatgt    3120
tacccccatc caacgggct gcccctgcct tcacggcagc accaagacta aagttatagc    3180
cagaaatgtt gatgctggac tgctgttcag tgatgacccc cagaactggg tgcttgtctt    3240
tcagcctttc aagatcatta agatttggat acttgactgt gtaaagcaag ccaaggtctg    3300
tgagcgcttg tacaacgtca ttgagcggag tctgtgactg tttggccata caagccatag    3360
ttagacttgg cattgtgcca aattgattgt tcaaaagtga tgagtctttc acatcccaaa    3420
ctcttaccac accacttgca ccctgctgag gctttctcat cccaactatc tgtaggatct    3480
gagatctttg gtctagttgc tgtgttgtta agttccccat atataccct gaagcctggg    3540 gcctttcaga cctcatgatc ttggccttca gcttctcaag gtcagccgca agagacatca    3600
gttcttctgc actgagcctc cccactttca aaacattctt ctttgatgtt gactttaaat    3660
ccacaagaga atgtacagtc tggttgagac ttctgagtct ctgtaggtct ttgtcatctc    3720
tcttttcctt cctcatgatc ctctgaacat tgctgacctc agagaagtcc aacccattca    3780
gaaggttggt tgcatcctta atgacagcag ccttcacatc tgatgtgaag ctctgcaatt    3840
ctcttctcaa tgcttgcgtc cattggaagc tcttaacttc cttagacaag gacatcttgt    3900
tgctcaatgg tttctcaaga caaatgcgca atcaaatgcc taggatccac tgtgcg    3956
```

<210> SEQ ID NO 11
<211> LENGTH: 2076
<212> TYPE: DNA
<213> ORGANISM: Artificial Sequence
<220> FEATURE:
<223> OTHER INFORMATION: HgB(1-691) cDNA sequence

<400> SEQUENCE: 11

```
atggaatcca ggatctggtg cctggtagtc tgcgttaacc tgtgtatcgt ctgtctgggt     60
gctgcggttt cctcttctag tacttcccat gcaacttctt ctactcacaa tggaagccat    120
acttctcgta cgacgtctgc tcaaacccgg tcagtctatt tcaacacgt aacgtcttct     180 gaagccgtca gtcatagagc caacgagact atctacaaca ctaccctcaa gtacggagat    240
gtggtgggag tcaacactac caagtacccc tatcgcgtgt gttctatggc ccagggtacg    300
gatcttattc gctttgaacg taatatcatc tgcacctcga tgaagcctat caatgaagac    360
ttggatgagg gcatcatggt ggtctacaag cgcaacatcg tggcgcacac ctttaaggta    420
cgggtctacc aaaaggtttt gacgtttcgt cgtagctacg cttacatcta caccactat   480 ctgctgggca gcaatacgga atacgtggcg cctcctatgt gggagattca tcacatcaac    540
aagtttgctc aatgctacag ttcctacagc cgcgttatag gaggcacggt tttcgtggca    600
```

-continued

```
tatcataggg acagttatga aaacaaaacc atgcaattaa ttcccgacga ttattccaac      660
acccacagta cccgttacgt gacggtcaag gatcagtggc acagccgcgg cagcacctgg      720
ctctatcgtg agacctgtaa tctgaactgt atgctgacca tcactactgc gcgctccaag      780
tatccttatc attttttgc aacttccacg ggtgatgtgg tttacatttc tcctttctac      840
aacggaacca atcgcaatgc cagctacttt ggagaaaacg ccgacaagtt tttcattttc      900
ccgaactaca ccatcgtttc cgactttgga gacccaacg ctgcgccaga aacccatagg      960
ttggtggctt ttctcgaacg tgccgactcg gtgatctctt gggatataca ggacgagaag     1020
aatgtcacct gccagctcac cttctgggaa gcctcggaac gtactatccg ttccgaagcc     1080
gaagactcgt accactttc ttctgccaaa atgactgcaa ctttctgtc taagaaacaa      1140 gaagtgaaca tgtccgactc cgcgctggac tgcgtacgtg atgaggctat aaataagtta     1200
cagcagattt tcaatacttc atacaatcaa acatatgaaa aatacggaaa cgtgtccgtc     1260
ttcgaaacca gcggcggtct ggtggtgttc tggcaaggca tcaagcaaaa atctttggtg     1320
gaattggaac gtttggccaa tcgatccagt ctgaatatca ctcataggac cagaagaagt     1380
acgagtgaca taatacaac tcatttgtcc agcatggaat cggtgcacaa tctggtctac     1440
gcccagctgc agttcaccta tgacacgttg cgcggttaca tcaaccgggc gctggcgcaa     1500
atcgcagaag cctggtgtgt ggatcaacgg cgcaccctag aggtcttcaa ggaactcagc     1560
aagatcaacc cgtcagccat tctctcggcc atttacaaca aaccgattgc cgcgcgtttc     1620
atgggtgatg tcttgggcct ggccagctgc gtgaccatca accaaaccag cgtcaaggtg     1680
ctgcgtgata tgaacgtgaa ggaatcgcca ggacgctgct actcacgacc cgtggtcatc     1740
tttaatttcg ccaacagctc gtacgtgcag tacggtcaac tgggcgagga caacgaaatc     1800
ctgttgggca ccaccgcac tgaggaatgt cagcttccca gcctcaagat cttcatcgcc     1860
gggaactcgg cctacgagta cgtggactac ctcttcaaac gcatgattga cctcagcagt     1920
atctccaccg tcgacagcat gatcgccctg gatatcgacc cgctggaaaa taccgacttc     1980
agggtactgg aactttactc gcagaaagag ctgcgttcca gcaacgtttt tgacctcgaa     2040
gagatcatgc gcgaattcaa ctcgtacaag cagtga                             2076
```

<210> SEQ ID NO 12
<211> LENGTH: 691
<212> TYPE: PRT
<213> ORGANISM: Artificial Sequence
<220> FEATURE:
<223> OTHER INFORMATION: HgB(1-691) amino acid sequence

<400> SEQUENCE: 12

```
Met Glu Ser Arg Ile Trp Cys Leu Val Val Cys Val Asn Leu Cys Ile
 1               5                  10                  15

Val Cys Leu Gly Ala Ala Val Ser Ser Ser Thr Ser His Ala Thr
                20                  25                  30

Ser Ser Thr His Asn Gly Ser His Thr Ser Arg Thr Thr Ser Ala Gln
            35                  40                  45

Thr Arg Ser Val Tyr Ser Gln His Val Thr Ser Glu Ala Val Ser
        50                  55                  60

His Arg Ala Asn Glu Thr Ile Tyr Asn Thr Thr Leu Lys Tyr Gly Asp
 65                  70                  75                  80

Val Val Gly Val Asn Thr Thr Lys Tyr Pro Tyr Arg Val Cys Ser Met
                85                  90                  95
```

```
Ala Gln Gly Thr Asp Leu Ile Arg Phe Glu Arg Asn Ile Ile Cys Thr
                100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
                180                 185                 190

Ile Gly Gly Thr Val Phe Val Ala Tyr His Arg Asp Ser Tyr Glu Asn
                195                 200                 205

Lys Thr Met Gln Leu Ile Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
                260                 265                 270

Val Val Tyr Ile Ser Pro Phe Tyr Asn Gly Thr Asn Arg Asn Ala Ser
                275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
                340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
                420                 425                 430

Gly Ile Lys Gln Lys Ser Leu Val Glu Leu Glu Arg Leu Ala Asn Arg
        435                 440                 445

Ser Ser Leu Asn Ile Thr His Arg Thr Arg Ser Thr Ser Asp Asn
        450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
                500                 505                 510

Leu Glu Val Phe Lys Glu Leu Ser Lys Ile Asn Pro Ser Ala Ile Leu
```

```
                515                 520                 525
Ser Ala Ile Tyr Asn Lys Pro Ile Ala Ala Arg Phe Met Gly Asp Val
    530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
            580                 585                 590

Gln Leu Gly Glu Asp Asn Glu Ile Leu Leu Gly Asn His Arg Thr Glu
        595                 600                 605

Glu Cys Gln Leu Pro Ser Leu Lys Ile Phe Ile Ala Gly Asn Ser Ala
    610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
        675                 680                 685

Tyr Lys Gln
    690

<210> SEQ ID NO 13
<211> LENGTH: 3224
<212> TYPE: DNA
<213> ORGANISM: Artificial Sequence
<220> FEATURE:
<223> OTHER INFORMATION: HK1-HgB(1-447)

<400> SEQUENCE: 13
gcgcaccggg gatcctaggc tttttggatt gcgctttcct ctagatcaac tgggtgtcag      60
gccctatcct acagaaggat ggaatccagg atctggtgcc tggtagtctg cgttaacctg     120
tgtatcgtct gtctgggtgc tgcggtttcc tcttctagta cttcccatgc aacttcttct     180
actcacaatg gaagccatac ttctcgtacg acgtctgctc aaacccggtc agtctattct     240 caaacgtaa cgtcttctga agccgtcagt catagagcca acgagactat ctacaacact      300
accctcaagt acggagatgt ggtgggagtc aacactacca gtaccccta tcgcgtgtgt      360 tctatggccc agggtacgga tcttattcgc tttgaacgta atatcatctg cacctcgatg     420
aagcctatca tgaagactt ggatgagggc atcatggtgg tctacaagcg caacatcgtg      480
gcgcacacct ttaaggtacg ggtctaccaa aaggttttga cgtttcgtcg tagctacgct     540
tacatctaca ccacttatct actgggcagc aatacggaat acgtggcgcc tcctatgtgg     600
gagattcatc acatcaacaa gtttgctcaa tgctacagtt cctacagccg cgttatagga     660
ggcacggttt tcgtggcata tcatagggac agttatgaaa acaaaaccat gcaattaatt     720
cccgacgatt attccaacac ccacagtacc cgttacgtga cggtcaagga tcagtggcac     780
agccgcggca gcacctggct ctatcgtgag acctgtaatc tgaactgtat gctgaccatc     840
actactgcgc gctccaagta tccttatcat ttttttgcaa cttccacggg tgatgtggtt     900
tacatttctc ctttctacaa cggaaccaat cgcaatgcca gctactttgg agaaaacgcc     960
gacaagtttt tcattttccc gaactacacc atcgtttccg actttggaag acccaacgct    1020
```

```
gcgccagaaa cccataggtt ggtggctttt ctcgaacgtg ccgactcggt gatctcttgg   1080
gatatacagg acgagaagaa tgtcacctgc cagctcacct tctgggaagc tcggaacgt    1140 actatccgtt ccgaagccga agactcgtac cacttttctt ctgccaaaat gactgcaact   1200
tttctgtcta agaaacaaga agtgaacatg tccgactccg cgctggactg cgtacgtgat   1260
gaggctataa ataagttaca gcagattttc aatacttcat acaatcaaac atatgaaaaa   1320 tacgaaacg tgtccgtctt cgaaaccagc ggcggtctgg tggtgttctg gcaaggcatc    1380
aagcaaaaat ctttggtgga attggaacgt ttggccaatt gaagaacagc gcctccctga   1440
ctctccacct cgaaagaggt ggagagtcag ggaggcccag agggtcttag agtgtcacaa   1500
catttgggcc tctaaaaatt aggtcatgtg gcagaatgtt gtgaacagtt ttcagatctg   1560
ggagccttgc tttggaggcg cttttcaaaaa tgatgcagtc catgagtgca cagtgcgggg   1620
tgatctcttt cttcttttg tcccttacta ttccagtatg catcttacac aaccagccat    1680
atttgtccca cactttatct tcatactccc tcgaagcttc cctggtcatt tcaacatcga   1740
taagcttaat gtccttccta ttttgtgagt ccagaagctt tctgatgtca tcggagcctt   1800
gacagcttag aaccatcccc tgcggaagag cacctataac tgacgaggtc aacccgggtt   1860
gcgcattgaa gaggtcggca agatccatgc cgtgtgagta cttggaatct tgcttgaatt   1920 gttttgatc aacgggttcc ctgtaaaagt gtatgaactg cccgttctgt ggttggaaaa    1980
ttgctatttc cactggatca ttaaatctac cctcaatgtc aatccatgta ggagcgttgg   2040
ggtcaattcc tcccatgagg tcttttaaaa gcattgtctg gctgtagctt aagcccacct   2100
gaggtggacc tgctgctcca ggcgctggcc tgggtgagtt gactgcaggt ttctcgcttg   2160
tgagatcaat tgttgtgttt tcccatgctc tccccacaat cgatgttcta caagctatgt   2220
atggccatct tcacctgaa aggcaaactt tatagaggat gttttcataa gggttcctgt    2280
ccccaacttg gtctgaaaca aacatgttga gttttctctt ggccccgaga actgccttca   2340
agagatcctc gctgttgctt ggcttgatca aaattgactc taacatgtta ccccccatcca  2400 acagggctgc ccctgccttc acggcagcac caagactaaa gttatagcca gaaatgttga   2460
tgctggactg ctgttcagtg atgaccccca gaactgggtg cttgtctttc agcctttcaa   2520
gatcattaag atttggatac ttgactgtgt aaagcaagcc aaggtctgtg agcgcttgta   2580
caacgtcatt gagcggagtc tgtgactgtt tggccataca agccatagtt agacttggca   2640 tgtgccaaa ttgattgttc aaaagtgatg agtctttcac atcccaaact cttaccacac    2700
cacttgcacc ctgctgaggc tttctcatcc caactatctg taggatctga gatctttggt   2760
ctagttgctg tgttgttaag ttccccatat atacccctga agcctggggc ctttcagacc   2820
tcatgatctt ggccttcagc ttctcaaggt cagccgcaag agacatcagt tcttctgcac   2880
tgagcctccc cactttcaaa acattcttct ttgatgttga ctttaaatcc acaagagaat   2940
gtacagtctg gttgagactt ctgagtctct gtaggtcttt gtcatctctc ttttccttcc   3000
tcatgatcct ctgaacattg ctgacctcag agaagtccaa cccattcaga aggttggttg   3060
catccttaat gacagcagcc ttcacatctg atgtgaagct ctgcaattct cttctcaatg   3120
cttgcgtcca ttggaagctc ttaacttcct tagacaagga catcttgttg ctcaatggtt   3180
tctcaagaca aatgcgcaat caaatgccta ggatccactg tgcg              3224

<210> SEQ ID NO 14
<211> LENGTH: 1344
<212> TYPE: DNA
<213> ORGANISM: Artificial Sequence
```

```
<220> FEATURE:
<223> OTHER INFORMATION: HgB(1-447) cDNA sequence

<400> SEQUENCE: 14
atggaatcca ggatctggtg cctggtagtc tgcgttaacc tgtgtatcgt ctgtctgggt     60
gctgcggttt cctcttctag tacttcccat gcaacttctt ctactcacaa tggaagccat    120
acttctcgta cgacgtctgc tcaaacccgg tcagtctatt ctcaacacgt aacgtcttct    180
gaagccgtca gtcatagagc caacgagact atctacaaca ctaccctcaa gtacggagat    240
gtggtgggag tcaacactac caagtacccc tatcgcgtgt gttctatggc ccagggtacg    300
gatcttattc gctttgaacg taatatcatc tgcacctcga tgaagcctat caatgaagac    360
ttggatgagg gcatcatggt ggtctacaag cgcaacatcg tggcgcacac ctttaaggta    420
cgggtctacc aaaaggtttt gacgtttcgt cgtagctacg cttacatcta caccacttat    480
ctactgggca gcaatacgga atacgtggcg cctcctatgt gggagattca tcacatcaac    540
aagtttgctc aatgctacag ttcctacagc cgcgttatag gaggcacggt tttcgtggca    600
tatcataggg acagttatga aaacaaaacc atgcaattaa ttcccgacga ttattccaac    660
acccacagta cccgttacgt gacggtcaag gatcagtggc acagccgcgg cagcacctgg    720
ctctatcgtg agacctgtaa tctgaactgt atgctgacca tcactactgc gcgctccaag    780
tatccttatc attttttttgc aacttccacg ggtgatgtgg tttacatttc tcctttctac    840
aacggaacca atcgcaatgc cagctacttt ggagaaaacg ccgacaagtt tttcattttc    900
ccgaactaca ccatcgtttc cgactttgga gacccaacg ctgcgccaga aacccatagg    960
ttggtggctt ttctcgaacg tgccgactcg gtgatctctt gggatataca ggacgagaag   1020
aatgtcacct gccagctcac cttctgggaa gcctcggaac gtactatccg ttccgaagcc   1080
gaagactcgt accactttttc ttctgccaaa atgactgcaa cttttctgtc taagaaacaa   1140
gaagtgaaca tgtccgactc cgcgctggac tgcgtacgtg atgaggctat aaataagtta   1200
cagcagattt tcaatacttc atacaatcaa acatatgaaa aatacggaaa cgtgtccgtc   1260
ttcgaaacca gcggcggtct ggtggtgttc tggcaaggca tcaagcaaaa atctttggtg   1320
gaattggaac gtttggccaa ttga                                          1344

<210> SEQ ID NO 15
<211> LENGTH: 447
<212> TYPE: PRT
<213> ORGANISM: Artificial Sequence
<220> FEATURE:
<223> OTHER INFORMATION: HgB(1-447) amino acid sequence

<400> SEQUENCE: 15

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95
```

Ala Gln Gly Thr Asp Leu Ile Arg Phe Glu Arg Asn Ile Ile Cys Thr
                100                 105                 110

Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
        130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
            420                 425                 430

Gly Ile Lys Gln Lys Ser Leu Val Glu Leu Glu Arg Leu Ala Asn
        435                 440                 445

<210> SEQ ID NO 16
<211> LENGTH: 4202
<212> TYPE: DNA
<213> ORGANISM: Artificial Sequence
<220> FEATURE:
<223> OTHER INFORMATION: HK1-HgB(dCt)

<400> SEQUENCE: 16
gcgcaccggg gatcctaggc ttttggatt gcgctttcct ctagatcaac tgggtgtcag     60
gccctatcct acagaaggat ggaatccagg atctggtgcc tggtagtctg cgttaacttg    120

```
tgtatcgtct gtctgggtgc tgcggtttcc tcatcttcta ctcgtggaac ttctgctact    180
cacagtcacc attcctctca tacgacgtct gctgctcact ctcgatccgg ttcagtctct    240
caacgcgtaa cttcttccca aacggtcagc catggtgtta acgagaccat ctacaacact    300
accctcaagt acggagatgt ggtgggggtc aataccacca agtaccccta tcgcgtgtgt    360
tctatggccc agggtacgga tcttattcgc tttgaacgta atatcgtctg cacctcgatg    420
aagcccatca atgaagacct ggacgagggc atcatggtgg tctacaaacg caacatcgtc    480
gcgcacacct ttaaggtacg agtctaccag aaggttttga cgtttcgtcg tagctacgct    540
tacatccaca ccactatct gctgggcagc aacacggaat acgtggcgcc tcctatgtgg    600
gagattcatc atatcaacag ccacagtcag tgctacagtt cctacagccg cgttatagca    660
ggcacggttt tcgtggctta tcatagggac agctatgaaa acaaaaccat gcaattaatg    720
cccgacgatt attccaacac ccacagtacc cgttacgtga cggtcaagga tcaatggcac    780
agccgcggca gcacctggct ctatcgtgag acctgtaatc tgaattgtat ggtgaccatc    840
actactgcgc gctccaaata tccttatcat tttttcgcca cttccacggg tgacgtggtt    900
gacatttctc ctttctacaa cggaaccaat cgcaatgcca gctactttgg agaaaacgcc    960
gacaagtttt tcattttcc gaactacact attgtctccg actttggaag accgaattct   1020
gcgttagaga cccacaggtt ggtggctttt cttgaacgtg cggactcggt gatctcctgg   1080
gatatacagg acgaaaagaa tgtcacttgt caactcactt tctgggaagc ctcggaacgc   1140
accattcgtt ccgaagccga ggactcgtat cacttttctt ctgccaaaat gaccgccact   1200
ttcttatcta agaagcaaga ggtgaacatg tccgactctg cgctggactg cgtacgtgat   1260
gaggctataa ataagttaca gcagattttc aatacttcat acaatcaaac atatgaaaaa   1320
tatggaaacg tgtccgtctt tgaaaccact ggtggtttgg tagtgttctg gcaaggtatc   1380
aagcaaaaat ctctggtgga actcgaacgt ttggccaacc gctccagtct gaatcttact   1440
cataatagaa ccaaaagaag tacagatggc aacaatgcaa ctcatttatc caacatggaa   1500
tcggtgcaca atctggtcta cgcccagctg cagttcacct atgacacgtt gcgcggttac   1560
atcaaccggg cgctggcgca aatcgcagaa gcctggtgtg tggatcaacg cgcacccta   1620 gaggtcttca aggaactcag caagatcaac ccgtcagcca ttctctcggc catttacaac   1680
aaaccgattg ccgcgcgttt catgggtgat gtcttgggcc tggccagctg cgtgaccatc   1740
aaccaaacca gcgtcaaggt gctgcgtgat atgaacgtga aggagtcgcc aggacgctgc   1800
tactcacgac ccgtggtcat ctttaatttc gccaacagct cgtacgtgca gtacggtcaa   1860
ctgggcgagg acaacgaaat cctgttgggc aaccaccgca ctgaggaatg tcagcttccc   1920
agcctcaaga tcttcatcgc cgggaactcg gcctacgagt acgtggacta cctcttcaaa   1980
cgcatgattg acctcagcag tatctccacc gtcgacagca tgatcgccct ggatatcgac   2040
ccgctggaaa ataccgactt cagggtactg gaactttact cgcagaaaga gctgcgttcc   2100
agcaacgttt ttgacctcga agagatcatg cgcgaattca actcgtacaa gcagcgggta   2160
aagtacgtgg aggacaaggt agtcgacccg ctaccgccct acctcaaggg tctgacgac   2220 ctcatgagcg gcctgggcgc cgcgggaaag gccgttggcg tagccattgg ggccgtgggt   2280
ggcgcggtgg cctccgtggt cgaaggcgtt gccaccttcc tcaaaaaccc cttcggagcg   2340
ttcaccatca tcctcgtggc catagctgta gtcattatca cttatttgat ctatcgatga   2400
agaacagcgc ctccctgact ctccacctcg aaagaggtgg agagtcaggg aggcccagag   2460
```

| | | | | |
|---|---|---|---|---|
| ggtcttagag | tgtcacaaca | tttgggcctc | taaaaattag | gtcatgtggc agaatgttgt | 2520 |
| gaacagtttt | cagatctggg | agccttgctt | tggaggcgct | ttcaaaaatg atgcagtcca | 2580 |
| tgagtgcaca | gtgcggggtg | atctctttct | tcttttttgtc | ccttactatt ccagtatgca | 2640 |
| tcttacacaa | ccagccatat | ttgtcccaca | ctttatcttc | atactccctc gaagcttccc | 2700 |
| tggtcatttc | aacatcgata | agcttaatgt | ccttcctatt | ttgtgagtcc agaagctttc | 2760 |
| tgatgtcatc | ggagccttga | cagcttagaa | ccatcccctg | cggaagagca cctataactg | 2820 |
| acgaggtcaa | cccgggttgc | gcattgaaga | ggtcggcaag | atccatgccg tgtgagtact | 2880 |
| tggaatcttg | cttgaattgt | ttttgatcaa | cgggttccct | gtaaaagtgt atgaactgcc | 2940 |
| cgttctgtgg | ttggaaaatt | gctatttcca | ctggatcatt | aaatctaccc tcaatgtcaa | 3000 |
| tccatgtagg | agcgttgggg | tcaattcctc | ccatgaggtc | ttttaaaagc attgtctggc | 3060 |
| tgtagcttaa | gcccacctga | ggtggacctg | ctgctccagg | cgctggcctg ggtgagttga | 3120 |
| ctgcaggttt | ctcgcttgtg | agatcaattg | ttgtgttttc | ccatgctctc cccacaatcg | 3180 |
| atgttctaca | agctatgtat | ggccatcctt | cacctgaaag | gcaaactta tagaggatgt | 3240 |
| tttcataagg | gttcctgtcc | ccaacttggt | ctgaaacaaa | catgttgagt tttctcttgg | 3300 |
| ccccgagaac | tgccttcaag | agatcctcgc | tgttgcttgg | cttgatcaaa attgactcta | 3360 |
| acatgttacc | cccatccaac | agggctgccc | ctgccttcac | ggcagcacca agactaaagt | 3420 |
| tatagccaga | aatgttgatg | ctggactgct | gttcagtgat | gacccccaga actgggtgct | 3480 |
| tgtctttcag | cctttcaaga | tcattaagat | ttggatactt | gactgtgtaa agcaagccaa | 3540 |
| ggtctgtgag | cgcttgtaca | acgtcattga | gcggagtctg | tgactgtttg gccatacaag | 3600 |
| ccatagttag | acttggcatt | gtgccaaatt | gattgttcaa | agtgatgag tctttcacat | 3660 |
| cccaaactct | taccacacca | cttgcaccct | gctgaggctt | tctcatccca actatctgta | 3720 |
| ggatctgaga | tctttggtct | agttgctgtg | ttgttaagtt | ccccatatat accccctgaag | 3780 |
| cctggggcct | ttcagacctc | atgatcttgg | ccttcagctt | ctcaaggtca gccgcaagag | 3840 |
| acatcagttc | ttctgcactg | agcctcccca | cttttcaaaac | attcttcttt gatgttgact | 3900 |
| ttaaatccac | aagagaatgt | acagtctggt | tgagacttct | gagtctctgt aggtctttgt | 3960 |
| catctctctt | ttccttcctc | atgatcctct | gaacattgct | gacctcagag aagtccaacc | 4020 |
| cattcagaag | gttggttgca | tccttaatga | cagcagcctt | cacatctgat gtgaagctct | 4080 |
| gcaattctct | tctcaatgct | tgcgtccatt | ggaagctctt | aacttcctta gacaaggaca | 4140 |
| tcttgttgct | caatggtttc | tcaagacaaa | tgcgcaatca | aatgcctagg atccactgtg | 4200 |
| cg | | | | | 4202 |

<210> SEQ ID NO 17
<211> LENGTH: 2319
<212> TYPE: DNA
<213> ORGANISM: Artificial Sequence
<220> FEATURE:
<223> OTHER INFORMATION: HgB(dCt) cDNA sequence

<400> SEQUENCE: 17

| | | | | |
|---|---|---|---|---|
| atggaatcca | ggatctggtg | cctggtagtc | tgcgttaact | tgtgtatcgt ctgtctgggt | 60 |
| gctgcggttt | cctcatcttc | tactcgtgga | acttctgcta | ctcacagtca ccattcctct | 120 |
| catacgacgt | ctgctgctca | ctctcgatcg | ggttcagtct | ctcaacgcgt aacttcttcc | 180 |
| caaacggtca | gccatggtgt | taacgagacc | atctacaaca | ctaccctcaa gtacggagat | 240 |
| gtggtggggg | tcaataccac | caagtacccc | tatcgcgtgt | gttctatggc ccagggtacg | 300 |

```
gatcttattc gctttgaacg taatatcgtc tgcacctcga tgaagcccat caatgaagac    360
ctggacgagg gcatcatggt ggtctacaaa cgcaacatcg tcgcgcacac ctttaaggta    420
cgagtctacc agaaggtttt gacgtttcgt cgtagctacg cttacatcca caccacttat    480
ctgctgggca gcaacacgga atacgtggcg cctcctatgt gggagattca tcatatcaac    540
agccacagtc agtgctacag ttcctacagc cgcgttatag caggcacggt tttcgtggct    600
tatcataggg acagctatga aaacaaaacc atgcaattaa tgcccgacga ttattccaac    660
acccacagta cccgttacgt gacggtcaag gatcaatggc acagccgcgg cagcacctgg    720
ctctatcgtg agacctgtaa tctgaattgt atggtgacca tcactactgc gcgctccaaa    780
tatccttatc attttttcgc cacttccacg ggtgacgtgg ttgacatttc tcctttctac    840
aacggaacca atcgcaatgc cagctacttt ggagaaaacg ccgacaagtt tttcattttt    900
ccgaactaca ctattgtctc cgactttgga agaccgaatt ctgcgttaga gacccacagg    960
ttggtggctt ttcttgaacg tgcggactcg gtgatctcct gggatataca ggacgaaaag   1020
aatgtcactt gtcaactcac tttctgggaa gcctcggaac gcaccattcg ttccgaagcc   1080
gaggactcgt atcactttc ttctgccaaa atgaccgcca ctttcttatc taagaagcaa   1140
gaggtgaaca tgtccgactc tgcgctggac tgcgtacgtg atgaggctat aaataagtta   1200
cagcagattt tcaatacttc atacaatcaa acatatgaaa aatatggaaa cgtgtccgtc   1260
tttgaaacca ctggtggttt ggtagtgttc tggcaaggta tcaagcaaaa atctctggtg   1320
gaactcgaac gtttggccaa ccgctccagt ctgaatctta ctcataatag aaccaaaaga   1380
agtacagatg gcaacaatgc aactcattta tccaacatgg aatcggtgca caatctggtc   1440
tacgcccagc tgcagttcac ctatgacacg ttgcgcggtt acatcaaccg ggcgctggcg   1500
caaatcgcag aagcctggtg tgtggatcaa cggcgcaccc tagaggtctt caaggaactc   1560
agcaagatca cccgtcagc cattctctcg gccatttaca acaaaccgat tgccgcgcgt   1620
ttcatgggtg atgtcttggg cctggccagc tgcgtgacca tcaaccaaac cagcgtcaag   1680
gtgctgcgtg atatgaacgt gaaggagtcg ccaggacgct gctactcacg acccgtggtc   1740
atctttaatt tcgccaacag ctcgtacgtg cagtacggtc aactgggcga ggacaacgaa   1800
atcctgttgg gcaaccaccg cactgaggaa tgtcagcttc ccagcctcaa gatcttcatc   1860
gccgggaact cggcctacga gtacgtggac tacctcttca aacgcatgat tgacctcagc   1920
agtatctcca ccgtcgacag catgatcgcc ctggatatcg acccgctgga aaataccgac   1980
ttcagggtac tggaacttta ctcgcagaaa gagctgcgtt ccagcaacgt ttttgacctc   2040
gaagagatca tgcgcgaatt caactcgtac aagcagcggg taaagtacgt ggaggacaag   2100
gtagtcgacc cgctaccgcc ctacctcaag ggtctggacg acctcatgag cggcctgggc   2160
gccgcgggaa aggccgttgg cgtagccatt ggggccgtgg gtggcgcggt ggcctccgtg   2220
gtcgaaggcg ttgccacctt cctcaaaaac cccttcggag cgttcaccat catcctcgtg   2280
gccatagctg tagtcattat cacttatttg atctatcga                         2319
```

<210> SEQ ID NO 18
<211> LENGTH: 773
<212> TYPE: PRT
<213> ORGANISM: Artificial Sequence
<220> FEATURE:
<223> OTHER INFORMATION: HgB(dCt) amino acid sequence

<400> SEQUENCE: 18

-continued

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
```

```
            420                 425                 430
Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
                500                 505                 510

Thr Leu Glu Val Phe Lys Glu Leu Ser Lys Ile Asn Pro Ser Ala Ile
            515                 520                 525

Leu Ser Ala Ile Tyr Asn Lys Pro Ile Ala Ala Arg Phe Met Gly Asp
        530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
                580                 585                 590

Gly Gln Leu Gly Glu Asp Asn Glu Ile Leu Leu Gly Asn His Arg Thr
            595                 600                 605

Glu Glu Cys Gln Leu Pro Ser Leu Lys Ile Phe Ile Ala Gly Asn Ser
        610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
                660                 665                 670

Arg Ser Ser Asn Val Phe Asp Leu Glu Glu Ile Met Arg Glu Phe Asn
            675                 680                 685

Ser Tyr Lys Gln Arg Val Lys Tyr Val Glu Asp Lys Val Val Asp Pro
        690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
                740                 745                 750

Gly Ala Phe Thr Ile Ile Leu Val Ala Ile Ala Val Val Ile Ile Thr
            755                 760                 765

Tyr Leu Ile Tyr Arg
    770

<210> SEQ ID NO 19
<211> LENGTH: 4283
<212> TYPE: DNA
<213> ORGANISM: Artificial Sequence
<220> FEATURE:
<223> OTHER INFORMATION: HK1-HgB(VSV-G-1)

<400> SEQUENCE: 19
gcgcaccggg gatcctaggc tttttggatt gcgctttcct ctagatcaac tgggtgtcag      60
```

```
gccctatcct acagaaggat ggaatccagg atctggtgcc tggtagtctg cgttaacttg      120
tgtatcgtct gtctgggtgc tgcggtttcc tcatcttcta ctcgtggaac ttctgctact      180
cacagtcacc attcctctca tacgacgtct gctgctcact ctcgatccgg ttcagtctct      240
caacgcgtaa cttcttccca aacggtcagc catggtgtta acgagaccat ctacaacact      300
accctcaagt acggagatgt ggtgggggtc aataccacca agtacccta tcgcgtgtgt      360 tctatggccc agggtacgga tcttattcgc tttgaacgta atatcgtctg cacctcgatg      420
aagcccatca atgaagacct ggacgagggc atcatggtgg tctacaaacg caacatcgtc      480
gcgcacacct ttaaggtacg agtctaccag aaggttttga cgtttcgtcg tagctacgct      540
tacatccaca ccacttatct gctgggcagc aacacggaat acgtggcgcc tcctatgtgg      600
gagattcatc atatcaacag ccacagtcag tgctacagtt cctacagccg cgttatagca      660
ggcacggttt tcgtggctta tcatagggac agctatgaaa acaaaaccat gcaattaatg      720
cccgacgatt attccaacac ccacagtacc cgttacgtga cggtcaagga tcaatggcac      780
agccgcggca gcacctggct ctatcgtgag acctgtaatc tgaattgtat ggtgaccatc      840
actactgcgc gctccaaata tccttatcat tttttcgcca cttccacggg tgacgtggtt      900
gacatttctc ctttctacaa cggaaccaat cgcaatgcca gctactttgg agaaaacgcc      960
gacaagtttt tcattttttcc gaactacact attgtctccg actttggaag accgaattct     1020
gcgttagaga cccacaggtt ggtggctttt cttgaacgtg cggactcggt gatctcctgg     1080
gatatacagg acgaaaagaa tgtcacttgt caactcactt tctgggaagc ctcggaacgc     1140
accattcgtt ccgaagccga ggactcgtat cactttttctt ctgccaaaat gaccgccact     1200
ttcttatcta agaagcaaga ggtgaacatg tccgactctg cgctggactg cgtacgtgat     1260
gaggctataa ataagttaca gcagattttc aatacttcat acaatcaaac atatgaaaaa     1320
tatggaaacg tgtccgtctt tgaaaccact ggtggtttgg tagtgttctg gcaaggtatc     1380
aagcaaaaat ctctggtgga actcgaacgt ttggccaacc gctccagtct gaatcttact     1440
cataatagaa ccaaaagaag tacagatggc aacaatgcaa ctcatttatc caacatggaa     1500
tcggtgcaca atctggtcta cgcccagctg cagttcacct atgacacgtt gcgcggttac     1560
atcaaccggg cgctggcgca aatcgcagaa gcctggtgtg tggatcaacg gcgcacccta     1620
gaggtcttca aggaactcag caagatcaac ccgtcagcca ttctctcggc catttacaac     1680
aaaccgattg ccgcgcgttt catgggtgat gtcttgggcc tggccagctg cgtgaccatc     1740
aaccaaacca gcgtcaaggt gctgcgtgat atgaacgtga aggagtcgcc aggacgctgc     1800
tactcacgac ccgtggtcat ctttaatttc gccaacagct cgtacgtgca gtacggtcaa     1860
ctgggcgagg acaacgaaat cctgttgggc aaccaccgca ctgaggaatg tcagcttccc     1920
agcctcaaga tcttcatcgc cgggaactcg gcctacgagt acgtggacta cctcttcaaa     1980
cgcatgattg acctcagcag tatctccacc gtcgacagca tgatcgccct ggatatcgac     2040
ccgctggaaa ataccgactt cagggtactg gaactttact cgcagaaaga gctgcgttcc     2100
agcaacgttt ttgacctcga agagatcatg cgcgaattca actcgtacaa gcagcgggta     2160
aagtacgtga aggacaaggt agtcgacccg ctaccgccct acctcaaggg tctgacgac      2220 ctcatgagcg gcctgggcgc cgcgggaaag gccgttggcg tagccattgg ggccgtgggt     2280
ggcgcggtgg cctccgtggt cgaaggcgtt gccaccttcc tcaaaaaccc cagcagcatc     2340
gccagcttct tcttcatcat cggcctgatc atcggcctgt tcctggtgct gcgcgtgggc     2400
```

-continued

| | |
|---|---|
| atccacctgt gcatcaagct gaagcacacc aagaagcgcc agatctacac cgacatcgag | 2460 |
| atgaaccgcc tgggcaagtg aagaacagcg cctccctgac tctccacctc gaaagaggtg | 2520 |
| gagagtcagg gaggcccaga gggtcttaga gtgtcacaac atttgggcct ctaaaaatta | 2580 |
| ggtcatgtgg cagaatgttg tgaacagttt tcagatctgg gagccttgct ttggaggcgc | 2640 |
| tttcaaaaat gatgcagtcc atgagtgcac agtgcgggt gatctctttc ttcttttttgt | 2700 |
| cccttactat tccagtatgc atcttacaca accagccata tttgtcccac actttatctt | 2760 |
| catactccct cgaagcttcc ctggtcattt caacatcgat aagcttaatg tccttcctat | 2820 |
| tttgtgagtc cagaagcttt ctgatgtcat cggagccttg acagcttaga accatcccct | 2880 |
| gcggaagagc acctataact gacgaggtca acccgggttg cgcattgaag aggtcggcaa | 2940 |
| gatccatgcc gtgtgagtac ttggaatctt gcttgaattg tttttgatca acgggttccc | 3000 |
| tgtaaaagtg tatgaactgc ccgttctgtg gttggaaaat tgctatttcc actggatcat | 3060 |
| taaatctacc ctcaatgtca atccatgtag gagcgttggg gtcaattcct cccatgaggt | 3120 |
| cttttaaaag cattgtctgg ctgtagctta agcccacctg aggtggacct gctgctccag | 3180 |
| gcgctggcct gggtgagttg actgcaggtt tctcgcttgt gagatcaatt gttgtgtttt | 3240 |
| cccatgctct ccccacaatc gatgttctac aagctatgta tggccatcct tcacctgaaa | 3300 |
| ggcaaacttt atagaggatg ttttcataag ggttcctgtc cccaacttgg tctgaaacaa | 3360 |
| acatgttgag ttttctcttg gccccgagaa ctgccttcaa gagatcctcg ctgttgcttg | 3420 |
| gcttgatcaa aattgactct aacatgttac ccccatccaa cagggctgcc cctgccttca | 3480 |
| cggcagcacc aagactaaag ttatagccag aaatgttgat gctggactgc tgttcagtga | 3540 |
| tgacccccag aactgggtgc ttgtctttca gcctttcaag atcattaaga tttggatact | 3600 |
| tgactgtgta aagcaagcca aggtctgtga gcgcttgtac aacgtcattg agcggagtct | 3660 |
| gtgactgttt ggccatacaa gccatagtta gacttggcat tgtgccaaat tgattgttca | 3720 |
| aaagtgatga gtctttcaca tcccaaactc ttaccacacc acttgcaccc tgctgaggct | 3780 |
| ttctcatccc aactatctgt aggatctgag atctttggtc tagttgctgt gttgttaagt | 3840 |
| tccccatata taccccctgaa gcctggggcc tttcagacct catgatcttg gccttcagct | 3900 |
| tctcaaggtc agccgcaaga gacatcagtt cttctgcact gagcctcccc actttcaaaa | 3960 |
| cattcttctt tgatgttgac tttaaatcca caagagaatg tacagtctgg ttgagacttc | 4020 |
| tgagtctctg taggtctttg tcatctctct tttccttcct catgatcctc tgaacattgc | 4080 |
| tgacctcaga gaagtccaac ccattcagaa ggttggttgc atccttaatg acagcagcct | 4140 |
| tcacatctga tgtgaagctc tgcaattctc ttctcaatgc ttgcgtccat ggaagctct | 4200 |
| taacttcctt agacaaggac atcttgttgc tcaatggttt ctcaagacaa atgcgcaatc | 4260 |
| aaatgcctag gatccactgt gcg | 4283 |

<210> SEQ ID NO 20
<211> LENGTH: 2400
<212> TYPE: DNA
<213> ORGANISM: Artificial Sequence
<220> FEATURE:
<223> OTHER INFORMATION: HgB(VSV-G-1) cDNA sequence

<400> SEQUENCE: 20

| | |
|---|---|
| atggaatcca ggatctggtg cctggtagtc tgcgttaact tgtgtatcgt ctgtctgggt | 60 |
| gctgcggttt cctcatcttc tactcgtgga acttctgcta ctcacagtca ccattcctct | 120 |
| catacgacgt ctgctgctca ctctcgatcc ggttcagtct ctcaacgcgt aacttcttcc | 180 |

```
caaacggtca gccatggtgt taacgagacc atctacaaca ctaccctcaa gtacggagat      240
gtggtggggg tcaataccac caagtacccc tatcgcgtgt gttctatggc ccagggtacg     300
gatcttattc gctttgaacg taatatcgtc tgcacctcga tgaagcccat caatgaagac     360
ctggacgagg gcatcatggt ggtctacaaa cgcaacatcg tcgcgcacac ctttaaggta    420
cgagtctacc agaaggtttt gacgtttcgt cgtagctacg cttacatcca caccacttat    480
ctgctgggca gcaacacgga atacgtggcg cctcctatgt gggagattca tcatatcaac    540
agccacagtc agtgctacag ttcctacagc cgcgttatag caggcacggt tttcgtggct    600
tatcataggg acagctatga aaacaaaacc atgcaattaa tgcccgacga ttattccaac    660
acccacagta cccgttacgt gacggtcaag gatcaatggc acagccgcgg cagcacctgg    720
ctctatcgtg agacctgtaa tctgaattgt atggtgacca tcactactgc gcgctccaaa    780
tatccttatc attttttcgc cacttccacg ggtgacgtgg ttgacatttc tcctttctac    840
aacggaacca atcgcaatgc cagctacttt ggagaaaacg ccgacaagtt tttcattttt    900
ccgaactaca ctattgtctc cgactttgga agaccgaatt ctgcgttaga gacccacagg    960
ttggtggctt ttcttgaacg tgcggactcg gtgatctcct gggatataca ggacgaaaag   1020
aatgtcactt gtcaactcac tttctgggaa gcctcggaac gcaccattcg ttccgaagcc   1080
gaggactcgt atcactttc ttctgccaaa atgaccgcca cttcttatc taagaagcaa     1140 gaggtgaaca tgtccgactc tgcgctggac tgcgtacgtg atgaggctat aaataagtta   1200
cagcagattt tcaatacttc atacaatcaa acatatgaaa aatatggaaa cgtgtccgtc   1260
tttgaaacca ctggtggttt ggtagtgttc tggcaaggta tcaagcaaaa atctctggtg   1320
gaactcgaac gtttggccaa ccgctccagt ctgaatctta ctcataatag aaccaaaaga   1380
agtacagatg gcaacaatgc aactcattta tccaacatgg aatcggtgca caatctggtc   1440
tacgcccagc tgcagttcac ctatgacacg ttgcgcggtt acatcaaccg ggcgctggcg   1500
caaatcgcag aagcctggtg tgtggatcaa cggcgcaccc tagaggtctt caaggaactc   1560
agcaagatca acccgtcagc cattctctcg gccatttaca acaaaccgat tgccgcgcgt   1620
ttcatgggtg atgtcttggg cctggccagc tgcgtgacca tcaaccaaac cagcgtcaag   1680
gtgctgcgtg atatgaacgt gaaggagtcg ccaggacgct gctactcacg acccgtggtc   1740
atctttaatt tcgccaacag ctcgtacgtg cagtacggtc aactgggcga ggacaacgaa   1800
atcctgttgg gcaaccaccg cactgaggaa tgtcagcttc ccagcctcaa gatcttcatc   1860
gccgggaact cggcctacga gtacgtggac tacctcttca aacgcatgat tgacctcagc   1920
agtatctcca ccgtcgacag catgatcgcc ctggatatcg acccgctgga aaataccgac   1980
ttcagggtac tggaactta ctcgcagaaa gagctgcgtt ccagcaacgt tttgacctc    2040 gaagagatca tgcgcgaatt caactcgtac aagcagcggg taaagtacgt ggaggacaag   2100
gtagtcgacc cgctaccgcc ctacctcaag ggtctggacg acctcatgag cggcctgggc   2160
gccgcgggaa aggccgttgg cgtagccatt ggggccgtgg gtggcgcggt ggcctccgtg   2220
gtcgaaggcg ttgccacctt cctcaaaaac cccagcagca tcgccagctt cttcttcatc   2280
atcggcctga tcatcggcct gttcctggtg ctgcgcgtgg gcatccacct gtgcatcaag   2340
ctgaagcaca ccaagaagcg ccagatctac accgacatcg agatgaaccg cctgggcaag   2400
```

<210> SEQ ID NO 21
<211> LENGTH: 800
<212> TYPE: PRT

<213> ORGANISM: Artificial Sequence
<220> FEATURE:
<223> OTHER INFORMATION: HgB(VSV-G-1) amino acid sequence

<400> SEQUENCE: 21

```
Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
```

```
            385                 390                 395                 400
        Gln Gln Ile Phe Asn Thr Ser Tyr Asn Gln Thr Tyr Glu Lys Tyr Gly
                        405                 410                 415

Asn Val Ser Val Phe Glu Thr Thr Gly Gly Leu Val Val Phe Trp Gln
                        420                 425                 430

Gly Ile Lys Gln Lys Ser Leu Val Glu Leu Glu Arg Leu Ala Asn Arg
                        435                 440                 445

Ser Ser Leu Asn Leu Thr His Asn Arg Thr Lys Arg Ser Thr Asp Gly
        450                 455                 460

Asn Asn Ala Thr His Leu Ser Asn Met Glu Ser Val His Asn Leu Val
        465                 470                 475                 480

Tyr Ala Gln Leu Gln Phe Thr Tyr Asp Thr Leu Arg Gly Tyr Ile Asn
                        485                 490                 495

Arg Ala Leu Ala Gln Ile Ala Glu Ala Trp Cys Val Asp Gln Arg Arg
                        500                 505                 510

Thr Leu Glu Val Phe Lys Glu Leu Ser Lys Ile Asn Pro Ser Ala Ile
                        515                 520                 525

Leu Ser Ala Ile Tyr Asn Lys Pro Ile Ala Arg Phe Met Gly Asp
        530                 535                 540

Val Leu Gly Leu Ala Ser Cys Val Thr Ile Asn Gln Thr Ser Val Lys
        545                 550                 555                 560

Val Leu Arg Asp Met Asn Val Lys Glu Ser Pro Gly Arg Cys Tyr Ser
                        565                 570                 575

Arg Pro Val Val Ile Phe Asn Phe Ala Asn Ser Ser Tyr Val Gln Tyr
                        580                 585                 590

Gly Gln Leu Gly Glu Asp Asn Glu Ile Leu Leu Gly Asn His Arg Thr
                        595                 600                 605

Glu Glu Cys Gln Leu Pro Ser Leu Lys Ile Phe Ile Ala Gly Asn Ser
                        610                 615                 620

Ala Tyr Glu Tyr Val Asp Tyr Leu Phe Lys Arg Met Ile Asp Leu Ser
        625                 630                 635                 640

Ser Ile Ser Thr Val Asp Ser Met Ile Ala Leu Asp Ile Asp Pro Leu
                        645                 650                 655

Glu Asn Thr Asp Phe Arg Val Leu Glu Leu Tyr Ser Gln Lys Glu Leu
                        660                 665                 670

Arg Ser Ser Asn Val Phe Asp Leu Glu Glu Ile Met Arg Glu Phe Asn
                        675                 680                 685

Ser Tyr Lys Gln Arg Val Lys Tyr Val Glu Asp Lys Val Val Asp Pro
                        690                 695                 700

Leu Pro Pro Tyr Leu Lys Gly Leu Asp Asp Leu Met Ser Gly Leu Gly
        705                 710                 715                 720

Ala Ala Gly Lys Ala Val Gly Val Ala Ile Gly Ala Val Gly Gly Ala
                        725                 730                 735

Val Ala Ser Val Val Glu Gly Val Ala Thr Phe Leu Lys Asn Pro Ser
                        740                 745                 750

Ser Ile Ala Ser Phe Phe Ile Ile Gly Leu Ile Ile Gly Leu Phe
                        755                 760                 765

Leu Val Leu Arg Val Gly Ile His Leu Cys Ile Lys Leu Lys His Thr
                        770                 775                 780

Lys Lys Arg Gln Ile Tyr Thr Asp Ile Glu Met Asn Arg Leu Gly Lys
        785                 790                 795                 800

<210> SEQ ID NO 22
```

<211> LENGTH: 4151
<212> TYPE: DNA
<213> ORGANISM: Artificial Sequence
<220> FEATURE:
<223> OTHER INFORMATION: HK1-HgB(VSV-G-2)

<400> SEQUENCE: 22

| | | | | | |
|---|---|---|---|---|---|
| gcgcaccggg | gatcctaggc | tttttggatt | gcgctttcct | ctagatcaac | tgggtgtcag | 60 |
| gccctatcct | acagaaggat | ggaatccagg | atctggtgcc | tggtagtctg | cgttaacttg | 120 |
| tgtatcgtct | gtctgggtgc | tgcggtttcc | tcatcttcta | ctcgtggaac | ttctgctact | 180 |
| cacagtcacc | attcctctca | tacgacgtct | gctgctcact | ctcgatccgg | ttcagtctct | 240 |
| caacgcgtaa | cttcttccca | acggtcagc | catggtgtta | acgagaccat | ctacaacact | 300 |
| accctcaagt | acggagatgt | ggtggggtc | aataccacca | agtacccta | tcgcgtgtgt | 360 |
| tctatggccc | agggtacgga | tcttattcgc | tttgaacgta | atatcgtctg | cacctcgatg | 420 |
| aagcccatca | atgaagacct | ggacgagggc | atcatggtgg | tctacaaacg | caacatcgtc | 480 |
| gcgcacacct | ttaaggtacg | agtctaccag | aaggttttga | cgtttcgtcg | tagctacgct | 540 |
| tacatccaca | ccacttatct | gctgggcagc | aacacggaat | acgtggcgcc | tcctatgtgg | 600 |
| gagattcatc | atatcaacag | ccacagtcag | tgctacagtt | cctacagccg | cgttatagca | 660 |
| ggcacggttt | tcgtggctta | tcatagggac | agctatgaaa | acaaaaccat | gcaattaatg | 720 |
| cccgacgatt | attccaacac | ccacagtacc | cgttacgtga | cggtcaagga | tcaatggcac | 780 |
| agccgcggca | gcacctggct | ctatcgtgag | acctgtaatc | tgaattgtat | ggtgaccatc | 840 |
| actactgcgc | gctccaaata | tccttatcat | tttttcgcca | cttccacggg | tgacgtggtt | 900 |
| gacatttctc | ctttctacaa | cggaaccaat | cgcaatgcca | gctactttgg | agaaaacgcc | 960 |
| gacaagtttt | tcatttttcc | gaactacact | attgtctccg | actttggaag | accgaattct | 1020 |
| gcgttagaga | cccacaggtt | ggtggctttt | cttgaacgtg | cggactcggt | gatctcctgg | 1080 |
| gatatacaga | cgaaaagaa | tgtcacttgt | caactcactt | tctgggaagc | ctcggaacgc | 1140 |
| accattcgtt | ccgaagccga | ggactcgtat | cacttttctt | ctgccaaaat | gaccgccact | 1200 |
| ttcttatcta | agaagcaaga | ggtgaacatg | tccgactctg | cgctggactg | cgtacgtgat | 1260 |
| gaggctataa | ataagttaca | gcagattttc | aatacttcat | acaatcaaac | atatgaaaaa | 1320 |
| tatggaaacg | tgtccgtctt | tgaaaccact | ggtggtttgg | tagtgttctg | gcaaggtatc | 1380 |
| aagcaaaaat | ctctggtgga | actcgaacgt | ttggccaacc | gctccagtct | gaatcttact | 1440 |
| cataatagaa | ccaaaagaag | tacagatggc | aacaatgcaa | ctcatttatc | caacatggaa | 1500 |
| tcggtgcaca | atctggtcta | cgcccagctg | cagttcacct | atgacacgtt | gcgcggttac | 1560 |
| atcaaccggg | cgctggcgca | aatcgcagaa | gcctggtgtg | tggatcaacg | gcgcacccta | 1620 |
| gaggtcttca | aggaactcag | caagatcaac | ccgtcagcca | ttctctcggc | catttacaac | 1680 |
| aaaccgattg | ccgcgcgttt | catgggtgat | gtcttgggcc | tggccagctg | cgtgaccatc | 1740 |
| aaccaaacca | gcgtcaaggt | gctgcgtgat | atgaacgtga | aggagtcgcc | aggacgctgc | 1800 |
| tactcacgac | ccgtggtcat | ctttaatttc | gccaacagct | cgtacgtgca | gtacggtcaa | 1860 |
| ctgggcgagac | acaacgaaat | cctgttgggc | aaccaccgca | ctgaggaatg | tcagcttccc | 1920 |
| agcctcaaga | tcttcatcgc | cgggaactcg | gcctacgagt | acgtggacta | cctcttcaaa | 1980 |
| cgcatgattg | acctcagcag | tatctccacc | gtcgacagca | tgatcgccct | ggatatcgac | 2040 |
| ccgctggaaa | ataccgactt | cagggtactg | gaactttact | cgcagaaaga | gctgcgttcc | 2100 |
| agcaacgttt | ttgacctcga | agagatcatg | cgcgaattca | actcgtacaa | gcagcgggta | 2160 |

```
aagtacgtgg aggacaaggt agtcgacccg ctaccgccca gcagcatcgc cagcttcttc    2220
ttcatcatcg gcctgatcat cggcctgttc ctggtgctgc gcgtgggcat ccacctgtgc    2280
atcaagctga agcacaccaa gaagcgccag atctacaccg acatcgagat gaaccgcctg    2340
ggcaagtgaa gaacagcgcc tccctgactc tccacctcga aagaggtgga gagtcaggga    2400
ggcccagagg gtcttagagt gtcacaacat ttgggcctct aaaaattagg tcatgtggca    2460
gaatgttgtg aacagttttc agatctggga gccttgcttt ggaggcgctt tcaaaaatga    2520
tgcagtccat gagtgcacag tgcggggtga tctctttctt cttttgtcc cttactattc    2580 cagtatgcat cttacacaac cagccatatt tgtcccacac tttatcttca tactccctcg    2640
aagcttccct ggtcatttca acatcgataa gcttaatgtc cttcctattt tgtgagtcca    2700
gaagctttct gatgtcatcg gagccttgac agcttagaac catcccctgc ggaagagcac    2760
ctataactga cgaggtcaac ccgggttgcg cattgaagag gtcggcaaga tccatgccgt    2820
gtgagtactt ggaatcttgc ttgaattgtt tttgatcaac gggttccctg taaaagtgta    2880
tgaactgccc gttctgtggt tggaaaattg ctatttccac tggatcatta aatctaccct    2940
caatgtcaat ccatgtagga gcgttggggt caattcctcc catgaggtct tttaaaagca    3000
ttgtctggct gtagcttaag cccacctgag gtggacctgc tgctccaggc gctggcctgg    3060
gtgagttgac tgcaggtttc tcgcttgtga gatcaattgt tgtgttttcc catgctctcc    3120
ccacaatcga tgttctacaa gctatgtatg ccatccttc acctgaaagg caaactttat    3180
agaggatgtt ttcataaggg ttcctgtccc caacttggtc tgaaacaaac atgttgagtt    3240
ttctcttggc cccgagaact gccttcaaga gatcctcgct gttgcttggc ttgatcaaaa    3300
ttgactctaa catgttaccc ccatccaaca gggctgcccc tgccttcacg gcagcaccaa    3360
gactaaagtt atagccagaa atgttgatgc tggactgctg ttcagtgatg acccccagaa    3420
ctgggtgctt gtcttttcagc ctttcaagat cattaagatt tggatacttg actgtgtaaa    3480
gcaagccaag gtctgtgagc gcttgtacaa cgtcattgag cggagtctgt gactgtttgg    3540
ccatacaagc catagttaga cttggcattg tgccaaattg attgttcaaa agtgatgagt    3600 cttttcacatc ccaaactctt accacaccac ttgcaccctg ctgaggcttt ctcatcccaa    3660
ctatctgtag gatctgagat cttttggtcta gttgctgtgt tgttaagttc cccatatata    3720
cccctgaagc ctggggcctt tcagacctca tgatcttggc cttcagcttc tcaaggtcag    3780
ccgcaagaga catcagttct tctgcactga gcctccccac tttcaaaaca ttcttctttg    3840
atgttgactt taaatccaca agagaatgta cagtctggtt gagacttctg agtctctgta    3900
ggtctttgtc atctctcttt tccttcctca tgatcctctg aacattgctg acctcagaga    3960
agtccaaccc attcagaagg ttggttgcat ccttaatgac agcagcctc acatctgatg    4020 tgaagctctg caattctctt ctcaatgctt gcgtccattg gaagctctta acttccttag    4080
acaaggacat cttgttgctc aatggttttct caagacaaat gcgcaatcaa atgcctagga    4140
tccactgtgc g                                                        4151
```

<210> SEQ ID NO 23
<211> LENGTH: 2268
<212> TYPE: DNA
<213> ORGANISM: Artificial Sequence
<220> FEATURE:
<223> OTHER INFORMATION: HgB(VSV-G-2) cDNA sequence

<400> SEQUENCE: 23

```
atggaatcca ggatctggtg cctggtagtc tgcgttaact tgtgtatcgt ctgtctgggt    60
gctgcggttt cctcatcttc tactcgtgga acttctgcta ctcacagtca ccattcctct   120
catacgacgt ctgctgctca ctctcgatcc ggttcagtct ctcaacgcgt aacttcttcc   180
caaacggtca gccatggtgt aacgagacc atctacaaca ctaccctcaa gtacggagat   240
gtggtggggg tcaataccac caagtacccc tatcgcgtgt gttctatggc ccagggtacg   300
gatcttattc gctttgaacg taatatcgtc tgcacctcga tgaagcccat caatgaagac   360
ctggacgagg gcatcatggt ggtctacaaa cgcaacatcg tcgcgcacac ctttaaggta   420
cgagtctacc agaaggtttt gacgtttcgt cgtagctacg cttacatcca caccacttat   480
ctgctgggca gcaacacgga atacgtggcg cctcctatgt gggagattca tcatatcaac   540
agccacagtc agtgctacag ttcctacagc cgcgttatag caggcacggt tttcgtggct   600
tatcataggg acagctatga aaacaaaacc atgcaattaa tgcccgacga ttattccaac   660
acccacagta cccgttacgt gacggtcaag gatcaatggc acagccgcgg cagcacctgg   720
ctctatcgtg agacctgtaa tctgaattgt atggtgacca tcactactgc gcgctccaaa   780
tatccttatc atttttttcgc cacttccacg ggtgacgtgg ttgacatttc tcctttctac   840
aacggaacca atcgcaatgc cagctacttt ggagaaaacg ccgacaagtt tttcattttt   900
ccgaactaca ctattgtctc cgactttgga agaccgaatt ctgcgttaga cccacagg    960
ttggtggctt ttcttgaacg tgcggactcg gtgatctcct gggatataca ggacgaaaag  1020
aatgtcactt gtcaactcac tttctgggaa gcctcggaac gcaccattcg ttccgaagcc  1080
gaggactcgt atcactttc ttctgccaaa atgaccgcca ctttcttatc taagaagcaa  1140
gaggtgaaca tgtccgactc tgcgctggac tgcgtacgtg atgaggctat aaataagtta  1200
cagcagattt tcaatacttc atacaatcaa acatatgaaa aatatggaaa cgtgtccgtc  1260
tttgaaacca ctggtggttt ggtagtgttc tggcaaggta tcaagcaaaa atctctggtg  1320
gaactcgaac gtttggccaa ccgctccagt ctgaatctta ctcataatag aaccaaaaga  1380
agtacagatg caacaatgc aactcattta tccaacatgg aatcggtgca atctggtc   1440
tacgcccagc tgcagttcac ctatgacacg ttgcgcggtt acatcaaccg ggcgctggcg  1500
caaatcgcag aagcctggtg tgtggatcaa cggcgcaccc tagaggtctt caaggaactc  1560
agcaagatca cccgtcagc cattctctcg gccatttaca acaaaccgat tgccgcgcgt  1620
ttcatgggtg atgtcttggg cctggccagc tgcgtgacca tcaaccaaac cagcgtcaag  1680
gtgctgcgtg atatgaacgt gaaggagtcg ccaggacgct gctactcacg acccgtggtc  1740
atctttaatt tcgccaacag ctcgtacgtg cagtacggtc aactgggcga ggacaacgaa  1800
atcctgttgg gcaaccaccg cactgaggaa tgtcagcttc ccagcctcaa gatcttcatc  1860
gccgggaact cggcctacga gtacgtggac tacctcttca aacgcatgat tgacctcagc  1920
agtatctcca ccgtcgacag catgatcgcc ctggatatcg acccgctgga aaataccgac  1980
ttcagggtac tggaacttta ctcgcagaaa gagctgcgtt ccagcaacgt ttttgacctc  2040
gaagagatca tgcgcgaatt caactcgtac aagcagcggg taaagtacgt ggaggacaag  2100
gtagtcgacc cgctaccgcc cagcagcatc gccagcttct tcttcatcat cggcctgatc  2160
atcggcctgt tcctggtgct gcgcgtgggc atccacctgt gcatcaagct gaagcacacc  2220
aagaagcgcc agatctacac cgacatcgag atgaaccgcc tgggcaag              2268
```

<210> SEQ ID NO 24
<211> LENGTH: 756

<212> TYPE: PRT
<213> ORGANISM: Artificial Sequence
<220> FEATURE:
<223> OTHER INFORMATION: HgB(VSV-G-2) amino acid sequence

<400> SEQUENCE: 24

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
                35                  40                  45

Arg Ser Gly Ser Val Ser Gln Arg Val Thr Ser Ser Gln Thr Val Ser
            50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
            195                 200                 205

Lys Thr Met Gln Leu Met Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
            275                 280                 285

Tyr Phe Gly Glu Asn Ala Asp Lys Phe Ile Phe Pro Asn Tyr Thr
            290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
            355                 360                 365

Ala Lys Met Thr Ala Thr Phe Leu Ser Lys Lys Gln Glu Val Asn Met
            370                 375                 380
```

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
            405                 410                 415

Asn Val Ser Val Phe Glu Thr Thr Gly Gly Leu Val Val Phe Trp Gln
        420                 425                 430

Gly Ile Lys Gln Lys Ser Leu Val Glu Leu Glu Arg Leu Ala Asn Arg
    435                 440                 445

Ser Ser Leu Asn Leu Thr His Asn Arg Thr Lys Arg Ser Thr Asp Gly
450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
690                 695                 700

Leu Pro Pro Ser Ser Ile Ala Ser Phe Phe Ile Ile Gly Leu Ile
705                 710                 715                 720

Ile Gly Leu Phe Leu Val Leu Arg Val Gly Ile His Leu Cys Ile Lys
                725                 730                 735

Leu Lys His Thr Lys Lys Arg Gln Ile Tyr Thr Asp Ile Glu Met Asn
            740                 745                 750

Arg Leu Gly Lys
        755

<210> SEQ ID NO 25
<211> LENGTH: 4247
<212> TYPE: DNA
<213> ORGANISM: Artificial Sequence
<220> FEATURE:
<223> OTHER INFORMATION: HK1-HgB(H3-1)

<400> SEQUENCE: 25

```
gcgcaccggg gatcctaggc tttttggatt gcgctttcct ctagatcaac tgggtgtcag    60
gccctatcct acagaaggat ggaatccagg atctggtgcc tggtagtctg cgttaacttg   120
tgtatcgtct gtctgggtgc tgcggtttcc tcatcttcta ctcgtggaac ttctgctact   180
cacagtcacc attcctctca tacgacgtct gctgctcact ctcgatccgg ttcagtctct   240
caacgcgtaa cttcttccca aacggtcagc catggtgtta acgagaccat ctacaacact   300
accctcaagt acggagatgt ggtgggggtc aataccacca agtacccta tcgcgtgtgt    360
tctatggccc agggtacgga tcttattcgc tttgaacgta atatcgtctg cacctcgatg   420
aagcccatca atgaagacct ggacgagggc atcatggtgg tctacaaacg caacatcgtc   480
gcgcacacct ttaaggtacg agtctaccag aaggttttga cgtttcgtcg tagctacgct   540
tacatccaca ccacttatct gctgggcagc aacacggaat acgtggcgcc tcctatgtgg   600
gagattcatc atatcaacag ccacagtcag tgctacagtt cctacagccg cgttatagca   660
ggcacggttt tcgtggctta tcatagggac agctatgaaa acaaaaccat gcaattaatg   720
cccgacgatt attccaacac ccacagtacc cgttacgtga cggtcaagga tcaatggcac   780
agccgcggca gcacctggct ctatcgtgag acctgtaatc tgaattgtat ggtgaccatc   840
actactgcgc gctccaaata tccttatcat ttttttcgcca cttccacggg tgacgtggtt   900
gacatttctc ctttctacaa cggaaccaat cgcaatgcca gctactttgg agaaaacgcc   960
gacaagtttt tcatttttcc gaactacact attgtctccg actttggaag accgaattct  1020
gcgttagaga cccacaggtt ggtggctttt cttgaacgtg cggactcggt gatctcctgg  1080
gatatacagg acgaaaagaa tgtcacttgt caactcactt tctgggaagc ctcggaacgc  1140
accattcgtt ccgaagccga ggactcgtat cacttttctt ctgccaaaat gaccgccact  1200
ttcttatcta agaagcaaga ggtgaacatg tccgactctg cgctggactg cgtacgtgat  1260
gaggctataa ataagttaca gcagatttt aatacttcat acaatcaaac atatgaaaaa   1320
tatgaaaacg tgtccgtctt tgaaaccact ggtggtttgg tagtgttctg gcaaggtatc  1380
aagcaaaaat ctctggtgga actcgaacgt ttggccaacc gctccagtct gaatcttact  1440
cataatagaa ccaaaagaag tacagatggc aacaatgcaa ctcatttatc caacatggaa  1500
tcggtgcaca atctggtcta cgcccagctg cagttcacct atgacacgtt gcgcggttac  1560
atcaaccggg cgctggcgca aatcgcagaa gcctggtgtg tggatcaacg gcgcacccta  1620
gaggtcttca aggaactcag caagatcaac ccgtcagcca ttctctcggc catttacaac  1680
aaaccgattg ccgcgcgttt catgggtgat gtcttgggcc tggccagctg cgtgaccatc  1740
aaccaaacca gcgtcaaggt gctgcgtgat atgaacgtga aggagtcgcc aggacgctgc  1800
tactcacgac ccgtggtcat ctttaatttc gccaacagct cgtacgtgca gtacggtcaa  1860
ctgggcgaga caacgaaat cctgttgggc aaccaccgca ctgaggaatg tcagcttccc    1920
agcctcaaga tcttcatcgc cgggaactcg gcctacgagt acgtggacta cctcttcaaa   1980
cgcatgattg acctcagcag tatctccacc gtcgacagca tgatcgccct ggatatcgac   2040
ccgctggaaa ataccgactt cagggtactg gaactttact cgcagaaaga gctgcgttcc   2100
agcaacgttt ttgacctcga agagatcatg cgcgaattca actcgtacaa gcagcgggta   2160
aagtacgtgg aggacaaggt agtcgacccg ctaccgccct acctcaaggg tctggacgac   2220
ctcatgagcg gcctgggcgc cgcgggaaag gccgttggcg tagccattgg ggccgtgggt   2280
```

```
ggcgcggtgg cctccgtggt cgaaggcgtt gccaccttcc tcaaaaaccc ctggatccta    2340
tggatttcct ttgccatatc atgcttttg ctttgtgttg ttctgttggg gttcattatg    2400
tgggcctgcc aaaagggcaa cattaggtgc aacatttgca tttgaagaac agcgcctccc    2460
tgactctcca cctcgaaaga ggtggagagt cagggaggcc cagagggtct tagagtgtca    2520
caacatttgg gcctctaaaa attaggtcat gtggcagaat gttgtaaca gttttcagat    2580 ctgggagcct tgctttggag gcgctttcaa aaatgatgca gtccatgagt gcacagtgcg    2640
gggtgatctc tttcttcttt ttgtccctta ctattccagt atgcatctta cacaaccagc    2700
catatttgtc ccacacttta tcttcatact ccctcgaagc ttccctggtc atttcaacat    2760
cgataagctt aatgtccttc ctattttgtg agtccagaag ctttctgatg tcatcggagc    2820
cttgacagct tagaaccatc ccctgcggaa gagcacctat aactgacgag gtcaacccgg    2880
gttgcgcatt gaagaggtcg gcaagatcca tgccgtgtga gtacttggaa tcttgcttga    2940 attgttttg atcaacgggt tccctgtaaa agtgtatgaa ctgcccgttc tgtggttgga    3000
aaattgctat ttccactgga tcattaaatc taccctcaat gtcaatccat gtaggagcgt    3060
tggggtcaat tcctcccatg aggtctttta aaagcattgt ctggctgtag cttaagccca    3120
cctgaggtgg acctgctgct ccaggcgctg gcctgggtga gttgactgca ggtttctcgc    3180
ttgtgagatc aattgttgtg ttttcccatg ctctccccac aatcgatgtt ctacaagcta    3240
tgtatggcca tccttcacct gaaaggcaaa ctttatagag gatgttttca taagggttcc    3300
tgtccccaac ttggtctgaa acaaacatgt tgagttttct cttggccccg agaactgcct    3360
tcaagagatc ctcgctgttg cttggcttga tcaaaattga ctctaacatg ttacccccat    3420
ccaacagggc tgcccctgcc ttcacggcag caccaagact aaagttatag ccagaaatgt    3480
tgatgctgga ctgctgttca gtgatgaccc ccagaactgg gtgcttgtct ttcagccttt    3540
caagatcatt aagatttgga tacttgactg tgtaaagcaa gccaaggtct gtgagcgctt    3600
gtacaacgtc attgagcgga gtctgtgact gtttggccat acaagccata gttagacttg    3660
gcattgtgcc aaattgattg ttcaaaagtg atgagtcttt cacatcccaa actcttacca    3720
caccacttgc accctgctga ggctttctca tcccaactat ctgtaggatc tgagatcttt    3780
ggtctagttg ctgtgttgtt aagttcccca tatataccc tgaagcctgg ggcctttcag    3840
acctcatgat cttggccttc agcttctcaa ggtcagccgc aagagacatc agttcttctg    3900
cactgagcct ccccactttc aaaacattct tctttgatgt tgactttaaa tccacaagag    3960
aatgtacagt ctggttgaga cttctgagtc tctgtaggtc tttgtcatct ctcttttcct    4020
tcctcatgat cctctgaaca ttgctgacct cagagaagtc caacccattc agaaggttgg    4080
ttgcatcctt aatgacagca gccttcacat ctgatgtgaa gctctgcaat tctcttctca    4140
atgcttgcgt ccattggaag ctcttaactt ccttagacaa ggacatcttg ttgctcaatg    4200
gtttctcaag acaaatgcgc aatcaaatgc ctaggatcca ctgtgcg                 4247
```

<210> SEQ ID NO 26
<211> LENGTH: 2364
<212> TYPE: DNA
<213> ORGANISM: Artificial Sequence
<220> FEATURE:
<223> OTHER INFORMATION: HgB(H3-1) cDNA sequence

<400> SEQUENCE: 26

```
atggaatcca ggatctggtg cctggtagtc tgcgttaact tgtgtatcgt ctgtctgggt      60
gctgcggttt cctcatcttc tactcgtgga acttctgcta ctcacagtca ccattcctct     120
```

```
catacgacgt ctgctgctca ctctcgatcc ggttcagtct ctcaacgcgt aacttcttcc      180
caaacggtca gccatggtgt taacgagacc atctacaaca ctaccctcaa gtacggagat      240
gtggtggggg tcaataccac caagtacccc tatcgcgtgt gttctatggc ccagggtacg      300
gatcttattc gctttgaacg taatatcgtc tgcacctcga tgaagcccat caatgaagac      360
ctggacgagg gcatcatggt ggtctacaaa cgcaacatcg tcgcgcacac ctttaaggta      420
cgagtctacc agaaggtttt gacgtttcgt cgtagctacg cttacatcca caccacttat      480
ctgctgggca gcaacacgga atacgtggcg cctcctatgt gggagattca tcatatcaac      540
agccacagtc agtgctacag ttcctacagc cgcgttatag caggcacggt tttcgtggct      600
tatcataggg acagctatga aaacaaaacc atgcaattaa tgcccgacga ttattccaac      660
acccacagta cccgttacgt gacggtcaag gatcaatggc acagccgcgg cagcacctgg      720
ctctatcgtg agacctgtaa tctgaattgt atggtgacca tcactactgc gcgctccaaa      780
tatccttatc attttttcgc cacttccacg ggtgacgtgg ttgacatttc tcctttctac      840
aacggaacca atcgcaatgc cagctacttt ggagaaaacg ccgacaagtt tttcattttt      900
ccgaactaca ctattgtctc cgactttgga agaccgaatt ctgcgttaga gacccacagg      960
ttggtggctt ttcttgaacg tgcggactcg gtgatctcct gggatataca ggacgaaaag     1020
aatgtcactt gtcaactcac tttctgggaa gcctcggaac gcaccattcg ttccgaagcc     1080
gaggactcgt atcactttc ttctgccaaa atgaccgcca ctttcttatc taagaagcaa     1140
gaggtgaaca tgtccgactc tgcgctggac tgcgtacgtg atgaggctat aaataagtta     1200
cagcagattt tcaatacttc atacaatcaa acatatgaaa aatatggaaa cgtgtccgtc     1260
tttgaaacca ctggtggttt ggtagtgttc tggcaaggta tcaagcaaaa atctctggtg     1320
gaactcgaac gtttggccaa ccgctccagt ctgaatctta ctcataatag aaccaaaaga     1380
agtacagatg caacaatgc aactcattta tccaacatgg aatcggtgca caatctggtc     1440
tacgcccagc tgcagttcac ctatgacacg ttgcgcggtt acatcaaccg ggcgctggcg     1500
caaatcgcag aagcctggtg tgtggatcaa cggcgcaccc tagaggtctt caaggaactc     1560
agcaagatca acccgtcagc cattctctcg gccatttaca acaaaccgat tgccgcgcgt     1620
ttcatgggtg atgtcttggg cctggccagc tgcgtgacca tcaaccaaac cagcgtcaag     1680
gtgctgcgtg atatgaacgt gaaggagtcg ccaggacgct gctactcacg acccgtggtc     1740
atctttaatt tcgccaacag ctcgtacgtg cagtacggtc aactgggcga ggacaacgaa     1800
atcctgttgg gcaaccaccg cactgaggaa tgtcagcttc ccagcctcaa gatcttcatc     1860
gccgggaact cggcctacga gtacgtggac tacctcttca aacgcatgat tgacctcagc     1920
agtatctcca ccgtcgacag catgatcgcc ctggatatcg acccgctgga aaataccgac     1980
ttcagggtac tggaacttta ctcgcagaaa gagctgcgtt ccagcaacgt ttttgacctc     2040
gaagagatca tgcgcgaatt caactcgtac aagcagcggg taaagtacgt ggaggacaag     2100
gtagtcgacc cgctaccgcc ctacctcaag ggtctggacg acctcatgag cggcctgggc     2160
gccgcgggaa aggccgttgg cgtagccatt ggggccgtgg gtggcgcggt ggcctccgtg     2220
gtcgaaggcg ttgccacctt cctcaaaaac ccctggatcc tatggatttc ctttgccata     2280
tcatgctttt tgctttgtgt tgttctgttg gggttcatta tgtgggcctg ccaaaagggc     2340
aacattaggt gcaacatttg catt                                            2364
```

<210> SEQ ID NO 27

<211> LENGTH: 788
<212> TYPE: PRT
<213> ORGANISM: Artificial Sequence
<220> FEATURE:
<223> OTHER INFORMATION: HgB(H3-1) amino acid sequence

<400> SEQUENCE: 27

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
            35                  40                  45

Arg Ser Gly Ser Val Ser Gln Arg Val Thr Ser Ser Gln Thr Val Ser
        50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Ile Phe Pro Asn Tyr Thr
290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
370                 375                 380
```

```
Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
            405                 410                 415

Asn Val Ser Val Phe Glu Thr Thr Gly Gly Leu Val Val Phe Trp Gln
        420                 425                 430

Gly Ile Lys Gln Lys Ser Leu Val Glu Leu Glu Arg Leu Ala Asn Arg
            435                 440                 445

Ser Ser Leu Asn Leu Thr His Asn Arg Thr Lys Arg Ser Thr Asp Gly
        450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
            485                 490                 495

Arg Ala Leu Ala Gln Ile Ala Glu Ala Trp Cys Val Asp Gln Arg Arg
        500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Arg Phe Met Gly Asp
530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
            565                 570                 575

Arg Pro Val Val Ile Phe Asn Phe Ala Asn Ser Ser Tyr Val Gln Tyr
        580                 585                 590

Gly Gln Leu Gly Glu Asp Asn Glu Ile Leu Leu Gly Asn His Arg Thr
    595                 600                 605

Glu Glu Cys Gln Leu Pro Ser Leu Lys Ile Phe Ile Ala Gly Asn Ser
610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
            645                 650                 655

Glu Asn Thr Asp Phe Arg Val Leu Glu Leu Tyr Ser Gln Lys Glu Leu
        660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
            725                 730                 735

Val Ala Ser Val Val Glu Gly Val Ala Thr Phe Leu Lys Asn Pro Trp
        740                 745                 750

Ile Leu Trp Ile Ser Phe Ala Ile Ser Cys Phe Leu Leu Cys Val Val
        755                 760                 765

Leu Leu Gly Phe Ile Met Trp Ala Cys Gln Lys Gly Asn Ile Arg Cys
    770                 775                 780

Asn Ile Cys Ile
785
```

<210> SEQ ID NO 28
<211> LENGTH: 4115
<212> TYPE: DNA
<213> ORGANISM: Artificial Sequence
<220> FEATURE:
<223> OTHER INFORMATION: HK1-HgB(H3-2)

<400> SEQUENCE: 28

| | | | | | |
|---|---|---|---|---|---|
| gcgcaccggg | gatcctaggc | tttttggatt | gcgctttcct | ctagatcaac | tgggtgtcag | 60 |
| gccctatcct | acagaaggat | ggaatccagg | atctggtgcc | tggtagtctg | cgttaacttg | 120 |
| tgtatcgtct | gtctgggtgc | tgcggtttcc | tcatcttcta | ctcgtggaac | ttctgctact | 180 |
| cacagtcacc | attcctctca | tacgacgtct | gctgctcact | ctcgatccgg | ttcagtctct | 240 |
| caacgcgtaa | cttcttccca | aacggtcagc | atggtgtta | acgagaccat | ctacaacact | 300 |
| accctcaagt | acggagatgt | ggtggggtc | aataccacca | agtacccta | tcgcgtgtgt | 360 |
| tctatggccc | agggtacgga | tcttattcgc | tttgaacgta | atatcgtctg | cacctcgatg | 420 |
| aagcccatca | atgaagacct | ggacgagggc | atcatggtgg | tctacaaacg | caacatcgtc | 480 |
| gcgcacacct | ttaaggtacg | agtctaccag | aaggttttga | cgtttcgtcg | tagctacgct | 540 |
| tacatccaca | ccacttatct | gctgggcagc | aacacggaat | acgtggcgcc | tcctatgtgg | 600 |
| gagattcatc | atatcaacag | ccacagtcag | tgctacagtt | cctacagccg | cgttatagca | 660 |
| ggcacggttt | tcgtggctta | tcatagggac | agctatgaaa | acaaaaccat | gcaattaatg | 720 |
| cccgacgatt | attccaacac | ccacagtacc | cgttacgtga | cggtcaagga | tcaatggcac | 780 |
| agccgcggca | gcacctggct | ctatcgtgag | acctgtaatc | tgaattgtat | ggtgaccatc | 840 |
| actactgcgc | gctccaaata | tccttatcat | tttttcgcca | cttccacggg | tgacgtggtt | 900 |
| gacatttctc | ctttctacaa | cggaaccaat | cgcaatgcca | gctactttgg | agaaaacgcc | 960 |
| gacaagtttt | tcattttttcc | gaactacact | attgtctccg | actttggaag | accgaattct | 1020 |
| gcgttagaga | cccacaggtt | ggtggctttt | cttgaacgtg | cggactcggt | gatcctctgg | 1080 |
| gatatacagg | acgaaaagaa | tgtcacttgt | caactcactt | tctgggaagc | ctcggaacgc | 1140 |
| accattcgtt | ccgaagccga | ggactcgtat | cactttttctt | ctgccaaaat | gaccgccact | 1200 |
| ttcttatcta | agaagcaaga | ggtgaacatg | tccgactctg | cgctggactg | cgtacgtgat | 1260 |
| gaggctataa | ataagttaca | gcagattttc | aatacttcat | acaatcaaac | atatgaaaaa | 1320 |
| tatggaaacg | tgtccgtctt | tgaaaccact | ggtggtttgg | tagtgttctg | gcaaggtatc | 1380 |
| aagcaaaaat | ctctggtgga | actcgaacgt | ttggccaacc | gctccagtct | gaatcttact | 1440 |
| cataatagaa | ccaaaagaag | tacagatggc | aacaatgcaa | ctcatttatc | caacatggaa | 1500 |
| tcggtgcaca | atctggtcta | cgcccagctg | cagttcacct | atgacacgtt | gcgcggttac | 1560 |
| atcaaccggg | cgctggcgca | aatcgcagaa | gcctggtgtg | tggatcaacg | gcgcacccta | 1620 |
| gaggtcttca | aggaactcag | caagatcaac | ccgtcagcca | ttctctcggc | catttacaac | 1680 |
| aaaccgattg | ccgcgcgttt | catgggtgat | gtcttgggcc | tggccagctg | cgtgaccatc | 1740 |
| aaccaaacca | gcgtcaaggt | gctgcgtgat | atgaacgtga | aggagtcgcc | aggacgctgc | 1800 |
| tactcacgac | ccgtggtcat | ctttaatttc | gccaacagct | cgtacgtgca | gtacggtcaa | 1860 |
| ctgggcgagg | acaacgaaat | cctgttgggc | aaccaccgca | ctgaggaatg | tcagcttccc | 1920 |
| agcctcaaga | tcttcatcgc | cgggaactcg | gcctacgagt | acgtggacta | cctcttcaaa | 1980 |
| cgcatgattg | acctcagcag | tatctccacc | gtcgacagca | tgatcgccct | ggatatcgac | 2040 |
| ccgctggaaa | ataccgactt | cagggtactg | gaactttact | cgcagaaaga | gctgcgttcc | 2100 |

```
agcaacgttt ttgacctcga agagatcatg cgcgaattca actcgtacaa gcagcgggta    2160
aagtacgtgg aggacaaggt agtcgacccg ctaccgccct ggatcctatg gatttccttt    2220
gccatatcat gcttttgct ttgtgttgtt ctgttggggt tcattatgtg ggcctgccaa    2280
aagggcaaca ttaggtgcaa catttgcatt tgaagaacag cgcctccctg actctccacc    2340
tcgaaagagg tggagagtca gggaggccca gagggtctta gagtgtcaca catttgggc     2400 ctctaaaaat taggtcatgt ggcagaatgt tgtgaacagt tttcagatct gggagccttg    2460
ctttggaggc gctttcaaaa atgatgcagt ccatgagtgc acagtgcggg gtgatctctt    2520
tcttcttttt gtcccttact attccagtat gcatcttaca caaccagcca tatttgtccc    2580
acactttatc ttcatactcc ctcgaagctt ccctggtcat ttcaacatcg ataagcttaa    2640
tgtccttcct attttgtgag tccagaagct ttctgatgtc atcggagcct tgacagctta    2700
gaaccatccc ctgcggaaga gcacctataa ctgacgaggt caacccgggt tgcgcattga    2760
agaggtcggc aagatccatg ccgtgtgagt acttggaatc ttgcttgaat tgttttgat    2820 caacgggttc cctgtaaaag tgtatgaact gcccgttctg tggttggaaa attgctattt    2880
ccactggatc attaaatcta ccctcaatgt caatccatgt aggagcgttg gggtcaattc    2940
ctcccatgag gtcttttaaa agcattgtct ggctgtagct taagcccacc tgaggtggac    3000
ctgctgctcc aggcgctggc ctgggtgagt tgactgcagg tttctcgctt gtgagatcaa    3060
ttgttgtgtt ttcccatgct ctcccacaa tcgatgttct acaagctatg tatggccatc     3120
cttcacctga aagcaaact ttatagagga tgttttcata agggttcctg tccccaactt     3180
ggtctgaaac aaacatgttg agttttctct tggccccgag aactgccttc aagagatcct    3240
cgctgttgct tggcttgatc aaaattgact ctaacatgtt accccatcc aacagggctg     3300 cccctgcctt cacggcagca ccaagactaa agttatagcc agaaatgttg atgctggact    3360
gctgttcagt gatgaccccc agaactgggt gcttgtcttt cagcctttca agatcattaa    3420
gatttggata cttgactgtg taaagcaagc caaggtctgt gagcgcttgt acaacgtcat    3480
tgagcggagt ctgtgactgt ttggccatac aagccatagt tagacttggc attgtgccaa    3540
attgattgtt caaaagtgat gagtctttca catcccaaac tcttaccaca ccacttgcac    3600
cctgctgagg cttctcatc ccaactatct gtaggatctg agatctttgg tctagttgct     3660
gtgttgttaa gttccccata tatacccctg aagcctgggg cctttcagac ctcatgatct    3720
tggccttcag cttctcaagg tcagccgcaa gagacatcag ttcttctgca ctgagcctcc    3780
ccactttcaa acattcttc tttgatgttg actttaaatc cacaagagaa tgtacagtct     3840
ggttgagact tctgagtctc tgtaggtctt tgtcatctct ctttccttc ctcatgatcc      3900 tctgaacatt gctgacctca gagaagtcca accattcag aaggttggtt gcatccttaa     3960
tgacagcagc cttcacatct gatgtgaagc tctgcaattc tcttctcaat gcttgcgtcc    4020
attggaagct cttaacttcc ttagacaagg acatcttgtt gctcaatggt ttctcaagac    4080
aaatgcgcaa tcaaatgcct aggatccact gtgcg                               4115
```

<210> SEQ ID NO 29
<211> LENGTH: 2232
<212> TYPE: DNA
<213> ORGANISM: Artificial Sequence
<220> FEATURE:
<223> OTHER INFORMATION: HgB(H3-2) cDNA sequence

<400> SEQUENCE: 29

```
atggaatcca ggatctggtg cctggtagtc tgcgttaact tgtgtatcgt ctgtctgggt    60
gctgcggttt cctcatcttc tactcgtgga acttctgcta ctcacagtca ccattcctct   120
catacgacgt ctgctgctca ctctcgatcc ggttcagtct ctcaacgcgt aacttcttcc   180
caaacggtca gccatggtgt taacgagacc atctacaaca ctaccctcaa gtacggagat   240
gtggtggggg tcaataccac caagtacccc tatcgcgtgt gttctatggc ccagggtacg   300
gatcttattc gctttgaacg taatatcgtc tgcacctcga tgaagcccat caatgaagac   360
ctggacgagg gcatcatggt ggtctacaaa cgcaacatcg tcgcgcacac ctttaaggta   420
cgagtctacc agaaggtttt gacgtttcgt cgtagctacg cttacatcca caccacttat   480
ctgctgggca gcaacacgga atacgtggcg cctcctatgt gggagattca tcatatcaac   540
agccacagtc agtgctacag ttcctacagc cgcgttatag caggcacggt tttcgtggct   600
tatcataggg acagctatga aaacaaaacc atgcaattaa tgcccgacga ttattccaac   660
acccacagta cccgttacgt gacggtcaag gatcaatggc acagccgcgg cagcacctgg   720
ctctatcgtg agacctgtaa tctgaattgt atggtgacca tcactactgc gcgctccaaa   780
tatccttatc attttttcgc cacttccacg ggtgacgtgg ttgacatttc tcctttctac   840
aacggaacca atcgcaatgc cagctacttt ggagaaaacg ccgacaagtt tttcattttt   900
ccgaactaca ctattgtctc cgactttgga agaccgaatt ctgcgttaga gacccacagg   960
ttggtggctt ttcttgaacg tgcggactcg gtgatctcct gggatataca ggacgaaaag  1020
aatgtcactt gtcaactcac tttctgggaa gcctcggaac gcaccattcg ttccgaagcc  1080
gaggactcgt atcactttc ttctgccaaa atgaccgcca ctttcttatc taagaagcaa  1140
gaggtgaaca tgtccgactc tgcgctggac tgcgtacgtg atgaggctat aaataagtta  1200
cagcagattt tcaatacttc atacaatcaa acatatgaaa aatatggaaa cgtgtccgtc  1260
tttgaaacca ctggtggttt ggtagtgttc tggcaaggta tcaagcaaaa atctctggtg  1320
gaactcgaac gtttggccaa ccgctccagt ctgaatctta ctcataatag aaccaaaaga  1380
agtacagatg gcaacaatgc aactcattta tccaacatgg aatcggtgca atctggtc   1440
tacgcccagc tgcagttcac ctatgacacg ttgcgcggtt acatcaaccg ggcgctggcg  1500
caaatcgcag aagcctggtg tgtggatcaa cggcgcaccc tagaggtctt caaggaactc  1560
agcaagatca cccgtcagc cattctctcg gccatttaca acaaaccgat tgccgcgcgt  1620
ttcatgggtg atgtcttggg cctggccagc tgcgtgacca tcaaccaaac cagcgtcaag  1680
gtgctgcgtg atatgaacgt gaaggagtcg ccaggacgct gctactcacg acccgtggtc  1740
atctttaatt tcgccaacag ctcgtacgtg cagtacggtc aactgggcga ggacaacgaa  1800
atcctgttgg gcaaccaccg cactgaggaa tgtcagcttc ccagcctcaa gatcttcatc  1860
gccgggaact cggcctacga gtacgtggac tacctcttca aacgcatgat tgacctcagc  1920
agtatctcca ccgtcgacag catgatcgcc ctggatatcg acccgctgga aaataccgac  1980
ttcagggtac tggaacttta ctcgcagaaa gagctgcgtt ccagcaacgt ttttgacctc  2040
gaagagatca tgcgcgaatt caactcgtac aagcagcggg taaagtacgt ggaggacaag  2100
gtagtcgacc cgctaccgcc ctggatccta tggatttcct ttgccatatc atgcttttg   2160
ctttgtgttg ttctgttggg gttcattatg tgggcctgcc aaaagggcaa cattaggtgc  2220
aacatttgca tt                                                      2232
```

<210> SEQ ID NO 30
<211> LENGTH: 744

```
<212> TYPE: PRT
<213> ORGANISM: Artificial Sequence
<220> FEATURE:
<223> OTHER INFORMATION: HgB(H3-2) amino acid sequence

<400> SEQUENCE: 30

Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
            35                  40                  45

Arg Ser Gly Ser Val Ser Gln Arg Val Thr Ser Ser Gln Thr Val Ser
        50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Ile Phe Pro Asn Tyr Thr
290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380
```

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
            405                 410                 415

Asn Val Ser Val Phe Glu Thr Thr Gly Gly Leu Val Val Phe Trp Gln
        420                 425                 430

Gly Ile Lys Gln Lys Ser Leu Val Glu Leu Glu Arg Leu Ala Asn Arg
            435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
                500                 505                 510

Thr Leu Glu Val Phe Lys Glu Leu Ser Lys Ile Asn Pro Ser Ala Ile
            515                 520                 525

Leu Ser Ala Ile Tyr Asn Lys Pro Ile Ala Ala Arg Phe Met Gly Asp
530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
                580                 585                 590

Gly Gln Leu Gly Glu Asp Asn Glu Ile Leu Leu Gly Asn His Arg Thr
            595                 600                 605

Glu Glu Cys Gln Leu Pro Ser Leu Lys Ile Phe Ile Ala Gly Asn Ser
610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
                660                 665                 670

Arg Ser Ser Asn Val Phe Asp Leu Glu Glu Ile Met Arg Glu Phe Asn
            675                 680                 685

Ser Tyr Lys Gln Arg Val Lys Tyr Val Glu Asp Lys Val Val Asp Pro
    690                 695                 700

Leu Pro Pro Trp Ile Leu Trp Ile Ser Phe Ala Ile Ser Cys Phe Leu
705                 710                 715                 720

Leu Cys Val Val Leu Leu Gly Phe Ile Met Trp Ala Cys Gln Lys Gly
                725                 730                 735

Asn Ile Arg Cys Asn Ile Cys Ile
            740

<210> SEQ ID NO 31
<211> LENGTH: 3376
<212> TYPE: DNA
<213> ORGANISM: Lymphocytic choriomeningitis virus
<220> FEATURE:
<223> OTHER INFORMATION: Lymphocytic choriomeningitis virus segment S,
      complete sequence

<400> SEQUENCE: 31

```
cgcaccgggg atcctaggct ttttggattg cgctttcctc tagatcaact gggtgtcagg    60
ccctatccta cagaaggatg ggtcagattg tgacaatgtt tgaggctctg cctcacatca   120
tcgatgaggt gatcaacatt gtcattattg tgcttatcgt gatcacgggt atcaaggctg   180
tctacaattt tgccacctgt gggatattcg cattgatcag tttcctactt ctggctggca   240
ggtcctgtgg catgtacggt cttaagggac ccgacattta caaggagtt taccaattta    300 agtcagtgga gtttgatatg tcacatctga acctgaccat gcccaacgca tgttcagcca   360
acaactccca ccattacatc agtatgggga cttctggact agaattgacc ttcaccaatg   420
attccatcat cagtcacaac ttttgcaatc tgacctctgc cttcaacaaa aagacctttg   480
accacacact catgagtata gtttcgagcc tacacctcag tatcagaggg aactccaact   540
ataaggcagt atcctgcgac ttcaacaatg gcataaccat ccaatacaac ttgacattct   600
cagatcgaca aagtgctcag agccagtgta gaaccttcag aggtagagtc ctagatatgt   660
ttagaactgc cttcgggggg aaatacatga ggagtggctg gggctggaca ggctcagatg   720
gcaagaccac ctggtgtagc cagacgagtt accaatacct gattatacaa aatagaacct   780
gggaaaacca ctgcacatat gcaggtcctt ttgggatgtc caggattctc ctttcccaag   840
agaagactaa gttcttcact aggagactag cgggcacatt cacctggact ttgtcagact   900
cttcaggggt ggagaatcca ggtggttatt gcctgaccaa atggatgatt cttgctgcag   960
agcttaagtg tttcgggaac acagcagttg cgaaatgcaa tgtaaatcat gatgccgaat  1020
tctgtgacat gctgcgacta attgactaca caaggctgc tttgagtaag ttcaaagagg  1080
acgtagaatc tgccttgcac ttattcaaaa caacagtgaa ttctttgatt tcagatcaac  1140
tactgatgag gaaccacttg agagatctga tgggggtgcc atattgcaat tactcaaagt  1200
tttggtacct agaacatgca aagaccggcg aaactagtgt ccccaagtgc tggcttgtca  1260
ccaatggttc ttacttaaat gagacccact tcagtgatca aatcgaacag gaagccgata  1320
acatgattac agagatgttg aggaaggatt acataaagag gcaggggagt accccctag  1380 cattgatgga ccttctgatg ttttccacat ctgcatatct agtcagcatc ttcctgcacc  1440
ttgtcaaaat accaacacac aggcacataa aaggtggctc atgtccaaag ccacaccgat  1500
taaccaacaa aggaatttgt agttgtggtg catttaaggt gcctggtgta aaaaccgtct  1560
ggaaaagacg ctgaagaaca gcgcctccct gactctccac ctcgaaagag gtggagagtc  1620
agggaggccc agagggtctt agagtgtcac aacatttggg cctctaaaaa ttaggtcatg  1680
tggcagaatg ttgtgaacag ttttcagatc tgggagcctt gctttggagg cgctttcaaa  1740
aatgatgcag tccatgagtg cacagtgcgg ggtgatctct ttcttctttt tgtcccttac  1800
tattccagta tgcatcttac acaaccagcc atatttgtcc cacactttgt cttcatactc  1860
cctcgaagct tccctggtca tttcaacatc gataagctta atgtccttcc tattctgtga  1920
gtccagaagc tttctgatgt catcggagcc ttgacagctt agaaccatcc cctgcggaag  1980
agcacctata actgacgagg tcaacccggg ttgcgcattg aagaggtcgg caagatccat  2040
gccgtgtgag tacttggaat cttgcttgaa ttgttttga tcaacgggtt ccctgtaaaa   2100
gtgtatgaac tgcccgttct gtggttggaa aattgctatt tccactggat cattaaatct  2160
accctcaatg tcaatccatg taggagcgtt ggggtcaatt cctcccatga ggtcttttaa  2220
aagcattgtc tggctgtagc ttaagcccac ctgaggtgga cctgctgctc caggcgctgg  2280
cctgggtgaa ttgactgcag gtttctcgct tgtgagatca attgttgtgt tttcccatgc  2340
```

```
tctccccaca atcgatgttc tacaagctat gtatggccat ccttcacctg aaaggcaaac    2400
tttatagagg atgttttcat aagggttcct gtccccaact tggtctgaaa caaacatgtt    2460
gagttttctc ttggccccga gaactgcctt caagaggtcc tcgctgttgc ttggcttgat    2520
caaaattgac tctaacatgt taccccatc aacagggct gccctgcct tcacggcagc      2580 accaagacta aagttatagc cagaaatgtt gatgctggac tgctgttcag tgatgacccc    2640
cagaactggg tgcttgtctt tcagccttc aagatcatta agatttggat acttgactgt    2700
gtaaagcaag ccaaggtctg tgagcgcttg tacaacgtca ttgagcggag tctgtgactg    2760
tttggccata caagccatag ttagacttgg cattgtgcca aattgattgt tcaaaagtga    2820
tgagtctttc acatcccaaa ctcttaccac accacttgca ccctgctgag ctttctcat    2880 cccaactatc tgtaggatct gagatctttg gtctagttgc tgtgttgtta agttccccat    2940 atataccct gaagcctggg gcctttcaga cctcatgatc ttggccttca gcttctcaag    3000
gtcagccgca agagacatca gttcttctgc actgagcctc cccactttca aaacattctt    3060
ctttgatgtt gactttaaat ccacaagaga atgtacagtc tggttgagac ttctgagtct    3120
ctgtaggtct ttgtcatctc tcttttcctt cctcatgatc ctctgaacat tgctgacctc    3180
agagaagtcc aacccattca gaaggttggt tgcatcctta atgacagcag ccttcacatc    3240
tgatgtgaag ctctgcaatt ctcttctcaa tgcttgcgtc cattggaagc tcttaacttc    3300
cttagacaag gacatcttgt tgctcaatgg tttctcaaga caaatgcgca atcaaatgcc    3360
taggatccac tgtgcg                                                   3376
```

<210> SEQ ID NO 32
<211> LENGTH: 3377
<212> TYPE: DNA
<213> ORGANISM: Lymphocytic choriomeningitis virus
<220> FEATURE:
<223> OTHER INFORMATION: Lymphocytic choriomeningitis virus segment S, complete sequence

<400> SEQUENCE: 32

```
gcgcaccggg gatcctaggc tttttggatt gcgctttcct ctagatcaac tgggtgtcag     60
gccctatcct acagaaggat gggtcagatt gtgacaatgt tgaggctct gcctcacatc    120 atcgatgagg tgatcaacat tgtcattatt gtgcttatcg tgatcacggg tatcaaggct    180
gtctacaatt ttgccacctg tgggatattc gcattgatca gtttcctact tctggctggc    240
aggtcctgtg gcatgtacgg tcttaaggga cccgacattt acaaaggagt ttaccaattt    300
aagtcagtgg agtttgatat gtcacatctg aacctgacca tgcccaacgc atgttcagcc    360
aacaactccc accattacat cagtatgggg acttctggac tagaattgac cttcaccaat    420
gattccatca tcagtcacaa cttttgcaat ctgacctctg ccttcaacaa aaagaccttt    480
gaccacacac tcatgagtat agtttcgagc ctacacctca gtatcagagg gaactccaac    540
tataaggcag tatcctgcga cttcaacaat ggcataacca tccaatacaa cttgacattc    600
tcagatgcac aaagtgctca gagccagtgt agaaccttca gaggtagagt cctagatatg    660
tttagaactg ccttcggggg gaaatacatg aggagtggct ggggctggac aggctcagat    720
ggcaagacca cctggtgtag ccagacgagt taccaatacc tgattataca aaatagaacc    780
tgggaaaacc actgcacata tgcaggtcct ttgggatgt ccaggattct cctttcccaa    840
gagaagacta agttcctcac taggagacta gcgggcacat tcacctggac tttgtcagac    900
tcttcagggg tggagaatcc aggtggttat tgcctgacca aatggatgat tcttgctgca    960
```

```
gagcttaagt gtttcgggaa cacagcagtt gcgaaatgca atgtaaatca tgatgaagaa    1020
ttctgtgaca tgctgcgact aattgactac aacaaggctg ctttgagtaa gttcaaagag    1080
gacgtagaat ctgccttgca cttattcaaa acaacagtga attctttgat ttcagatcaa    1140
ctactgatga ggaaccactt gagagatctg atggggggtgc catattgcaa ttactcaaag    1200
ttttggtacc tagaacatgc aaagaccggc gaaactagtg tccccaagtg ctggcttgtc    1260
accaatggtt cttacttaaa tgagacccac ttcagtgacc aaatcgaaca ggaagccgat    1320
aacatgatta cagagatgtt gaggaaggat tacataaaga ggcaggggag tacccccta     1380
gcattgatgg accttctgat gttttccaca tctgcatatc tagtcagcat cttcctgcac    1440
cttgtcaaaa taccaacaca caggcacata aaaggtggct catgtccaaa gccacaccga    1500
ttaaccaaca aaggaatttg tagttgtggt gcatttaagg tgcctggtgt aaaaaccgtc    1560
tggaaaagac gctgaagaac agcgcctccc tgactctcca cctcgaaaga ggtggagagt    1620
cagggaggcc cagagggtct tagagtgtca acacatttgg gcctctaaaa attaggtcat    1680
gtggcagaat gttgtgaaca gttttcagat ctgggagcct tgctttggag gcgctttcaa    1740
aaatgatgca gtccatgagt gcacagtgcg gggtgatctc tttcttctttt tgtcccttta   1800
ctattccagt atgcatctta cacaaccagc catatttgtc ccacactttg tcttcatact    1860
ccctcgaagc ttccctggtc atttcaacat cgataagctt aatgtcccttc ctattctgtg   1920
agtccagaag ctttctgatg tcatcggagc cttgacagct tagaaccatc ccctgcggaa    1980
gagcacctat aactgacgag gtcaacccgg gttgcgcatt gaagaggtcg gcaagatcca    2040
tgccgtgtga gtacttggaa tcttgcttga attgttttg atcaacgggt tccctgtaaa     2100
agtgtatgaa ctgcccgttc tgtggttgga aaattgctat ttccactgga tcattaaatc    2160
taccctcaat gtcaatccat gtaggagcgt tggggtcaat tcctcccatg aggtctttta    2220
aaagcattgt ctggctgtag cttaagccca cctgaggtgg acctgctgct ccaggcgctg    2280
gcctgggtga attgactgca ggtttctcgc ttgtgagatc aattgttgtg ttttcccatg    2340
ctctccccac aatcgatgtt ctacaagcta tgtatggcca tccttcacct gaaaggcaaa    2400
ctttatagag gatgttttca taagggttcc tgtccccaac ttggtctgaa acaaacatgt    2460
tgagttttct cttggccccg agaactgcct tcaagaggtc ctcgctgttg cttggcttga    2520
tcaaaattga ctctaacatg ttaccccccat ccaacagggc tgcccctgcc ttcacggcag   2580
caccaagact aaagttatag ccagaaatgt tgatgctgga ctgctgttca gtgatgaccc    2640
ccagaactgg gtgcttgtct ttcagccttt caagatcatt aagatttgga tacttgactg    2700
tgtaaagcaa gccaaggtct gtgagcgctt gtacaacgtc attgagcgga gtctgtgact    2760
gtttggccat acaagccata gttagacttg gcattgtgcc aaattgattg ttcaaaagtg    2820
atgagtcttt cacatcccaa actcttacca caccacttgc accctgctga ggctttctca    2880
tcccaactat ctgtaggatc tgagatcttt ggtctagttg ctgtgttgtt aagttcccca    2940
tatataccccc tgaagcctgg ggcctttcag acctcatgat cttggccttc agcttctcaa   3000
ggtcagccgc aagagacatc agttcttctg cactgagcct ccccactttc aaaacattct    3060
tctttgatgt tgactttaaa tccacaagag aatgtacagt ctggttgaga cttctgagtc    3120
tctgtaggtc tttgtcatct ctcttttcct tcctcatgat cctctgaaca ttgctgacct    3180
cagagaagtc caacccattc agaaggttgg ttgcatcctt aatgacagca gccttcacat    3240
ctgatgtgaa gctctgcaat tctcttctca atgcttgcgt ccattggaag ctcttaactt    3300
ccttagacaa ggacatcttg ttgctcaatg gtttctcaag acaaatgcgc aatcaaatgc    3360
```
ctaggatcca ctgtgcg 3377

<210> SEQ ID NO 33
<211> LENGTH: 7229
<212> TYPE: DNA
<213> ORGANISM: Lymphocytic choriomeningitis virus
<220> FEATURE:
<223> OTHER INFORMATION: Lymphocytic choriomeningitis virus segment L, complete sequence

<400> SEQUENCE: 33
gcgcaccggg gatcctaggc gtttagttgc gctgtttggt tgcacaactt tcttcgtgag 60
gctgtcagaa gtggacctgg ctgatagcga tgggtcaagg caagtccaga gaggagaaag 120
gcaccaatag tacaaacagg gccgaaatcc taccagatac cacctatctt ggccctttaa 180
gctgcaaatc ttgctggcag aaatttgaca gcttggtaag atgccatgac cactaccttt 240
gcaggcactg tttaaacctt ctgctgtcag tatccgacag gtgtcctctt tgtaaatatc 300
cattaccaac cagattgaag atatcaacag ccccaagctc tccacctccc tacgaagagt 360
aacaccgtcc ggccccggcc ccgacaaaca gcccagcaca agggaaccgc acgtcaccca 420
acgcacacag acacagcacc caacacagaa cacgcacaca cacacacaca cacacccaca 480
cgcacgcgcc cccaccaccg gggggcgccc ccccccgggg ggcggccccc cgggagcccg 540
ggcggagccc cacggagatg cccatcagtc gatgtcctcg gccaccgacc cgcccagcca 600
atcgtcgcag gacctcccct tgagtctaaa cctgcccccc actgtttcat acatcaaagt 660
gctcctagat ttgctaaaac aaagtctgca atccttaaag gcgaaccagt ctggcaaaag 720
cgacagtgga atcagcagaa tagatctgtc tatacatagt tcctggagga ttacacttat 780
ctctgaaccc aacaaatgtt caccagttct gaatcgatgc aggaagaggt tcccaaggac 840
atcactaatc ttttcatagc cctcaagtcc tgctagaaag actttcatgt ccttggtctc 900
cagcttcaca atgatatttt ggacaaggtt tcttccttca aaaagggcac ccatctttac 960
agtcagtggc acaggctccc actcaggtcc aactctctca aagtcaatag atctaatccc 1020
atccagtatt cttttggagc ccaacaactc aagctcaaga gaatcaccaa gtatcaaggg 1080
atcttccatg taatcctcaa actcttcaga tctgatatca aagacaccat cgttcacctt 1140
gaagacagag tctgtcctca gtaagtggag gcattcatcc aacattcttc tatctatctc 1200
acccttaaag aggtgagagc atgataaaag ttcagccaca cctggattct gtaattggca 1260
cctaaccaag aatatcaatg aaaatttcct taaacagtca gtattattct gattgtgcgt 1320
aaagtccact gaaattgaaa actccaatac cccttttgtg tagttgagca tgtagtccca 1380
cagatccttt aaggatttaa atgcctttgg gtttgtcagg ccctgcctaa tcaacatggc 1440
agcattacac acaacatctc ccattcggta agagaaccac ccaaaaccaa actgcaaatc 1500
attcctaaac ataggcctct ccacattttt gttcaccacc tttgagacaa atgattgaaa 1560
ggggcccagt gcctcagcac catcttcaga tggcatcatt tctttatgag ggaaccatga 1620
aaaattgcct aatgtcctgg ttgttgcaac aaattctcga acaaatgatt caaaatacac 1680
ctgttttaag aagttcttgc agacatccct cgtgctaaca acaaattcat caaccagact 1740
ggagtcagat cgctgatgag aattggcaag gtcagaaaac agaacagtgt aatgttcatc 1800
ccttttccac ttaacaacat gagaaatgag tgacaaggat tctgagttaa tatcaattaa 1860
aacacagagg tcaaggaatt taattctggg actccacctc atgttttttg agctcatgtc 1920
agacataaat ggaagaagct gatcctcaaa gatcttggga tatagccgcc tcacagattg 1980

```
aatcacttgg ttcaaattca ctttgtcctc cagtagcctt gagctctcag gctttcttgc    2040
tacataatca catgggttta agtgcttaag agttaggttc tcactgttat tcttcccttt    2100
ggtcggttct gctaggaccc aaacacccaa ctcaaaagag ttgctcaatg aaatacaaat    2160
gtagtcccaa agaagaggcc ttaaaaggca tatatgatca cggtgggctt ctggatgaga    2220
ctgtttgtca caaatgtaca gcgttatacc atcccgattg caaactcttg tcacatgatc    2280
atctgtggtt agatcctcaa gcagcttttt gatatacaga ttttccctat ttttgtttct    2340
cacacacctg cttcctagag ttttgcaaag gcctataaag ccagatgaga tacaactctg    2400
gaaagctgac ttgttgattg cttctgacag cagcttctgt gcaccccttg tgaatttact    2460
acaaagtttg ttctggagtg tcttgatcaa tgatgggatt cttcctctt ggaaagtcat     2520 cactgatgga taaaccacct tttgtcttaa aaccatcctt aatgggaaca tttcattcaa    2580
attcaaccag ttaacatctg ctaactgatt cagatcttct tcaagaccga ggaggtctcc    2640
caattgaaga atggcctcct ttttatctct gttaaatagg tctaagaaaa attcttcatt    2700
aaattcacca tttttgagct tatgatgcag tttccttaca agctttctta caacctttgt    2760
ttcattagga cacagttcct caatgagtct ttgtattctg taacctctag aaccatccag    2820
ccaatctttc acatcagtgt tggtattcag tagaaatgga tccaaaggga aattggcata    2880
ctttaggagg tccagtgttc tcctttggat actattaact agggagactg ggacgccatt    2940
tgcgatggct tgatctgcaa ttgtatctat tgtttcacaa agttgatgtg gctctttaca    3000
cttgacattg tgtagcgctg cagatacaaa ctttgtgaga gagggactt cctccccccca    3060 tacatagaat ctagatttaa attctgcagc gaacctccca gccacacttt ttgggctgat    3120
aaatttgttt aacaagccgc tcagatgaga ttggaattcc aacaggacaa ggacttcctc    3180
cggatcactt acaaccaggt cactcagcct cctatcaaat aaagtgatct gatcatcact    3240
tgatgtgtaa gcctctggtc tttcgccaaa gataacacca atgcagtagt tgatgaacct    3300
ctcgctaagc aaaccataga agtcagaagc attatgcaag attccctgcc ccatatcaat    3360
aaggctggat atatgggatg gcactatccc catttcaaaa tattgtctga aaattctctc    3420
agtaacagtt gtttctgaac ccctgagaag ttttagcttc gacttgacat atgatttcat    3480
cattgcattc acaacaggaa aggggacctc gacaagctta tgcatgtgcc aagttaacaa    3540
agtgctaaca tgatctttcc cggaacgcac atactggtca tcacctagtt tgagattttg    3600
tagaaacatt aagaacaaaa atgggcacat cattggtccc catttgctgt gatccatact    3660
atagtttaag aacccttccc gcacattgat agtcattgac aagattgcat tttcaaattc    3720
cttatcattg tttaaacagg agcctgaaaa gaaacttgaa aaagactcaa ataatcttc     3780 tattaacctt gtgaacattt ttgtcctcaa atctccaata tagagttctc tatttccccc    3840
aacctgctct ttataagata gtgcaaattt cagccttcca gagtcaggac ctactgaggt    3900
gtatgatgtt ggtgattctt ctgagtagaa gcacagattt ttcaaagcag cactcataca    3960
ttgtgtcaac gacagagctt tactaaggga ctcagaatta cttccctct cactgattct     4020 cacgtcttct tccagtttgt cccagtcaaa tttgaaattc aagccttgcc tttgcatatg    4080
cctgtatttc cctgagtacg catttgcatt catttgcaac agaatcatct tcatgcaaga    4140
aaaccaatca ttctcagaaa agaactttct acaaaggttt tttgccatct catcgaggcc    4200
acactgatct ttaatgactg aggtgaaata caaaggtgac agctctgtgg aaccctcaac    4260
agcctcacag ataaatttca tgtcatcatt ggttagacat gatgggtcaa agtcttctac    4320
```

| | | | | | |
|---|---|---|---|---|---|
| taaatggaaa | gatatttctg | acaagataac | ttttcttaag | tgagccatct | tccctgttag | 4380 |
| aataagctgt | aaatgatgta | gtccttttgt | atttgtaagt | ttttctccat | ctcctttgtc | 4440 |
| attggccctc | ctacctcttc | tgtaccgtgc | tattgtggtg | ttgacctttt | cttcgagact | 4500 |
| tttgaagaag | cttgtctctt | cttctccatc | aaaacatatt | tctgccaggt | tgtcttccga | 4560 |
| tctccctgtc | tcttctccct | tggaaccgat | gaccaatcta | gagactaact | tggaaacttt | 4620 |
| atattcatag | tctgagtggc | tcaacttata | cttttgtttt | cttacgaaac | tctccgtaat | 4680 |
| ttgactcaca | gcactaacaa | gcaatttgtt | aaagtcatat | tccagaagtc | gttctccatt | 4740 |
| tagatgctta | ttaaccacca | cacttttgtt | actagcaaga | tctaatgctg | tcgcacatcc | 4800 |
| agagttagtc | atgggatcta | ggctgtttag | cttcttctct | cctttgaaaa | ttaaagtgcc | 4860 |
| gttgttaaat | gaagacacca | ttaggctaaa | ggcttccaga | ttaacacctg | gagttgtatg | 4920 |
| ctgacagtca | atttctttac | tagtgaatct | cttcatttgc | tcatagaaca | cacattcttc | 4980 |
| ctcaggagtg | attgcttcct | tggggttgac | aaaaaaacca | aattgacttt | tgggctcaaa | 5040 |
| gaacttttca | aaacatttta | tctgatctgt | tagcctgtca | ggggtctcct | ttgtgatcaa | 5100 |
| atgacacagg | tatgacacat | tcaacataaa | tttaaatttt | gcactcaaca | acaccttctc | 5160 |
| accagtacca | aaaatagttt | ttattaggaa | tctaagcagc | ttatacacca | ccttctcagc | 5220 |
| aggtgtgatc | agatcctccc | tcaacttatc | cattaatgat | gtagatgaaa | aatctgacac | 5280 |
| tattgccatc | accaaatatc | tgacactctg | tacctgcttt | tgatttctct | ttgttgggtt | 5340 |
| ggtgagcatt | agcaacaata | gggtcctcag | tgcaacctca | atgtcggtga | gacagtcttt | 5400 |
| caaatcagga | catgatctaa | tccatgaaat | catgatgtct | atcatattgt | ataagacctc | 5460 |
| atctgaaaaa | attggtaaaa | agaacctttt | aggatctgca | tagaaggaaa | ttaaatgacc | 5520 |
| atccgggcct | tgtatggagt | agcaccttga | agattctcca | gtcttctggt | ataataggtg | 5580 |
| gtattcttca | gagtccagtt | ttattacttg | gcaaaacact | tctttgcatt | ctaccacttg | 5640 |
| atatctcaca | gaccctattt | gattttgcct | tagtctagca | actgagctag | ttttcatact | 5700 |
| gtttgttaag | gccagacaaa | cagatgataa | tcttctcagg | ctctgtatgt | tcttcagctg | 5760 |
| ctctgtgctg | ggttggaaat | tgtaatcttc | aaacttcgta | taatacatta | tcgggtgagc | 5820 |
| tccaattttc | ataaagttct | caaattcagt | gaatggtatg | tggcattctt | gctcaaggtg | 5880 |
| ttcagacagt | ccgtaatgct | cgaaactcag | tcccaccact | aacaggcatt | tttgaatttt | 5940 |
| tgcaatgaac | tcactaatag | atgccctaaa | caattcctca | aaagacacct | ttctaaacac | 6000 |
| ctttgacttt | tttctattcc | tcaaaagtct | aatgaactcc | tctttagtgc | tgtgaaagct | 6060 |
| taccagccta | tcattcacac | tactatagca | acaacccacc | cagtgtttat | catttttaa | 6120 |
| cccttttgaat | ttcgactgtt | ttatcaatga | ggaaagacac | aaaacatcca | gatttaacaa | 6180 |
| ctgtctcctt | ctagtattca | acagtttcaa | actcttgact | ttgtttaaca | tagagaggag | 6240 |
| cctctcatat | tcagtgctag | tctcacttcc | cctttcgtgc | ccatgggtct | ctgcagttat | 6300 |
| gaatctcatc | aaaggacagg | attcgactgc | ctccctgctt | aatgttaaga | tatcatcact | 6360 |
| atcagcaagg | ttttcataga | gctcagagaa | ttccttgatc | aagccttcag | ggtttacttt | 6420 |
| ctgaaagttt | ctcttttaatt | tcccactttc | taaatctctt | ctaaacctgc | tgaaaagaga | 6480 |
| gtttattcca | aaaaccacat | catcacagct | catgttgggg | ttgatgcctt | cgtggcacat | 6540 |
| cctcataatt | tcatcattgt | gagttgacct | cgcatctttc | agaattttca | tagagtccat | 6600 |
| accggagcgc | ttgtcgatag | tagtcttcag | ggactcacag | agtctaaaat | attcagactc | 6660 |
| ttcaaagact | ttctcatttt | ggttagaata | ctccaaaagt | ttgaataaaa | ggtctctaaa | 6720 |

```
tttgaagttt gcccactctg gcataaaact attatcataa tcacaacgac catctactat    6780
tggaactaat gtgacacccg caacagcaag gtcttccctg atgcatgcca atttgttagt    6840
gtcctctata aatttcttct caaaactggc tggagtgctc ctaacaaaac actcaagaag    6900
aatgagagaa ttgtctatca gcttgtaacc atcaggaatg ataagtggta gtcctgggca    6960
tacaattcca gactccacca aaattgtttc cacagactta tcgtcgtggt tgtgtgtgca    7020
gccactcttg tctgcactgt ctatttcaat gcagcgtgac agcaacttga gtccctcaat    7080
cagaaccatt ctgggttccc tttgtcccag aaagttgagt ttctgccttg acaacctctc    7140
atcctgttct atatagttta aacataactc tctcaattct gagatgattt catccattgc    7200
gcatcaaaaa gcctaggatc ctcggtgcg                                      7229

<210> SEQ ID NO 34
<211> LENGTH: 3566
<212> TYPE: DNA
<213> ORGANISM: Unknown
<220> FEATURE:
<223> OTHER INFORMATION: HK1-Hpp65 genomic segment

<400> SEQUENCE: 34
gcgcaccggg gatcctaggc ttttggatt gcgctttcct ctagatcaac tgggtgtcag      60
gccctatcct acagaaggat ggaatctagg gacgccgct gtcccgaaat gatcagtgtt     120
ctggggccaa tatccggaca tgtcctgaaa ccgttttca gtcgaggtga cactcccgtg     180
ctcccgcatg agacaagact ccttcagact gggatacacg tgagggtcag ccagccgagt    240
ctgatcctgg ttagccagta caccccagac agtacacctt gtcacagagg ggacaatcag    300
ctgcaagtgc agcatacata ctttaccggt agtgaggtgg agaatgtgtc cgtgaacgtc    360 cataaccca ctggtcggag catttgcccc agccaagagc ccatgagcat ctacgtgtat     420
gcactccctc tgaagatgct gaacattcca tccatcaacg tccatcacta ccccagcgct    480
gctgaaagga acacaggca cttgcccgtt gcggatgcgg taattcacgc ttctggaaag    540
cagatgtggc aggccaggtt gacggtgtct ggccttgcct ggaccaggca gcagaatcag    600
tggaaagagc cagacgtgta ctacacttca gccttcgtgt ttccaaccaa ggatgtggca    660
ctccggcacg tcgtatgtgc acacgaactc gtgtgctcca tggagaacac acgagccacc    720
aagatgcaag tgatagggga tcaatacgta aaagtctacc tggagagctt ttgcgaagat    780
gtcccatcag gcaagctctt catgcatgtg actctggggt ctgatgttga ggaagatctg    840
actatgacaa gaaatccgca acctttcatg cgccctcatg agcgaaacgg atttaccgtt    900
ctgtgtccaa agaacatgat tatcaaaccc ggcaaaatca gccacattat gctggatgtg    960
gctttcacat ctcacgaaca ctttgggctg cctttgccctc agtctattcc aggcctgtcc   1020
atttcaggca acctcttgat gaacgggcaa cagatctttc tggaagttca ggccattcgg   1080
gagactgtcg agctgagaca gtatgacccc gtcgctgccc tgttcttctt cgacatcgat   1140
ctgctgcttc agagaggccc tcagtatagc gagcatccca cctttaccag ccagtatcgg   1200
atccagggaa agttggagta tcggcacact tgggacagac acgatgaagg cgcagcacag   1260
ggcgacgatg acgtgtggac ctcggctca gacagcgacg aagagttggt caccacagag    1320
cgtaaaaccc caagagtgac cggaggtgga gccatggctg gcgcctcaac atccgctgga   1380
cgcaagcgga aatccgcaag ctcagccaca ggctgtacat ccggggtcat gacgaggggt   1440
cgtctgaagg ccgagtccac agtagctccc gaagaagata cggatgagga ctctgacaac   1500
```

```
gagatacaca atccagccgt gttcacttgg ccaccttggc aggctgggat ccttgctcgt    1560
aatctggttc ccatggtggc gaccgtacaa ggccagaatc tcaagtatca ggagttcttc    1620
tgggatgcca atgacattta ccgaatcttt gcggagctgg aaggagtgtg cagcctgca     1680 gctcaaccga agaggcggag acatcgccag gacgcacttc ctggcccttg catcgcaagt    1740
acgcctaaga aacatcgcgg ttgaagaaca gcgcctccct gactctccac ctcgaaagag    1800
gtggagagtc agggaggccc agagggtctt agagtgtcac aacatttggg cctctaaaaa    1860
ttaggtcatg tggcagaatg ttgtgaacag ttttcagatc tgggagcctt gctttggagg    1920
cgctttcaaa aatgatgcag tccatgagtg cacagtgcgg ggtgatctct ttcttctttt    1980
tgtcccttac tattccagta tgcatcttac acaaccagcc atatttgtcc cacactttat    2040
cttcatactc cctcgaagct tccctggtca tttcaacatc gataagctta atgtccttcc    2100
tattttgtga gtccagaagc tttctgatgt catcggagcc ttgacagctt agaaccatcc    2160
cctgcggaag agcacctata actgacgagg tcaacccggg ttgcgcattg aagaggtcgg    2220
caagatccat gccgtgtgag tacttggaat cttgcttgaa ttgttttga tcaacggggtt    2280 ccctgtaaaa gtgtatgaac tgcccgttct gtggttggaa aattgctatt tccactggat    2340
cattaaatct accctcaatg tcaatccatg taggagcgtt ggggtcaatt cctcccatga    2400
ggtcttttaa aagcattgtc tggctgtagc ttaagcccac ctgaggtgga cctgctgctc    2460
caggcgctgg cctgggtgag ttgactgcag gtttctcgct tgtgagatca attgttgtgt    2520
tttcccatgc tctccccaca atcgatgttc tacaagctat gtatggccat ccttcacctg    2580
aaaggcaaac tttatagagg atgttttcat aagggttcct gtccccaact tggtctgaaa    2640
caaacatgtt gagttttctc ttggccccga gaactgcctt caagagatcc tcgctgttgc    2700
ttggcttgat caaaattgac tctaacatgt taccccatc caacagggct gcccctgcct    2760
tcacggcagc accaagacta aagttatagc cagaaatgtt gatgctggac tgctgttcag    2820
tgatgacccc cagaactggg tgcttgtctt tcagcctttc aagatcatta agatttggat    2880
acttgactgt gtaaagcaag ccaaggtctg tgagcgcttg tacaacgtca ttgagcggag    2940
tctgtgactg tttggccata caagccatag ttagacttgg cattgtgcca aattgattgt    3000
tcaaaagtga tgagtctttc acatcccaaa ctcttaccac accacttgca ccctgctgag    3060
gctttctcat cccaactatc tgtaggatct gagatctttg gtctagttgc tgtgttgtta    3120
agttccccat atataccct gaagcctggg gcctttcaga cctcatgatc ttggccttca    3180
gcttctcaag gtcagccgca agagacatca gttcttctgc actgagcctc cccactttca    3240
aaacattctt ctttgatgtt gactttaaat ccacaagaga atgtacagtc tggttgagac    3300
ttctgagtct ctgtaggtct ttgtcatctc tcttttcctt cctcatgatc ctctgaacat    3360
tgctgacctc agagaagtcc aacccattca gaaggttggt tgcatcctta atgacagcag    3420
ccttcacatc tgatgtgaag ctctgcaatt ctcttctcaa tgcttgcgtc cattggaagc    3480
tcttaacttc cttagacaag gacatcttgt tgctcaatgg tttctcaaga caaatgcgca    3540
atcaaatgcc taggatccac tgtgcg                                         3566
```

<210> SEQ ID NO 35
<211> LENGTH: 1686
<212> TYPE: DNA
<213> ORGANISM: Unknown
<220> FEATURE:
<223> OTHER INFORMATION: Hpp65 cDNA

<400> SEQUENCE: 35

```
atggaatcta ggggacgccg ctgtcccgaa atgatcagtg ttctgggcc aatatccgga       60
catgtcctga aagccgtttt cagtcgaggt gacactccg tgctcccgca tgagacaaga      120
ctccttcaga ctgggataca cgtgagggtc agccagccga gtctgatcct ggttagccag     180
tacaccccag acagtacacc ttgtcacaga ggggacaatc agctgcaagt gcagcataca     240
tactttaccg gtagtgaggt ggagaatgtg tccgtgaacg tccataaccc tactggtcgg     300
agcatttgcc ccagccaaga gcccatgagc atctacgtgt atgcactccc tctgaagatg     360
ctgaacattc catccatcaa cgtccatcac taccccagcg ctgctgaaag gaaacacagg     420
cacttgcccg ttgcggatgc ggtaattcac gcttctggaa agcagatgtg gcaggccagg     480
ttgacggtgt ctggccttgc ctggaccagg cagcagaatc agtggaaaga gccagacgtg     540
tactacactt cagccttcgt gtttccaacc aaggatgtgg cactccggca cgtcgtatgt     600
gcacacgaac tcgtgtgctc catggagaac acacgagcca ccaagatgca agtgataggg     660
gatcaatacg taaaagtcta cctggagagc ttttgcgaag atgtcccatc aggcaagctc     720
ttcatgcatg tgactctggg gtctgatgtt gaggaagatc tgactatgac aagaaatccg     780
caacctttca tgcgccctca tgagcgaaac ggatttaccg ttctgtgtcc aaagaacatg     840
attatcaaac ccggcaaaat cagccacatt atgctggatg tggctttcac atctcacgaa     900
cactttgggc tgcttttgccc taagtctatt ccaggcctgt ccatttcagg caacctcttg     960
atgaacgggc aacagatctt tctggaagtt caggccattc gggagactgt cgagctgaga    1020
cagtatgacc ccgtcgctgc cctgttcttc ttcgacatcg atctgctgct tcagagaggc    1080
cctcagtata gcgagcatcc cacctttacc agccagtatc ggatccaggg aaagttggag    1140
tatcggcaca cttgggacag acacgatgaa ggcgcagcac agggcgacga tgacgtgtgg    1200
acctctggct cagacagcga cgaagagttg gtcaccacag agcgtaaaac cccaagagtg    1260
accggaggtg gagccatggc tggcgcctca acatccgctg gacgcaagcg gaaatccgca    1320
agctcagcca cagcctgtac atccggggtc atgacgaggg gtcgtctgaa ggccgagtcc    1380
acagtagctc ccgaagaaga tacgatgag gactctgaca acgagataca caatccagcc    1440
gtgttcactt ggccaccttg gcaggctggg atccttgctc gtaatctggt tcccatggtg    1500
gcgaccgtac aaggccagaa tctcaagtat caggagttct ctgggatgc caatgacatt    1560
taccgaatct ttgcggagct ggaaggagtg tggcagcctg cagctcaacc gaagaggcgg    1620
agacatcgcc aggacgcact tcctggccct tgcatcgcaa gtacgcctaa gaaacatcgc    1680
ggttga                                                               1686
```

<210> SEQ ID NO 36
<211> LENGTH: 561
<212> TYPE: PRT
<213> ORGANISM: Unknown
<220> FEATURE:
<223> OTHER INFORMATION: Hpp65

<400> SEQUENCE: 36

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp

```
             50                  55                  60
Ser Thr Pro Cys His Arg Gly Asp Asn Gln Leu Gln Val Gln His Thr
 65                  70                  75                  80

Tyr Phe Thr Gly Ser Glu Val Glu Asn Val Ser Val Asn Val His Asn
                 85                  90                  95

Pro Thr Gly Arg Ser Ile Cys Pro Ser Gln Glu Pro Met Ser Ile Tyr
                100                 105                 110

Val Tyr Ala Leu Pro Leu Lys Met Leu Asn Ile Pro Ser Ile Asn Val
                115                 120                 125

His His Tyr Pro Ser Ala Ala Glu Arg Lys His Arg His Leu Pro Val
                130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
                180                 185                 190

Val Ala Leu Arg His Val Val Cys Ala His Glu Leu Val Cys Ser Met
                195                 200                 205

Glu Asn Thr Arg Ala Thr Lys Met Gln Val Ile Gly Asp Gln Tyr Val
                210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
                260                 265                 270

Thr Val Leu Cys Pro Lys Asn Met Ile Ile Lys Pro Gly Lys Ile Ser
                275                 280                 285

His Ile Met Leu Asp Val Ala Phe Thr Ser His Glu His Phe Gly Leu
                290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
                340                 345                 350

Ile Asp Leu Leu Leu Gln Arg Gly Pro Gln Tyr Ser Glu His Pro Thr
                355                 360                 365

Phe Thr Ser Gln Tyr Arg Ile Gln Gly Lys Leu Glu Tyr Arg His Thr
                370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser Ser
                420                 425                 430

Ala Gly Arg Lys Arg Lys Ser Ala Ser Ser Ala Thr Ala Cys Thr Ser
                435                 440                 445

Gly Val Met Thr Arg Gly Arg Leu Lys Ala Glu Ser Thr Val Ala Pro
                450                 455                 460

Glu Glu Asp Thr Asp Glu Asp Ser Asp Asn Glu Ile His Asn Pro Ala
465                 470                 475                 480
```

```
Val Phe Thr Trp Pro Pro Trp Gln Ala Gly Ile Leu Ala Arg Asn Leu
            485                 490                 495

Val Pro Met Val Ala Thr Val Gln Gly Gln Asn Leu Lys Tyr Gln Glu
        500                 505                 510

Phe Phe Trp Asp Ala Asn Asp Ile Tyr Arg Ile Phe Ala Glu Leu Glu
            515                 520                 525

Gly Val Trp Gln Pro Ala Ala Gln Pro Lys Arg Arg Arg His Arg Gln
        530                 535                 540

Asp Ala Leu Pro Gly Pro Cys Ile Ala Ser Thr Pro Lys Lys His Arg
545                 550                 555                 560

Gly

<210> SEQ ID NO 37
<211> LENGTH: 4112
<212> TYPE: DNA
<213> ORGANISM: Unknown
<220> FEATURE:
<223> OTHER INFORMATION: HK1-HgH genomic segment

<400> SEQUENCE: 37
gcgcaccggg gatcctaggc tttttggatt gcgctttcct ctagatcaac tgggtgtcag      60
gccctatcct acagaaggat gcggcccggc ctcccttct  acctcaccgt cttcgccgtc     120
tacctcctta gtcacctacc ttcgcaacga tatggcgcag acgccgcatc cgaagcgctg     180
gaccctcacg cgtttcacct actactcaac acctatggga gacccatccg tttcctgcgt     240
gaaaacacca cccagtgcac ctacaacagc agcctccgta acagcacggt cgtcagggaa     300
aacgccatca gtttcaactt tttccaaagc tataatcaat actatgtatt ccatatgcct     360
cgatgtcttt ttgcgggtcc tctggcggag cagtttctga accaggtaga tctgaccgaa     420
accctagaaa gataccaaca gagacttaac acctacgcat tggtatccaa agacctggct     480
agctaccgat cttttcgca gcagctgaag gcacaagaca gcctgggtca gcagcccacc     540
accgtgccac cgcccattga tctgtcaata cctcacgtct ggatgccacc caaaccact     600 ccacacgact ggaagggatc gcacaccacc tcgggactac atcggccaca ctttaaccag     660
acctgtatcc tcttttgatgg acacgatctg cttttcagca ccgttacgcc ctgtctgcac     720
cagggctttt acctcatgga cgaactacgt tacgttaaaa tcacactgac cgaggacttc     780
ttcgtagtta cggtatccat agacgacgac acacccatgc tgcttatctt cggtcatctt     840
ccacgcgtac tcttcaaagc gccctatcaa cgcgacaact ttatactacg acaaactgaa     900
aaacacgagc tcctggtact agttaagaaa actcaactga accgtcactc ctatctcaaa     960
gactcggact ttctcgacgc cgcactcgac ttcaactacc tggacctcag cgcactgcta    1020
cgtaacagct ttcaccgtta cgctgtagac gtactcaaaa gcggtcgatg tcaaatgctg    1080
gaccgccgca cggtagaaat ggcctttgcc tacgcattag cactgttcgc ggcagcccga    1140
caagaagagg ccggcaccga aatctccatc ccacgggccc tagaccgcca ggccgcactc    1200
ttacaaatac aagaatttat gatcacctgc ctctcacaaa caccaccacg caccacattg    1260
ctgctatatc ccacggccgt ggacctgcc  aaacgagccc tctggacgcc ggaccagatc    1320
accgacatca ccagcctcgt acgcctggtc tacatacttt ctaaacagaa tcagcaacat    1380
ctcattcccc agtgggcact acgacagatc gccgactttg ccctacaatt acacaaaacg    1440
cacctggcct ctttttcttc agccttcgcg cgccaagaac tctacctcat gggcagcctc    1500
gtccactcca tgctggtgca tacgacggag aggcgcgaaa tcttcatcgt agaaacgggc    1560
```

```
ctctgttcat tggccgagct atcacacttt acgcagttgc tagctcatcc gcaccacgaa   1620
tacctcagcg acctgtacac accctgttcc agtagcgggc gacgcgatca ctcgctcgaa   1680
cgccttacgc gcctcttccc cgatgccacc gtccccgcta ccgttcccgc cgccctctcc   1740
atcctatcta ccatgcaacc aagcacgctg gaaaccttcc ccgacctgtt ttgtctgcca   1800
ctaggcgaat ccttctccgc gctcaccgtt tccgaacacg tcagctacgt cgtaacaaac   1860
caatacctga tcaaaggtat ctcctaccct gtctccacca ccgtcgtagg ccagagcctc   1920
atcatcaccc agacggacag tcaaagtaaa tgcgaactga cgcgcaacat gcacaccaca   1980
cacagcatca cagcggcgct caacatttcg ctagaaaact gcgccttctg ccaaagcgcc   2040
ttactagaat acgacgacac gcaaggcgtc attaatatca tgtacatgca cgactcggac   2100
gacgtccttt tgccctgga tccctacaac gaagtggtgg tctcatctcc acgaactcac   2160
tacctcatgc tgttgaaaaa cggtacggtc ctggaagtaa ctgacgtcgt cgtggacgcc   2220
accgacagcc gcctcctcat gatgtccgtc tacgcgttgt cggccatcat cggcatctat   2280
ctgctctacc gcatgctcaa gacatgctga agaacagcgc ctccctgact ctccacctcg   2340
aaagaggtgg agagtcaggg aggcccagag ggtcttagag tgtcacaaca tttgggcctc   2400
taaaaattag gtcatgtggc agaatgttgt gaacagtttt cagatctggg agccttgctt   2460
tggaggcgct ttcaaaaatg atgcagtcca tgagtgcaca gtgcggggtg atctctttct   2520 tcttttgtc ccttactatt ccagtatgca tcttacacaa ccagccatat ttgtcccaca   2580 cttatcttc atactccctc gaagcttccc tggtcatttc aacatcgata agcttaatgt   2640
ccttcctatt ttgtgagtcc agaagctttc tgatgtcatc ggagccttga cagcttagaa   2700
ccatcccctg cggaagagca cctataactg acgaggtcaa cccgggttgc gcattgaaga   2760
ggtcggcaag atccatgccg tgtgagtact tggaatcttg cttgaattgt ttttgatcaa   2820
cgggttccct gtaaaagtgt atgaactgcc cgttctgtgg ttggaaaatt gctatttcca   2880
ctggatcatt aaatctaccc tcaatgtcaa tccatgtagg agcgttgggg tcaattcctc   2940
ccatgaggtc ttttaaaagc attgtctggc tgtagcttaa gcccacctga ggtggacctg   3000
ctgctccagg cgctggcctg ggtgagttga ctgcaggttt ctcgcttgtg agatcaattg   3060
ttgtgttttc ccatgctctc cccacaatcg atgttctaca agctatgtat ggccatcctt   3120
cacctgaaag gcaaacttta tagaggatgt tttcataagg gttcctgtcc ccaacttggt   3180
ctgaaacaaa catgttgagt tttctcttgg ccccgagaac tgccttcaag agatcctcgc   3240
tgttgcttgg cttgatcaaa attgactcta acatgttacc cccatccaac agggctgccc   3300
ctgccttcac ggcagcacca agactaaagt tatagccaga aatgttgatg ctggactgct   3360
gttcagtgat gaccccagag actgggtgct tgtctttcag ccttcaagaa tcattaagat   3420
ttggatactt gactgtgtaa agcaagccaa ggtctgtgag cgcttgtaca acgtcattga   3480
gcggagtctg tgactgtttg gccatacaag ccatagttag acttggcatt gtgccaaatt   3540
gattgttcaa aagtgatgag tctttcacat cccaaactct taccacacca cttgcaccct   3600
gctgaggctt tctcatccca actatctgta ggatctgaga tctttggtct agttgctgtg   3660
ttgttaagtt ccccatatat accctgaag cctggggcct ttcagacctc atgatcttgg   3720
ccttcagctt ctcaaggtca gccgcaagag acatcagttc ttctgcactg agcctcccca   3780
ctttcaaaac attcttcttt gatgttgact ttaaatccac aagagaatgt acagtctggt   3840
tgagacttct gagtctctgt aggtctttgt catctctctt ttccttcctc atgatcctct   3900
```

| | |
|---|---:|
| gaacattgct gacctcagag aagtccaacc cattcagaag gttggttgca tccttaatga | 3960 |
| cagcagcctt cacatctgat gtgaagctct gcaattctct tctcaatgct tgcgtccatt | 4020 |
| ggaagctctt aacttcctta gacaaggaca tcttgttgct caatggtttc tcaagacaaa | 4080 |
| tgcgcaatca aatgcctagg atccactgtg cg | 4112 |

<210> SEQ ID NO 38
<211> LENGTH: 2232
<212> TYPE: DNA
<213> ORGANISM: Unknown
<220> FEATURE:
<223> OTHER INFORMATION: HgH cDNA

<400> SEQUENCE: 38

| | |
|---|---:|
| atgcggcccg gcctcccctt ctacctcacc gtcttcgccg tctacctcct tagtcaccta | 60 |
| ccttcgcaac gatatggcgc agacgccgca tccgaagcgc tggaccctca cgcgtttcac | 120 |
| ctactactca acacctatgg gagacccatc cgtttcctgc gtgaaaacac cacccagtgc | 180 |
| acctacaaca gcagcctccg taacagcacg gtcgtcaggg aaaacgccat cagtttcaac | 240 |
| tttttccaaa gctataatca atactatgta ttccatatgc ctcgatgtct ttttgcgggt | 300 |
| cctctggcgg agcagtttct gaaccaggta gatctgaccg aaaccctaga agataccaa | 360 |
| cagagactta acacctacgc attggtatcc aaagacctgg ctagctaccg atcttttcg | 420 |
| cagcagctga aggcacaaga cagcctgggt cagcagccca ccaccgtgcc accgcccatt | 480 |
| gatctgtcaa tacctcacgt ctggatgcca ccccaaacca ctccacacga ctggaaggga | 540 |
| tcgcacacca cctcgggact acatcggcca cactttaacc agacctgtat cctctttgat | 600 |
| ggacacgatc tgcttttcag caccgttacg ccctgtctgc accagggctt ttacctcatg | 660 |
| gacgaactac gttacgttaa atcacactg accgaggact tcttcgtagt tacggtatcc | 720 |
| atagacgacg acacacccat gctgcttatc ttcggtcatc ttccacgcgt actcttcaaa | 780 |
| gcgcccatc aacgcgacaa ctttatacta cgacaaactg aaaaacacga gctcctggta | 840 |
| ctagttaaga aaactcaact gaaccgtcac tcctatctca aagactcgga ctttctcgac | 900 |
| gccgcactcg acttcaacta cctggacctc agcgcactgc tacgtaacag cttttcaccgt | 960 |
| tacgctgtag acgtactcaa aagcggtcga tgtcaaatgc tggaccgccg cacggtagaa | 1020 |
| atggcctttg cctacgcatt agcactgttc gcggcagccc gacaagaaga ggccggcacc | 1080 |
| gaaatctcca tcccacgggc cctagaccgc caggccgcac tcttacaaat acaagaattt | 1140 |
| atgatcacct gcctctcaca aacaccacca cgcaccacat gctgctata tcccacggcc | 1200 |
| gtggacctgg ccaaacgagc cctctggacg ccggaccaga tcaccgacat caccagcctc | 1260 |
| gtacgcctgg tctacatact ttctaaacag aatcagcaac atctcattcc ccagtgggca | 1320 |
| ctacgacaga tcgccgactt tgccctacaa ttacacaaaa cgcacctggc ctcttttctt | 1380 |
| tcagccttcg cgcgccaaga actctacctc atgggcagcc tcgtccactc catgctggtg | 1440 |
| catacgacgg agaggcgcga atcttcatc gtagaaacgg gcctctgttc attggccgag | 1500 |
| ctatcacact ttacgcagtt gctagctcat ccgcaccacg aatacctcag cgacctgtac | 1560 |
| acaccctgtt ccagtagcgg gcgacgcgat cactcgctcg aacgcttac gcgcctcttc | 1620 |
| cccgatgcca ccgtccccgc taccgttccc gccgccctct ccatcctatc taccatgcaa | 1680 |
| ccaagcacgc tggaaacctt ccccgacctg ttttgtctgc cactaggcga atccttctcc | 1740 |
| gcgctcaccg tttccgaaca cgtcagctac gtcgtaacaa accaatacct gatcaaaggt | 1800 |
| atctcctacc ctgtctccac caccgtcgta ggccagagcc tcatcatcac ccagacggac | 1860 |

-continued

```
agtcaaagta aatgcgaact gacgcgcaac atgcacacca cacacagcat cacagcggcg    1920
ctcaacattt cgctagaaaa ctgcgccttc tgccaaagcg ccttactaga atacgacgac    1980
acgcaaggcg tcattaatat catgtacatg cacgactcgg acgacgtcct ttttgccctg    2040
gatccctaca acgaagtggt ggtctcatct ccacgaactc actacctcat gctgttgaaa    2100
aacggtacgg tcctggaagt aactgacgtc gtcgtggacg ccaccgacag ccgcctcctc    2160
atgatgtccg tctacgcgtt gtcggccatc atcggcatct atctgctcta ccgcatgctc    2220
aagacatgct ga                                                        2232
```

<210> SEQ ID NO 39
<211> LENGTH: 743
<212> TYPE: PRT
<213> ORGANISM: Unknown
<220> FEATURE:
<223> OTHER INFORMATION: HgH

<400> SEQUENCE: 39

```
Met Arg Pro Gly Leu Pro Phe Tyr Leu Thr Val Phe Ala Val Tyr Leu
1               5                   10                  15

Leu Ser His Leu Pro Ser Gln Arg Tyr Gly Ala Asp Ala Ala Ser Glu
            20                  25                  30

Ala Leu Asp Pro His Ala Phe His Leu Leu Asn Thr Tyr Gly Arg
        35                  40                  45

Pro Ile Arg Phe Leu Arg Glu Asn Thr Thr Gln Cys Thr Tyr Asn Ser
    50                  55                  60

Ser Leu Arg Asn Ser Thr Val Val Arg Glu Asn Ala Ile Ser Phe Asn
65                  70                  75                  80

Phe Phe Gln Ser Tyr Asn Gln Tyr Tyr Val Phe His Met Pro Arg Cys
                85                  90                  95

Leu Phe Ala Gly Pro Leu Ala Glu Gln Phe Leu Asn Gln Val Asp Leu
            100                 105                 110

Thr Glu Thr Leu Glu Arg Tyr Gln Gln Arg Leu Asn Thr Tyr Ala Leu
        115                 120                 125

Val Ser Lys Asp Leu Ala Ser Tyr Arg Ser Phe Ser Gln Gln Leu Lys
    130                 135                 140

Ala Gln Asp Ser Leu Gly Gln Gln Pro Thr Thr Val Pro Pro Pro Ile
145                 150                 155                 160

Asp Leu Ser Ile Pro His Val Trp Met Pro Pro Gln Thr Thr Pro His
                165                 170                 175

Asp Trp Lys Gly Ser His Thr Thr Ser Gly Leu His Arg Pro His Phe
            180                 185                 190

Asn Gln Thr Cys Ile Leu Phe Asp Gly His Asp Leu Leu Phe Ser Thr
        195                 200                 205

Val Thr Pro Cys Leu His Gln Gly Phe Tyr Leu Met Asp Glu Leu Arg
    210                 215                 220

Tyr Val Lys Ile Thr Leu Thr Glu Asp Phe Val Val Thr Val Ser
225                 230                 235                 240

Ile Asp Asp Asp Thr Pro Met Leu Leu Ile Phe Gly His Leu Pro Arg
                245                 250                 255

Val Leu Phe Lys Ala Pro Tyr Gln Arg Asp Asn Phe Ile Leu Arg Gln
            260                 265                 270

Thr Glu Lys His Glu Leu Leu Val Leu Val Lys Thr Gln Leu Asn
        275                 280                 285
```

-continued

```
Arg His Ser Tyr Leu Lys Asp Ser Asp Phe Leu Asp Ala Ala Leu Asp
    290                 295                 300

Phe Asn Tyr Leu Asp Leu Ser Ala Leu Leu Arg Asn Ser Phe His Arg
305                 310                 315                 320

Tyr Ala Val Asp Val Leu Lys Ser Gly Arg Cys Gln Met Leu Asp Arg
                325                 330                 335

Arg Thr Val Glu Met Ala Phe Ala Tyr Ala Leu Ala Leu Phe Ala Ala
            340                 345                 350

Ala Arg Gln Glu Glu Ala Gly Thr Glu Ile Ser Ile Pro Arg Ala Leu
        355                 360                 365

Asp Arg Gln Ala Ala Leu Leu Gln Ile Gln Glu Phe Met Ile Thr Cys
370                 375                 380

Leu Ser Gln Thr Pro Pro Arg Thr Thr Leu Leu Leu Tyr Pro Thr Ala
385                 390                 395                 400

Val Asp Leu Ala Lys Arg Ala Leu Trp Thr Pro Asp Gln Ile Thr Asp
                405                 410                 415

Ile Thr Ser Leu Val Arg Leu Val Tyr Ile Leu Ser Lys Gln Asn Gln
            420                 425                 430

Gln His Leu Ile Pro Gln Trp Ala Leu Arg Gln Ile Ala Asp Phe Ala
        435                 440                 445

Leu Gln Leu His Lys Thr His Leu Ala Ser Phe Leu Ser Ala Phe Ala
    450                 455                 460

Arg Gln Glu Leu Tyr Leu Met Gly Ser Leu Val His Ser Met Leu Val
465                 470                 475                 480

His Thr Thr Glu Arg Arg Glu Ile Phe Ile Val Glu Thr Gly Leu Cys
                485                 490                 495

Ser Leu Ala Glu Leu Ser His Phe Thr Gln Leu Leu Ala His Pro His
            500                 505                 510

His Glu Tyr Leu Ser Asp Leu Tyr Thr Pro Cys Ser Ser Ser Gly Arg
        515                 520                 525

Arg Asp His Ser Leu Glu Arg Leu Thr Arg Leu Phe Pro Asp Ala Thr
    530                 535                 540

Val Pro Ala Thr Val Pro Ala Ala Leu Ser Ile Leu Ser Thr Met Gln
545                 550                 555                 560

Pro Ser Thr Leu Glu Thr Phe Pro Asp Leu Phe Cys Leu Pro Leu Gly
                565                 570                 575

Glu Ser Phe Ser Ala Leu Thr Val Ser Glu His Val Ser Tyr Val Val
            580                 585                 590

Thr Asn Gln Tyr Leu Ile Lys Gly Ile Ser Tyr Pro Val Ser Thr Thr
        595                 600                 605

Val Val Gly Gln Ser Leu Ile Ile Thr Gln Thr Asp Ser Gln Ser Lys
    610                 615                 620

Cys Glu Leu Thr Arg Asn Met His Thr Thr His Ser Ile Thr Ala Ala
625                 630                 635                 640

Leu Asn Ile Ser Leu Glu Asn Cys Ala Phe Cys Gln Ser Ala Leu Leu
                645                 650                 655

Glu Tyr Asp Asp Thr Gln Gly Val Ile Asn Ile Met Tyr Met His Asp
            660                 665                 670

Ser Asp Asp Val Leu Phe Ala Leu Asp Pro Tyr Asn Glu Val Val Val
        675                 680                 685

Ser Ser Pro Arg Thr His Tyr Leu Met Leu Leu Lys Asn Gly Thr Val
    690                 695                 700

Leu Glu Val Thr Asp Val Val Val Asp Ala Thr Asp Ser Arg Leu Leu
```

```
                705                 710                 715                 720
Met Met Ser Val Tyr Ala Leu Ser Ala Ile Ile Gly Ile Tyr Leu Leu
                    725                 730                 735

Tyr Arg Met Leu Lys Thr Cys
            740

<210> SEQ ID NO 40
<211> LENGTH: 837
<212> TYPE: DNA
<213> ORGANISM: Unknown
<220> FEATURE:
<223> OTHER INFORMATION: HgL cDNA

<400> SEQUENCE: 40
atgtgccgcc gcccggattg cggcttctct ttctcacctg gaccggtggt actgctgtgg      60
tgttgccttc tgctgcccat tgtttcctca gtcgccgtca gcgtcgctcc taccgccgcc     120
gagaaagtcc ccgcggagtg tcccgaacta acgcgccgat gcctgttggg tgaggtgttt     180
cagggtgaca agtatgaaag ttggctgcgt ccgttggtga atgttaccgg cgcaatggc      240 ccgctatcgc aacttatccg ttaccgtccc gttacgccgg aggccgccaa ctccgtgctg     300
ttggacgatg ctttcctgga cactctggcc ctgctgtaca acaatccgga tcaattgcgg     360
gccctgctga cactgttgag ctcggacaca gcgccgcgct ggatgacggt gatgcgcggc     420
tacagcgagt gcggcgatgg ctcgccggcc gtgtacacgt gcgtggacga cctgcccgc      480 ggctacgacc tcacgcgact gtcatacggg cgcagcatct tcacggaaca cgtgttaggc     540
ttcgagctgt gccaccgtc cctctttaac gtggtggtgg ccatacgcaa cgaagccacg      600
cgtaccaacc gcgccgtgcg tctgcccgtg agcaccgctg ccgcgcccga gggcatcacg     660
ctcttttacg gcctgtacaa cgcagtgaag gaattttgcc tgcgtcacca gctggacccg     720
ccgctgctac gccacctaga taaatactac gccggactgc cgcccgagct gaagcagacg     780
cgcgtcaacc tgccggctca ctcgcgctat ggccctcaag cagtggatgc tcgctga       837

<210> SEQ ID NO 41
<211> LENGTH: 278
<212> TYPE: PRT
<213> ORGANISM: Unknown
<220> FEATURE:
<223> OTHER INFORMATION: HgL

<400> SEQUENCE: 41

Met Cys Arg Arg Pro Asp Cys Gly Phe Ser Phe Ser Pro Gly Pro Val
1               5                   10                  15

Val Leu Leu Trp Cys Cys Leu Leu Leu Pro Ile Val Ser Ser Val Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Gln Gly Asp Lys
    50                  55                  60

Tyr Glu Ser Trp Leu Arg Pro Leu Val Asn Val Thr Gly Arg Asn Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Asp Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125
```

```
Asp Thr Ala Pro Arg Trp Met Thr Val Met Arg Gly Tyr Ser Glu Cys
            130                 135                 140
Gly Asp Gly Ser Pro Ala Val Tyr Thr Cys Val Asp Asp Leu Cys Arg
145                 150                 155                 160
Gly Tyr Asp Leu Thr Arg Leu Ser Tyr Gly Arg Ser Ile Phe Thr Glu
                165                 170                 175
His Val Leu Gly Phe Glu Leu Val Pro Pro Ser Leu Phe Asn Val Val
            180                 185                 190
Val Ala Ile Arg Asn Glu Ala Thr Arg Thr Asn Arg Ala Val Arg Leu
        195                 200                 205
Pro Val Ser Thr Ala Ala Pro Glu Gly Ile Thr Leu Phe Tyr Gly
        210                 215                 220
Leu Tyr Asn Ala Val Lys Glu Phe Cys Leu Arg His Gln Leu Asp Pro
225                 230                 235                 240
Pro Leu Leu Arg His Leu Asp Lys Tyr Tyr Ala Gly Leu Pro Pro Glu
                245                 250                 255
Leu Lys Gln Thr Arg Val Asn Leu Pro Ala His Ser Arg Tyr Gly Pro
            260                 265                 270
Gln Ala Val Asp Ala Arg
            275

<210> SEQ ID NO 42
<211> LENGTH: 513
<212> TYPE: DNA
<213> ORGANISM: Unknown
<220> FEATURE:
<223> OTHER INFORMATION: HUL128 cDNA

<400> SEQUENCE: 42
atgagtccca aaaacctgac gccgttcttg acggcgttgt ggctgttatt ggatcacagc      60
cgcgtgccgc gggtacgcgc agaagaatgt tgcgaattca taaacgtcaa ccacccgccg     120
gaacgctgtt acgatttcaa aatgtgcaat cgcttcaccg tcgcgctgcg gtgtccggac     180
ggcgaagtct gctacagtcc gagaaaacg gctgagattc gcgggatcgt caccaccatg     240
acccattcat tgacacgcca ggtcgtacac aacaaactga cgagctgcaa ctacaatccg     300
ttatacctcg aagctgacgg gcgaatacgc tgcggcaaag tgaacgacaa ggcgcagtac     360
ctgctgggcg ccgctggcag cgttccctat cgatggatca acctggaata cgacaagata     420
acccggatcg tgggcctgga tcagtacctg gagagcgtta agaaacacaa acggctggat     480
gtgtgccgcg ctaaaatggg ctatatgctg cag                                  513

<210> SEQ ID NO 43
<211> LENGTH: 171
<212> TYPE: PRT
<213> ORGANISM: Unknown
<220> FEATURE:
<223> OTHER INFORMATION: HUL128

<400> SEQUENCE: 43

Met Ser Pro Lys Asn Leu Thr Pro Phe Leu Thr Ala Leu Trp Leu Leu
1               5                   10                  15
Leu Asp His Ser Arg Val Pro Arg Val Arg Ala Glu Glu Cys Cys Glu
            20                  25                  30
Phe Ile Asn Val Asn His Pro Pro Glu Arg Cys Tyr Asp Phe Lys Met
        35                  40                  45
Cys Asn Arg Phe Thr Val Ala Leu Arg Cys Pro Asp Gly Glu Val Cys
```

```
                50                 55                 60
Tyr Ser Pro Glu Lys Thr Ala Glu Ile Arg Gly Ile Val Thr Thr Met
 65                 70                 75                 80

Thr His Ser Leu Thr Arg Gln Val Val His Asn Lys Leu Thr Ser Cys
                 85                 90                 95

Asn Tyr Asn Pro Leu Tyr Leu Glu Ala Asp Gly Arg Ile Arg Cys Gly
                100                105                110

Lys Val Asn Asp Lys Ala Gln Tyr Leu Leu Gly Ala Ala Gly Ser Val
            115                120                125

Pro Tyr Arg Trp Ile Asn Leu Glu Tyr Asp Lys Ile Thr Arg Ile Val
        130                135                140

Gly Leu Asp Gln Tyr Leu Glu Ser Val Lys Lys His Lys Arg Leu Asp
145                150                155                160

Val Cys Arg Ala Lys Met Gly Tyr Met Leu Gln
                165                170

<210> SEQ ID NO 44
<211> LENGTH: 2525
<212> TYPE: DNA
<213> ORGANISM: Unknown
<220> FEATURE:
<223> OTHER INFORMATION: HK1-HUL130 genomic segment

<400> SEQUENCE: 44
gcgcaccggg gatcctaggc tttttggatt gcgctttcct ctagatcaac tgggtgtcag      60
gccctatcct acagaaggat gctacggctt ctgcttcgtc accactttca ctgcctgctt     120
ctgtgcgcgg tttgggcaac gccctgtctg gcgtccccgt ggtcaacgct aacggcgaac     180
cagaatccgt ccccgctatg gtctaaactg acgtattcca aaccgcatga cgcggcgacg     240
ttttactgtc cttttatcta tccctcgccc ccacggtccc ccttgcaatt ctcggggttc     300
cagcgggtat taacgggtcc cgagtgtcgc aacgagaccc tgtatctgct gtacaaccgg     360
gaaggccaga ccttggtgga gagaagctcc acctgggtga aaaaggtgat ctggtacctg     420
agcggtcgca accagaccat cctccaacgg atgccccgaa cggcttcaaa accgagcgac     480
ggaaacgtgc agatcagcgt ggaagacgcc aagatttttg agcgcacat ggtgcccaag     540 cagaccaagc tgctacgctt cgtcgtcaac gatggcacac gttatcagat gtgtgtgatg     600
aagctggaga gctgggctca cgtcttccgg gactacagcg tgtcttttca ggtgcgattg     660
acgttcaccg aggccaataa ccagacttac accttctcca cccatcccaa tctcatcgtt     720
tgaagaacag cgcctcccctg actctccacc tcgaaagagg tggagagtca gggaggccca     780
gagggtctta gagtgtcaca acatttgggc ctctaaaaat taggtcatgt ggcagaatgt     840
tgtgaacagt tttcagatct gggagccttg ctttggaggc gctttcaaaa atgatgcagt     900
ccatgagtgc acagtgcggg gtgatctctt tcttcttttt gtcccttact attccagtat     960
gcatcttaca caaccagcca tatttgtccc acactttatc ttcatactcc ctcgaagctt    1020
ccctggtcat ttcaacatcg ataagcttaa tgtccttcct attttgtgag tccagaagct    1080
ttctgatgtc atcggagcct tgacagctta gaaccatccc ctgcggaaga gcacctataa    1140
ctgacgaggt caacccgggt tgcgcattga agaggtcggc aagatccatg ccgtgtgagt    1200
acttggaatc ttgcttgaat tgttttttgat caacgggttc cctgtaaaag tgtatgaact    1260
gcccgttctg tggttggaaa attgctattt ccactggatc attaaatcta ccctcaatgt    1320
caatccatgt aggagcgttg gggtcaattc ctcccatgag gtcttttaaa agcattgtct    1380
```

```
ggctgtagct taagcccacc tgaggtggac ctgctgctcc aggcgctggc ctgggtgagt       1440
tgactgcagg tttctcgctt gtgagatcaa ttgttgtgtt ttcccatgct ctccccacaa       1500
tcgatgttct acaagctatg tatggccatc cttcacctga aaggcaaact ttatagagga       1560
tgttttcata agggttcctg tccccaactt ggtctgaaac aaacatgttg agttttctct       1620
tggccccgag aactgccttc aagagatcct cgctgttgct tggcttgatc aaaattgact       1680
ctaacatgtt accccatcc aacagggctg ccctgcctt cacggcagca ccaagactaa        1740
agttatagcc agaaatgttg atgctggact gctgttcagt gatgacccc agaactgggt       1800 gcttgtcttt cagcctttca agatcattaa gatttggata cttgactgtg taaagcaagc       1860
caaggtctgt gagcgcttgt acaacgtcat tgagcggagt ctgtgactgt ttggccatac       1920
aagccatagt tagacttggc attgtgccaa attgattgtt caaaagtgat gagtcttttca      1980 catcccaaac tcttaccaca ccacttgcac cctgctgagg ctttctcatc ccaactatct       2040
gtaggatctg atctttggg tctagttgct gtgttgttaa gttccccata tatacccctg       2100
aagcctgggg ccttttcagac ctcatgatct tggccttcag cttctcaagg tcagccgcaa     2160
gagacatcag ttcttctgca ctgagcctcc ccactttcaa aacattcttc tttgatgttg       2220
actttaaatc cacaagagaa tgtacagtct ggttgagact tctgagtctc tgtaggtctt      2280
tgtcatctct cttttccttc ctcatgatcc tctgaacatt gctgacctca gagaagtcca      2340
acccattcag aaggttggtt gcatccttaa tgacagcagc cttcacatct gatgtgaagc      2400
tctgcaattc tcttctcaat gcttgcgtcc attggaagct cttaacttcc ttagacaagg      2460
acatcttgtt gctcaatggt ttctcaagac aaatgcgcaa tcaaatgcct aggatccact      2520
gtgcg                                                                  2525
```

<210> SEQ ID NO 45
<211> LENGTH: 642
<212> TYPE: DNA
<213> ORGANISM: Unknown
<220> FEATURE:
<223> OTHER INFORMATION: HUL130 cDNA

<400> SEQUENCE: 45

```
atgctacggc ttctgcttcg tcaccacttt cactgcctgc ttctgtgcgc ggtttgggca        60 acgcccgtc tggcgtcccc gtggtcaacg ctaacggcga accagaatcc gtccccgcta       120
tggtctaaac tgacgtattc caaaccgcat gacgcggcga cgttttactg tccttttatc      180
tatccctcgc ccccacggtc ccccttgcaa ttctcggggt tccagcgggt attaacgggt       240
cccgagtgtc gcaacgagac cctgtatctg ctgtacaacc gggaaggcca gaccttggtg       300
gagagaagct ccacctgggt gaaaaaggtg atctggtacc tgagcggtcg caaccagacc       360
atcctccaac ggatgccccg aacggcttca aaaccgagcg acggaaacgt gcagatcagc       420
gtggaagacg ccaagatttt tggagcgcac atggtgccca agcagaccaa gctgctacgc      480
ttcgtcgtca acgatggcac acgttatcag atgtgtgtga tgaagctgga gagctgggct     540
cacgtcttcc gggactacag cgtgtctttt caggtgcgat tgacgttcac cgaggccaat      600
aaccagactt acaccttctc cacccatccc aatctcatcg tt                          642
```

<210> SEQ ID NO 46
<211> LENGTH: 214
<212> TYPE: PRT
<213> ORGANISM: Unknown
<220> FEATURE:
<223> OTHER INFORMATION: HUL130

<400> SEQUENCE: 46

| Met | Leu | Arg | Leu | Leu | Arg | His | His | Phe | His | Cys | Leu | Leu | Leu | Cys |
| 1 | | | | 5 | | | | | 10 | | | | | 15 |

| Ala | Val | Trp | Ala | Thr | Pro | Cys | Leu | Ala | Ser | Pro | Trp | Ser | Thr | Leu | Thr |
| | | | | 20 | | | | | 25 | | | | | 30 | |

| Ala | Asn | Gln | Asn | Pro | Ser | Pro | Leu | Trp | Ser | Lys | Leu | Thr | Tyr | Ser | Lys |
| | | | 35 | | | | | 40 | | | | | 45 | | |

| Pro | His | Asp | Ala | Ala | Thr | Phe | Tyr | Cys | Pro | Phe | Ile | Tyr | Pro | Ser | Pro |
| | 50 | | | | | 55 | | | | | 60 | | | | |

| Pro | Arg | Ser | Pro | Leu | Gln | Phe | Ser | Gly | Phe | Gln | Arg | Val | Leu | Thr | Gly |
| 65 | | | | | 70 | | | | | 75 | | | | | 80 |

| Pro | Glu | Cys | Arg | Asn | Glu | Thr | Leu | Tyr | Leu | Leu | Tyr | Asn | Arg | Glu | Gly |
| | | | | 85 | | | | | 90 | | | | | 95 | |

| Gln | Thr | Leu | Val | Glu | Arg | Ser | Ser | Thr | Trp | Val | Lys | Lys | Val | Ile | Trp |
| | | | 100 | | | | | 105 | | | | | 110 | | |

| Tyr | Leu | Ser | Gly | Arg | Asn | Gln | Thr | Ile | Leu | Gln | Arg | Met | Pro | Arg | Thr |
| | | 115 | | | | | 120 | | | | | 125 | | | |

| Ala | Ser | Lys | Pro | Ser | Asp | Gly | Asn | Val | Gln | Ile | Ser | Val | Glu | Asp | Ala |
| | 130 | | | | | 135 | | | | | 140 | | | | |

| Lys | Ile | Phe | Gly | Ala | His | Met | Val | Pro | Lys | Gln | Thr | Lys | Leu | Leu | Arg |
| 145 | | | | | 150 | | | | | 155 | | | | | 160 |

| Phe | Val | Val | Asn | Asp | Gly | Thr | Arg | Tyr | Gln | Met | Cys | Val | Met | Lys | Leu |
| | | | | 165 | | | | | 170 | | | | | 175 | |

| Glu | Ser | Trp | Ala | His | Val | Phe | Arg | Asp | Tyr | Ser | Val | Ser | Phe | Gln | Val |
| | | | 180 | | | | | 185 | | | | | 190 | | |

| Arg | Leu | Thr | Phe | Thr | Glu | Ala | Asn | Asn | Gln | Thr | Tyr | Thr | Phe | Ser | Thr |
| | | 195 | | | | | 200 | | | | | 205 | | | |

| His | Pro | Asn | Leu | Ile | Val |
| | | | 210 | | |

```
<210> SEQ ID NO 47
<211> LENGTH: 387
<212> TYPE: DNA
<213> ORGANISM: Unknown
<220> FEATURE:
<223> OTHER INFORMATION: HUL131  cDNA

<400> SEQUENCE: 47
atgcggctgt gtcgggtgtg gctgtctgtt tgtctgtgcg ccgtggtgct gggtcagtgc       60
cagcgggaga ccgcagaaaa aaacgattat taccgagtac cgcattactg ggacgcgtgc      120
tctcgcgcgc tgcccgacca aacccgttac aagtatgtgg aacagctcgt ggacctcacg      180
ttgaactacc actacgatgc gagccacggc ttggacaact tgacgtgct  caagagaatc      240 aacgtgaccg aggtgtcgtt gctcatcagc gactttagac gtcagaaccg tcgcggcggc      300
accaacaaaa ggaccacgtt caacgccgcc ggttcgctgg cgccgcacgc ccggagcctc      360
gagttcagcg tgcggctctt tgccaac                                         387

<210> SEQ ID NO 48
<211> LENGTH: 129
<212> TYPE: PRT
<213> ORGANISM: Unknown
<220> FEATURE:
<223> OTHER INFORMATION: HUL131

<400> SEQUENCE: 48
```

```
Met Arg Leu Cys Arg Val Trp Leu Ser Val Cys Leu Cys Ala Val Val
1               5                   10                  15
Leu Gly Gln Cys Gln Arg Glu Thr Ala Glu Lys Asn Asp Tyr Tyr Arg
            20                  25                  30
Val Pro His Tyr Trp Asp Ala Cys Ser Arg Ala Leu Pro Asp Gln Thr
        35                  40                  45
Arg Tyr Lys Tyr Val Glu Gln Leu Val Asp Leu Thr Leu Asn Tyr His
    50                  55                  60
Tyr Asp Ala Ser His Gly Leu Asp Asn Phe Asp Val Leu Lys Arg Ile
65                  70                  75                  80
Asn Val Thr Glu Val Ser Leu Leu Ile Ser Asp Phe Arg Arg Gln Asn
                85                  90                  95
Arg Arg Gly Gly Thr Asn Lys Arg Thr Thr Phe Asn Ala Ala Gly Ser
            100                 105                 110
Leu Ala Pro His Ala Arg Ser Leu Glu Phe Ser Val Arg Leu Phe Ala
        115                 120                 125

Asn
```

<210> SEQ ID NO 49
<211> LENGTH: 7205
<212> TYPE: DNA
<213> ORGANISM: Unknown
<220> FEATURE:
<223> OTHER INFORMATION: lymphocytic choriomeningitis strain MP segment L complete sequence

<400> SEQUENCE: 49

```
gcgcaccggg gatcctaggc atttttgttg cgcattttgt tgtgttattt gttgcacagc     60
ccttcatcgt gggaccttca caaacaaacc aaaccaccag ccatgggcca aggcaagtcc    120
aaagagggaa gggatgccag caatacgagc agagctgaaa ttctgccaga caccacctat    180
ctcggacctc tgaactgcaa gtcatgctgg cagagatttg acagtttagt cagatgccat    240
gaccactatc tctgcagaca ctgcctgaac ctcctgctgt cagtctccga caggtgccct    300
ctctgcaaac atccattgcc aaccaaactg aaaatatcca cggccccaag ctctccaccc    360
ccttacgagg agtgacgccc cgagccccaa caccgacaca aggaggccac caacacaacg    420
cccaacacgg aacacacaca cacacaccca cacacacatc cacacacacg cgcccccaca    480
acgggggcgc ccccccgggg gtggcccccc gggtgctcgg gcggagcccc acggagaggc    540
caattagtcg atctcctcga ccaccgactt ggtcagccag tcatcacagg acttgccctt    600
aagtctgtac ttgcccacaa ctgtttcata catcaccgtg ttctttgact tactgaaaca    660
tagcctacag tctttgaaag tgaaccagtc aggcacaagt gacagcggta ccagtagaat    720
ggatctatct atacacaact cttggagaat tgtgctaatt tccgacccct gtagatgctc    780
accagttctg aatcgatgta gaagaaggct cccaaggacg tcatcaaaat ttccataacc    840
ctcgagctct gccaagaaaa ctctcatatc cttggtctcc agtttcacaa cgatgttctg    900
aacaaggctt cttccctcaa aaagagcacc cattctcaca gtcaagggca caggctccca    960
ttcaggccca atcctctcaa aatcaaggga tctgatcccg tccagtattt tccttgagcc   1020
tatcagctca agctcaagag agtcaccgag tatcaggggg tcctccatat agtcctcaaa   1080
ctcttcagac ctaatgtcaa aaacaccatc gttcaccttg aagatagagt ctgatctcaa   1140
caggtggagg cattcgtcca agaaccttct gtccacctca cctttaaaga ggtgagagca   1200
tgataggaac tcagctacac ctggaccttg taactggcac ttcactaaaa agatcaatga   1260
```

-continued

```
aaacttcctc aaacaatcag tgttattctg gttgtgagtg aaatctactg taattgagaa      1320
ctctagcact ccctctgtat tatttatcat gtaatcccac aagtttctca aagacttgaa      1380
tgcctttgga tttgtcaagc cttgtttgat tagcatggca gcattgcaca caatatctcc      1440
caatcggtaa gagaaccatc caaatccaaa ttgcaagtca ttcctaaaca tgggcctctc      1500
catatttttg ttcactactt ttaagatgaa tgattggaaa ggccccaatg cttcagcgcc      1560
atcttcagat ggcatcatgt ctttatgagg gaaccatgaa aaacttccta gagttctgct      1620
tgttgctaca aattctcgta caaatgactc aaaatacact tgttttaaaa agtttttgca      1680
gacatccctt gtactaacga caaattcatc aacaaggctt gagtcagagc gctgatggga      1740
atttacaaga tcagaaaata gaacagtgta gtgttcgtcc ctcttccact taactacatg      1800
agaaatgagc gataaagatt ctgaattgat atcgatcaat acgcaaaggt caaggaattt      1860
gattctggga ctccatctca tgttttttga gctcatatca gacatgaagg gaagcagctg      1920
atcttcatag attttagggt acaatcgcct cacagattgg attacatggt ttaaacttat      1980
cttgtcctcc agtagccttg aactctcagg cttccttgct acataatcac atgggttcaa      2040
gtgcttgagg cttgagcttc cctcattctt ccctttcaca ggttcagcta agacccaaac      2100
acccaactca aaggaattac tcagtgagat gcaaatatag tcccaaagga ggggcctcaa      2160
gagactgatg tggtcgcagt gagcttctgg atgactttgc ctgtcacaaa tgtacaacat      2220
tatgccatca tgtctgtgga ttgctgtcac atgcgcatcc atagctagat cctcaagcac      2280
ttttctaatg tatagattgt ccctatttttt atttctcaca catctacttc ccaaagttttt     2340 gcaaagacct ataagcctg atgagatgca actttgaaag gctgacttat tgattgcttc      2400
tgacagcaac ttctgtgcac ctcttgtgaa cttactgcag agcttgttct ggagtgtctt      2460
gattaatgat gggattcttt cctcttggaa agtcattact gatggataaa ccactttctg      2520
cctcaagacc attcttaatg ggaacaactc attcaaattc agccaattta tgtttgccaa      2580
ttgacttaga tcctcttcga ggccaaggat gtttcccaac tgaagaatgg cttccttttt      2640
atccctattg aagaggtcta agaagaattc ttcattgaac tcaccattct tgagcttatg      2700
atgtagtctc cttacaagcc ttctcatgac cttcgtttca ctaggacaca attcttcaat      2760
aagcctttgg attctgtaac ctctagagcc atccaaccaa tccttgacat cagtattagt      2820
gttaagcaaa aatgggtcca agggaaagtt ggcatatttt aagaggtcta atgttctctt      2880
ctggatgcag tttaccaatg aaactggaac accatttgca acagcttgat cggcaattgt      2940
atctattgtt tcacagagtt ggtgtggctc tttacactta acgttgtgta atgctgctga      3000
cacaaatttt gttaaaagtg ggacctcttc cccccacaca taaaatctgg atttaaattc      3060
tgcagcaaat cgccccacca cacttttcgg actgatgaac ttgttaagca agccactcaa      3120
atgagaatga aattccagca atacaaggac ttcctcaggg tcactatcaa ccagttcact      3180
caatctccta tcaaataagg tgatctgatc atcacttgat gtgtaagatt ctggtctctc      3240
accaaaaatg acaccgatac aataattaat gaatctctca ctgattaagc cgtaaaagtc      3300
agaggcatta tgtaagattc cctgtcccat gtcaatgaga ctgcttatat gggaaggcac      3360
tattcctaat tcaaaatatt ctcgaaagat tctttcagtc acagttgtct ctgaaccct        3420 aagaagtttc agctttgatt tgatatatga tttcatcatt gcattcacaa caggaaaagg      3480
gacctcaaca agtttgtgca tgtgccaagt taataaggtg ctgatatgat cctttccgga      3540
acgcacatac tggtcatcac ccagtttgag attttgaagg agcattaaaa acaaaaatgg      3600
gcacatcatt ggcccccatt tgctatgatc catactgtag ttcaacaacc cctctcgcac      3660
```

```
attgatggtc attgatagaa ttgcatttc  aaattcttg  tcattgttta agcatgaacc   3720
tgagaagaag ctagaaaaag actcaaaata atcctctatc aatcttgtaa acattttgt    3780
tctcaaatcc ccaatataaa gttctctgtt tcctccaacc tgctctttgt atgataacgc   3840
aaacttcaac cttccggaat caggaccaac tgaagtgtat gacgttggtg actcctctga   3900
gtaaaaacat aaattcttta aagcagcact catgcatttt gtcaatgata gagccttact   3960
tagagactca gaattacttt ccctttcact aattctaaca tcttcttcta gtttgtccca   4020
gtcaaacttg aaattcagac cttgtctttg catgtgcctg tatttccctg agtatgcatt   4080
tgcattcatt tgcagtagaa tcattttcat acacgaaaac caatcaccct ctgaaaaaaa   4140
cttcctgcag aggttttttg ccatttcatc cagaccacat tgttctttga cagctgaagt   4200
gaaatacaat ggtgacagtt ctgtagaagt ttcaatagcc tcacagataa atttcatgtc   4260
atcattggtg agacaagatg ggtcaaaatc ttccacaaga tgaaaagaaa tttctgataa   4320
gatgaccttc cttaaatatg ccattttacc tgacaatata gtctgaaggt gatgcaatcc   4380
ttttgtattt tcaaaccca cctcattttc cccttcattg gtcttcttgc ttctttcata    4440
ccgcttatt gtggagttga ccttatcttc taaattcttg aagaaacttg tctcttcttc    4500
cccatcaaag catatgtctg ctgagtcacc ttctagtttc ccagcttctg tttctttaga   4560
gccgataacc aatctagaga ccaactttga aaccttgtac tcgtaatctg agtggttcaa   4620
tttgtacttc tgctttctca tgaagctctc tgtgatctga ctcacagcac taacaagcaa   4680
tttgttaaaa tcatactcta ggagccgttc cccatttaaa tgtttgttaa caaccacact   4740
tttgttgctg gcaaggtcta atgctgttgc acacccagag ttagtcatgg gatccaagct   4800
attgagcctc ttctcccctt tgaaaatcaa agtgccattg ttgaatgagg acaccatcat   4860
gctaaaggcc tccagattga cacctggggt tgtgcgctga cagtcaactt ctttcccagt   4920
gaacttcttc atttggtcat aaaaaacaca ctcttcctca ggggtgattg actcttagg    4980
gttaacaaag aagccaaact cacttttagg ctcaaagaat ttctcaaagc atttaatttg   5040
atctgtcagc ctatcagggg tttcctttgt gattaaatga cacaggtatg acacattcaa   5100
catgaacttg aactttgcgc tcaacagtac cttttcacca gtcccaaaaa cagttttgat   5160
caaaaatctg agcaatttgt acactacttt ctcagcaggt gtgatcaaat cctccttcaa   5220
cttgtccatc aatgatgtgg atgagaagtc tgagacaatg ccatcacta  aatacctaat   5280
gttttgaacc tgttttgat  tcctctttgt tgggttggtg agcatgagta ataatagggt   5340
tctcaatgca atctcaacat catcaatgct gtccttcaag tcaggacatg atctgatcca   5400
tgagatcatg gtgtcaatca tgttgtgcaa cacttcatct gagaagattg gtaaaagaa    5460
ccttttggg  tctgcataaa aagagattag atggccattg ggaccttgta tagaataaca   5520
ccttgaggat tctccagtct tttgatacag caggtgatat tcctcagagt ccaattttat   5580
cacttggcaa ataccttctt tacattccac cacttgatac cttacagagc ccaattggtt   5640
ttgtcttaat ctagcaactg aacttgtttt catactgttt gtcaaagcta gacagacaga   5700
tgacaatctt ttcaaactat gcatgttcct taattgttcc gtattaggct ggaaatcata   5760
atcttcaaac tttgtataat acattatagg atgagttccg gacctcatga aattctcaaa   5820
ctcaataaat ggtatgtggc actcatgctc aagatgttca gacagaccat agtgcccaaa   5880
actaagtccc accactgaca agcacctttg aacttttaaa atgaactcat ttatggatgt   5940
tctaaacaaa tcctcaagag ataccttct atacgccttt gactttctcc tgttccttag    6000
```

| | | | | | |
|---|---|---|---|---|---|
| aagtctgatg | aactcttcct | tggtgctatg | aaagctcacc | aacctatcat | tcacactccc | 6060 |
| atagcaacaa | ccaacccagt | gcttatcatt | ttttgaccct | ttgagtttag | actgtttgat | 6120 |
| caacgaagag | agacacaaga | catccaaatt | cagtaactgt | ctccttctgg | tgttcaataa | 6180 |
| ttttaaactt | ttaactttgt | tcaacataga | gaggagcctc | tcatactcag | tgctagtctc | 6240 |
| acttcctctc | tcataaccat | gggtatctgc | tgtgataaat | ctcatcaaag | gacaggattc | 6300 |
| aactgcctcc | ttgcttagtg | ctgaaatgtc | atcactgtca | gcaagagtct | cataaagctc | 6360 |
| agagaattcc | ttaattaaat | ttccggggtt | gattttctga | aaactcctct | tgagcttccc | 6420 |
| agtttccaag | tctcttctaa | acctgctgta | aagggagttt | atgccaagaa | ccacatcatc | 6480 |
| gcagttcatg | tttgggttga | caccatcatg | gcacattttc | ataatttcat | cattgtgaaa | 6540 |
| tgatcttgca | tctttcaaga | ttttcataga | gtctataccg | gaacgcttat | caacagtggt | 6600 |
| cttgagagat | tcgcaaagtc | tgaagtactc | agattcctca | aagactttct | catcttggct | 6660 |
| agaatactct | aaaagtttaa | acagaaggtc | tctgaacttg | aaattcaccc | actctggcat | 6720 |
| aaagctgtta | tcataatcac | accgaccatc | cactattggg | accaatgtga | tacccgcaat | 6780 |
| ggcaaggtct | tctttgatac | aggctagttt | attggtgtcc | tctataaatt | tcttctcaaa | 6840 |
| actagctggt | gtgcttctaa | cgaagcactc | aagaagaatg | agggaattgt | caatcagttt | 6900 |
| ataaccatca | ggaatgatca | aaggcagtcc | cgggcacaca | atcccagact | ctattagaat | 6960 |
| tgcctcaaca | gatttatcat | catggttgtg | tatgcagccg | ctcttgtcag | cactgtctat | 7020 |
| ctctatacaa | cgcgacaaaa | gtttgagtcc | ctctatcaat | accattctgg | gttctctttg | 7080 |
| ccctaaaaag | ttgagcttct | gccttgacaa | cctctcatct | tgttctatgt | ggtttaagca | 7140 |
| caactctctc | aactccgaaa | tagcctcatc | cattgcgcat | caaaaagcct | aggatcctcg | 7200 |
| gtgcg | | | | | 7205 |

<210> SEQ ID NO 50
<211> LENGTH: 4037
<212> TYPE: DNA
<213> ORGANISM: Unknown
<220> FEATURE:
<223> OTHER INFORMATION: HK1-HgH(dTM) genomic segment

<400> SEQUENCE: 50

| | | | | | |
|---|---|---|---|---|---|
| gcgcaccggg | gatcctaggc | tttttggatt | gcgctttcct | ctagatcaac | tgggtgtcag | 60 |
| gccctatcct | acagaaggat | gcggcccggc | ctccccttct | acctcaccgt | cttcgccgtc | 120 |
| tacctcctta | gtcacctacc | ttcgcaacga | tatggcgcag | acgccgcatc | cgaagcgctg | 180 |
| gaccctcacg | cgtttcacct | actactcaac | acctatggga | gacccatccg | tttcctgcgt | 240 |
| gaaaacacca | cccagtgcac | ctacaacagc | agcctccgta | acagcacggt | cgtcagggaa | 300 |
| aacgccatca | gtttcaactt | ttttccaaagc | tataatcaat | actatgtatt | ccatatgcct | 360 |
| cgatgtcttt | ttgcgggtcc | tctggcggag | cagtttctga | accaggtaga | tctgaccgaa | 420 |
| acccctagaaa | gataccaaca | gagacttaac | acctacgcat | tggtatccaa | agacctggct | 480 |
| agctaccgat | ctttttcgca | gcagctgaag | gcacaagaca | gcctgggtca | gcagcccacc | 540 |
| accgtgccac | cgcccattga | tctgtcaata | cctcacgtct | ggatgccacc | ccaaaccact | 600 |
| ccacacgact | ggaagggatc | gcacaccacc | tcgggactac | atcggccaca | ctttaaccag | 660 |
| acctgtatcc | tctttgatgg | acacgatctg | cttttcagca | ccgttacgcc | ctgtctgcac | 720 |
| cagggctttt | acctcatgga | cgaactacgt | tacgttaaaa | tcacactgac | cgaggacttc | 780 |
| ttcgtagtta | cggtatccat | agacgacgac | acacccatgc | tgcttatctt | cggtcatctt | 840 |

```
ccacgcgtac tcttcaaagc gccctatcaa cgcgacaact ttatactacg acaaactgaa      900
aaacacgagc tcctggtact agttaagaaa actcaactga accgtcactc ctatctcaaa      960
gactcggact ttctcgacgc cgcactcgac ttcaactacc tggacctcag cgcactgcta     1020
cgtaacagct ttcaccgtta cgctgtagac gtactcaaaa gcggtcgatg tcaaatgctg     1080
gaccgccgca cggtagaaat ggcctttgcc tacgcattag cactgttcgc ggcagcccga     1140
caagaagagg ccggcaccga aatctccatc ccacgggccc tagaccgcca ggccgcactc     1200
ttacaaatac aagaatttat gatcacctgc ctctcacaaa caccaccacg caccacattg     1260
ctgctatatc ccacggccgt ggacctggcc aaacgagccc tctggacgcc ggaccagatc     1320
accgacatca ccagcctcgt acgcctggtc tacatacttt ctaaacagaa tcagcaacat     1380
ctcattcccc agtgggcact acgacagatc gccgactttg ccctacaatt acacaaaacg     1440
cacctggcct cttttctttc agccttcgcg cgccaagaac tctacctcat gggcagcctc     1500
gtccactcca tgctggtgca tacgacggag aggcgcgaaa tcttcatcgt agaaacgggc     1560
ctctgttcat tggccgagct atcacacttt acgcagttgc tagctcatcc gcaccacgaa     1620
tacctcagcg acctgtacac accctgttcc agtagcgggc gacgcgatca ctcgctcgaa     1680
cgccttacgc gcctcttccc cgatgccacc gtccccgcta ccgttcccgc cgccctctcc     1740
atcctatcta ccatgcaacc aagcacgctg gaaaccttcc ccgacctgtt ttgtctgcca     1800
ctaggcgaat ccttctccgc gctcaccgtt tccgaacacg tcagctacgt cgtaacaaac     1860
caatacctga tcaaaggtat ctcctaccct gtctccacca ccgtcgtagg ccagagcctc     1920
atcatcaccc agacggacag tcaaagtaaa tgcgaactga cgcgcaacat gcacaccaca     1980
cacagcatca cagcggcgct caacatttcg ctagaaaact gcgccttctg ccaaagcgcc     2040
ttactagaat acgacgacac gcaaggcgtc attaatatca tgtacatgca cgactcggac     2100
gacgtccttt ttgccctgga tccctacaac gaagtggtgg tctcatctcc acgaactcac     2160
tacctcatgc tgttgaaaaa cggtacggtc ctggaagtaa ctgacgtcgt cgtggacgcc     2220
accgacagcc gctgaagaac agcgcctccc tgactctcca cctcgaaaga ggtgagagt     2280
cagggaggcc cagagggtct tagagtgtca caacatttgg gcctctaaaa attaggtcat     2340
gtggcagaat gttgtgaaca gttttcagat ctgggagcct tgctttggag gcgctttcaa     2400
aaaatgatgca gtccatgagt gcacagtgcg gggtgatctc tttcttcttt ttgtccctta     2460
ctattccagt atgcatctta cacaaccagc catatttgtc ccacacttta tcttcatact     2520
ccctcgaagc ttccctggtc atttcaacat cgataagctt aatgtccttc ctattttgtg     2580
agtccagaag ctttctgatg tcatcggagc cttgacagct tagaaccatc cctgcggaa     2640
gagcacctat aactgacgag gtcaacccgg gttgcgcatt gaagaggtcg gcaagatcca     2700
tgccgtgtga gtacttggaa tcttgcttga attgttttg atcaacgggt tccctgtaaa     2760
agtgtatgaa ctgcccgttc tgtggttgga aaattgctat ttccactgga tcattaaatc     2820
taccctcaat gtcaatccat gtaggagcgt tggggtcaat tcctcccatg aggtctttta     2880
aaagcattgt ctggctgtag cttaagccca cctgaggtgg acctgctgct ccaggcgctg     2940
gcctgggtga gttgactgca ggtttctcgc ttgtgagatc aattgttgtg ttttcccatg     3000
ctctccccac aatcgatgtt ctacaagcta tgtatggcca tccttcacct gaaaggcaaa     3060
ctttatagag gatgttttca taggggttcc tgtcccaac ttggtctgaa acaaacatgt      3120
tgagttttct cttggccccg agaactgcct tcaagagatc ctcgctgttg cttggcttga     3180
```

| | | | | |
|---|---|---|---|---|
| tcaaaattga | ctctaacatg | ttaccccat | ccaacagggc | tgcccctgcc ttcacggcag | 3240 |
| caccaagact | aaagttatag | ccagaaatgt | tgatgctgga | ctgctgttca gtgatgaccc | 3300 |
| ccagaactgg | gtgcttgtct | ttcagccttt | caagatcatt | aagatttgga tacttgactg | 3360 |
| tgtaaagcaa | gccaaggtct | gtgagcgctt | gtacaacgtc | attgagcgga gtctgtgact | 3420 |
| gtttggccat | acaagccata | gttagacttg | gcattgtgcc | aaattgattg ttcaaaagtg | 3480 |
| atgagtcttt | cacatcccaa | actcttacca | caccacttgc | accctgctga ggctttctca | 3540 |
| tcccaactat | ctgtaggatc | tgagatcttt | ggtctagttg | ctgtgttgtt aagttcccca | 3600 |
| tatataccc | tgaagcctgg | ggcctttcag | acctcatgat | cttggccttc agcttctcaa | 3660 |
| ggtcagccgc | aagagacatc | agttcttctg | cactgagcct | ccccactttc aaaacattct | 3720 |
| tctttgatgt | tgactttaaa | tccacaagag | aatgtacagt | ctggttgaga cttctgagtc | 3780 |
| tctgtaggtc | tttgtcatct | ctcttttcct | tcctcatgat | cctctgaaca ttgctgacct | 3840 |
| cagagaagtc | caacccattc | agaaggttgg | ttgcatcctt | aatgacagca gccttcacat | 3900 |
| ctgatgtgaa | gctctgcaat | tctcttctca | atgcttgcgt | ccattggaag ctcttaactt | 3960 |
| ccttagacaa | ggacatcttg | ttgctcaatg | gtttctcaag | acaaatgcgc aatcaaatgc | 4020 |
| ctaggatcca | ctgtgcg | | | | 4037 |

<210> SEQ ID NO 51
<211> LENGTH: 2154
<212> TYPE: DNA
<213> ORGANISM: Unknown
<220> FEATURE:
<223> OTHER INFORMATION: HgH(dTM) cDNA

<400> SEQUENCE: 51

| | | | | |
|---|---|---|---|---|
| atgcggcccg | gcctccctt | ctacctcacc | gtcttcgccg | tctacctcct tagtcaccta | 60 |
| ccttcgcaac | gatatggcgc | agacgccgca | tccgaagcgc | tggaccctca cgcgtttcac | 120 |
| ctactactca | cacctatgg | gagacccatc | cgtttcctgc | gtgaaaacac cacccagtgc | 180 |
| acctacaaca | gcagcctccg | taacagcacg | gtcgtcaggg | aaaacgccat cagtttcaac | 240 |
| ttttccaaa | gctataatca | atactatgta | ttccatatgc | ctcgatgtct ttttgcgggt | 300 |
| cctctggcgg | agcagtttct | gaaccaggta | gatctgaccg | aaaccctaga agataccaa | 360 |
| cagagactta | cacctacgc | attggtatcc | aaagacctgg | ctagctaccg atcttttcg | 420 |
| cagcagctga | aggcacaaga | cagcctgggt | cagcagccca | ccaccgtgcc accgcccatt | 480 |
| gatctgtcaa | tacctcacgt | ctggatgcca | ccccaaacca | ctccacacga ctggaaggga | 540 |
| tcgcacacca | cctcgggact | acatcggcca | cactttaacc | agacctgtat cctctttgat | 600 |
| ggacacgatc | tgcttttcag | caccgttacg | ccctgtctgc | accagggctt ttacctcatg | 660 |
| gacgaactac | gttacgttaa | aatcacactg | accgaggact | tcttcgtagt tacggtatcc | 720 |
| atagcgacg | acacacccat | gctgcttatc | ttcggtcatc | ttccacgcgt actcttcaaa | 780 |
| gcgccctatc | aacgcgacaa | ctttatacta | cgacaaactg | aaaaacacga gctcctggta | 840 |
| ctagttaaga | aaactcaact | gaaccgtcac | tcctatctca | aagactcgga ctttctcgac | 900 |
| gccgcactcg | acttcaacta | cctggacctc | agcgcactgc | tacgtaacag ctttcaccgt | 960 |
| tacgctgtag | acgtactcaa | aagcggtcga | tgtcaaatgc | tggaccgccg cacggtagaa | 1020 |
| atggcctttg | cctacgcatt | agcactgttc | gcggcagccc | gacaagaaga ggccggcacc | 1080 |
| gaaatctcca | tcccacgggc | cctagaccgc | caggccgcac | tcttacaaat acaagaattt | 1140 |
| atgatcaccct | gcctctcaca | aacaccacca | cgcaccacat | tgctgctata tcccacggcc | 1200 |

-continued

```
gtggacctgg ccaaacgagc cctctggacg ccggaccaga tcaccgacat caccagcctc  1260
gtacgcctgg tctacatact ttctaaacag aatcagcaac atctcattcc ccagtgggca  1320
ctacgacaga tcgccgactt tgccctacaa ttacacaaaa cgcacctggc ctcttttctt  1380
tcagccttcg cgcgccaaga actctacctc atgggcagcc tcgtccactc catgctggtg  1440
catacgacgg agaggcgcga aatcttcatc gtagaaacgg gcctctgttc attggccgag  1500
ctatcacact ttacgcagtt gctagctcat ccgcaccacg aataccggag cgacctgtac  1560
acaccctgtt ccagtagcgg gcgacgcgat cactcgctcg aacgccttac gcgcctcttc  1620
cccgatgcca ccgtccccgc taccgttccc gccgccctct ccatcctatc taccatgcaa  1680
ccaagcacgc tggaaacctt ccccgacctg ttttgtctgc cactaggcga atccttctcc  1740
gcgctcaccg tttccgaaca cgtcagctac gtcgtaacaa accaataccct gatcaaaggt  1800
atctcctacc ctgtctccac caccgtcgta ggccagagcc tcatcatcac ccagacggac  1860
agtcaaagta aatgcgaact gacgcgcaac atgcacacca cacacagcat cacagcggcg  1920
ctcaacattt cgctagaaaa ctgcgccttc tgccaaagcg ccttactaga atacgacgac  1980
acgcaaggcg tcattaatat catgtacatg cacgactcgg acgacgtcct ttttgccctg  2040
gatccctaca cgaagtggt ggtctcatct ccacgaactc actacctcat gctgttgaaa  2100
aacggtacgg tcctggaagt aactgacgtc gtcgtggacg ccaccgacag ccgc         2154
```

<210> SEQ ID NO 52
<211> LENGTH: 718
<212> TYPE: PRT
<213> ORGANISM: Unknown
<220> FEATURE:
<223> OTHER INFORMATION: HgH(dTM)

<400> SEQUENCE: 52

```
Met Arg Pro Gly Leu Pro Phe Tyr Leu Thr Val Phe Ala Val Tyr Leu
1               5                   10                  15

Leu Ser His Leu Pro Ser Gln Arg Tyr Gly Ala Asp Ala Ala Ser Glu
            20                  25                  30

Ala Leu Asp Pro His Ala Phe His Leu Leu Asn Thr Tyr Gly Arg
        35                  40                  45

Pro Ile Arg Phe Leu Arg Glu Asn Thr Thr Gln Cys Thr Tyr Asn Ser
    50                  55                  60

Ser Leu Arg Asn Ser Thr Val Val Arg Glu Asn Ala Ile Ser Phe Asn
65                  70                  75                  80

Phe Phe Gln Ser Tyr Asn Gln Tyr Tyr Val Phe His Met Pro Arg Cys
                85                  90                  95

Leu Phe Ala Gly Pro Leu Ala Glu Gln Phe Leu Asn Gln Val Asp Leu
            100                 105                 110

Thr Glu Thr Leu Glu Arg Tyr Gln Gln Arg Leu Asn Thr Tyr Ala Leu
        115                 120                 125

Val Ser Lys Asp Leu Ala Ser Tyr Arg Ser Phe Ser Gln Gln Leu Lys
    130                 135                 140

Ala Gln Asp Ser Leu Gly Gln Gln Pro Thr Thr Val Pro Pro Pro Ile
145                 150                 155                 160

Asp Leu Ser Ile Pro His Val Trp Met Pro Gln Thr Thr Pro His
                165                 170                 175

Asp Trp Lys Gly Ser His Thr Thr Ser Gly Leu His Arg Pro His Phe
            180                 185                 190
```

-continued

```
Asn Gln Thr Cys Ile Leu Phe Asp Gly His Asp Leu Leu Phe Ser Thr
            195                 200                 205
Val Thr Pro Cys Leu His Gln Gly Phe Tyr Leu Met Asp Glu Leu Arg
    210                 215                 220
Tyr Val Lys Ile Thr Leu Thr Glu Asp Phe Phe Val Thr Val Ser
225                 230                 235                 240
Ile Asp Asp Asp Thr Pro Met Leu Leu Ile Phe Gly His Leu Pro Arg
                245                 250                 255
Val Leu Phe Lys Ala Pro Tyr Gln Arg Asp Asn Phe Ile Leu Arg Gln
            260                 265                 270
Thr Glu Lys His Glu Leu Leu Val Leu Lys Lys Thr Gln Leu Asn
    275                 280                 285
Arg His Ser Tyr Leu Lys Asp Ser Asp Phe Leu Asp Ala Ala Leu Asp
    290                 295                 300
Phe Asn Tyr Leu Asp Leu Ser Ala Leu Leu Arg Asn Ser Phe His Arg
305                 310                 315                 320
Tyr Ala Val Asp Val Leu Lys Ser Gly Arg Cys Gln Met Leu Asp Arg
                325                 330                 335
Arg Thr Val Glu Met Ala Phe Ala Tyr Ala Leu Ala Leu Phe Ala Ala
            340                 345                 350
Ala Arg Gln Glu Glu Ala Gly Thr Glu Ile Ser Ile Pro Arg Ala Leu
    355                 360                 365
Asp Arg Gln Ala Ala Leu Leu Gln Ile Gln Glu Phe Met Ile Thr Cys
    370                 375                 380
Leu Ser Gln Thr Pro Pro Arg Thr Thr Leu Leu Leu Tyr Pro Thr Ala
385                 390                 395                 400
Val Asp Leu Ala Lys Arg Ala Leu Trp Thr Pro Asp Gln Ile Thr Asp
                405                 410                 415
Ile Thr Ser Leu Val Arg Leu Val Tyr Ile Leu Ser Lys Gln Asn Gln
            420                 425                 430
Gln His Leu Ile Pro Gln Trp Ala Leu Arg Gln Ile Ala Asp Phe Ala
    435                 440                 445
Leu Gln Leu His Lys Thr His Leu Ala Ser Phe Leu Ser Ala Phe Ala
450                 455                 460
Arg Gln Glu Leu Tyr Leu Met Gly Ser Leu Val His Ser Met Leu Val
465                 470                 475                 480
His Thr Thr Glu Arg Arg Glu Ile Phe Ile Val Glu Thr Gly Leu Cys
                485                 490                 495
Ser Leu Ala Glu Leu Ser His Phe Thr Gln Leu Leu Ala His Pro His
            500                 505                 510
His Glu Tyr Leu Ser Asp Leu Tyr Thr Pro Cys Ser Ser Ser Gly Arg
    515                 520                 525
Arg Asp His Ser Leu Glu Arg Leu Thr Arg Leu Phe Pro Asp Ala Thr
    530                 535                 540
Val Pro Ala Thr Val Pro Ala Leu Ser Ile Leu Ser Thr Met Gln
545                 550                 555                 560
Pro Ser Thr Leu Glu Thr Phe Pro Asp Leu Phe Cys Leu Pro Leu Gly
                565                 570                 575
Glu Ser Phe Ser Ala Leu Thr Val Ser Glu His Val Ser Tyr Val Val
            580                 585                 590
Thr Asn Gln Tyr Leu Ile Lys Gly Ile Ser Tyr Pro Val Ser Thr Thr
    595                 600                 605
Val Val Gly Gln Ser Leu Ile Ile Thr Gln Thr Asp Ser Gln Ser Lys
```

```
    610                 615                 620

Cys Glu Leu Thr Arg Asn Met His Thr Thr His Ser Ile Thr Ala Ala
625                 630                 635                 640

Leu Asn Ile Ser Leu Glu Asn Cys Ala Phe Cys Gln Ser Ala Leu Leu
                645                 650                 655

Glu Tyr Asp Asp Thr Gln Gly Val Ile Asn Ile Met Tyr Met His Asp
            660                 665                 670

Ser Asp Asp Val Leu Phe Ala Leu Asp Pro Tyr Asn Glu Val Val Val
        675                 680                 685

Ser Ser Pro Arg Thr His Tyr Leu Met Leu Leu Lys Asn Gly Thr Val
    690                 695                 700

Leu Glu Val Thr Asp Val Val Val Asp Ala Thr Asp Ser Arg
705                 710                 715

<210> SEQ ID NO 53
<211> LENGTH: 3359
<212> TYPE: DNA
<213> ORGANISM: Unknown
<220> FEATURE:
<223> OTHER INFORMATION: lymphocytic choriomeningitis strain MP segment
      S, complete sequence

<400> SEQUENCE: 53
cgcaccgggg atcctaggct tttggattg cgctttcctc agctccgtct tgtgggagaa     60
tgggtcaaat tgtgacgatg tttgaggctc tgcctcacat cattgatgag gtcattaaca    120
ttgtcattat cgtgcttatt atcatcacga gcatcaaagc tgtgtacaat ttcgccacct    180
gcgggatact tgcattgatc agctttcttt ttctggctgg caggtcctgt ggaatgtatg    240
gtcttgatgg gcctgacatt tacaaagggg tttaccgatt caagtcagtg gagtttgaca    300
tgtcttacct taacctgacg atgcccaatg catgttcggc aaacaactcc catcattata    360
taagtatggg gacttctgga ttggagttaa ccttcacaaa tgactccatc atcacccaca    420
acttttgtaa tctgacttcc gccctcaaca agaggacttt tgaccacaca cttatgagta    480
tagtctcaag tctgcacctc agcattagag ggtccccag ctacaaagca gtgtcctgtg    540
attttaacaa tggcatcact attcaataca acctgtcatt ttctaatgca cagagcgctc    600
tgagtcaatg taagaccttc agggggagag tcctggatat gttcagaact gcttttggag    660
gaaagtacat gaggagtggc tggggctgga caggttcaga tggcaagact acttggtgca    720
gccagacaaa ctaccaatat ctgattatac aaaacaggac ttgggaaaac cactgcaggt    780
acgcaggccc tttcggaatg tctagaattc tcttcgctca agaaaagaca aggtttctaa    840
ctagaaggct tgcaggcaca ttcacttgga ctttatcaga ctcatcagga gtggagaatc    900
caggtggtta ctgcttgacc aagtggatga tcctcgctgc agagctcaag tgttttggga    960
acacagctgt tgcaaagtgc aatgtaaatc atgatgaaga gttctgtgat atgctacgac   1020
tgattgatta caacaaggct gctttgagta aattcaaaga agatgtagaa tccgctctac   1080
atctgttcaa gacaacagtg aattctttga tttctgatca gcttttgatg agaaatcacc   1140
taagagactt gatgggagtg ccatactgca attactcgaa attctggtat ctagagcatg   1200
caaagactgg tgagactagt gtccccaagt gctggcttgt cagcaatggt tcttatttga   1260
atgaaaccca tttcagcgac caaattgagc aggaagcaga taatatgatc acagaaatgc   1320
tgagaaagga ctacataaaa aggcaaggga gtacccctct agccttgatg gatctattga   1380
tgttttctac atcagcatat ttgatcagca tctttctgca tcttgtgagg ataccaacac   1440
```

| acagacacat aaagggcggc tcatgcccaa aaccacatcg gttaaccagc aagggaatct | 1500 |
| gtagttgtgg tgcatttaaa gtaccaggtg tggaaaccac ctggaaaaga cgctgaacag | 1560 |
| cagcgcctcc ctgactcacc acctcgaaag aggtggtgag tcagggaggc ccagagggtc | 1620 |
| ttagagtgtt acgacatttg gacctctgaa gattaggtca tgtggtagga tattgtggac | 1680 |
| agttttcagg tcggggagcc ttgccttgga ggcgctttca aagatgatac agtccatgag | 1740 |
| tgcacagtgt ggggtgacct ctttctttt cttgtccctc actattccag tgtgcatctt | 1800 |
| gcatagccag ccatatttgt cccagacttt gtcctcatat tctcttgaag cttctttagt | 1860 |
| catctcaaca tcgatgagct taatgtctct tctgttttgt gaatctagga gtttcctgat | 1920 |
| gtcatcagat ccctgacaac ttaggaccat tccctgtgga agagcaccta ttactgaaga | 1980 |
| tgtcagccca ggttgtgcat tgaagaggtc agcaaggtcc atgccatgtg agtatttgga | 2040 |
| gtcctgcttg aattgttttt gatcagtggg ttctctatag aaatgtatgt actgcccatt | 2100 |
| ctgtggctga atattgcta tttctaccgg gtcattaaat ctgccctcaa tgtcaatcca | 2160 |
| tgtaggagcg ttagggtcaa tacctcccat gaggtccttc agcaacattg tttggctgta | 2220 |
| gcttaagccc acctgaggtg ggcccgctgc cccaggcgct ggtttgggtg agttggccat | 2280 |
| aggcctctca tttgtcagat caattgttgt gttctcccat gctctcccta caactgatgt | 2340 |
| tctacaagct atgtatggcc acccctcccc tgaaagacag actttgtaga ggatgttctc | 2400 |
| gtaaggattc ctgtctccaa cctgatcaga aacaaacatg ttgagtttct tcttggcccc | 2460 |
| aagaactgct tcaggagat cctcactgtt gcttggctta attaagatgg attccaacat | 2520 |
| gttaccccca tctaacaagg ctgccctgc tttcacagca gcaccgagac tgaaattgta | 2580 |
| gccagatatg ttgatgctag actgctgctc agtgatgact cccaagactg ggtgcttgtc | 2640 |
| tttcagcctt tcaaggtcac ttaggttcgg tacttgact gtgtaaagca gcccaaggtc | 2700 |
| tgtgagtgct tgcacaacgt cattgagtga ggtttgtgat tgtttggcca tacaagccat | 2760 |
| tgttaagctt ggcattgtgc cgaattgatt gttcagaagt gatgagtcct tcacatccca | 2820 |
| gaccctcacc acaccatttg cactctgctg aggtctcctc attccaacca tttgcagaat | 2880 |
| ctgagatctt tggtcaagct gttgtgctgt taagttcccc atgtagactc cagaagttag | 2940 |
| aggcctttca gacctcatga ttttagccctt cagttttca aggtcagctg caagggacat | 3000 |
| cagttcttct gcactaagcc tccctacttt tagaacattc ttttttgatg ttgactttag | 3060 |
| gtccacaagg gaatacacag tttggttgag gcttctgagt ctctgtaaat ctttgtcatc | 3120 |
| cctcttctct ttcctcatga tcctctgaac attgctcacc tcagagaagt ctaatccatt | 3180 |
| cagaaggctg gtggcatcct tgatcacagc agctttcaca tctgatgtga agccttgaag | 3240 |
| ctctctcctc aatgcctggg tccattgaaa gcttttaact tctttggaca gagacatttt | 3300 |
| gtcactcagt ggatttccaa gtcaaatgcg caatcaaaat gcctaggatc cactgtgcg | 3359 |

<210> SEQ ID NO 54
<211> LENGTH: 558
<212> TYPE: PRT
<213> ORGANISM: Unknown
<220> FEATURE:
<223> OTHER INFORMATION: NP protein of the MP strain of LCMV

<400> SEQUENCE: 54

Met Ser Leu Ser Lys Glu Val Lys Ser Phe Gln Trp Thr Gln Ala Leu
1               5                   10                  15

Arg Arg Glu Leu Gln Gly Phe Thr Ser Asp Val Lys Ala Ala Val Ile
            20                  25                  30

Lys Asp Ala Thr Ser Leu Leu Asn Gly Leu Asp Phe Ser Glu Val Ser
            35                  40                  45

Asn Val Gln Arg Ile Met Arg Lys Glu Lys Arg Asp Lys Asp Leu
 50                  55                  60

Gln Arg Leu Arg Ser Leu Asn Gln Thr Val Tyr Ser Leu Val Asp Leu
 65                  70                  75                  80

Lys Ser Thr Ser Lys Lys Asn Val Leu Lys Val Gly Arg Leu Ser Ala
                 85                  90                  95

Glu Glu Leu Met Ser Leu Ala Ala Asp Leu Glu Lys Leu Lys Ala Lys
                100                 105                 110

Ile Met Arg Ser Glu Arg Pro Leu Thr Ser Gly Val Tyr Met Gly Asn
                115                 120                 125

Leu Thr Ala Gln Gln Leu Asp Gln Arg Ser Gln Ile Leu Gln Met Val
    130                 135                 140

Gly Met Arg Arg Pro Gln Gln Ser Ala Asn Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Ser Leu Asn
                180                 185                 190

Asp Val Val Gln Ala Leu Thr Asp Leu Gly Leu Leu Tyr Thr Val Lys
                195                 200                 205

Tyr Pro Asn Leu Ser Asp Leu Glu Arg Leu Lys Asp Lys His Pro Val
210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
                260                 265                 270

Asp Leu Leu Lys Ala Val Leu Gly Ala Lys Lys Leu Asn Met Phe
                275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Arg Pro Met Ala Asn Ser Pro Lys Pro Ala Pro Gly Ala Ala Gly
                340                 345                 350

Pro Pro Gln Val Gly Leu Ser Tyr Ser Gln Thr Met Leu Leu Lys Asp
            355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Tyr Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
                420                 425                 430

Asn Ala Gln Pro Gly Leu Thr Ser Ser Val Ile Gly Ala Leu Pro Gln
            435                 440                 445

```
Gly Met Val Leu Ser Cys Gln Gly Ser Asp Asp Ile Arg Lys Leu Leu
            450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Ile Val Arg Asp Lys Lys Lys
            500                 505                 510

Glu Val Thr Pro His Cys Ala Leu Met Asp Cys Ile Ile Phe Glu Ser
            515                 520                 525

Ala Ser Lys Ala Arg Leu Pro Asp Leu Lys Thr Val His Asn Ile Leu
530                 535                 540

Pro His Asp Leu Ile Phe Arg Gly Pro Asn Val Val Thr Leu
545                 550                 555

<210> SEQ ID NO 55
<211> LENGTH: 498
<212> TYPE: PRT
<213> ORGANISM: Unknown
<220> FEATURE:
<223> OTHER INFORMATION: GP protein of the MP strain of LCMV

<400> SEQUENCE: 55

Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
                20                  25                  30

Lys Ala Val Tyr Asn Phe Ala Thr Cys Gly Ile Leu Ala Leu Ile Ser
            35                  40                  45

Phe Leu Phe Leu Ala Gly Arg Ser Cys Gly Met Tyr Gly Leu Asp Gly
50                  55                  60

Pro Asp Ile Tyr Lys Gly Val Tyr Arg Phe Lys Ser Val Glu Phe Asp
65                  70                  75                  80

Met Ser Tyr Leu Asn Leu Thr Met Pro Asn Ala Cys Ser Ala Asn Asn
                85                  90                  95

Ser His His Tyr Ile Ser Met Gly Thr Ser Gly Leu Glu Leu Thr Phe
            100                 105                 110

Thr Asn Asp Ser Ile Ile Thr His Asn Phe Cys Asn Leu Thr Ser Ala
        115                 120                 125

Leu Asn Lys Arg Thr Phe Asp His Thr Leu Met Ser Ile Val Ser Ser
130                 135                 140

Leu His Leu Ser Ile Arg Gly Val Pro Ser Tyr Lys Ala Val Ser Cys
145                 150                 155                 160

Asp Phe Asn Asn Gly Ile Thr Ile Gln Tyr Asn Leu Ser Phe Ser Asn
                165                 170                 175

Ala Gln Ser Ala Leu Ser Gln Cys Lys Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Thr Gly Ser Asp Gly Lys Thr Thr Trp Cys Ser Gln Thr Asn
210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255
```

Thr Arg Phe Leu Thr Arg Arg Leu Ala Gly Thr Phe Thr Trp Thr Leu
                260                 265                 270

Ser Asp Ser Ser Gly Val Glu Asn Pro Gly Gly Tyr Cys Leu Thr Lys
            275                 280                 285

Trp Met Ile Leu Ala Ala Glu Leu Lys Cys Phe Gly Asn Thr Ala Val
290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Ser Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Met Phe Ser Thr Ser Ala Tyr Leu
        435                 440                 445

Ile Ser Ile Phe Leu His Leu Val Arg Ile Pro Thr His Arg His Ile
    450                 455                 460

Lys Gly Gly Ser Cys Pro Lys Pro His Arg Leu Thr Ser Lys Gly Ile
465                 470                 475                 480

Cys Ser Cys Gly Ala Phe Lys Val Pro Gly Val Glu Thr Thr Trp Lys
                485                 490                 495

Arg Arg

<210> SEQ ID NO 56
<211> LENGTH: 2209
<212> TYPE: PRT
<213> ORGANISM: Unknown
<220> FEATURE:
<223> OTHER INFORMATION: L protein of the MP strain of LCMV

<400> SEQUENCE: 56

Met Asp Glu Ala Ile Ser Glu Leu Arg Glu Leu Cys Leu Asn His Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Ile His Asn His
    50                  55                  60

Asp Asp Lys Ser Val Glu Ala Ile Leu Ile Glu Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu

```
            115                 120                 125
Asp Leu Ala Ile Ala Gly Ile Thr Leu Val Pro Ile Val Asp Gly Arg
    130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr
            180                 185                 190

Thr Val Asp Lys Arg Ser Gly Ile Asp Ser Met Lys Ile Leu Lys Asp
        195                 200                 205

Ala Arg Ser Phe His Asn Asp Glu Ile Met Lys Met Cys His Asp Gly
    210                 215                 220

Val Asn Pro Asn Met Asn Cys Asp Asp Val Val Leu Gly Ile Asn Ser
225                 230                 235                 240

Leu Tyr Ser Arg Phe Arg Arg Asp Leu Glu Thr Gly Lys Leu Lys Arg
                245                 250                 255

Ser Phe Gln Lys Ile Asn Pro Gly Asn Leu Ile Lys Glu Phe Ser Glu
            260                 265                 270

Leu Tyr Glu Thr Leu Ala Asp Ser Asp Ile Ser Ala Leu Ser Lys
        275                 280                 285

Glu Ala Val Glu Ser Cys Pro Leu Met Arg Phe Ile Thr Ala Asp Thr
    290                 295                 300

His Gly Tyr Glu Arg Gly Ser Glu Thr Ser Thr Glu Tyr Glu Arg Leu
305                 310                 315                 320

Leu Ser Met Leu Asn Lys Val Lys Ser Leu Lys Leu Asn Thr Arg
                325                 330                 335

Arg Arg Gln Leu Leu Asn Leu Asp Val Leu Cys Leu Ser Ser Leu Ile
            340                 345                 350

Lys Gln Ser Lys Leu Lys Gly Ser Lys Asn Asp Lys His Trp Val Gly
        355                 360                 365

Cys Cys Tyr Gly Ser Val Asn Asp Arg Leu Val Ser Phe His Ser Thr
    370                 375                 380

Lys Glu Glu Phe Ile Arg Leu Leu Arg Asn Arg Arg Lys Ser Lys Ala
385                 390                 395                 400

Tyr Arg Lys Val Ser Leu Glu Asp Leu Phe Arg Thr Ser Ile Asn Glu
                405                 410                 415

Phe Ile Leu Lys Val Gln Arg Cys Leu Ser Val Val Gly Leu Ser Phe
            420                 425                 430

Gly His Tyr Gly Leu Ser Glu His Leu Glu His Glu Cys His Ile Pro
        435                 440                 445

Phe Ile Glu Phe Glu Asn Phe Met Arg Ser Gly Thr His Pro Ile Met
    450                 455                 460

Tyr Tyr Thr Lys Phe Glu Asp Tyr Asp Phe Gln Pro Asn Thr Glu Gln
465                 470                 475                 480

Leu Arg Asn Met His Ser Leu Lys Arg Leu Ser Ser Val Cys Leu Ala
                485                 490                 495

Leu Thr Asn Ser Met Lys Thr Ser Val Ala Arg Leu Arg Gln Asn
            500                 505                 510

Gln Leu Gly Ser Val Arg Tyr Gln Val Val Glu Cys Lys Glu Val Phe
        515                 520                 525

Cys Gln Val Ile Lys Leu Asp Ser Glu Glu Tyr His Leu Leu Tyr Gln
    530                 535                 540
```

-continued

```
Lys Thr Gly Glu Ser Ser Arg Cys Tyr Ser Ile Gln Gly Pro Asn Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Ile Asp Asp Val Glu Ile
                595                 600                 605

Ala Leu Arg Thr Leu Leu Leu Met Leu Thr Asn Pro Thr Lys Arg
610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Lys Leu Leu Arg Phe Leu Ile
            660                 665                 670

Lys Thr Val Phe Gly Thr Gly Glu Lys Val Leu Leu Ser Ala Lys Phe
                675                 680                 685

Lys Phe Met Leu Asn Val Ser Tyr Leu Cys His Leu Ile Thr Lys Glu
690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Ser Ile
                725                 730                 735

Thr Pro Glu Glu Glu Cys Val Phe Tyr Asp Gln Met Lys Lys Phe Thr
            740                 745                 750

Gly Lys Glu Val Asp Cys Gln Arg Thr Thr Pro Gly Val Asn Leu Glu
                755                 760                 765

Ala Phe Ser Met Met Val Ser Ser Phe Asn Asn Gly Thr Leu Ile Phe
            770                 775                 780

Lys Gly Glu Lys Arg Leu Asn Ser Leu Asp Pro Met Thr Asn Ser Gly
785                 790                 795                 800

Cys Ala Thr Ala Leu Asp Leu Ala Ser Asn Lys Ser Val Val Val Asn
                805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Ser Phe Met Arg Lys Gln
                835                 840                 845

Lys Tyr Lys Leu Asn His Ser Asp Tyr Glu Tyr Lys Val Ser Lys Leu
            850                 855                 860

Val Ser Arg Leu Val Ile Gly Ser Lys Glu Thr Glu Ala Gly Lys Leu
865                 870                 875                 880

Glu Gly Asp Ser Ala Asp Ile Cys Phe Asp Gly Glu Glu Thr Ser
                885                 890                 895

Phe Phe Lys Asn Leu Glu Asp Lys Val Asn Ser Thr Ile Lys Arg Tyr
            900                 905                 910

Glu Arg Ser Lys Lys Thr Asn Glu Gly Glu Asn Glu Val Gly Phe Glu
                915                 920                 925

Asn Thr Lys Gly Leu His His Leu Gln Thr Ile Leu Ser Gly Lys Met
            930                 935                 940

Ala Tyr Leu Arg Lys Val Ile Leu Ser Glu Ile Ser Phe His Leu Val
945                 950                 955                 960
```

-continued

```
Glu Asp Phe Asp Pro Ser Cys Leu Thr Asn Asp Met Lys Phe Ile
            965                 970                 975
Cys Glu Ala Ile Glu Thr Ser Thr Glu Leu Ser Pro Leu Tyr Phe Thr
            980                 985                 990
Ser Ala Val Lys Glu Gln Cys Gly Leu Asp Glu Met Ala Lys Asn Leu
            995                 1000                1005
Cys Arg Lys Phe Phe Ser Glu Gly Asp Trp Phe Ser Cys Met Lys
        1010                1015                1020
Met Ile Leu Leu Gln Met Asn Ala Asn Ala Tyr Ser Gly Lys Tyr
        1025                1030                1035
Arg His Met Gln Arg Gln Gly Leu Asn Phe Lys Phe Asp Trp Asp
        1040                1045                1050
Lys Leu Glu Glu Asp Val Arg Ile Ser Glu Arg Glu Ser Asn Ser
        1055                1060                1065
Glu Ser Leu Ser Lys Ala Leu Ser Leu Thr Lys Cys Met Ser Ala
        1070                1075                1080
Ala Leu Lys Asn Leu Cys Phe Tyr Ser Glu Glu Ser Pro Thr Ser
        1085                1090                1095
Tyr Thr Ser Val Gly Pro Asp Ser Gly Arg Leu Lys Phe Ala Leu
        1100                1105                1110
Ser Tyr Lys Glu Gln Val Gly Gly Asn Arg Glu Leu Tyr Ile Gly
        1115                1120                1125
Asp Leu Arg Thr Lys Met Phe Thr Arg Leu Ile Glu Asp Tyr Phe
        1130                1135                1140
Glu Ser Phe Ser Ser Phe Ser Gly Ser Cys Leu Asn Asn Asp
        1145                1150                1155
Lys Glu Phe Glu Asn Ala Ile Leu Ser Met Thr Ile Asn Val Arg
        1160                1165                1170
Glu Gly Leu Leu Asn Tyr Ser Met Asp His Ser Lys Trp Gly Pro
        1175                1180                1185
Met Met Cys Pro Phe Leu Phe Leu Met Leu Leu Gln Asn Leu Lys
        1190                1195                1200
Leu Gly Asp Asp Gln Tyr Val Arg Ser Gly Lys Asp His Ile Ser
        1205                1210                1215
Thr Leu Leu Thr Trp His Met His Lys Leu Val Glu Val Pro Phe
        1220                1225                1230
Pro Val Val Asn Ala Met Met Lys Ser Tyr Ile Lys Ser Lys Leu
        1235                1240                1245
Lys Leu Leu Arg Gly Ser Glu Thr Thr Val Thr Glu Arg Ile Phe
        1250                1255                1260
Arg Glu Tyr Phe Glu Leu Gly Ile Val Pro Ser His Ile Ser Ser
        1265                1270                1275
Leu Ile Asp Met Gly Gln Gly Ile Leu His Asn Ala Ser Asp Phe
        1280                1285                1290
Tyr Gly Leu Ile Ser Glu Arg Phe Ile Asn Tyr Cys Ile Gly Val
        1295                1300                1305
Ile Phe Gly Glu Arg Pro Glu Ser Tyr Thr Ser Ser Asp Asp Gln
        1310                1315                1320
Ile Thr Leu Phe Asp Arg Arg Leu Ser Glu Leu Val Asp Ser Asp
        1325                1330                1335
Pro Glu Glu Val Leu Val Leu Leu Glu Phe His Ser His Leu Ser
        1340                1345                1350
Gly Leu Leu Asn Lys Phe Ile Ser Pro Lys Ser Val Val Gly Arg
```

-continued

|  | 1355 |  |  |  | 1360 |  |  |  | 1365 |  |
| --- | --- | --- | --- | --- | --- | --- | --- | --- | --- | --- |
| Phe | Ala | Ala | Glu | Phe | Lys | Ser | Arg | Phe | Tyr | Val | Trp | Gly | Glu | Glu |
|  | 1370 |  |  |  | 1375 |  |  |  | 1380 |  |

Val Pro Leu Leu Thr Lys Phe Val Ser Ala Ala Leu His Asn Val
 1385             1390              1395

Lys Cys Lys Glu Pro His Gln Leu Cys Glu Thr Ile Asp Thr Ile
 1400             1405              1410

Ala Asp Gln Ala Val Ala Asn Gly Val Pro Val Ser Leu Val Asn
 1415             1420              1425

Cys Ile Gln Lys Arg Thr Leu Asp Leu Leu Lys Tyr Ala Asn Phe
 1430             1435              1440

Pro Leu Asp Pro Phe Leu Leu Asn Thr Asn Thr Asp Val Lys Asp
 1445             1450              1455

Trp Leu Asp Gly Ser Arg Gly Tyr Arg Ile Gln Arg Leu Ile Glu
 1460             1465              1470

Glu Leu Cys Pro Ser Glu Thr Lys Val Met Arg Arg Leu Val Arg
 1475             1480              1485

Arg Leu His His Lys Leu Lys Asn Gly Glu Phe Asn Glu Glu Phe
 1490             1495              1500

Phe Leu Asp Leu Phe Asn Arg Asp Lys Lys Glu Ala Ile Leu Gln
 1505             1510              1515

Leu Gly Asn Ile Leu Gly Leu Glu Glu Asp Leu Ser Gln Leu Ala
 1520             1525              1530

Asn Ile Asn Trp Leu Asn Leu Asn Glu Leu Phe Pro Leu Arg Met
 1535             1540              1545

Val Leu Arg Gln Lys Val Val Tyr Pro Ser Val Met Thr Phe Gln
 1550             1555              1560

Glu Glu Arg Ile Pro Ser Leu Ile Lys Thr Leu Gln Asn Lys Leu
 1565             1570              1575

Cys Ser Lys Phe Thr Arg Gly Ala Gln Lys Leu Leu Ser Glu Ala
 1580             1585              1590

Ile Asn Lys Ser Ala Phe Gln Ser Cys Ile Ser Ser Gly Phe Ile
 1595             1600              1605

Gly Leu Cys Lys Thr Leu Gly Ser Arg Cys Val Arg Asn Lys Asn
 1610             1615              1620

Arg Asp Asn Leu Tyr Ile Arg Lys Val Leu Glu Asp Leu Ala Met
 1625             1630              1635

Asp Ala His Val Thr Ala Ile His Arg His Asp Gly Ile Met Leu
 1640             1645              1650

Tyr Ile Cys Asp Arg Gln Ser His Pro Glu Ala His Cys Asp His
 1655             1660              1665

Ile Ser Leu Leu Arg Pro Leu Leu Trp Asp Tyr Ile Cys Ile Ser
 1670             1675              1680

Leu Ser Asn Ser Phe Glu Leu Gly Val Trp Val Leu Ala Glu Pro
 1685             1690              1695

Val Lys Gly Lys Asn Glu Gly Ser Ser Ser Leu Lys His Leu Asn
 1700             1705              1710

Pro Cys Asp Tyr Val Ala Arg Lys Pro Glu Ser Ser Arg Leu Leu
 1715             1720              1725

Glu Asp Lys Ile Ser Leu Asn His Val Ile Gln Ser Val Arg Arg
 1730             1735              1740

Leu Tyr Pro Lys Ile Tyr Glu Asp Gln Leu Leu Pro Phe Met Ser
 1745             1750              1755

```
Asp Met Ser Ser Lys Asn Met Arg Trp Ser Pro Arg Ile Lys Phe
    1760            1765                1770
Leu Asp Leu Cys Val Leu Ile Asp Ile Asn Ser Glu Ser Leu Ser
    1775            1780                1785
Leu Ile Ser His Val Val Lys Trp Lys Arg Asp Glu His Tyr Thr
    1790            1795                1800
Val Leu Phe Ser Asp Leu Val Asn Ser His Gln Arg Ser Asp Ser
    1805            1810                1815
Ser Leu Val Asp Glu Phe Val Val Ser Thr Arg Asp Val Cys Lys
    1820            1825                1830
Asn Phe Leu Lys Gln Val Tyr Phe Glu Ser Phe Val Arg Glu Phe
    1835            1840                1845
Val Ala Thr Ser Arg Thr Leu Gly Ser Phe Ser Trp Phe Pro His
    1850            1855                1860
Lys Asp Met Met Pro Ser Glu Asp Gly Ala Glu Ala Leu Gly Pro
    1865            1870                1875
Phe Gln Ser Phe Ile Leu Lys Val Val Asn Lys Asn Met Glu Arg
    1880            1885                1890
Pro Met Phe Arg Asn Asp Leu Gln Phe Gly Phe Gly Trp Phe Ser
    1895            1900                1905
Tyr Arg Leu Gly Asp Ile Val Cys Asn Ala Ala Met Leu Ile Lys
    1910            1915                1920
Gln Gly Leu Thr Asn Pro Lys Ala Phe Lys Ser Leu Arg Asn Leu
    1925            1930                1935
Trp Asp Tyr Met Ile Asn Asn Thr Glu Gly Val Leu Glu Phe Ser
    1940            1945                1950
Ile Thr Val Asp Phe Thr His Asn Gln Asn Asn Thr Asp Cys Leu
    1955            1960                1965
Arg Lys Phe Ser Leu Ile Phe Leu Val Lys Cys Gln Leu Gln Gly
    1970            1975                1980
Pro Gly Val Ala Glu Phe Leu Ser Cys Ser His Leu Phe Lys Gly
    1985            1990                1995
Glu Val Asp Arg Arg Phe Leu Asp Glu Cys Leu His Leu Leu Arg
    2000            2005                2010
Ser Asp Ser Ile Phe Lys Val Asn Asp Gly Val Phe Asp Ile Arg
    2015            2020                2025
Ser Glu Glu Phe Glu Asp Tyr Met Glu Asp Pro Leu Ile Leu Gly
    2030            2035                2040
Asp Ser Leu Glu Leu Glu Leu Ile Gly Ser Arg Lys Ile Leu Asp
    2045            2050                2055
Gly Ile Arg Ser Leu Asp Phe Glu Arg Ile Gly Pro Glu Trp Glu
    2060            2065                2070
Pro Val Pro Leu Thr Val Arg Met Gly Ala Leu Phe Glu Gly Arg
    2075            2080                2085
Ser Leu Val Gln Asn Ile Val Val Lys Leu Glu Thr Lys Asp Met
    2090            2095                2100
Arg Val Phe Leu Ala Glu Leu Glu Gly Tyr Gly Asn Phe Asp Asp
    2105            2110                2115
Val Leu Gly Ser Leu Leu Leu His Arg Phe Arg Thr Gly Glu His
    2120            2125                2130
Leu Gln Gly Ser Glu Ile Ser Thr Ile Leu Gln Glu Leu Cys Ile
    2135            2140                2145
```

```
Asp Arg Ser Ile Leu Leu Val Pro Leu Ser Leu Val Pro Asp Trp
    2150                2155                2160
Phe Thr Phe Lys Asp Cys Arg Leu Cys Phe Ser Lys Ser Lys Asn
    2165                2170                2175
Thr Val Met Tyr Glu Thr Val Val Gly Lys Tyr Arg Leu Lys Gly
    2180                2185                2190
Lys Ser Cys Asp Asp Trp Leu Thr Lys Ser Val Val Glu Glu Ile
    2195                2200                2205
Asp
```

<210> SEQ ID NO 57
<211> LENGTH: 90
<212> TYPE: PRT
<213> ORGANISM: Unknown
<220> FEATURE:
<223> OTHER INFORMATION: Z protein of the MP strain of LCMV

<400> SEQUENCE: 57

```
Met Gly Gln Gly Lys Ser Lys Glu Gly Arg Asp Ala Ser Asn Thr Ser
1               5                   10                  15
Arg Ala Glu Ile Leu Pro Asp Thr Thr Tyr Leu Gly Pro Leu Asn Cys
                20                  25                  30
Lys Ser Cys Trp Gln Arg Phe Asp Ser Leu Val Arg Cys His Asp His
            35                  40                  45
Tyr Leu Cys Arg His Cys Leu Asn Leu Leu Leu Ser Val Ser Asp Arg
    50                  55                  60
Cys Pro Leu Cys Lys His Pro Leu Pro Thr Lys Leu Lys Ile Ser Thr
65                  70                  75                  80
Ala Pro Ser Ser Pro Pro Pro Tyr Glu Glu
                85                  90
```

<210> SEQ ID NO 58
<211> LENGTH: 4604
<212> TYPE: DNA
<213> ORGANISM: Artificial Sequence
<220> FEATURE:
<223> OTHER INFORMATION: LCMV clone 13 S-Segment encoding HCMV strain
      Merlin gB

<400> SEQUENCE: 58

```
gcgcaccggg gatcctaggc tttttggatt gcgctttcct ctagatcaac tgggtgtcag      60
gccctatcct acagaaggat ggaatccagg atctggtgcc tggtagtctg cgttaacttg     120
tgtatcgtct gtctgggtgc tgcggtttcc tcatcttcta ctcgtggaac ttctgctact     180
cacagtcacc attcctctca tacgacgtct gctgctcact ctcgatccgg ttcagtctct     240
caacgcgtaa cttcttccca acggtcagc atggtgtta acgagaccat ctacaacact       300
accctcaagt acggagatgt ggtggggtc aataccacca gtaccccta tcgcgtgtgt       360
tctatggccc agggtacgga tcttattcgc tttgaacgta atatcgtctg cacctcgatg     420
aagcccatca tgaagacct ggacgagggc atcatggtgg tctacaaacg caacatcgtc      480
gcgcacacct ttaaggtacg agtctaccag aaggttttga cgtttcgtcg tagctacgct     540
tacatccaca ccactatct gctgggcagc aacacggaat acgtggcgcc tcctatgtgg     600
gagattcatc atatcaacag ccacagtcag tgctacagtt cctacagccg cgttatagca     660
ggcacggttt tcgtggctta tcatagggac agctatgaaa acaaaaccat gcaattaatg     720
cccgacgatt attccaacac ccacagtacc cgttacgtga cggtcaagga tcaatggcac     780
```

```
agccgcggca gcacctggct ctatcgtgag acctgtaatc tgaattgtat ggtgaccatc      840
actactgcgc gctccaaata tccttatcat tttttcgcca cttccacggg tgacgtggtt      900
gacatttctc ctttctacaa cggaaccaat cgcaatgcca gctactttgg agaaaacgcc      960
gacaagtttt tcattttttcc gaactacact attgtctccg actttggaag accgaattct     1020
gcgttagaga cccacaggtt ggtggctttt cttgaacgtg cggactcggt gatctcctgg     1080
gatatacagg acgaaaagaa tgtcacttgt caactcactt tctgggaagc tcggaacgc     1140 accattcgtt ccgaagccga ggactcgtat cacttttctt ctgccaaaat gaccgccact     1200
ttcttatcta agaagcaaga ggtgaacatg tccgactctg cgctggactg cgtacgtgat     1260
gaggctataa ataagttaca gcagattttc aatacttcat acaatcaaac atatgaaaaa     1320
tatggaaacg tgtccgtctt tgaaaccact ggtggtttgg tagtgttctg gcaaggtatc     1380
aagcaaaaat ctctggtgga actcgaacgt ttggccaacc gctccagtct gaatcttact     1440
cataatagaa ccaaaagaag tacagatggc aacaatgcaa ctcatttatc caacatggaa     1500
tcggtgcaca atctggtcta cgcccagctg cagttcacct atgacgtt gcgcggttac     1560 atcaaccggg cgctggcgca aatcgcagaa gcctggtgtg tggatcaacg gcgcacccta     1620
gaggtcttca aggaactcag caagatcaac ccgtcagcca ttctctcggc catttacaac     1680
aaaccgattg ccgcgcgttt catgggtgat gtcttgggcc tggccagctg cgtgaccatc     1740
aaccaaacca gcgtcaaggt gctgcgtgat atgaacgtga aggagtcgcc aggacgctgc     1800
tactcacgac ccgtggtcat ctttaatttc gccaacagct cgtacgtgca gtacggtcaa     1860
ctgggcgagg acaacgaaat cctgttgggc aaccaccgca ctgaggaatg tcagcttccc     1920
agcctcaaga tcttcatcgc cgggaactcg gcctacgagt acgtggacta cctcttcaaa     1980
cgcatgattg acctcagcag tatctccacc gtcgacagca tgatcgccct ggatatcgac     2040
ccgctggaaa ataccgactt cagggtactg gaactttact cgcagaaaga gctgcgttcc     2100
agcaacgttt ttgacctcga agagatcatg cgcgaattca actcgtacaa gcagcgggta     2160
aagtacgtgg aggacaaggt agtcgacccg ctaccgccct acctcaaggg tctggacgac     2220
ctcatgagcg gcctgggcgc cgcgggaaag gccgttggcg tagccattgg ggccgtgggt     2280
ggcgcggtgg cctccgtggt cgaaggcgtt gccaccttcc tcaaaaaccc cttcggagcg     2340
ttcaccatca tcctcgtggc catagctgta gtcattatca cttatttgat ctatactcga     2400
cagcggcgtt tgtgcacgca gccgctgcag aacctctttc cctatctggt gtccgccgac     2460
gggaccaccg tgacgtcggg cagcaccaaa gacacgtcgt tacaggctcc gccttcctac     2520
gaggaaagtg tttataattc tggtcgcaaa ggaccgggac caccgtcgtc tgatgcatcc     2580
acggcggctc cgccttacac caacgagcag gcttaccaga tgcttctggc cctggcccgt     2640
ctggacgcag agcagcgagc gcagcagaac ggtacagatt ctttggacgg acggactggc     2700
acgcaggaca agggacagaa gcccaaccta ctagaccgac tgcgacatcg caaaaacggc     2760
taccgacact tgaaagactc tgacgaagaa gagaacgtct gaagaacagc gcctccctga     2820
ctctccacct cgaaagaggt ggagagtcag ggaggcccag agggtcttag agtgtcacaa     2880
catttgggcc tctaaaaatt aggtcatgtg gcagaatgtt gtgaacagtt ttcagatctg     2940
ggagccttgc tttggaggcg cttttcaaaaa tgatgcagtc catgagtgca cagtgcgggg     3000
tgatctcttt cttcttttttg tcccttacta ttccagtatg catcttacac aaccagccat     3060
atttgtccca cactttatct tcatactccc tcgaagcttc cctggtcatt tcaacatcga     3120
taagcttaat gtccttccta ttttgtgagt ccagaagctt tctgatgtca tcggagcctt     3180
```

-continued

```
gacagcttag aaccatcccc tgcggaagag cacctataac tgacgaggtc aacccgggtt    3240
gcgcattgaa gaggtcggca agatccatgc cgtgtgagta cttggaatct tgcttgaatt    3300
gtttttgatc aacgggttcc ctgtaaaagt gtatgaactg cccgttctgt ggttggaaaa    3360
ttgctatttc cactggatca ttaaatctac cctcaatgtc aatccatgta ggagcgttgg    3420
ggtcaattcc tcccatgagg tcttttaaaa gcattgtctg gctgtagctt aagcccacct    3480
gaggtggacc tgctgctcca ggcgctggcc tgggtgagtt gactgcaggt ttctcgcttg    3540
tgagatcaat tgttgtgttt tcccatgctc tccccacaat cgatgttcta caagctatgt    3600
atggccatcc ttcacctgaa aggcaaactt tatagaggat gttttcataa gggttcctgt    3660
ccccaacttg gtctgaaaca acatgttga gttttctctt ggccccgaga actgccttca    3720
agagatcctc gctgttgctt ggcttgatca aaattgactc taacatgtta ccccccatcca    3780 acagggctgc ccctgccttc acggcagcac caagactaaa gttatagcca gaaatgttga    3840
tgctggactc tgttcagtg atgaccccca gaactgggtg cttgtctttc agcctttcaa    3900
gatcattaag atttggatac ttgactgtgt aaagcaagcc aaggtctgtg agcgcttgta    3960
caacgtcatt gagcggagtc tgtgactgtt tggccataca agccatagtt agacttggca    4020
ttgtgccaaa ttgattgttc aaaagtgatg agtctttcac atcccaaact cttaccacac    4080
cacttgcacc ctgctgaggc tttctcatcc caactatctg taggatctga gatctttggt    4140
ctagttgctg tgttgttaag ttccccatat ataccctga agcctggggc ctttcagacc    4200
tcatgatctt ggccttcagc ttctcaaggt cagccgcaag agacatcagt tcttctgcac    4260
tgagcctccc cactttcaaa acattcttct ttgatgttga ctttaaatcc acaagagaat    4320
gtacagtctg gttgagactt ctgagtctct gtaggtcttt gtcatctctc tttccttcc    4380 tcatgatcct ctgaacattg ctgaccctcag agaagtccaa cccattcaga aggttggttg    4440
catccttaat gacagcagcc ttcacatctg atgtgaagct ctgcaattct cttctcaatg    4500
cttgcgtcca ttggaagctc ttaacttcct tagacaagga catcttgttg ctcaatggtt    4560
tctcaagaca aatgcgcaat caaatgccta ggatccactg tgcg    4604
```

<210> SEQ ID NO 59
<211> LENGTH: 2724
<212> TYPE: DNA
<213> ORGANISM: Human cytomegalovirus
<220> FEATURE:
<223> OTHER INFORMATION: HCMV strain Merlin gB(FL) cDNA

<400> SEQUENCE: 59

```
atggaatcca ggatctggtg cctggtagtc tgcgttaact tgtgtatcgt ctgtctgggt      60
gctgcggttt cctcatcttc tactcgtgga acttctgcta ctcacagtca ccattcctct     120
catacgacgt ctgctgctca ctctcgatcc ggttcagtct ctcaacgcgt aacttcttcc     180
caaacggtca gccatggtgt aacgagacc atctacaaca ctaccctcaa gtacggagat     240
gtggtggggg tcaataccac caagtacccc tatcgcgtgt gttctatggc ccagggtacg     300
gatcttattc gctttgaacg taatatcgtc tgcacctcga tgaagcccat caatgaagac     360
ctggacgagg catcatggt ggtctacaaa cgcaacatcg tcgcgcacac ctttaaggta     420
cgagtctacc agaaggtttt gacgtttcgt cgtagctacg cttacatcca ccaccttat     480 ctgctgggca gcaacacgga atacgtagcg cctcctatgt gggagattca tcatatcaac     540
agccacagtc agtgctacag ttcctacagc cgcgttatag caggcacggt tttcgtggct     600
```

| | |
|---|---|
| tatcataggg acagctatga aaacaaaacc atgcaattaa tgcccgacga ttattccaac | 660 |
| acccacagta cccgttacgt gacggtcaag gatcaatggc acagccgcgg cagcacctgg | 720 |
| ctctatcgtg agacctgtaa tctgaattgt atggtgacca tcactactgc gcgctccaaa | 780 |
| tatccttatc attttttcgc cacttccacg ggtgacgtgg ttgacatttc tcctttctac | 840 |
| aacggaacca atcgcaatgc cagctacttt ggagaaaacg ccgacaagtt tttcattttt | 900 |
| ccgaactaca ctattgtctc cgactttgga gaccgaatt ctgcgttaga gacccacagg | 960 |
| ttggtggctt ttcttgaacg tgcggactcg gtgatctcct gggatataca ggacgaaaag | 1020 |
| aatgtcactt gtcaactcac tttctgggaa gcctcggaac gcaccattcg ttccgaagcc | 1080 |
| gaggactcgt atcactttc ttctgccaaa atgaccgcca ctttcttatc taagaagcaa | 1140 |
| gaggtgaaca tgtccgactc tgcgctggac tgcgtacgtg atgaggctat aaataagtta | 1200 |
| cagcagattt tcaatacttc atacaatcaa acatatgaaa aatatggaaa cgtgtccgtc | 1260 |
| tttgaaacca ctggtggttt ggtagtgttc tggcaaggta tcaagcaaaa atctctggtg | 1320 |
| gaactcgaac gtttggccaa ccgctccagt ctgaatctta ctcataatag aaccaaaaga | 1380 |
| agtacagatg caacaatgc aactcattta tccaacatgg aatcggtgca caatctggtc | 1440 |
| tacgcccagc tgcagttcac ctatgacacg ttgcgcggtt acatcaaccg ggcgctggcg | 1500 |
| caaatcgcag aagcctggtg tgtggatcaa cggcgcaccc tagaggtctt caaggaactc | 1560 |
| agcaagatca cccgtcagc cattctctcg gccatttaca caaaccgat tgccgcgcgt | 1620 |
| ttcatgggtg atgtcttggg cctggccagc tgcgtgacca tcaaccaaac cagcgtcaag | 1680 |
| gtgctgcgtg atatgaacgt gaaggagtcg ccaggacgct gctactcacg acccgtggtc | 1740 |
| atctttaatt cgccaacag ctcgtacgtg cagtacggtc aactgggcga ggacaacgaa | 1800 |
| atcctgttgg gcaaccaccg cactgaggaa tgtcagcttc ccagcctcaa gatcttcatc | 1860 |
| gccgggaact cggcctacga gtacgtggac tacctcttca aacgcatgat tgacctcagc | 1920 |
| agtatctcca ccgtcgacag catgatcgcc ctggatatcg acccgctgga aaataccgac | 1980 |
| ttcagggtac tggaacttta ctcgcagaaa gagctgcgtt ccagcaacgt ttttgacctc | 2040 |
| gaagagatca tgcgcgaatt caactcgtac aagcagcggg taaagtacgt ggaggacaag | 2100 |
| gtagtcgacc cgctaccgcc ctacctcaag ggtctggacg acctcatgag cggcctgggc | 2160 |
| gccgcgggaa aggccgttgg cgtagccatt ggggccgtgg gtggcgcggt ggcctccgtg | 2220 |
| gtcgaaggcg ttgccacctt cctcaaaaac cccttcggag cgttcaccat catcctcgtg | 2280 |
| gccatagctg tagtcattat cacttatttg atctatactc gacagcggcg tttgtgcacg | 2340 |
| cagccgctgc agaacctctt tcccctatctg gtgtccgccg acgggaccac cgtgacgtcg | 2400 |
| ggcagcacca agacacgtc gttacaggct ccgccttcct acgaggaaag tgtttataat | 2460 |
| tctggtcgca aaggaccggg accaccgtcg tctgatgcat ccacggcggc tccgccttac | 2520 |
| accaacgagc aggcttacca gatgcttctg gccctggccc gtctggacgc agagcagcga | 2580 |
| gcgcagcaga acggtacaga ttcttttggac ggacggactg gcacgcagga caagggacag | 2640 |
| aagcccaacc tactagaccg actgcgacat cgcaaaaacg gctaccgaca cttgaaagac | 2700 |
| tctgacgaag aagagaacgt ctga | 2724 |

<210> SEQ ID NO 60
<211> LENGTH: 907
<212> TYPE: PRT
<213> ORGANISM: Human cytomegalovirus
<220> FEATURE:
<223> OTHER INFORMATION: HCMV strain Merlin gB(FL)

<400> SEQUENCE: 60

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
            35                  40                  45

Arg Ser Gly Ser Val Ser Gln Arg Val Thr Ser Ser Gln Thr Val Ser
        50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
        130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
            370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
```

```
            405                 410                 415
Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
            435                 440                 445

Ser Ser Leu Asn Leu Thr His Asn Arg Thr Lys Arg Ser Thr Asp Gly
            450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
            485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
            515                 520                 525

Leu Ser Ala Ile Tyr Asn Lys Pro Ile Ala Ala Arg Phe Met Gly Asp
            530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                    565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
            595                 600                 605

Glu Glu Cys Gln Leu Pro Ser Leu Lys Ile Phe Ile Ala Gly Asn Ser
610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
            645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
            675                 680                 685

Ser Tyr Lys Gln Arg Val Lys Tyr Val Glu Asp Lys Val Val Asp Pro
            690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
            725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
            755                 760                 765

Tyr Leu Ile Tyr Thr Arg Gln Arg Arg Leu Cys Thr Gln Pro Leu Gln
            770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
            805                 810                 815

Ser Val Tyr Asn Ser Gly Arg Lys Gly Pro Gly Pro Pro Ser Ser Asp
            820                 825                 830
```

```
Ala Ser Thr Ala Ala Pro Pro Tyr Thr Asn Glu Gln Ala Tyr Gln Met
            835                 840                 845

Leu Leu Ala Leu Ala Arg Leu Asp Ala Glu Gln Ala Gln Gln Asn
    850                 855                 860

Gly Thr Asp Ser Leu Asp Gly Arg Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Glu Asn Val
            900                 905

<210> SEQ ID NO 61
<211> LENGTH: 4376
<212> TYPE: DNA
<213> ORGANISM: Artificial Sequence
<220> FEATURE:
<223> OTHER INFORMATION: LCMV clone 13 S-Segment encoding HCMV strain
      Merlin gB (dTM)

<400> SEQUENCE: 61
gcgcaccggg gatcctaggc ttttggatt gcgctttcct ctagatcaac tgggtgtcag      60
gccctatcct acagaaggat ggaatccagg atctggtgcc tggtagtctg cgttaacttg    120
tgtatcgtct gtctgggtgc tgcggttttcc tcatcttcta ctcgtggaac ttctgctact   180
cacagtcacc attcctctca tacgacgtct gctgctcact ctcgatccgg ttcagtctct    240
caacgcgtaa cttcttccca aacggtcagc atggtgtta acgagaccat ctacaacact    300
accctcaagt acggagatgt ggtgggggtc aataccacca gtacccccta tcgcgtgtgt   360
tctatggccc agggtacgga tcttattcgc tttgaacgta atatcgtctg cacctcgatg    420
aagcccatca atgaagacct ggacgagggc atcatggtgg tctacaaacg caacatcgtc    480
gcgcacacct ttaaggtacg agtctaccag aaggttttga cgtttcgtcg tagctacgct    540
tacatccaca ccacttatct gctgggcagc aacacggaat acgtggcgcc tcctatgtgg    600
gagattcatc atatcaacag ccacagtcag tgctacagtt cctacagccg cgttatagca    660
ggcacggttt tcgtggctta tcatagggac agctatgaaa caaaaccat gcaattaatg     720 cccgacgatt attccaacac ccacagtacc cgttacgtga cggtcaagga tcaatggcac    780
agccgcggca gcacctggct ctatcgtgag acctgtaatc tgaattgtat ggtgaccatc    840
actactgcgc gctccaaata tccttatcat tttttcgcca cttccacggg tgacgtggtt    900
gacatttctc ctttctacaa cggaaccaat cgcaatgcca gctactttgg agaaaacgcc    960
gacaagtttt tcattttttcc gaactacact attgtctccg actttggaag accgaattct   1020
gcgttagaga cccacaggtt ggtggctttt cttgaacgtg cggactcggt gatctcctgg    1080
gatatacagg acgaaaagaa tgtcacttgt caactcactt tctgggaagc ctcggaacgc    1140
accattcgtt ccgaagccga ggactcgtat cacttttctt ctgccaaaat gaccgccact   1200
ttcttatcta agaagcaaga ggtgaacatg tccgactctg cgctggactg cgtacgtgat   1260
gaggctataa ataagttaca gcagattttc aatacttcat acaatcaaac atatgaaaaa    1320
tatggaaacg tgtccgtctt tgaaaccact ggtggtttgg tagtgttctg gcaaggtatc   1380
aagcaaaaat ctctggtgga actcgaacgt ttggccaacc gctccagtct gaatcttact   1440
cataatagaa ccaaaagaag tacagatggc aacaatgcaa ctcatttatc caacatggaa   1500
tcggtgcaca atctggtcta cgcccagctg cagttcaccct atgacacgtt gcgcggttac   1560
```

```
atcaaccggg cgctggcgca aatcgcagaa gcctggtgtg tggatcaacg gcgcacccta    1620
gaggtcttca aggaactcag caagatcaac ccgtcagcca ttctctcggc catttacaac    1680
aaaccgattg ccgcgcgttt catgggtgat gtcttgggcc tggccagctg cgtgaccatc    1740
aaccaaacca gcgtcaaggt gctgcgtgat atgaacgtga aggagtcgcc aggacgctgc    1800
tactcacgac ccgtggtcat ctttaatttc gccaacagct cgtacgtgca gtacggtcaa    1860
ctgggcgagg acaacgaaat cctgttgggc aaccaccgca ctgaggaatg tcagcttccc    1920
agcctcaaga tcttcatcgc cgggaactcg gcctacgagt acgtggacta cctcttcaaa    1980
cgcatgattg acctcagcag tatctccacc gtcgacagca tgatcgccct ggatatcgac    2040
ccgctggaaa ataccgactt cagggtactg aactttact cgcagaaaga gctgcgttcc     2100
agcaacgttt ttgacctcga agagatcatg cgcgaattca actcgtacaa gcagcgggta    2160
aagtacgtgg aggaccggcg tttgtgcacg cagccgctgc agaacctctt tccctatctg    2220
gtgtccgccg acgggaccac cgtgacgtcg ggcagcacca agacacgtc gttacaggct     2280 ccgccttcct acgaggaaag tgtttataat tctggtcgca aaggaccggg accaccgtcg    2340
tctgatgcat ccacggcggc tccgccttac accaacgagc aggcttacca gatgcttctg    2400
gccctggccc gtctggacgc agagcagcga gcgcagcaga acgtacaga ttctttggac     2460 ggacggactg gcacgcagga caagggacag aagcccaacc tactagaccg actgcgacat    2520
cgcaaaaacg gctaccgaca cttgaaagac tctgacgaag aagagaacgt ctgaagaaca    2580
gcgcctccct gactctccac ctcgaaagag gtggagagtc agggaggccc agagggtctt    2640
agagtgtcac aacatttggg cctctaaaaa ttaggtcatg tggcagaatg ttgtgaacag    2700
ttttcagatc tgggagcctt gctttggagg cgctttcaaa aatgatgcag tccatgagtg    2760
cacagtgcgg ggtgatctct ttcttctttt tgtcccttac tattccagta tgcatcttac    2820
acaaccagcc atatttgtcc cacactttat cttcatactc cctcgaagct tccctggtca    2880
tttcaacatc gataagctta atgtccttcc tattttgtga gtccagaagc tttctgatgt    2940
catcggagcc ttgacagctt agaaccatcc cctgcggaag agcacctata actgacgagg    3000
tcaacccggg ttgcgcattg aagaggtcgg caagatccat gccgtgtgag tacttggaat    3060
cttgcttgaa ttgttttttga tcaacgggtt ccctgtaaaa gtgtatgaac tgcccgttct    3120
gtggttggaa aattgctatt tccactggat cattaaatct accctcaatg tcaatccatg    3180
taggagcgtt ggggtcaatt cctcccatga ggtcttttaa aagcattgtc tggctgtagc    3240
ttaagcccac ctgaggtgga cctgctgctc caggcgctgg cctgggtgag ttgactgcag    3300
gtttctcgct tgtgagatca attgttgtgt tttcccatgc tctccccaca atcgatgttc    3360
tacaagctat gtatggccat ccttcacctg aaaggcaaac tttatagagg atgttttcat    3420
aagggttcct gtccccaact tggtctgaaa caaacatgtt gagttttctc ttggccccga    3480
gaactgcctt caagagatcc tcgctgttgc ttggcttgat caaaattgac tctaacatgt    3540
tacccccatc caacagggct gcccctgcct tcacggcagc accaagacta aagttatagc    3600
cagaaatgtt gatgctggac tgctgttcag tgatgacccc cagaactggg tgcttgtctt    3660
tcagcctttc aagatcatta agatttggat acttgactgt gtaaagcaag ccaaggtctg    3720
tgagcgcttg tacaacgtca ttgagcggag tctgtgactg tttggccata caagccatag    3780
ttagacttgg cattgtgcca aattgattgt tcaaaagtga tgagtcttc acatcccaaa      3840 ctcttaccac accacttgca ccctgctgag gctttctcat cccaactatc tgtaggatct    3900
gagatctttg gtctagttgc tgtgttgtta agttccccat atataccct gaagcctggg      3960
```

| | |
|---|---|
| gcctttcaga cctcatgatc ttggccttca gcttctcaag gtcagccgca agagacatca | 4020 |
| gttcttctgc actgagcctc cccactttca aaacattctt ctttgatgtt gactttaaat | 4080 |
| ccacaagaga atgtacagtc tggttgagac ttctgagtct ctgtaggtct ttgtcatctc | 4140 |
| tcttttcctt cctcatgatc ctctgaacat tgctgacctc agagaagtcc aacccattca | 4200 |
| gaaggttggt tgcatcctta atgacagcag ccttcacatc tgatgtgaag ctctgcaatt | 4260 |
| ctcttctcaa tgcttgcgtc cattggaagc tcttaacttc cttagacaag acatcttgt | 4320 |
| tgctcaatgg tttctcaaga caaatgcgca atcaaatgcc taggatccac tgtgcg | 4376 |

<210> SEQ ID NO 62
<211> LENGTH: 2493
<212> TYPE: DNA
<213> ORGANISM: Human cytomegalovirus
<220> FEATURE:
<223> OTHER INFORMATION: HCMV strain Merlin gB(dTM) cDNA

<400> SEQUENCE: 62

| | |
|---|---|
| atggaatcca ggatctggtg cctggtagtc tgcgttaact tgtgtatcgt ctgtctgggt | 60 |
| gctgcggttt cctcatcttc tactcgtgga acttctgcta ctcacagtca ccattcctct | 120 |
| catacgacgt ctgctgctca ctctcgatcc ggttcagtct ctcaacgcgt aacttcttcc | 180 |
| caaacggtca gccatggtgt taacgagacc atctacaaca ctaccctcaa gtacggagat | 240 |
| gtggtggggg tcaataccac caagtacccc tatcgcgtgt gttctatggc ccagggtacg | 300 |
| gatcttattc gctttgaacg taatatcgtc tgcacctcga tgaagcccat caatgaagac | 360 |
| ctggacgagg gcatcatggt ggtctacaaa cgcaacatcg tcgcgcacac ctttaaggta | 420 |
| cgagtctacc agaaggtttt gacgtttcgt cgtagctacg cttacatcca caccacttat | 480 |
| ctgctgggca gcaacacgga atacgtggcg cctcctatgt gggagattca tcatatcaac | 540 |
| agccacagtc agtgctacag ttcctacagc cgcgttatag caggcacggt tttcgtggct | 600 |
| tatcataggg acagctatga aaacaaaacc atgcaattaa tgcccgacga ttattccaac | 660 |
| acccacagta cccgttacgt gacggtcaag gatcaatggc acagccgcgg cagcaccctgg | 720 |
| ctctatcgtg agacctgtaa tctgaattgt atggtgacca tcactactgc gcgctccaaa | 780 |
| tatccttatc atttttttcgc cacttccacg ggtgacgtgg ttgacattc tcctttctac | 840 |
| aacggaacca atcgcaatgc cagctacttt ggagaaaacg ccgacaagtt tttcattttt | 900 |
| ccgaactaca ctattgtctc cgactttgga agaccgaatt ctgcgttaga cccacagg | 960 |
| ttggtggctt ttcttgaacg tgcggactcg gtgatctcct gggatataca ggacgaaaag | 1020 |
| aatgtcactt gtcaactcac tttctgggaa gcctcggaac gcaccattcg ttccgaagcc | 1080 |
| gaggactcgt atcactttc ttctgccaaa atgaccgcca ctttcttatc taagaagcaa | 1140 |
| gaggtgaaca tgtccgactc tgcgctggac tgcgtacgtg atgaggctat aaataagtta | 1200 |
| cagcagattt tcaatacttc atacaatcaa acatatgaaa aatatggaaa cgtgtccgtc | 1260 |
| tttgaaacca ctggtggttt ggtagtgttc tggcaaggta tcaagcaaaa atctctggtg | 1320 |
| gaactcgaac gtttggccaa ccgctccagt ctgaatctta ctcataatag aaccaaaaga | 1380 |
| agtacagatg caacaatgc aactcattta tccaacatgg aatcggtgca aatctggtc | 1440 |
| tacgcccagc tgcagttcac ctatgacacg ttgcgcggtt acatcaaccg ggcgctggcg | 1500 |
| caaatcgcag aagcctggtg tgtggatcaa cggcgcaccc tagaggtctt caaggaactc | 1560 |
| agcaagatca cccgtcagc cattctctcg gccatttaca caaaccgat tgccgcgcgt | 1620 |

```
ttcatgggtg atgtcttggg cctggccagc tgcgtgacca tcaaccaaac cagcgtcaag    1680
gtgctgcgtg atatgaacgt gaaggagtcg ccaggacgct gctactcacg acccgtggtc    1740
atctttaatt tcgccaacag ctcgtacgtg cagtacggtc aactgggcga ggacaacgaa    1800
atcctgttgg gcaaccaccg cactgaggaa tgtcagcttc ccagcctcaa gatcttcatc    1860
gccgggaact cggcctacga gtacgtggac tacctcttca aacgcatgat tgacctcagc    1920
agtatctcca ccgtcgacag catgatcgcc ctggatatcg acccgctgga aaataccgac    1980
ttcagggtac tggaacttta ctcgcagaaa gagctgcgtt ccagcaacgt ttttgacctc    2040
gaagagatca tgcgcgaatt caactcgtac aagcagcggg taaagtacgt ggaggaccgg    2100
cgtttgtgca cgcagccgct gcagaacctc tttccctatc tggtgtccgc cgacgggacc    2160
accgtgacgt cggggcagcac caaagacacg tcgttacagg ctccgccttc ctacgaggaa    2220
agtgtttata attctggtcg caaaggaccg ggaccaccgt cgtctgatgc atccacggcg    2280
gctccgcctt acaccaacga gcaggcttac cagatgcttc tggccctggc ccgtctggac    2340
gcagagcagc gagcgcagca gaacggtaca gattctttgg acggacggac tggcacgcag    2400
gacaagggac agaagcccaa cctactagac cgactgcgac atcgcaaaaa cggctaccga    2460
cacttgaaag actctgacga agaagagaac gtc                                 2493
```

<210> SEQ ID NO 63
<211> LENGTH: 831
<212> TYPE: PRT
<213> ORGANISM: Human cytomegalovirus
<220> FEATURE:
<223> OTHER INFORMATION: HCMV strain Merlin gB(dTM)

<400> SEQUENCE: 63

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205
```

-continued

Lys Thr Met Gln Leu Met Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
            245                 250                 255

Ala Arg Ser Lys Tyr Pro Tyr His Phe Phe Ala Thr Ser Thr Gly Asp
                260                 265                 270

Val Val Asp Ile Ser Pro Phe Tyr Asn Gly Thr Asn Arg Asn Ala Ser
                275                 280                 285

Tyr Phe Gly Glu Asn Ala Asp Lys Phe Phe Ile Phe Pro Asn Tyr Thr
290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
            325                 330                 335

Gln Asp Glu Lys Asn Val Thr Cys Gln Leu Thr Phe Trp Glu Ala Ser
                340                 345                 350

Glu Arg Thr Ile Arg Ser Glu Ala Glu Asp Ser Tyr His Phe Ser Ser
355                 360                 365

Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
            405                 410                 415

Asn Val Ser Val Phe Glu Thr Thr Gly Gly Leu Val Val Phe Trp Gln
                420                 425                 430

Gly Ile Lys Gln Lys Ser Leu Val Glu Leu Glu Arg Leu Ala Asn Arg
            435                 440                 445

Ser Ser Leu Asn Leu Thr His Asn Arg Thr Lys Arg Ser Thr Asp Gly
450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
            485                 490                 495

Arg Ala Leu Ala Gln Ile Ala Glu Ala Trp Cys Val Asp Gln Arg Arg
                500                 505                 510

Thr Leu Glu Val Phe Lys Glu Leu Ser Lys Ile Asn Pro Ser Ala Ile
            515                 520                 525

Leu Ser Ala Ile Tyr Asn Lys Pro Ile Ala Ala Arg Phe Met Gly Asp
530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
            565                 570                 575

Arg Pro Val Val Ile Phe Asn Phe Ala Asn Ser Ser Tyr Val Gln Tyr
                580                 585                 590

Gly Gln Leu Gly Glu Asp Asn Glu Ile Leu Leu Gly Asn His Arg Thr
            595                 600                 605

Glu Glu Cys Gln Leu Pro Ser Leu Lys Ile Phe Ile Ala Gly Asn Ser
610                 615                 620

-continued

```
Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Arg Arg Leu Cys Thr
    690                 695                 700

Gln Pro Leu Gln Asn Leu Phe Pro Tyr Leu Val Ser Ala Asp Gly Thr
705                 710                 715                 720

Thr Val Thr Ser Gly Ser Thr Lys Asp Thr Ser Leu Gln Ala Pro Pro
                725                 730                 735

Ser Tyr Glu Glu Ser Val Tyr Asn Ser Gly Arg Lys Gly Pro Gly Pro
            740                 745                 750

Pro Ser Ser Asp Ala Ser Thr Ala Ala Pro Pro Tyr Thr Asn Glu Gln
        755                 760                 765

Ala Tyr Gln Met Leu Leu Ala Leu Ala Arg Leu Asp Ala Glu Gln Arg
    770                 775                 780

Ala Gln Gln Asn Gly Thr Asp Ser Leu Asp Gly Arg Thr Gly Thr Gln
785                 790                 795                 800

Asp Lys Gly Gln Lys Pro Asn Leu Leu Asp Arg Leu Arg His Arg Lys
                805                 810                 815

Asn Gly Tyr Arg His Leu Lys Asp Ser Asp Glu Glu Glu Asn Val
            820                 825                 830
```